(12) United States Patent
Foster et al.

(10) Patent No.: US 11,015,201 B2
(45) Date of Patent: May 25, 2021

(54) ANGIOTENSINOGEN (AGT) IRNA COMPOSITIONS AND METHODS OF USE THEREOF

(71) Applicant: Alnylam Pharmaceuticals, Inc., Cambridge, MA (US)

(72) Inventors: Donald Foster, Attleboro, MA (US); Gregory Hinkle, Cambridge, MA (US); Mark K. Schlegel, Boston, MA (US)

(73) Assignee: Alnylam Pharmaceuticals, Inc., Cambridge, MA (US)

( * ) Notice: Subject to any disclaimer, the term of this patent is extended or adjusted under 35 U.S.C. 154(b) by 0 days.

(21) Appl. No.: 17/093,816

(22) Filed: Nov. 10, 2020

(65) Prior Publication Data

US 2021/0095290 A1   Apr. 1, 2021

Related U.S. Application Data

(63) Continuation of application No. PCT/US2019/032150, filed on May 14, 2019.

(60) Provisional application No. 62/816,996, filed on Mar. 12, 2019, provisional application No. 62/727,141, filed on Sep. 5, 2018, provisional application No. 62/671,094, filed on May 14, 2018.

(51) Int. Cl.
*C12N 15/11* (2006.01)
*C12N 15/113* (2010.01)

(52) U.S. Cl.
CPC ...... *C12N 15/1136* (2013.01); *C12N 2310/14* (2013.01); *C12N 2310/315* (2013.01); *C12N 2310/3125* (2013.01); *C12N 2310/321* (2013.01); *C12N 2310/322* (2013.01); *C12N 2310/351* (2013.01)

(58) Field of Classification Search
CPC .......... C12N 15/1136; C12N 2310/315; C12N 2310/14; C12N 2310/321; C12N 2310/351
See application file for complete search history.

(56) References Cited

U.S. PATENT DOCUMENTS

| | | | |
|---|---|---|---|
| 10,238,749 | B2 | 3/2019 | Foster et al. |
| 10,709,728 | B2 | 7/2020 | Hinkle |
| 2014/0350071 | A1* | 11/2014 | Sehgal .................. A61P 43/00 514/44 A |
| 2017/0189541 | A1 | 7/2017 | Foster et al. |
| 2018/0169129 | A1 | 6/2018 | Hinkle |
| 2019/0298842 | A1 | 10/2019 | Foster et al. |

FOREIGN PATENT DOCUMENTS

| | | |
|---|---|---|
| WO | WO-2009/073809 A2 | 6/2009 |
| WO | WO-2010/042749 A2 | 4/2010 |
| WO | WO-2012/177949 A2 | 12/2012 |
| WO | WO-2014/018930 A1 | 1/2014 |
| WO | WO-2015/179724 A1 | 11/2015 |
| WO | WO-2017/062816 A2 | 4/2017 |

OTHER PUBLICATIONS

U.S. Appl. No. 15/313,145, filed Nov. 22, 2016, US 20170189541, Granted, U.S. Pat. No. 10,238,749, issued Mar. 26, 2019.
U.S. Appl. No. 16/274,393, filed Feb. 13, 2019, US 20190298842, Granted, U.S. Pat. No. 10,814,007, issued Oct. 27, 2020.
U.S. Appl. No. 17/020,954, filed Sep. 15, 2020, Pending.
U.S. Appl. No. 15/578,955, filed Dec. 1, 2017, US 20180169129, Granted, U.S. Pat. No. 10,709,728, issued Jul. 14, 2020.
U.S. Appl. No. 16/891,155, filed Jun. 3, 2020, Pending.
U.S. Appl. No. 16/998,046, filed Aug. 20, 2020, Pending.
PCT/US2020/059265, filed Nov. 6, 2020, Pending.
Olearczyk et al. "Targeting of hepatic angiotensinogen using chemically modified siRNAs results in significant and sustained blood pressure lowering in a rat model of hypertension", Hypertension Research vol. 37, pp. 405-412 (2013).
Anonymous: "ALN-AGT, an RNAi Therapeutic in Development for the Treatment of Hypertensive Disorders of Pregnancy", American Heart Association's High Blood Pressure Research 2014, Sep. 11, 2014.
Z-W Ye et al., "Knockdown of angiotensinogen by shRNA-mediated RNA interference inhibits human visceral preadipocytes differentiation", International Journal of Obesity, vol. 34, No. 1 (2009).
International Preliminary Report on Patentability from PCT/US2015/032099 dated Nov. 22, 2016.
Tomita et al., "Transient Decrease in High Blood Pressure by In Vivo Transfer of Antisense Oligodeoxynucleotides Against Rat Angiotensinogen", Hypertension. 1995; 26:131-136.
Choi et al., "Haplotype-based association of ACE I/D, AT1R 1166A>C, and AGT M235T polymorphisms in renin-angiotensin-aldosterone system genes in Korean women with idiopathic recurrent spontaneous abortions", European Journal of Obstetrics & Gynecology and Reproductive Biology, 2011; 158(2):225-228.
International Preliminary Report on Patentability from PCT/US2016/034062, dated Dec. 5, 2017.
Reynolds et al., "Rational siRNA design for RNA interference," Nature Biotechnology, vol. 22, pp. 326-330, 2004.
Corvol et al., "Molecular Genetics of Human Hypertension: Role of Angiotensinogen*", Endocrine Reviews 18(5): 662-677, 1997.
Olearczyk et al. Supplemental Table 1; Hypertension Research, 2013.

(Continued)

*Primary Examiner* — Ekaterina Poliakova-Georgantas
(74) *Attorney, Agent, or Firm* — McCarter & English, LLP; Maria Laccotripe Zacharakis; Deborah L. Nagle

(57) ABSTRACT

The present invention relates to RNAi agents, e.g., double stranded RNA (dsRNA) agents, targeting the AGT gene. The invention also relates to methods of using such RNAi agents to inhibit expression of an AGT gene and to methods of preventing and treating an AGT-associated disorder, e.g., high blood pressure.

15 Claims, 18 Drawing Sheets

Specification includes a Sequence Listing.

(56) References Cited

OTHER PUBLICATIONS

Imai et al., "Roles for host and tumor angiotensin II type 1 receptor in tumor growth and tumor-associated angiogenesis", Laboratory Investigation vol. 87, pp. 189-198 (2007).
Lu et al., "Structure and functions of angiotensinogen", Hypertens Res.; 39(7): 492-500 (2016).
Schlegel et al., "Chirality Dependent Potency Enhancement and Structural Impact of Glycol Nucleic Acid Modification on siRNA", J Am Chem Soc.; 139(25):8537-8546 (2017).
International Search Report and Written Opinion from PCT/US2019/032150, dated Oct. 9, 2019.

* cited by examiner

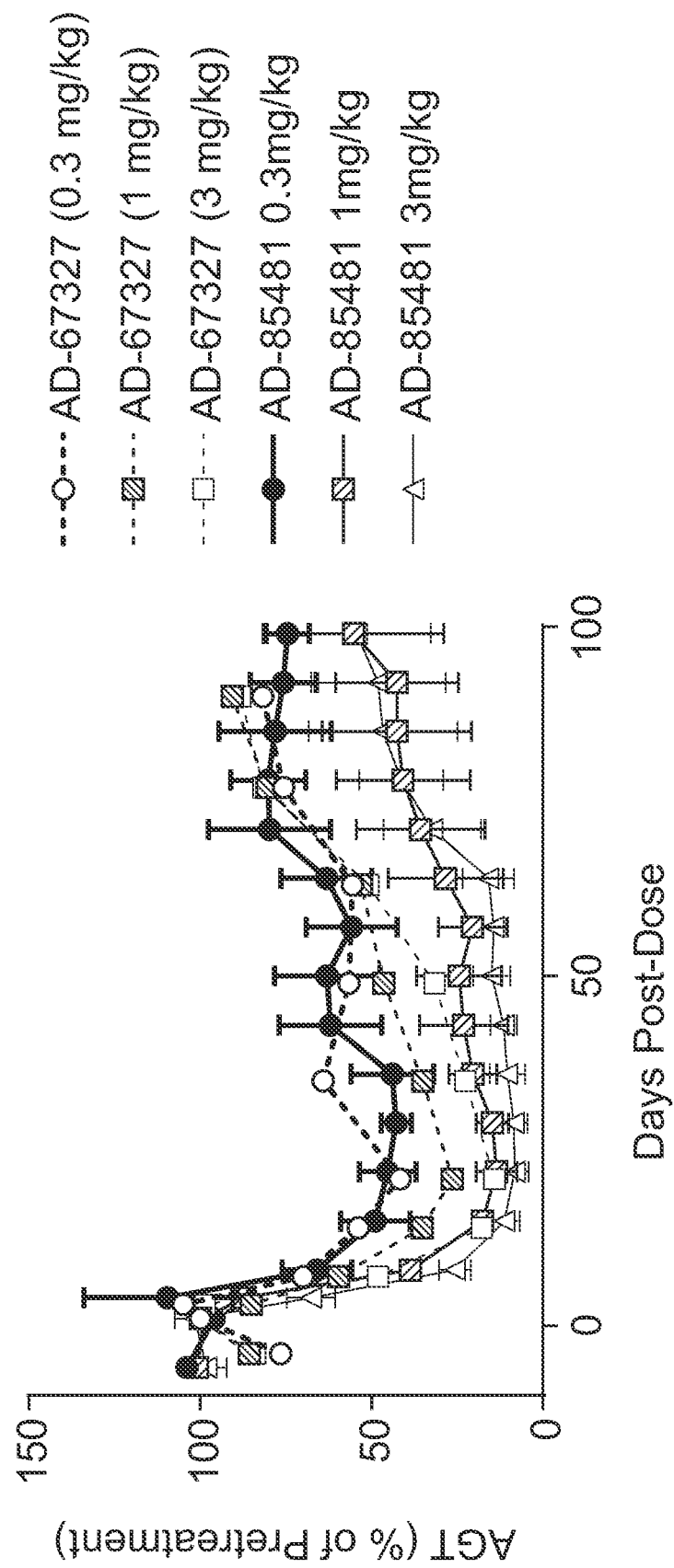

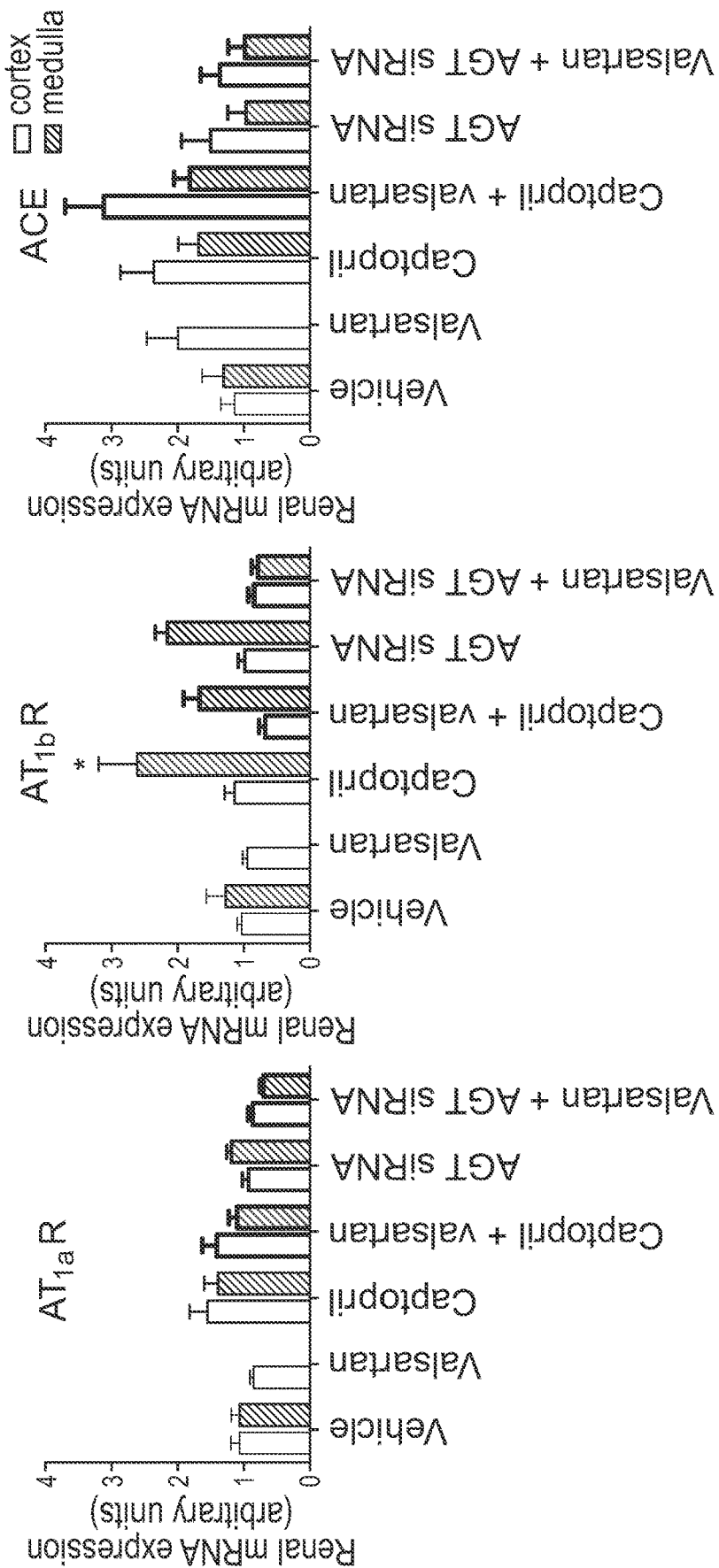

^ denotes value(s) above meter maximum (699)

ANGIOTENSINOGEN (AGT) IRNA COMPOSITIONS AND METHODS OF USE THEREOF

RELATED APPLICATIONS

This application is a 35 § U.S.C. 111(a) continuation application which claims the benefit of priority to PCT/US2019/032150, filed on May 14, 2019, which, in turn, claims the benefit of priority to U.S. Provisional Application No. 62/671,094, filed on May 14, 2018, U.S. Provisional Application No. 62/727,141, filed on Sep. 5, 2018, and U.S. Provisional Application No. 62/816,996, filed on Mar. 12, 2019. The entire contents of each of the foregoing applications are incorporated herein by reference.

SEQUENCE LISTING

The instant application contains a Sequence Listing which has been submitted electronically in ASCII format and is hereby incorporated by reference in its entirety. Said ASCII copy, created on Oct. 29, 2020, is named 121301_08604_SL.txt and is 272,533 bytes in size.

BACKGROUND OF THE INVENTION

The renin-angiotensin-aldosterone system (RAAS) plays a crucial role in the regulation of blood pressure. The RAAS cascade begins with the release of angiotensinogen from the liver, and renin by the juxtaglomerular cells of the kidney into the circulation. Renin secretion is stimulated by several factors, including Na+ load in the distal tubule, β-sympathetic stimulation, or reduced renal perfusion. Active renin in the plasma cleaves angiotensinogen (produced by the liver) to angiotensin I, which is then converted by circulating and locally expressed angiotensin-converting enzyme (ACE) to angiotensin II. Most of the effects of angiotensin II on the RAAS are exerted by its binding to angiotensin II type 1 receptors ($AT_1R$), leading to arterial vasoconstriction, tubular and glomerular effects, such as enhanced Na+ reabsorption or modulation of glomerular filtration rate. In addition, together with other stimuli such as adrenocorticotropin, anti-diuretic hormone, catecholamines, endothelin, serotonin, and levels of Mg2+ and K+, $AT_1R$ stimulation leads to aldosterone release which, in turn, promotes Na+ and K+ excretion in the renal distal convoluted tubule.

Dysregulation of the RAAS leading to, for example, excessive angiotensin II production or $AT_1R$ stimulation results in hypertension which can lead to, e.g., increased oxidative stress, promotion of inflammation, hypertrophy, and fibrosis in the heart, kidneys, and arteries, and result in, e.g., left ventricular fibrosis, arterial remodeling, and glomerulosclerosis.

Hypertension is the most prevalent, controllable disease in developed countries, affecting 20-50% of adult populations. Hypertension is a major risk factor for various diseases, disorders and conditions such as, shortened life expectancy, chronic kidney disease, stroke, myocardial infarction, heart failure, aneurysms (e.g. aortic aneurysm), peripheral artery disease, heart damage (e.g., heart enlargement or hypertrophy) and other cardiovascular related diseases, disorders, or conditions. In addition, hypertension has been shown to be an important risk factor for cardiovascular morbidity and mortality accounting for, or contributing to, 62% of all strokes and 49% of all cases of heart disease. In 2017, changes in the guidelines for diagnosis, prevention, and treatment of hypertension were developed providing goals for even lower blood pressure to further decrease risk of development of diseases and disorders associated with hypertension (see, e.g., Reboussin et al. Systematic Review for the 2017 ACC/AHA/AAPA/ABC/ACPM/AGS/APhA/ASH/ASPC/NMA/PCNA Guideline for the Prevention, Detection, Evaluation, and Management of High Blood Pressure in Adults: A Report of the American College of Cardiology/American Heart Association Task Force on Clinical Practice Guidelines. *J Am Coll Cardiol.* 2017 Nov. 7. pii: S0735-1097(17)41517-8. doi: 10.1016/j.jacc.2017.11.004; and Whelton et al. (2017 ACC/AHA/AAPA/ABC/ACPM/AGS/APhA/ASH/ASPC/NMA/PCNA Guideline for the Prevention, Detection, Evaluation, and Management of High Blood Pressure in Adults: A Report of the American College of Cardiology/American Heart Association Task Force on Clinical Practice Guidelines. *J Am Coll Cardiol.* 2017 Nov. 7. pii: S0735-1097(17)41519-1. doi: 10.1016/j.jacc.2017.11.006).

Despite the number of anti-hypertensive drugs available for treating hypertension, more than two-thirds of subjects are not controlled with one anti-hypertensive agent and require two or more anti-hypertensive agents selected from different drug classes. This further reduces the number of subjects with controlled blood pressure as adherence is reduced and side-effects are increased with increasing numbers of medications.

SUMMARY OF THE INVENTION

The present invention provides iRNA compositions which affect the RNA-induced silencing complex (RISC)-mediated cleavage of RNA transcripts of a gene encoding angiotensinogen (AGT). The AGT may be within a cell, e.g., a cell within a subject, such as a human subject.

In an aspect, the invention provides a double stranded ribonucleic acid (dsRNA) agent for inhibiting expression of angiotensinogen (AGT), wherein the dsRNA agent comprises a sense strand and an antisense strand forming a double stranded region, wherein the sense strand comprises at least 19 contiguous nucleotides from the nucleotide sequence of any one of nucleotides 635-658, 636-658, 642-667, 642-664, 645-667, 1248-1273, 1248-1272, 1248-1270, 1250-1272, 1251-1273, 1580-1602, 1584-1606, 1587-1609, 1601-1623, 1881-1903, 2074-2097, 2074-2096, 2075-2097, 2080-2102, 2272-2294, 2276-2298, 2281-2304, 2281-2303, or 2282-2304 of SEQ ID NO:1 and the antisense strand comprises at least 19 contiguous nucleotides from the nucleotide sequence of SEQ ID NO:2.

In certain embodiments, the sense strand comprises at least 21 contiguous nucleotides of any one of nucleotides 635-658, 636-658, 642-667, 642-664, 645-667, 1248-1273, 1248-1272, 1248-1270, 1250-1272, 1251-1273, 1580-1602, 1584-1606, 1587-1609, 1601-1623, 1881-1903, 2074-2097, 2074-2096, 2075-2097, 2080-2102, 2272-2294, 2276-2298, 2281-2304, 2281-2303, or 2282-2304 of SEQ ID NO:1. In certain embodiments, the antisense strand comprises at least 21 contiguous nucleotides from the nucleotide sequence of SEQ ID NO:2.

In certain embodiments, the antisense strand comprises at least 19 contiguous nucleotides from any one of the antisense strand nucleotide sequences of a duplex selected from the group consisting of AD-85481, AD-84701, AD-84703, AD-84704, AD-84705, AD-84707, AD-84715, AD-84716, AD-84739, AD-84741, AD-84746, AD-85432, AD-85434, AD-85435, AD-85436, AD-85437, AD-85438, AD-85441, AD-85442, AD-85443, AD-85444, AD-85446, AD-85447, AD-85482, AD-85485, AD-85493, AD-85496, AD-85504, AD-85517, AD-85519, AD-85524, AD-85622, AD-85623, AD-85625, AD-85626, AD-85634, AD-85635, AD-85637, AD-85655, AD-126306, AD-126307, AD-126308, AD-126310, AD133360, AD-133361, AD-133362, AD-133374, and AD-133385. In certain embodiments, the sense strand comprises at least 19 contiguous nucleotides from any one of the sense strand nucleotide sequences of a duplex selected from the group consisting of AD-85481, AD-84701, AD-84703, AD-84704, AD-84705, AD-84707, AD-84715, AD-84716, AD-84739, AD-84741, AD-84746, AD-85432, AD-85434, AD-85435, AD-85436, AD-85437, AD-85438, AD-85441, AD-85442, AD-85443, AD-85444, AD-85446, AD-85447, AD-85482, AD-85485, AD-85493, AD-85496, AD-85504, AD-85517, AD-85519, AD-85524, AD-85622, AD-85623, AD-85625, AD-85626, AD-85634, AD-85635, AD-85637, AD-85655, AD-126306, AD-126307, AD-126308, AD-126310, AD133360, AD-133361, AD-133362, AD-133374, and AD-133385. In certain embodiments, the sense and antisense strands comprise nucleotide sequences of a duplex selected from the group consisting of AD-85481, AD-84701, AD-84703, AD-84704, AD-84705, AD-84707, AD-84715, AD-84716, AD-84739, AD-84741, AD-84746, AD-85432, AD-85434, AD-85435, AD-85436, AD-85437, AD-85438, AD-85441, AD-85442, AD-85443, AD-85444, AD-85446, AD-85447, AD-85482, AD-85485, AD-85493, AD-85496, AD-85504, AD-85517, AD-85519, AD-85524, AD-85622, AD-85623, AD-85625, AD-85626, AD-85634, AD-85635, AD-85637, AD-85655, AD-126306, AD-126307, AD-126308, AD-126310, AD133360, AD-133361, AD-133362, AD-133374, and AD-133385.

In certain embodiments, the antisense strand comprises at least 19 contiguous nucleotides from nucleotide sequence of the antisense strand of AD-85481 (5'-UGUACUCUCAUU-GUGGAUGACGA-3' (SEQ ID NO: 9)). In certain embodiments, the sense strand comprises at least 19 contiguous nucleotides from the nucleotide sequences of the sense strand of AD-85481 (5'-GUCAUCCACAAUGAG-AGUACA-3' (SEQ ID NO: 10)). In certain embodiments, the sense and antisense strands comprise the nucleotide sequences of the sense and antisense strands of AD-85481 (5'-UGUACUCUCAUUGUGGAUGACGA-3' (SEQ ID NO: 9) and 5'-GUCAUCCACAAUGAGAGUACA-3' (SEQ ID NO: 10)).

In certain embodiments, the dsRNA agent comprises at least one modified nucleotide. In certain embodiments, substantially all of the nucleotides of the sense strand and substantially all of the nucleotides of the antisense strand comprise a modification. In certain embodiments, all of the nucleotides of the sense strand and all of the nucleotides of the antisense strand comprise a modification. In certain embodiments, at least one of the modified nucleotides is selected from the group of a deoxy-nucleotide, a 3'-terminal deoxy-thymine (dT) nucleotide, a 2'-O-methyl modified nucleotide, a 2'-fluoro modified nucleotide, a 2'-deoxy-modified nucleotide, a locked nucleotide, an unlocked nucleotide, a conformationally restricted nucleotide, a constrained ethyl nucleotide, an abasic nucleotide, a 2'-amino-modified nucleotide, a 2'-O-allyl-modified nucleotide, 2'-C-alkyl-modified nucleotide, 2'-hydroxly-modified nucleotide, a 2'-methoxyethyl modified nucleotide, a 2'-O-alkyl-modified nucleotide, a morpholino nucleotide, a phosphoramidate, a non-natural base comprising nucleotide, a tetrahydropyran modified nucleotide, a 1,5-anhydrohexitol modified nucleotide, a cyclohexenyl modified nucleotide, a nucleotide comprising a phosphorothioate group, a nucleotide comprising a methylphosphonate group, a nucleotide comprising a 5'-phosphate, a nucleotide comprising a 5'-phosphate mimic, a thermally destabilizing nucleotide, a glycol modified nucleotide (GNA), and a 2-O—(N-methylacetamide) modified nucleotide; and combinations thereof. In certain embodiments, the modifications on the nucleotides are selected from the group consisting of LNA, HNA, CeNA, 2'-methoxyethyl, 2'-O-alkyl, 2'-O-allyl, 2'-C-allyl, 2'-fluoro, 2'-deoxy, 2'-hydroxyl, GNA, and combinations thereof. In certain embodiments, the modifications on the nucleotides are 2'-O-methyl or 2'-fluoro modifications. In certain embodiments, at least one of the modified nucleotides is selected from the group consisting of a deoxynucleotide, a 2'-O-methyl modified nucleotide, a 2'-fluoro modified nucleotide, a 2'-deoxy-modified nucleotide, a glycol modified nucleotide (GNA), and a 2-O—(N-methylacetamide) modified nucleotide; and combinations thereof. In certain embodiments, at least one of the nucleotide modification is a thermally destabilizing nucleotide modification. In certain embodiments, the thermally destabilizing nucleotide modification is selected from the group consisting of of an abasic modification; a mismatch with the opposing nucleotide in the duplex; and destabilizing sugar modification, a 2'-deoxy modification, an acyclic nucleotide, an unlocked nucleic acids (UNA), and a glycerol nucleic acid (GNA) In certain embodiments, the double stranded region is 19-21 nucleotides in length. In certain embodiments, the double stranded region is 21 nucleotides in length. In certain embodiments, each strand of the dsRNA agent is independently no more than 30 nucleotides in length. In certain embodiments, at least one strand of the dsRNA agent comprises a 3' overhang of at least 1 nucleotide or at least 2 nucleotides.

In certain embodiments, dsRNA agent further comprises a ligand. In certain embodiments, the ligand is conjugated to the 3' end of the sense strand of the dsRNA agent. In certain embodiments, the ligand is an N-acetylgalactosamine (GaNAc) derivative, e.g., wherein the ligand is

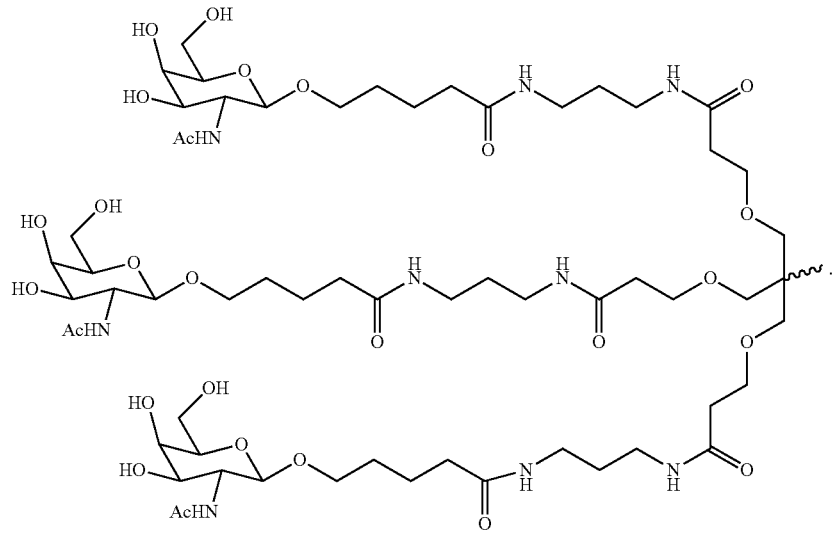 [SMILES: CC(=O)NC1C(OCCCCC(=O)NCCCNC(=O)CCOCC(C)(COCCC(=O)NCCCNC(=O)CCCCOC2OC(CO)C(O)C(O)C2NC(C)=O)COCCC(=O)NCCCNC(=O)CCCCOC2OC(CO)C(O)C(O)C2NC(C)=O)OC(CO)C(O)C1O]

In certain embodiments, the dsRNA agent is conjugated to the ligand as shown in the following schematic

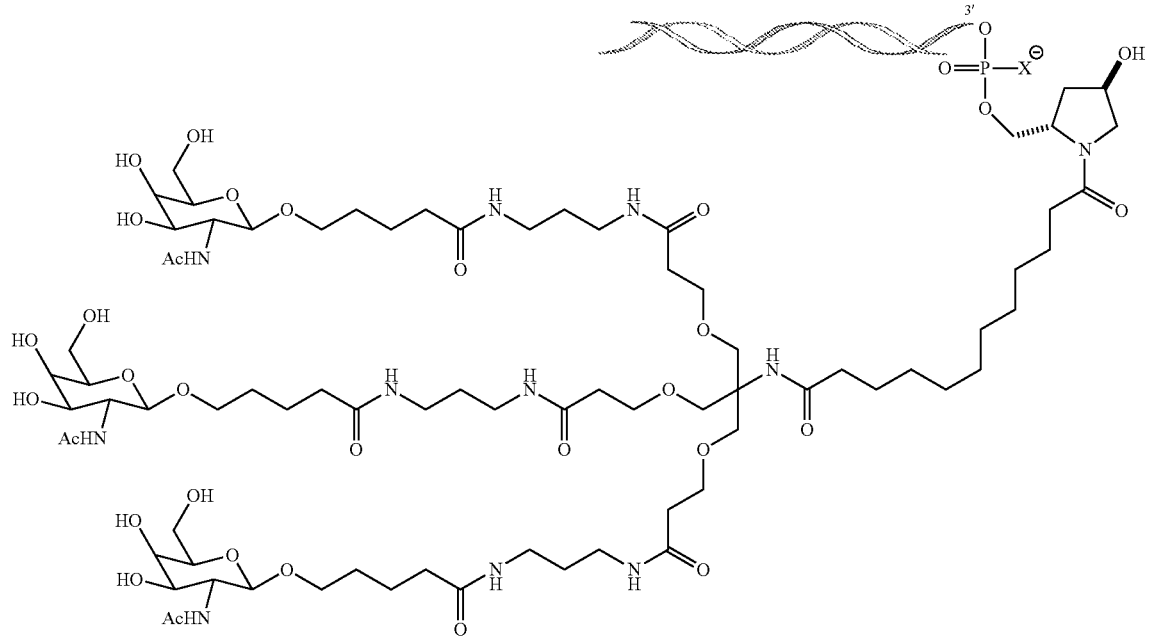

and, wherein X is O or S, e.g., wherein the X is O.

In certain embodiments, the invention provides a dsRNA agent, wherein the antisense strand comprises a region of complementarity to an mRNA encoding human AGT, wherein the region of complementarity comprises at least 19 nucleotides one of the antisense strand sequences of a duplex selected from the group consisting of AD-85481, AD-84701, AD-84703, AD-84704, AD-84705, AD-84707, AD-84715, AD-84716, AD-84739, AD-84741, AD-84746, AD-85432, AD-85434, AD-85435, AD-85436, AD-85437, AD-85438, AD-85441, AD-85442, AD-85443, AD-85444, AD-85446, AD-85447, AD-85482, AD-85485, AD-85493, AD-85496, AD-85504, AD-85517, AD-85519, AD-85524, AD-85622, AD-85623, AD-85625, AD-85626, AD-85634, AD-85635, AD-85637, AD-85655, AD-126306, AD-126307, AD-126308, AD-126310, AD133360, AD-133361, AD-133362, AD-133374, and AD-133385. In certain embodiments, the antisense strand comprises a region of complementarity to an mRNA encoding human AGT, wherein the region of complementarity comprises any one of the antisense strand sequences of a duplex selected from the group consisting of AD-85481, AD-84701, AD-84703, AD-84704, AD-84705, AD-84707, AD-84715, AD-84716, AD-84739, AD-84741, AD-84746, AD-85432, AD-85434, AD-85435, AD-85436, AD-85437, AD-85438, AD-85441, AD-85442, AD-85443, AD-85444, AD-85446, AD-85447, AD-85482, AD-85485, AD-85493, AD-85496, AD-85504, AD-85517, AD-85519, AD-85524, AD-85622, AD-85623, AD-85625, AD-85626, AD-85634, AD-85635, AD-85637, AD-85655, AD-126306, AD-126307, AD-126308, AD-126310, AD133360, AD-133361, AD-133362, AD-133374, and AD-133385. In certain embodiments, the region of complementarity consists of any one of the antisense strand sequences of a duplex selected from the group consisting of AD-85481, AD-84701, AD-84703, AD-84704, AD-84705, AD-84707, AD-84715, AD-84716, AD-84739, AD-84741, AD-84746, AD-85432, AD-85434, AD-85435, AD-85436, AD-85437, AD-85438, AD-85441, AD-85442, AD-85443, AD-85444, AD-85446, AD-85447, AD-85482, AD-85485, AD-85493, AD-85496, AD-85504, AD-85517, AD-85519, AD-85524, AD-85622, AD-85623, AD-85625, AD-85626, AD-85634, AD-85635, AD-85637, AD-85655, AD-126306, AD-126307, AD-126308, AD-126310, AD133360, AD-133361, AD-133362, AD-133374, and AD-133385.

In certain embodiments, the invention provides a dsRNA agent, wherein the antisense strand comprises the chemically modified nucleotide sequence of a duplex selected from the group consisting of AD-85481, AD-84701, AD-84703, AD-84704, AD-84705, AD-84707, AD-84715, AD-84716, AD-84739, AD-84741, AD-84746, AD-85432, AD-85434, AD-85435, AD-85436, AD-85437, AD-85438, AD-85441, AD-85442, AD-85443, AD-85444, AD-85446, AD-85447, AD-85482, AD-85485, AD-85493, AD-85496, AD-85504, AD-85517, AD-85519, AD-85524, AD-85622, AD-85623, AD-85625, AD-85626, AD-85634, AD-85635, AD-85637, AD-85655, AD-126306, AD-126307, AD-126308, AD-126310, AD133360, AD-133361, AD-133362, AD-133374, and AD-133385.

In certain embodiments, the invention provides a dsRNA agent, wherein the antisense strand comprises the chemically modified nucleotide sequence of the duplex AD-85481 (5'-usGfsuac(Tgn)cucauugUfgGfaugacsgsa-3' (SEQ ID NO: 11)) wherein a, c, g, and u are 2'-O-methyladenosine-3'-phosphate, 2'-O-methylcytidine-3'-phosphate, 2'-O-methylguanosine-3'-phosphate, and 2'-O-methyluridine-3'-phosphate, respectively; Af, Cf, Gf, and Uf are 2'-O-fluoroadenosine-3'-phosphate, 2'-O-fluorocytidine-3'-phosphate, 2'-O-fluoroguanosine-3'-phosphate, and 2'-O-fluorouridine-3'-phosphate, respectively; dT is a deoxythymine; s is a phosphorothioate linkage; and (Tgn) is thymidine-glycol nucleic acid (GNA) S-isomer.

In certain embodiments, the invention provides a dsRNA agent, wherein the antisense strand and the sense strand comprise the chemically modified nucleotide sequences of a duplex selected from the group consisting of AD-85481, AD-84701, AD-84703, AD-84704, AD-84705, AD-84707, AD-84715, AD-84716, AD-84739, AD-84741, AD-84746, AD-85432, AD-85434, AD-85435, AD-85436, AD-85437, AD-85438, AD-85441, AD-85442, AD-85443, AD-85444, AD-85446, AD-85447, AD-85482, AD-85485, AD-85493, AD-85496, AD-85504, AD-85517, AD-85519, AD-85524, AD-85622, AD-85623, AD-85625, AD-85626, AD-85634, AD-85635, AD-85637, AD-85655, AD-126306, AD-126307, AD-126308, AD-126310, AD133360, AD-133361, AD-133362, AD-133374, and AD-133385.

In certain embodiments, the invention provides a dsRNA agent, wherein the antisense strand and the sense strand comprise the chemically modified nucleotide sequences of the duplex AD-85481 (5'-usGfsuac(Tgn)cucauu-gUfgGfaugacsgsa-3' (SEQ ID NO: 11) and 5'-gsuscaucC-faCfAfAfugagaguaca-3' (SEQ ID NO: 12)) wherein a, c, g, and u are 2'-O-methyladenosine-3'-phosphate, 2'-O-methyl-cytidine-3'-phosphate, 2'-O-methylguanosine-3'-phosphate, and 2'-O-methyluridine-3'-phosphate, respectively; Af, Cf, Gf, and Uf are 2'-O-fluoroadenosine-3'-phosphate, 2'-O-fluorocytidine-3'-phosphate, 2'-O-fluoroguanosine-3'-phosphate, and 2'-O-fluorouridine-3'-phosphate, respectively; dT is a deoxy-thymine; s is a phosphorothioate linkage; and (Tgn) is thymidine-glycol nucleic acid (GNA) S-isomer; and wherein the 3'-end of the sense strand is optionally conjugated to an N-[tris(GaNAc-alkyl)-amidodecanoyl)]-4-hydroxyprolinol (L96) ligand.

In certain embodiments, the invention provides a dsRNA agent, wherein the antisense strand and the sense strand consist of the chemically modified nucleotide sequences of the duplex AD-85481 (5'-usGfsuac(Tgn)cucauu-gUfgGfaugacsgsa-3' (SEQ ID NO: 11) and 5'-gsuscaucC-faCfAfAfugagaguaca-3' (SEQ ID NO: 12)), wherein the 3'-end of the sense strand is conjugated to an N-[tris (GaNAc-alkyl)-amidodecanoyl)]-4-hydroxyprolinol (L96) ligand, wherein a, c, g, and u are 2'-O-methyladenosine-3'-phosphate, 2'-O-methylcytidine-3'-phosphate, 2'-O-methyl-guanosine-3'-phosphate, and 2'-O-methyluridine-3'-phosphate, respectively; Af, Cf, Gf, and Uf are 2'-O-fluoroadenosine-3'-phosphate, 2'-O-fluorocytidine-3'-phosphate, 2'-O-fluoroguanosine-3'-phosphate, and 2'-O-fluorouridine-3'-phosphate, respectively; dT is a deoxy-thymine; s is a phosphorothioate linkage; and (Tgn) is thymidine-glycol nucleic acid (GNA) S-isomer.

In certain embodiments, the double stranded region of the dsRNA agent is about 19-30 nucleotide pairs in length, about 19-25 nucleotide pairs in length, about 23-27 nucleotide pairs in length, about 19-23 nucleotide pairs in length, about 21-23 nucleotide pairs in length.

In certain embodiments, each strand of the dsRNA agent is independently 19-30 nucleotides in length.

In certain embodiments, the ligand is one or more GaNAc derivatives attached through a monovalent, bivalent, or trivalent branched linker.

In certain embodiments, the dsRNA agent further comprises at least one phosphorothioate or methylphosphonate internucleotide linkage. In certain embodiments, the phosphorothioate or methylphosphonate internucleotide linkage is at the 3'-terminus of one strand. In certain embodiments, the strand is the antisense strand. In certain embodiments, the strand is the sense strand.

In certain embodiments, the phosphorothioate or methylphosphonate internucleotide linkage is at the 5'-terminus of one strand. In certain embodiments, the strand is the antisense strand. In certain embodiments, the strand is the sense strand. In certain embodiments, the phosphorothioate or methylphosphonate internucleotide linkage is at the both the 5'- and 3'-terminus of one strand. In certain embodiments, the strand is the antisense strand.

In certain embodiments, the dsRNA agent at the 1 position of the 5'-end of the antisense strand of the duplex comprises a base pair that is an AU base pair.

In certain embodiments, the dsRNA agent comprises a sense strand has a total of 21 nucleotides and an antisense strand has a total of 23 nucleotides.

In an aspect, the invention provides a cell containing the dsRNA agent of the invention.

In an aspect, the invention provides a pharmaceutical composition for inhibiting expression of a gene encoding AGT comprising the dsRNA agent of the invention. In certain embodiments, the pharmaceutical composition comprises the dsRNA agent and a lipid formulation.

In an aspect, the invention provides a method of inhibiting expression of an AGT gene in a cell, the method comprising:
(a) contacting the cell with the dsRNA agent or a pharmaceutical composition of the invention; and
(b) maintaining the cell produced in step (a) for a time sufficient to obtain degradation of the mRNA transcript of the AGT gene, thereby inhibiting expression of the AGT gene in the cell.

In certain embodiments, the cell is within a subject. In certain embodiments, the subject is a human. In certain embodiments, the subject has been diagnosed with an AGT-associated disorder.

In certain embodiments, the AGT-associated disorder is selected from high blood pressure, hypertension, borderline hypertension, primary hypertension, secondary hypertension isolated systolic or diastolic hypertension, pregnancy-associated hypertension, diabetic hypertension, resistant hypertension, refractory hypertension, paroxysmal hypertension, renovascular hypertension, Goldblatt hypertension, ocular hypertension, glaucoma, pulmonary hypertension, portal hypertension, systemic venous hypertension, systolic hypertension, labile hypertension; hypertensive heart disease, hypertensive nephropathy, atherosclerosis, arteriosclerosis, vasculopathy, diabetic nephropathy, diabetic retinopathy, chronic heart failure, cardiomyopathy, diabetic cardiac myopathy, glomerulosclerosis, coarctation of the aorta, aortic aneurism, ventricular fibrosis, heart failure, myocardial infarction, angina, stroke, renal disease, renal failure, systemic sclerosis, intrauterine growth restriction (IUGR), fetal growth restriction, obesity, liver steatosis/fatty liver, non-alcoholic Steatohepatitis (NASH), non-alcoholic fatty liver disease (NAFLD); glucose intolerance, type 2 diabetes (non-insulin dependent diabetes), and metabolic syndrome.

In certain embodiments, the subject has a systolic blood pressure of at least 130 mm Hg or a diastolic blood pressure of at least 80 mm Hg. In certain embodiments, the subject has a systolic blood pressure of at least 140 mm Hg and a diastolic blood pressure of at least 80 mm Hg. In certain embodiments, the subject is part of a group susceptible to salt sensitivity, is overweight, is obese, or is pregnant.

In certain embodiments, contacting the cell with the dsRNA agent inhibits the expression of AGT by at least 50%, 60%, 70%, 80%, 90%, 95% (e.g., as compared to the level of expression of AGT prior to first contacting the cell with the dsRNA agent; e.g., prior to administration of a first dose of the dsRNA agent to the subject). In certain embodiments, inhibiting expression of AGT decreases an AGT protein level in a subject serum sample(s) by at least 50%, 60%, 70%, 80%, 90%, or 95%, e.g., as compared to the level of expression of AGT prior to first contacting the cell with the dsRNA agent.

In an aspect, the invention provides a method of treating an AGT-associated disorder in a subject, comprising administering to the subject the dsRNA agent or the pharmaceutical composition of the invention, thereby treating the AGT-associated disorder in the subject. In certain embodiments, the subject has a systolic blood pressure of at least 130 mm Hg or a diastolic blood pressure of at least 80 mm Hg. In certain embodiments, the subject has a systolic blood pressure of at least 140 mm Hg and diastolic blood pressure of at least 80 mm Hg. In certain embodiments, the subject is human. In certain embodiments, subject is part of a group susceptible to salt sensitivity, is overweight, is obese, or is pregnant.

In certain embodiments of the invention, the dsRNA agent is administered at a dose of about 0.01 mg/kg to about 50 mg/kg. In certain embodiments, the dsRNA agent is administered to the subject subcutaneously. In certain embodiments, the level of AGT is measured in the subject. In certain embodiments, the level of AGT in the subject is an AGT protein level in a subject blood sample(s), serum sample(s), or urine sample(s).

In certain embodiments, an additional therapeutic agent for treatment of hypertension is administered to the subject. In certain embodiments, the additional therapeutic agent is selected from the group consisting of of a diuretic, an angiotensin converting enzyme (ACE) inhibitor, an angiotensin II receptor antagonist, a beta-blocker, a vasodialator, a calcium channel blocker, an aldosterone antagonist, an alpha2-agonist, a renin inhibitor, an alpha-blocker, a peripheral acting adrenergic agent, a selective D1 receptor partial agonist, a nonselective alpha-adrenergic antagonist, a synthetic, and steroidal antimineralocorticoid agent; or a combination of any of the foregoing, and a hypertension therapeutic agent formulated as a combination of agents. In certain embodiments, the additional therapeutic agent comprises an angiotensin II receptor antagonist, e.g., losartan, valsartan, olmesartan, eprosartan, and azilsartan. In certain embodiments, the additional therapeutic agent is an angiotensin receptor-neprilysin inhibitor (ARNi), e.g., Entresto®, sacubitril/valsartan; or an endothelin receptor antagonist (ERA), e.g., sitaxentan, ambrisentan, atrasentan, BQ-123, zibotentan, bosentan, macitentan, and tezosentan.

The invention also provides uses of the dsRNA agents and the pharmaceutical compositions provided herein for treatment of an AGT-associated disorder. In certain embodiments, the uses include any of the methods provided by the invention.

The invention provides kits comprising a dsRNA agent of the invention. In certain embodiments, the invention provides kits for practicing a method of the invention.

BRIEF DESCRIPTION OF THE DRAWINGS

FIG. 1B is a graph showing serum AGT protein levels in cynomolgus monkeys (n=3 per group) treated with a single 0.3 mg/kg, 1 mg/kg, or 3 mg/kg dose of AD-85481 or AD-67327 on day 1. AGT levels are shown as a percent of AGT level prior to treatment.

FIG. 2A shows plasma AGT levels at the start (solid bars) and end (stippled bars) of the study (at four weeks).

FIG. 2B shows daily blood pressure readings compared to baseline.

FIG. 2C is a graph showing heart weight: tibial length ratios.

FIG. 2D is a graph showing plasma renin activity level at the start (solid bars) and end (stippled bars) of the study (at four weeks).

FIG. 2E is a graph of heart weight:tibial length graphed against mean arterial pressure (MAP) in mm Hg.

FIG. 2F is a graph of cardiomyocyte size.

FIG. 2G is a graph of N-terminal pro b-type natriuretic peptide (NT-proBNP) levels.

FIG. 6A is a graph showing the level of angiotensin receptor 1a in the kidney cortex and medulla in the spontaneous rat hypertensive study.

FIG. 6B is a graph showing the level of angiotensin 1b receptor in the kidney cortex and medulla in the spontaneous rat hypertensive study.

FIG. 6C is a graph showing the level of ACE in the kidney cortex and medulla in the spontaneous rat hypertensive study.

FIG. 11A is a graph showing alanine transaminase (ALT) levels in high fat high fructose (HF HFr) fed mice treated with either an AGT dsRNA agent or PBS, or normal chow fed (LFD) mice.

FIG. 11B is a graph showing aspartate transaminase (AST) levels in high fat high fructose (HF HFr) fed mice treated with either an AGT dsRNA agent or PBS, or normal chow fed (LFD) mice.

FIG. 11C is a graph showing glutamate dehydrogenase (GLDH) levels in high fat high fructose (HF HFr) fed mice treated with either an AGT dsRNA agent or PBS, or normal chow fed (LFD) mice.

DETAILED DESCRIPTION OF THE INVENTION

Figure 1A:
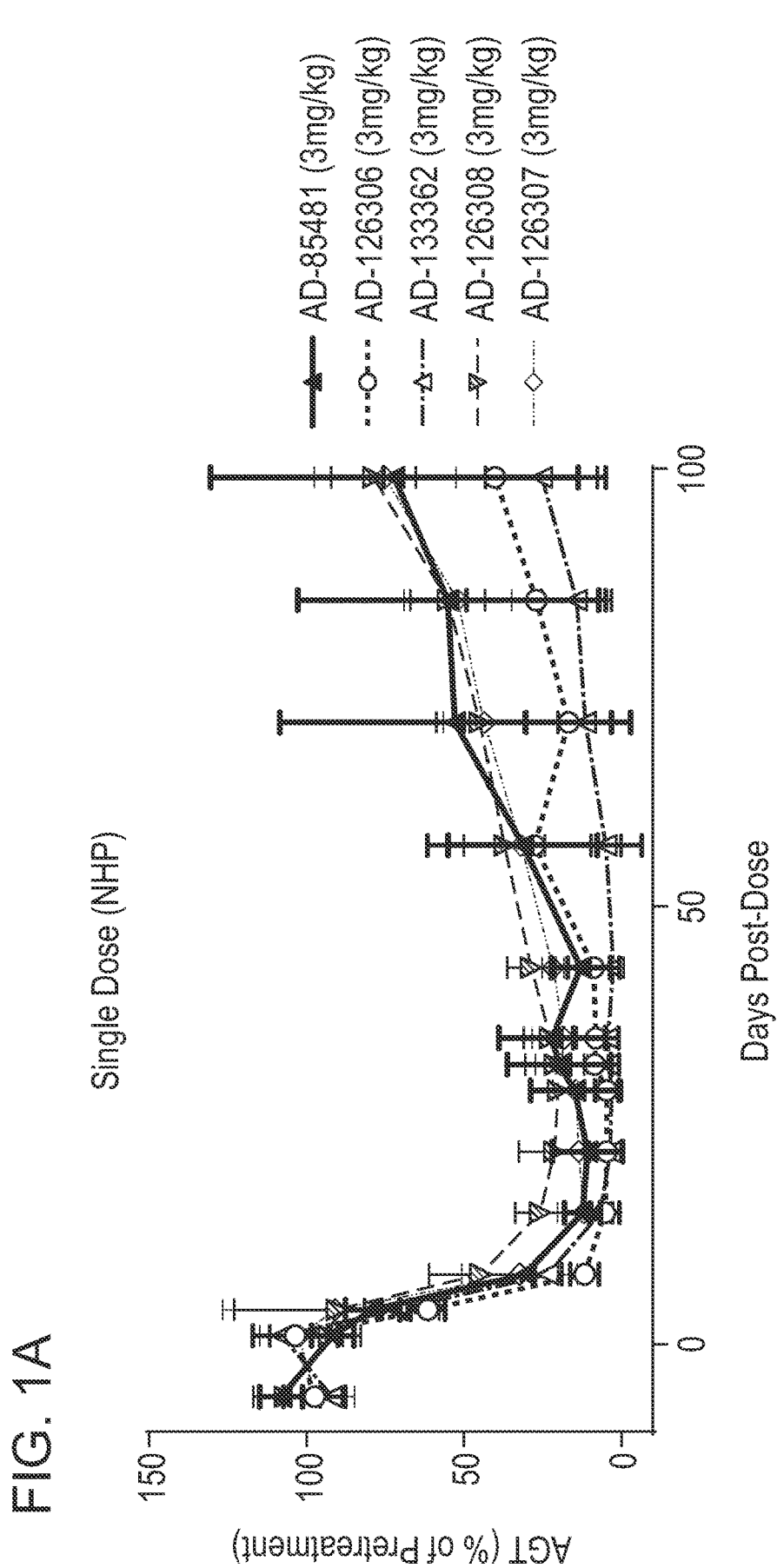
FIG. 1A is a graph showing serum AGT protein levels in cynomolgus monkeys (n=3 per group) treated with a single 3 mg/kg dose of the indicated siRNAs. AGT levels are shown as a percent of AGT level prior to treatment.

The present invention provides iRNA compositions which effect the RNA-induced silencing complex (RISC)-mediated cleavage of RNA transcripts of an AGT gene. The gene may be within a cell, e.g., a cell within a subject, such as a human. The use of these iRNAs enables the targeted degradation of mRNAs of the corresponding gene (AGT gene) in mammals.

The iRNAs of the invention have been designed to target the human AGT gene, including portions of the gene that are conserved in the AGT orthologs of other mammalian species. Without intending to be limited by theory, it is believed that a combination or sub-combination of the foregoing properties and the specific target sites or the specific modifications in these iRNAs confer to the iRNAs of the invention improved efficacy, stability, potency, durability, and safety.

Accordingly, the present invention provides methods for treating and preventing an AGT-associated disorder, e.g., hypertension, using iRNA compositions which effect the RNA-induced silencing complex (RISC)-mediated cleavage of RNA transcripts of an AGT gene.

The iRNAs of the invention include an RNA strand (the antisense strand) having a region which is up to about 30 nucleotides or less in length, e.g., 19-30, 19-29, 19-28, 19-27, 19-26, 19-25, 19-24, 19-23, 19-22, 19-21, 19-20, 20-30, 20-29, 20-28, 20-27, 20-26, 20-25, 20-24, 20-23, 20-22, 20-21, 21-30, 21-29, 21-28, 21-27, 21-26, 21-25, 21-24, 21-23, or 21-22 nucleotides in length, which region is substantially complementary to at least part of an mRNA transcript of an AGT gene.

In certain embodiments, one or both of the strands of the double stranded RNAi agents of the invention is up to 66 nucleotides in length, e.g., 36-66, 26-36, 25-36, 31-60, 22-43, 27-53 nucleotides in length, with a region of at least 19 contiguous nucleotides that is substantially complementary to at least a part of an mRNA transcript of an AGT gene. In some embodiments, such iRNA agents having longer length antisense strands preferably may include a second RNA strand (the sense strand) of 20-60 nucleotides in length wherein the sense and antisense strands form a duplex of 18-30 contiguous nucleotides.

The use of iRNAs of the invention enables the targeted degradation of mRNAs of the corresponding gene (AGT gene) in mammals. Using in vitro and in vivo assays, the present inventors have demonstrated that iRNAs targeting an AGT gene can mediate RNAi, resulting in significant inhibition of expression of AGT. Inhibition of expression of AGT in such a subject will prevent or treat development of a AGT-associated disorder, e.g., hypertension. Thus, methods and compositions including these iRNAs are useful for preventing and treating a subject susceptible to or diagnosed with an AGT-associated disorder, e.g., hypertension. The methods and compositions herein are useful for reducing the level of AGT in a subject.

The following detailed description discloses how to make and use compositions containing iRNAs to inhibit the expression of an AGT gene as well as compositions, uses, and methods for treating subjects that would benefit from reduction of the expression of an AGT gene, e.g., subjects susceptible to or diagnosed with an AGT-associated disorder, e.g., hypertension.

I. Definitions

In order that the present invention may be more readily understood, certain terms are first defined. In addition, it should be noted that whenever a value or range of values of a parameter are recited, it is intended that values and ranges intermediate to the recited values are also intended to be part of this invention.

The articles "a" and "an" are used herein to refer to one or to more than one (i.e., to at least one) of the grammatical object of the article. By way of example, "an element" means one element or more than one element, e.g., a plurality of elements.

The term "including" is used herein to mean, and is used interchangeably with, the phrase "including but not limited to".

The term "or" is used herein to mean, and is used interchangeably with, the term "and/or," unless context clearly indicates otherwise. For example, "sense strand or antisense strand" is understood as "sense strand or antisense strand or sense strand and antisense strand."

The term "about" is used herein to mean within the typical ranges of tolerances in the art. For example, "about" can be understood as about 2 standard deviations from the mean. In certain embodiments, about means ±10%. In certain embodiments, about means ±5%. When about is present before a series of numbers or a range, it is understood that "about" can modify each of the numbers in the series or range.

The term "at least" prior to a number or series of numbers is understood to include the number adjacent to the term "at least", and all subsequent numbers or integers that could logically be included, as clear from context. For example, the number of nucleotides in a nucleic acid molecule must be an integer. For example, "at least 19 nucleotides of a 21 nucleotide nucleic acid molecule" means that 19, 20, or 21 nucleotides have the indicated property. When at least is present before a series of numbers or a range, it is understood that "at least" can modify each of the numbers in the series or range.

As used herein, "no more than" or "less than" is understood as the value adjacent to the phrase and logical lower values or integers, as logical from context, to zero. For example, a duplex with an overhang of "no more than 2 nucleotides" has a 2, 1, or 0 nucleotide overhang. When "no more than" is present before a series of numbers or a range, it is understood that "no more than" can modify each of the numbers in the series or range. As used herein, ranges include both the upper and lower limit.

In the event of a conflict between a sequence and its indicated site on a transcript or other sequence, the nucleotide sequence recited in the specification takes precedence.

As used herein, "angiotensinogen," used interchangeably with the term "AGT" refers to the well-known gene and polypeptide, also known in the art as Serpin Peptidase Inhibitor, Clade A, Member 8; Alpha-1 Antiproteinase; Antitrypsin; SERPINA8; Angiotensin I; Serpin A8; Angiotensin II; Alpha-1 Antiproteinase angiotensinogen; antitrypsin; pre-angiotensinogen2; ANHU; Serine Proteinase Inhibitor; and Cysteine Proteinase Inhibitor.

The term "AGT" includes human AGT, the amino acid and complete coding sequence of which may be found in for example, GenBank Accession No. GI:188595658 (NM_000029.3; SEQ ID NO:1); Macacafascicularis AGT, the amino acid and complete coding sequence of which may be found in for example, GenBank Accession No. GI: 90075391 (AB170313.1: SEQ ID NO:3); mouse (*Mus musculus*) AGT, the amino acid and complete coding sequence of which may be found in for example, GenBank Accession No. GI: 113461997 (NM_007428.3; SEQ ID NO:5); and rat AGT (*Rattus norvegicus*) AGT the amino acid and complete coding sequence of which may be found in for example, for example GenBank Accession No. GI:51036672 (NM_134432; SEQ ID NO:7).

Additional examples of AGT mRNA sequences are readily available using publicly available databases, e.g., GenBank, UniProt, OMIM, and the *Macaca* genome project web site.

The term "AGT," as used herein, also refers to naturally occurring DNA sequence variations of the AGT gene, such as a single nucleotide polymorphism (SNP) in the AGT gene. Exemplary SNPs may be found in the dbSNP database available at www.ncbi.nlm.nih.gov/projects/SNP/snp-_refcgi?geneId=183. Non-limiting examples of sequence variations within the AGT gene include, for example, those described in U.S. Pat. No. 5,589,584, the entire contents of which are incorporated herein by reference. For example, sequence variations within the AGT gene may include as a C→T at position −532 (relative to the transcription start site); a G→A at position −386; a G→A at position −218; a C→T at position −18; a G→A and a A→C at position −6 and −10; a C→T at position +10 (untranslated); a C→T at position +521 (T174M); a T-C at position +597 (P199P); a T-C at position +704 (M235T; also see, e.g., Reference SNP (refSNP) Cluster Report: rs699, available at www.ncbi.nlm.nih.gov/SNP); a A-G at position +743 (Y248C); a C→T at position +813 (N271N); a G→A at position +1017 (L339L); a C-A at position +1075 (L359M); and/or a G→A at position +1162 (V388M).

As used herein, "target sequence" refers to a contiguous portion of the nucleotide sequence of an mRNA molecule formed during the transcription of an AGT gene, including mRNA that is a product of RNA processing of a primary transcription product. The target portion of the sequence will be at least long enough to serve as a substrate for iRNA-directed cleavage at or near that portion of the nucleotide sequence of an mRNA molecule formed during the transcription of an AGT gene. In one embodiment, the target sequence is within the protein coding region of AGT.

The target sequence may be from about 19-36 nucleotides in length, e.g., preferably about 19-30 nucleotides in length. For example, the target sequence can be about 19-30 nucleotides, 19-30, 19-29, 19-28, 19-27, 19-26, 19-25, 19-24, 19-23, 19-22, 19-21, 19-20, 20-30, 20-29, 20-28, 20-27, 20-26, 20-25, 20-24, 20-23, 20-22, 20-21, 21-30, 21-29, 21-28, 21-27, 21-26, 21-25, 21-24, 21-23, or 21-22 nucleotides in length. Ranges and lengths intermediate to the above recited ranges and lengths are also contemplated to be part of the invention.

As used herein, the term "strand comprising a sequence" refers to an oligonucleotide comprising a chain of nucleotides that is described by the sequence referred to using the standard nucleotide nomenclature.

"G," "C," "A," "T," and "U" each generally stand for a nucleotide that contains guanine, cytosine, adenine, thymidine, and uracil as a base, respectively. However, it will be understood that the term "ribonucleotide" or "nucleotide" can also refer to a modified nucleotide, as further detailed below, or a surrogate replacement moiety (see, e.g., Table 2). The skilled person is well aware that guanine, cytosine, adenine, and uracil can be replaced by other moieties without substantially altering the base pairing properties of an oligonucleotide comprising a nucleotide bearing such replacement moiety. For example, without limitation, a nucleotide comprising inosine as its base can base pair with nucleotides containing adenine, cytosine, or uracil. Hence, nucleotides containing uracil, guanine, or adenine can be replaced in the nucleotide sequences of dsRNA featured in the invention by a nucleotide containing, for example, inosine. In another example, adenine and cytosine anywhere in the oligonucleotide can be replaced with guanine and uracil, respectively to form G-U Wobble base pairing with the target mRNA. Sequences containing such replacement moieties are suitable for the compositions and methods featured in the invention.

The terms "iRNA", "RNAi agent," "iRNA agent,", "RNA interference agent" as used interchangeably herein, refer to an agent that contains RNA as that term is defined herein, and which mediates the targeted cleavage of an RNA transcript via an RNA-induced silencing complex (RISC) pathway. iRNA directs the sequence-specific degradation of mRNA through a process known as RNA interference (RNAi). The iRNA modulates, e.g., inhibits, the expression of an AGT gene in a cell, e.g., a cell within a subject, such as a mammalian subject.

In one embodiment, an RNAi agent of the invention includes a single stranded RNA that interacts with a target RNA sequence, e.g., an AGT target mRNA sequence, to direct the cleavage of the target RNA. Without wishing to be bound by theory it is believed that long double stranded RNA introduced into cells is broken down into siRNA by a Type III endonuclease known as Dicer (Sharp et al. (2001) *Genes Dev.* 15:485). Dicer, a ribonuclease-III-like enzyme, processes the dsRNA into 19-23 base pair short interfering RNAs with characteristic two base 3' overhangs (Bernstein, et al., (2001) *Nature* 409:363). The siRNAs are then incorporated into an RNA-induced silencing complex (RISC) where one or more helicases unwind the siRNA duplex, enabling the complementary antisense strand to guide target recognition (Nykanen, et al., (2001) *Cell* 107:309). Upon binding to the appropriate target mRNA, one or more endonucleases within the RISC cleave the target to induce silencing (Elbashir, et al., (2001) *Genes Dev.* 15:188). Thus, in one aspect the invention relates to a single stranded RNA (siRNA) generated within a cell and which promotes the formation of a RISC complex to effect silencing of the target gene, i.e., an AGT gene. Accordingly, the term "siRNA" is also used herein to refer to an iRNA as described above.

In certain embodiments, the RNAi agent may be a single-stranded siRNA (ssRNAi) that is introduced into a cell or organism to inhibit a target mRNA. Single-stranded RNAi agents bind to the RISC endonuclease, Argonaute 2, which then cleaves the target mRNA. The single-stranded siRNAs are generally 15-30 nucleotides and are chemically modified. The design and testing of single-stranded siRNAs are described in U.S. Pat. No. 8,101,348 and in Lima et al., (2012) Cell 150:883-894, the entire contents of each of which are hereby incorporated herein by reference. Any of the antisense nucleotide sequences described herein may be used as a single-stranded siRNA as described herein or as chemically modified by the methods described in Lima et al., (2012) Cell 150:883-894.

In certain embodiments, an "iRNA" for use in the compositions, uses, and methods of the invention is a double stranded RNA and is referred to herein as a "double stranded RNA agent," "double stranded RNA (dsRNA) molecule," "dsRNA agent," or "dsRNA". The term "dsRNA", refers to a complex of ribonucleic acid molecules, having a duplex structure comprising two anti-parallel and substantially complementary nucleic acid strands, referred to as having "sense" and "antisense" orientations with respect to a target RNA, i.e., an AGT gene. In some embodiments of the invention, a double stranded RNA (dsRNA) triggers the degradation of a target RNA, e.g., an mRNA, through a post-transcriptional gene-silencing mechanism referred to herein as RNA interference or RNAi.

In general, the majority of nucleotides of each strand of a dsRNA molecule are ribonucleotides, but as described in detail herein, each or both strands can also include one or more non-ribonucleotides, e.g., a deoxyribonucleotide or a modified nucleotide. In addition, as used in this specification, an "iRNA" may include ribonucleotides with chemical modifications; an iRNA may include substantial modifications at multiple nucleotides. As used herein, the term "modified nucleotide" refers to a nucleotide having, independently, a modified sugar moiety, a modified internucleotide linkage, or modified nucleobase, or any combination thereof. Thus, the term modified nucleotide encompasses substitutions, additions or removal of, e.g., a functional group or atom, to internucleoside linkages, sugar moieties, or nucleobases. The modifications suitable for use in the agents of the invention include all types of modifications disclosed herein or known in the art. Any such modifications, as used in a siRNA type molecule, are encompassed by "iRNA" or "RNAi agent" for the purposes of this specification and claims.

The duplex region may be of any length that permits specific degradation of a desired target RNA through a RISC pathway, and may range from about 19 to 36 base pairs in length, e.g., about 19-30 base pairs in length, for example, about 9, 10, 11, 12, 13, 14, 15, 16, 17, 18, 19, 20, 21, 22, 23, 24, 25, 26, 27, 28, 29, 30, 31, 32, 33, 34, 35, or 36 base pairs in length, such as about 19-30, 19-29, 19-28, 19-27, 19-26, 19-25, 19-24, 19-23, 19-22, 19-21, 19-20, 20-30, 20-29, 20-28, 20-27, 20-26, 20-25, 20-24, 20-23, 20-22, 20-21, 21-30, 21-29, 21-28, 21-27, 21-26, 21-25, 21-24, 21-23, or 21-22 base pairs in length. Ranges and lengths intermediate to the above recited ranges and lengths are also contemplated to be part of the invention.

The two strands forming the duplex structure may be different portions of one larger RNA molecule, or they may be separate RNA molecules. Where the two strands are part of one larger molecule, and therefore are connected by an uninterrupted chain of nucleotides between the 3'-end of one strand and the 5'-end of the respective other strand forming the duplex structure, the connecting RNA chain is referred to as a "hairpin loop." A hairpin loop can comprise at least one unpaired nucleotide. In some embodiments, the hairpin loop can comprise at least 2, 3, 4, 5, 6, 7, 8, 9, 10, 20, 23 or more unpaired nucleotides. In some embodiments, the hairpin loop can be 10 or fewer nucleotides. In some embodiments, the hairpin loop can be 8 or fewer unpaired nucleotides. In some embodiments, the hairpin loop can be 4-10 unpaired nucleotides. In some embodiments, the hairpin loop can be 4-8 nucleotides.

Where the two substantially complementary strands of a dsRNA are comprised by separate RNA molecules, those molecules need not be, but can be covalently connected. Where the two strands are connected covalently by means other than an uninterrupted chain of nucleotides between the 3'-end of one strand and the 5'-end of the respective other strand forming the duplex structure, the connecting structure is referred to as a "linker." The RNA strands may have the same or a different number of nucleotides. The maximum number of base pairs is the number of nucleotides in the shortest strand of the dsRNA minus any overhangs that are present in the duplex. In addition to the duplex structure, an RNAi may comprise one or more nucleotide overhangs.

In certain embodiments, an iRNA agent of the invention is a dsRNA, each strand of which comprises 19-23 nucleotides, that interacts with a target RNA sequence, e.g., an AGT gene, to direct cleavage of the target RNA.

In some embodiments, an iRNA of the invention is a dsRNA of 24-30 nucleotides that interacts with a target RNA sequence, e.g., an AGT target mRNA sequence, to direct the cleavage of the target RNA.

As used herein, the term "nucleotide overhang" refers to at least one unpaired nucleotide that protrudes from the duplex structure of a double stranded iRNA. For example, when a 3'-end of one strand of a dsRNA extends beyond the 5-end of the other strand, or vice versa, there is a nucleotide overhang. A dsRNA can comprise an overhang of at least one nucleotide; alternatively the overhang can comprise at least two nucleotides, at least three nucleotides, at least four nucleotides, at least five nucleotides or more. A nucleotide overhang can comprise or consist of a nucleotide/nucleoside analog, including a deoxynucleotide/nucleoside. The overhang(s) can be on the sense strand, the antisense strand, or any combination thereof. Furthermore, the nucleotide(s) of an overhang can be present on the 5-end, 3'-end, or both ends of either an antisense or sense strand of a dsRNA.

In certain embodiments, the antisense strand of a dsRNA has a 1-10 nucleotide, e.g., a 1, 2, 3, 4, 5, 6, 7, 8, 9, or 10 nucleotide, overhang at the 3'-end or the 5'-end. In certain embodiments, the overhang on the sense strand or the antisense strand, or both, can include extended lengths longer than 10 nucleotides, e.g., 1-30 nucleotides, 2-30 nucleotides, 10-30 nucleotides, 10-25 nucleotides, 10-20 nucleotides, or 10-15 nucleotides in length. In certain embodiments, an extended overhang is on the sense strand of the duplex. In certain embodiments, an extended overhang is present on the 3' end of the sense strand of the duplex. In certain embodiments, an extended overhang is present on the 5' end of the sense strand of the duplex. In certain embodiments, an extended overhang is on the antisense strand of the duplex. In certain embodiments, an extended overhang is present on the 3' end of the antisense strand of the duplex. In certain embodiments, an extended overhang is present on the 5' end of the antisense strand of the duplex. In certain embodiments, one or more of the nucleotides in the extended overhang is replaced with a nucleoside thiophosphate. In certain embodiments, the overhang includes a self-complementary portion such that the overhang is capable of forming a hairpin structure that is stable under physiological conditions.

"Blunt" or "blunt end" means that there are no unpaired nucleotides at that end of the double stranded RNA agent, i.e., no nucleotide overhang. A "blunt ended" double stranded RNA agent is double stranded over its entire length, i.e., no nucleotide overhang at either end of the molecule. The RNAi agents of the invention include RNAi agents with no nucleotide overhang at one end (i.e., agents with one overhang and one blunt end) or with no nucleotide overhangs at either end. Most often such a molecule will be double-stranded over its entire length.

The term "antisense strand" or "guide strand" refers to the strand of an iRNA, e.g., a dsRNA, which includes a region that is substantially complementary to a target sequence, e.g., an AGT mRNA. As used herein, the term "region of complementarity" refers to the region on the antisense strand that is substantially complementary to a sequence, for example a target sequence, e.g., an AGT nucleotide sequence, as defined herein. Where the region of complementarity is not fully complementary to the target sequence, the mismatches can be in the internal or terminal regions of the molecule. Generally, the most tolerated mismatches are in the terminal regions, e.g., within 5, 4, or 3 nucleotides of the 5'- or 3'-end of the iRNA. In some embodiments, a double stranded RNA agent of the invention includes a nucleotide mismatch in the antisense strand. In some embodiments, a double stranded RNA agent of the invention includes a nucleotide mismatch in the sense strand. In some embodiments, the nucleotide mismatch is, for example, within 5, 4, 3 nucleotides from the 3'-end of the iRNA. In another embodiment, the nucleotide mismatch is, for example, in the 3'-terminal nucleotide of the iRNA.

The term "sense strand" or "passenger strand" as used herein, refers to the strand of an iRNA that includes a region that is substantially complementary to a region of the antisense strand as that term is defined herein.

As used herein, "substantially all of the nucleotides are modified" are largely but not wholly modified and can include not more than 5, 4, 3, 2, or 1 unmodified nucleotides.

As used herein, the term "cleavage region" refers to a region that is located immediately adjacent to the cleavage site. The cleavage site is the site on the target at which cleavage occurs. In some embodiments, the cleavage region comprises three bases on either end of, and immediately adjacent to, the cleavage site. In some embodiments, the cleavage region comprises two bases on either end of, and immediately adjacent to, the cleavage site. In some embodiments, the cleavage site specifically occurs at the site bound by nucleotides 10 and 11 of the antisense strand, and the cleavage region comprises nucleotides 11, 12 and 13.

As used herein, and unless otherwise indicated, the term "complementary," when used to describe a first nucleotide sequence in relation to a second nucleotide sequence, refers to the ability of an oligonucleotide or polynucleotide comprising the first nucleotide sequence to hybridize and form a duplex structure under certain conditions with an oligonucleotide or polynucleotide comprising the second nucleotide sequence, as will be understood by the skilled person. Such conditions can, for example, be stringent conditions, where stringent conditions can include: 400 mM NaCl, 40 mM PIPES pH 6.4, 1 mM EDTA, 50° C. or 70° C. for 12-16 hours followed by washing (see, e.g., "Molecular Cloning: A Laboratory Manual, Sambrook, et al. (1989) Cold Spring Harbor Laboratory Press). Other conditions, such as physiologically relevant conditions as can be encountered inside an organism, can apply. The skilled person will be able to determine the set of conditions most appropriate for a test of complementarity of two sequences in accordance with the ultimate application of the hybridized nucleotides.

Complementary sequences within an iRNA, e.g., within a dsRNA as described herein, include base-pairing of the oligonucleotide or polynucleotide comprising a first nucleotide sequence to an oligonucleotide or polynucleotide comprising a second nucleotide sequence over the entire length of one or both nucleotide sequences. Such sequences can be referred to as "fully complementary" with respect to each other herein. However, where a first sequence is referred to as "substantially complementary" with respect to a second sequence herein, the two sequences can be fully complementary, or they can form one or more, but generally not more than 5, 4, 3, or 2 mismatched base pairs upon hybridization for a duplex up to 30 base pairs, while retaining the ability to hybridize under the conditions most relevant to their ultimate application, e.g., inhibition of gene expression via a RISC pathway. However, where two oligonucleotides are designed to form, upon hybridization, one or more single stranded overhangs, such overhangs shall not be regarded as mismatches with regard to the determination of complementarity. For example, a dsRNA comprising one oligonucleotide 21 nucleotides in length and another oligonucleotide 23 nucleotides in length, wherein the longer oligonucleotide comprises a sequence of 21 nucleotides that is fully complementary to the shorter oligonucleotide, can yet be referred to as "fully complementary" for the purposes described herein.

"Complementary" sequences, as used herein, can also include, or be formed entirely from, non-Watson-Crick base pairs or base pairs formed from non-natural and modified nucleotides, in so far as the above requirements with respect to their ability to hybridize are fulfilled. Such non-Watson-Crick base pairs include, but are not limited to, G:U Wobble or Hoogstein base pairing.

The terms "complementary," "fully complementary" and "substantially complementary" herein can be used with respect to the base matching between the sense strand and the antisense strand of a dsRNA, or between the antisense strand of a double stranded RNA agent and a target sequence, as will be understood from the context of their use.

As used herein, a polynucleotide that is "substantially complementary to at least part of" a messenger RNA (mRNA) refers to a polynucleotide that is substantially complementary to a contiguous portion of the mRNA of interest (e.g., an mRNA encoding an AGT gene). For example, a polynucleotide is complementary to at least a part of an AGT mRNA if the sequence is substantially complementary to a non-interrupted portion of an mRNA encoding an AGT gene.

Accordingly, in some embodiments, the sense strand polynucleotides and the antisense polynucleotides disclosed herein are fully complementary to the target AGT sequence. In other embodiments, the sense strand polynucleotides or the antisense polynucleotides disclosed herein are substantially complementary to the target AGT sequence and comprise a contiguous nucleotide sequence which is at least 80% complementary over its entire length to the equivalent region of the nucleotide sequence of any one of SEQ ID NOs:1 and 2, or a fragment of any one of SEQ ID NOs:1 and 2, such as at least 90%, or 95% complementary; or 100% complementary.

Accordingly, in some embodiments, the antisense strand polynucleotides disclosed herein are fully complementary to the target AGT sequence. In other embodiments, the antisense strand polynucleotides disclosed herein are substantially complementary to the target AGT sequence and comprise a contiguous nucleotide sequence which is at least about 90% complementary over its entire length to the equivalent region of the nucleotide sequence of SEQ ID NO:1, or a fragment of SEQ ID NO:1, such as about 90%, or about 95%, complementary. In certain embodiments, the fragment of SEQ ID NO: 1 is selected from the group of nucleotides 632-658, 635-658, 636-658, 1248-1273, 1248-1270, 1250-1272, 1251-1273, 1580-1602, 1584-1606, 1587-1609, 1601-1623, 1881-1903, 2074-2097, 2074-2096, 2075-2097, 2080-2102, 2272-2294, 2276-2298, 2281-2304, 2281-2303, or 2282-2304 of SEQ ID NO: 1. In preferred embodiments, the duplex does not consist of the sense strand consisting of uscsucccAfcCfUfUfuucuucuaauL96 (SEQ ID NO: 13) and the antisense strand consisting of asUfsuagAfagaaaagGfuGfggagascsu (SEQ ID NO: 14).

In some embodiments, an iRNA of the invention includes an antisense strand that is substantially complementary to the target AGT sequence and comprises a contiguous nucleotide sequence which is at least about 90% complementary over its entire length to the equivalent region of the nucleotide sequence of any one of the sense strands in Table 3, Table 5, or Table 6 or a fragment of any one of the sense strands in Table 3, Table 5, or Table 6, such as about 90%, 95%, or 100% complementary.

In some embodiments, an iRNA of the invention includes a sense strand that is substantially complementary to an antisense polynucleotide which, in turn, is complementary to a target AGT sequence, and wherein the sense strand polynucleotide comprises a contiguous nucleotide sequence which is at least about 90% complementary over its entire length to the equivalent region of the nucleotide sequence of any one of the antisense strands in Table 3, 5, or 6, or a fragment of any one of the antisense strands in Table 3 or 5, such as about 90%, 95%, or 100%.

In certain embodiments, the sense and antisense strands in Table 3 or Table 5 are selected from duplexes AD-85481, AD-84701, AD-84703, AD-84704, AD-84705, AD-84707, AD-84715, AD-84716, AD-84739, AD-84741, AD-84746, AD-85432, AD-85434, AD-85435, AD-85436, AD-85437, AD-85438, AD-85441, AD-85442, AD-85443, AD-85444, AD-85446, AD-85447, AD-85482, AD-85485, AD-85493, AD-85496, AD-85504, AD-85517, AD-85519, AD-85524, AD-85622, AD-85623, AD-85625, AD-85626, AD-85634, AD-85635, AD-85637, and AD-85655.

In general, an "iRNA" includes ribonucleotides with chemical modifications. Such modifications may include all types of modifications disclosed herein or known in the art. Any such modifications, as used in a dsRNA molecule, are encompassed by "iRNA" for the purposes of this specification and claims.

In an aspect of the invention, an agent for use in the methods and compositions of the invention is a single-stranded antisense oligonucleotide molecule that inhibits a target mRNA via an antisense inhibition mechanism. The single-stranded antisense oligonucleotide molecule is complementary to a sequence within the target mRNA. The single-stranded antisense oligonucleotides can inhibit translation in a stoichiometric manner by base pairing to the mRNA and physically obstructing the translation machinery, see Dias, N. et al., (2002) Mol Cancer Ther 1:347-355. The single-stranded antisense oligonucleotide molecule may be about 14 to about 30 nucleotides in length and have a sequence that is complementary to a target sequence. For example, the single-stranded antisense oligonucleotide molecule may comprise a sequence that is at least about 14, 15, 16, 17, 18, 19, 20, or more contiguous nucleotides from any one of the antisense sequences described herein.

The phrase "contacting a cell with an iRNA," such as a dsRNA, as used herein, includes contacting a cell by any possible means. Contacting a cell with an iRNA includes contacting a cell in vitro with the iRNA or contacting a cell in vivo with the iRNA. The contacting may be done directly or indirectly. Thus, for example, the iRNA may be put into physical contact with the cell by the individual performing the method, or alternatively, the iRNA may be put into a situation that will permit or cause it to subsequently come into contact with the cell.

Contacting a cell in vitro may be done, for example, by incubating the cell with the iRNA. Contacting a cell in vivo may be done, for example, by injecting the iRNA into or near the tissue where the cell is located, or by injecting the iRNA into another area, e.g., the bloodstream or the subcutaneous space, such that the agent will subsequently reach the tissue where the cell to be contacted is located. For example, the iRNA may contain or be coupled to a ligand, e.g., GaNAc, that directs the iRNA to a site of interest, e.g., the liver. Combinations of in vitro and in vivo methods of contacting are also possible. For example, a cell may also be contacted in vitro with an iRNA and subsequently transplanted into a subject.

In certain embodiments, contacting a cell with an iRNA includes "introducing" or "delivering the iRNA into the cell" by facilitating or effecting uptake or absorption into the cell. Absorption or uptake of an iRNA can occur through unaided diffusion or active cellular processes, or by auxiliary agents or devices. Introducing an iRNA into a cell may be in vitro or in vivo. For example, for in vivo introduction, iRNA can be injected into a tissue site or administered systemically. In vitro introduction into a cell includes methods known in the art such as electroporation and lipofection. Further approaches are described herein below or are known in the art.

The term "lipid nanoparticle" or "LNP" is a vesicle comprising a lipid layer encapsulating a pharmaceutically active molecule, such as a nucleic acid molecule, e.g., an iRNA or a plasmid from which an iRNA is transcribed. LNPs are described in, for example, U.S. Pat. Nos. 6,858,225, 6,815,432, 8,158,601, and 8,058,069, the entire contents of which are hereby incorporated herein by reference.

As used herein, a "subject" is an animal, such as a mammal, including a primate (such as a human, a non-human primate, e.g., a monkey, and a chimpanzee), a non-primate (such as a cow, a pig, a horse, a goat, a rabbit, a sheep, a hamster, a guinea pig, a cat, a dog, a rat, or a mouse), or a bird that expresses the target gene, either endogenously or heterologously. In an embodiment, the subject is a human, such as a human being treated or assessed for a disease or disorder that would benefit from reduction in AGT expression; a human at risk for a disease or disorder that would benefit from reduction in AGT expression; a human having a disease or disorder that would benefit from reduction in AGT expression; or human being treated for a disease or disorder that would benefit from reduction in AGT expression as described herein. The diagnostic criteria for an AGT-associated disorder, e.g., hypertension, are provided below. In some embodiments, the subject is a female human. In other embodiments, the subject is a male human. In certain embodiments, the subject is part of a group susceptible to salt sensitivity, e.g., black or an older adult (>65 years of age). In certain embodiments, the subject is overweight or obese, e.g., a subject that suffers from central obesity. In certain embodiments, the subject is sedentary. In certain embodiments, the subject is pregnant.

As used herein, the terms "treating" or "treatment" refer to a beneficial or desired result, such as reducing at least one sign or symptom of an AGT-associated disorder, e.g., hypertension in a subject. Treatment also includes a reduction of one or more sign or symptoms associated with unwanted AGT expression, e.g., angiotensin II type 1 receptor activation ($AT_1R$) (e.g., hypertension, chronic kidney disease, stroke, myocardial infarction, heart failure, aneurysms, peripheral artery disease, heart disease, increased oxidative stress, e.g., increased superoxide formation, inflammation, vasoconstriction, sodium and water retention, potassium and magnesium loss, renin suppression, myocyte and smooth muscle hypertrophy, increased collagen synthesis, stimulation of vascular, myocardial and renal fibrosis, increased rate and force of cardiac contractions, altered heart rate, e.g., increased arrhythmia, stimulation of plasminogen activator inhibitor 1 (PAI1), activation of the sympathetic nervous system, and increased endothelin secretion), symptoms of pregnancy-associated hypertension (e.g., preeclampsia, and eclampsia), including, but not limited to intrauterine growth restriction (IUGR) or fetal growth restriction, symptoms associated with malignant hypertension, symptoms associated with hyperaldosteronism; diminishing the extent of unwanted $AT_1R$ activation; stabilization (i.e., not worsening) of the state of chronic $AT_1R$ activation; amelioration or palliation of unwanted $AT_1R$ activation (e.g., hypertension, chronic kidney disease, stroke, myocardial infarction, heart failure, aneurysms, peripheral artery disease, heart disease, increased oxidative stress, e.g., increased superoxide formation, inflammation, vasoconstriction, sodium and water retention, potassium and magnesium loss, renin suppression, myocyte and smooth muscle hypertrophy, increased collagen synthesis, stimulation of vascular, myocardial and renal fibrosis, increased rate and force of cardiac contractions, altered heart rate, e.g., increased arrhythmia, stimulation of plasminogen activator inhibitor 1 (PAI1), activation of the sympathetic nervous system, and increased endothelin secretion) whether detectable or undetectable. AGT-associated disorders can also include obesity, liver steatosis/fatty liver, e.g., non-alcoholic Steatohepatitis (NASH) and non-alcoholic fatty liver disease (NAFLD), glucose intolerance, type 2 diabetes (non-insulin dependent diabetes), and metabolic syndrome. In certain embodiments, hypertension includes hypertension associated with low plasma renin activity or plasma renin concentration. "Treatment" can also mean prolonging survival as compared to expected survival in the absence of treatment.

The term "lower" in the context of the level of AGT gene expression or agt protein production in a subject, or a disease marker or symptom refers to a statistically significant decrease in such level. The decrease can be, for example, at least 50%, 55%, 60%, 65%, 70%, 75%, 80%, 85%, 90%, or 95%, or below the level of detection for the detection method in a relevant cell or tissue, e.g., a liver cell, or other subject sample, e.g., blood or serum derived therefrom, urine.

As used herein, "prevention" or "preventing," when used in reference to a disease or disorder, that would benefit from a reduction in expression of an AGT gene or production of agt protein, e.g., in a subject susceptible to an AGT-associated disorder due to, e.g., aging, genetic factors, hormone changes, diet, and a sedentary lifestyle. In certain embodiments, the disease or disorder is e.g., a symptom of unwanted $AT_1R$ activation, such as a hypertension, chronic kidney disease, stroke, myocardial infarction, heart failure, aneurysms, peripheral artery disease, heart disease, increased oxidative stress, e.g., increased superoxide formation, inflammation, vasoconstriction, sodium and water retention, potassium and magnesium loss, renin suppression, myocyte and smooth muscle hypertrophy, increased collagen synthesis, stimulation of vascular, myocardial and renal fibrosis, increased rate and force of cardiac contractions, altered heart rate, e.g., increased arrhythmia, stimulation of plasminogen activator inhibitor 1 (PAI1), activation of the sympathetic nervous system, and increased endothelin secretion. AGT-associated disorders can also include obesity, liver steatosis/fatty liver, e.g., non-alcoholic Steatohepatitis (NASH) and non-alcoholic fatty liver disease (NAFLD), glucose intolerance, type 2 diabetes (non-insulin dependent diabetes), and metabolic syndrome. In certain embodiments, hypertension includes hypertension associated with low plasma renin activity or plasma renin concentration. The likelihood of developing, e.g., hypertension, is reduced, for example, when an individual having one or more risk factors for a hypertension either fails to develop hypertension or develops hypertension with less severity relative to a population having the same risk factors and not receiving treatment as described herein. The failure to develop an AGT-associated disorder, e.g., hypertension or a delay in the time to develop hypertension by months or years is considered effective prevention. Prevention may require administration of more than one dose if the iRNA agent.

As used herein, the term "angiotensinogen-associated disease" or "AGT-associated disease," is a disease or disorder that is caused by, or associated with renin-angiotensin-aldosterone system (RAAS) activation, or a disease or disorder the symptoms of which or progression of which responds to RAAS inactivation. The term "angiotensinogen-associated disease" includes a disease, disorder or condition that would benefit from reduction in AGT expression. Such diseases are typically associated with high blood pressure. Non-limiting examples of angiotensinogen-associated diseases include hypertension, e.g., borderline hypertension (also known as prehypertension), primary hypertension (also known as essential hypertension or idiopathic hypertension), secondary hypertension (also known as inessential hypertension), isolated systolic or diastolic hypertension, pregnancy-associated hypertension (e.g., preeclampsia, eclampsia, and post-partum preeclampsia), diabetic hypertension, resistant hypertension, refractory hypertension, paroxysmal hypertension, renovascular hypertension (also known as renal hypertension), Goldblatt hypertension, ocular hypertension, glaucoma, pulmonary hypertension, portal hypertension, systemic venous hypertension, systolic hypertension, labile hypertension; hypertensive heart disease, hypertensive nephropathy, atherosclerosis, arteriosclerosis, vasculopathy (including peripheral vascular disease), diabetic nephropathy, diabetic retinopathy, chronic heart failure, cardiomyopathy, diabetic cardiac myopathy, glomerulosclerosis, coarctation of the aorta, aortic aneurism, ventricular fibrosis, sleep apnea, heart failure (e.g., left ventricular systolic dysfunction), myocardial infarction, angina, stroke, renal disease e.g., chronic kidney disease or diabetic nephropathy optionally in the context of pregnancy, renal failure, e.g., chronic renal failure, and systemic sclerosis (e.g., scleroderma renal crisis). In certain embodiments, AGT-associated disease includes intrauterine growth restriction (IUGR) or fetal growth restriction. In certain embodiments, AGT-associated disorders also include obesity, liver steatosis/fatty liver, e.g., non-alcoholic Steatohepatitis (NASH) and non-alcoholic fatty liver disease (NAFLD), glucose intolerance, type 2 diabetes (non-insulin dependent diabetes), and metabolic syndrome. In certain embodiments, hypertension includes hypertension associated with low plasma renin activity or plasma renin concentration.

Thresholds for high blood pressure and stages of hypertension are discussed in detail below.

In one embodiment, an angiotensinogen-associated disease is primary hypertension. "Primary hypertension" is a result of environmental or genetic causes (e.g., a result of no obvious underlying medical cause).

In one embodiment, an angiotensinogen-associated disease is secondary hypertension. "Secondary hypertension" has an identifiable underlying disorder which can be of multiple etiologies, including renal, vascular, and endocrine causes, e.g., renal parenchymal disease (e.g., polycystic kidneys, glomerular or interstitial disease), renal vascular disease (e.g., renal artery stenosis, fibromuscular dysplasia), endocrine disorders (e.g., adrenocorticosteroid or mineralocorticoid excess, pheochromocytoma, hyperthyroidism or hypothyroidism, growth hormone excess, hyperparathyroidism), coarctation of the aorta, or oral contraceptive use.

In one embodiment, an angiotensinogen-associated disease is pregnancy-associated hypertension, e.g., chronic hypertension of pregnancy, gestational hypertension, preeclampsia, eclampsia, preeclampsia superimposed on chronic hypertension, HELLP syndrome, and gestational hypertension (also known as transient hypertension of pregnancy, chronic hypertension identified in the latter half of pregnancy, and pregnancy-induced hypertension (PIH)). Diagnostic criteria for pregnancy-associated hypertension are provided below.

In one embodiment, an angiotensinogen-associated disease is resistant hypertension. "Resistant hypertension" is blood pressure that remains above goal (e.g., above 130 mm Hg systolic or above 90 diastolic) in spite of concurrent use of three antihypertensive agents of different classes, one of which is a thiazide diuretic. Subjects whose blood pressure is controlled with four or more medications are also considered to have resistant hypertension.

A "therapeutically-effective amount" or "prophylactically effective amount" also includes an amount of an RNAi agent that produces some desired effect at a reasonable benefit/risk ratio applicable to any treatment. The iRNA employed in the methods of the present invention may be administered in a sufficient amount to produce a reasonable benefit/risk ratio applicable to such treatment.

The phrase "pharmaceutically acceptable" is employed herein to refer to those compounds, materials, compositions, or dosage forms which are, within the scope of sound medical judgment, suitable for use in contact with the tissues of human subjects and animal subjects without excessive toxicity, irritation, allergic response, or other problem or complication, commensurate with a reasonable benefit/risk ratio.

The phrase "pharmaceutically-acceptable carrier" as used herein means a pharmaceutically-acceptable material, composition, or vehicle, such as a liquid or solid filler, diluent, excipient, manufacturing aid (e.g., lubricant, talc magnesium, calcium or zinc stearate, or steric acid), or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the subject being treated. Such carriers are known in the art. Pharmaceutically acceptable carriers include carriers for administration by injection.

The term "sample," as used herein, includes a collection of similar fluids, cells, or tissues isolated from a subject, as well as fluids, cells, or tissues present within a subject. Examples of biological fluids include blood, serum and serosal fluids, plasma, cerebrospinal fluid, ocular fluids, lymph, urine, saliva, and the like. Tissue samples may include samples from tissues, organs, or localized regions. For example, samples may be derived from particular organs, parts of organs, or fluids or cells within those organs. In certain embodiments, samples may be derived from the liver (e.g., whole liver or certain segments of liver or certain types of cells in the liver, such as, e.g., hepatocytes). In some embodiments, a "sample derived from a subject" refers to urine obtained from the subject. A "sample derived from a subject" can refer to blood or blood derived serum or plasma from the subject.

I. iRNAs of the Invention

The present invention provides iRNAs which inhibit the expression of an AGT gene. In preferred embodiments, the iRNA includes double stranded ribonucleic acid (dsRNA) molecules for inhibiting the expression of an AGT gene in a cell, such as a cell within a subject, e.g., a mammal, such as a human susceptible to developing an AGT-associated disorder, e.g., hypertension. The dsRNAi agent includes an antisense strand having a region of complementarity which is complementary to at least a part of an mRNA formed in the expression of an AGT gene. The region of complementarity is about 19-30 nucleotides in length (e.g., about 30, 29, 28, 27, 26, 25, 24, 23, 22, 21, 20, or 19 nucleotides in length). Upon contact with a cell expressing the AGT gene, the iRNA inhibits the expression of the AGT gene (e.g., a human, a primate, a non-primate, or a rat AGT gene) by at least about 50% as assayed by, for example, a PCR or branched DNA (bDNA)-based method, or by a protein-based method, such as by immunofluorescence analysis, using, for example, western blotting or flow cytometric techniques. In preferred embodiments, inhibition of expression is determined by the qPCR method provided in the examples, especially in Example 2 with the siRNA at a 10 nM concentration in an appropriate organism cell line provided therein. In preferred embodiments, inhibition of expression in vivo is determined by knockdown of the human gene in a rodent expressing the human gene, e.g., a mouse or an AAV-infected mouse expressing the human target gene, e.g., when administered a single dose at 3 mg/kg at the nadir of RNA expression. RNA expression in liver is determined using the PCR methods provided in Example 2.

A dsRNA includes two RNA strands that are complementary and hybridize to form a duplex structure under conditions in which the dsRNA will be used. One strand of a dsRNA (the antisense strand) includes a region of complementarity that is substantially complementary, and generally fully complementary, to a target sequence. The target sequence can be derived from the sequence of an mRNA formed during the expression of an AGT gene. The other strand (the sense strand) includes a region that is complementary to the antisense strand, such that the two strands hybridize and form a duplex structure when combined under suitable conditions. As described elsewhere herein and as known in the art, the complementary sequences of a dsRNA can also be contained as self-complementary regions of a single nucleic acid molecule, as opposed to being on separate oligonucleotides.

Generally, the duplex structure is 19 to 30 base pairs in length. Similarly, the region of complementarity to the target sequence is 19 to 30 nucleotides in length.

In some embodiments, the dsRNA is about 19 to about 23 nucleotides in length, or about 25 to about 30 nucleotides in length. In general, the dsRNA is long enough to serve as a substrate for the Dicer enzyme. For example, it is well-known in the art that dsRNAs longer than about 21-23 nucleotides in length may serve as substrates for Dicer. As the ordinarily skilled person will also recognize, the region of an RNA targeted for cleavage will most often be part of a larger RNA molecule, often an mRNA molecule. Where relevant, a "part" of an mRNA target is a contiguous sequence of an mRNA target of sufficient length to allow it to be a substrate for RNAi-directed cleavage (i.e., cleavage through a RISC pathway).

One of skill in the art will also recognize that the duplex region is a primary functional portion of a dsRNA, e.g., a duplex region of about 19 to about 30 base pairs, e.g., about 19-30, 19-29, 19-28, 19-27, 19-26, 19-25, 19-24, 19-23, 19-22, 19-21, 19-20, 20-30, 20-29, 20-28, 20-27, 20-26, 20-25, 20-24, 20-23, 20-22, 20-21, 21-30, 21-29, 21-28, 21-27, 21-26, 21-25, 21-24, 21-23, or 21-22 base pairs. Thus, in one embodiment, to the extent that it becomes processed to a functional duplex, of e.g., 15-30 base pairs, that targets a desired RNA for cleavage, an RNA molecule or complex of RNA molecules having a duplex region greater than 30 base pairs is a dsRNA. Thus, an ordinarily skilled artisan will recognize that in one embodiment, a miRNA is a dsRNA. In another embodiment, a dsRNA is not a naturally occurring miRNA. In another embodiment, an iRNA agent useful to target AGT gene expression is not generated in the target cell by cleavage of a larger dsRNA.

A dsRNA as described herein can further include one or more single-stranded nucleotide overhangs e.g., 1-4, 2-4, 1-3, 2-3, 1, 2, 3, or 4 nucleotides. dsRNAs having at least one nucleotide overhang can have superior inhibitory properties relative to their blunt-ended counterparts. A nucleotide overhang can comprise or consist of a nucleotide/nucleoside analog, including a deoxynucleotide/nucleoside. The overhang(s) can be on the sense strand, the antisense strand, or any combination thereof. Furthermore, the nucleotide(s) of an overhang can be present on the 5'-end, 3'-end, or both ends of an antisense or sense strand of a dsRNA.

A dsRNA can be synthesized by standard methods known in the art. Double stranded RNAi compounds of the invention may be prepared using a two-step procedure. First, the individual strands of the double stranded RNA molecule are prepared separately. Then, the component strands are annealed. The individual strands of the siRNA compound can be prepared using solution-phase or solid-phase organic synthesis or both. Organic synthesis offers the advantage that the oligonucleotide strands comprising unnatural or modified nucleotides can be easily prepared. Similarly, single-stranded oligonucleotides of the invention can be prepared using solution-phase or solid-phase organic synthesis or both.

In an aspect, a dsRNA of the invention includes at least two nucleotide sequences, a sense sequence and an antisense sequence. The sense strand is selected from the group of sequences provided in Tables 3, 5, and 6, and the corresponding antisense strand of the sense strand is selected from the group of sequences of Table 3, 5, and 6. In this aspect, one of the two sequences is complementary to the other of the two sequences, with one of the sequences being substantially complementary to a sequence of an mRNA generated in the expression of an AGT gene. As such, in this aspect, a dsRNA will include two oligonucleotides, where one oligonucleotide is described as the sense strand in Table, 5, or 6, and the second oligonucleotide is described as the corresponding antisense strand of the sense strand in Table 3, 5, or 6. In certain embodiments, the substantially complementary sequences of the dsRNA are contained on separate oligonucleotides. In other embodiments, the substantially complementary sequences of the dsRNA are contained on a single oligonucleotide. In certain embodiments, the sense or antisense strand in Table 3 or 5 is selected from AD-85481, AD-84701, AD-84703, AD-84704, AD-84705, AD-84707, AD-84715, AD-84716, AD-84739, AD-84741, AD-84746, AD-85432, AD-85434, AD-85435, AD-85436, AD-85437, AD-85438, AD-85441, AD-85442, AD-85443, AD-85444, AD-85446, AD-85447, AD-85482, AD-85485, AD-85493, AD-85496, AD-85504, AD-85517, AD-85519, AD-85524, AD-85622, AD-85623, AD-85625, AD-85626, AD-85634, AD-85635, AD-85637, and AD-85655.

It will be understood that, although the sequences in Table 3 are not described as modified or conjugated sequences, the RNA of the iRNA of the invention e.g., a dsRNA of the invention, may comprise any one of the sequences set forth in Table 3, or the sequences of Table 5 or 6 that are modified, or the sequences of Table 5 or 6 that are conjugated. In other words, the invention encompasses dsRNA of Table 3, 5, and 6 which are un-modified, un-conjugated, modified, or conjugated, as described herein.

The skilled person is well aware that dsRNAs having a duplex structure of about 20 to 23 base pairs, e.g., 21, base pairs have been hailed as particularly effective in inducing RNA interference (Elbashir et al., *EMBO* 2001, 20:6877-6888). However, others have found that shorter or longer RNA duplex structures can also be effective (Chu and Rana (2007) *RNA* 14:1714-1719; Kim et al. (2005) *Nat Biotech* 23:222-226). In the embodiments described above, by virtue of the nature of the oligonucleotide sequences provided in any one of Table 3, 5, and 6, dsRNAs described herein can include at least one strand of a length of minimally 21 nucleotides. It can be reasonably expected that shorter duplexes having one of the sequences of Table 3, 5, and 6 minus only a few nucleotides on one or both ends can be similarly effective as compared to the dsRNAs described above. Hence, dsRNAs having a sequence of at least 19, 20, or more contiguous nucleotides derived from one of the sequences of Table 3, 5, and 6, and differing in their ability to inhibit the expression of an AGT gene by not more than about 5, 10, 15, 20, 25, or 30% inhibition from a dsRNA comprising the full sequence, are contemplated to be within the scope of the present invention.

In addition, the RNAs provided in Table 3, 5, and 6 identify a site(s) in an AGT transcript that is susceptible to RISC-mediated cleavage. As such, the present invention further features iRNAs that target within one of these sites. As used herein, an iRNA is said to target within a particular site of an RNA transcript if the iRNA promotes cleavage of the transcript anywhere within that particular site. Such an iRNA will generally include at least about 19 contiguous nucleotides from one of the sequences provided in Table 3, 5, and 6 coupled to additional nucleotide sequences taken from the region contiguous to the selected sequence in an AGT gene.

II. Modified iRNAs of the Invention

In certain embodiments, the RNA of the iRNA of the invention e.g., a dsRNA, is un-modified, and does not comprise, e.g., chemical modifications or conjugations known in the art and described herein. In other embodiments, the RNA of an iRNA of the invention, e.g., a dsRNA, is chemically modified to enhance stability or other beneficial characteristics. In certain embodiments of the invention, substantially all of the nucleotides of an iRNA of the invention are modified. In other embodiments of the invention, all of the nucleotides of an iRNA or substantially all of the nucleotides of an iRNA are modified, i.e., not more than 5, 4, 3, 2, or 1 unmodified nucleotides are present in a strand of the iRNA.

The nucleic acids featured in the invention can be synthesized or modified by methods well established in the art, such as those described in "Current protocols in nucleic acid chemistry," Beaucage, S. L. et al. (Edrs.), John Wiley & Sons, Inc., New York, N.Y., USA, which is hereby incorporated herein by reference. Modifications include, for example, end modifications, e.g., 5'-end modifications (phosphorylation, conjugation, inverted linkages) or 3'-end modifications (conjugation, DNA nucleotides, inverted linkages, etc.); base modifications, e.g., replacement with stabilizing bases, destabilizing bases, or bases that base pair with an expanded repertoire of partners, removal of bases (abasic nucleotides), or conjugated bases; sugar modifications (e.g., at the 2'-position or 4'-position) or replacement of the sugar; or backbone modifications, including modification or replacement of the phosphodiester linkages. Specific examples of iRNA compounds useful in the embodiments described herein include, but are not limited to RNAs containing modified backbones or no natural internucleoside linkages. RNAs having modified backbones include, among others, those that do not have a phosphorus atom in the backbone. For the purposes of this specification, and as sometimes referenced in the art, modified RNAs that do not have a phosphorus atom in their internucleoside backbone can also be considered to be oligonucleosides. In some embodiments, a modified iRNA will have a phosphorus atom in its internucleoside backbone.

Modified RNA backbones include, for example, phosphorothioates, chiral phosphorothioates, phosphorodithioates, phosphotriesters, aminoalkylphosphotriesters, methyl and other alkyl phosphonates including 3'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, and boranophosphates having normal 3'-5' linkages, 2'-5'-linked analogs of these, and those having inverted polarity wherein the adjacent pairs of nucleoside units are linked 3'-5' to 5'-3' or 2'-5' to 5'-2'. Various salts, mixed salts and free acid forms are also included.

Representative U.S. Patents that teach the preparation of the above phosphorus-containing linkages include, but are not limited to, U.S. Pat. Nos. 3,687,808; 4,469,863; 4,476,301; 5,023,243; 5,177,195; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,316; 5,550,111; 5,563,253; 5,571,799; 5,587,361; 5,625,050; 6,028,188; 6,124,445; 6,160,109; 6,169,170; 6,172,209; 6,239,265; 6,277,603; 6,326,199; 6,346,614; 6,444,423; 6,531,590; 6,534,639; 6,608,035; 6,683,167; 6,858,715; 6,867,294; 6,878,805; 7,015,315; 7,041,816; 7,273,933; 7,321,029; and U.S. Pat. RE39464, the entire contents of each of which are hereby incorporated herein by reference.

Modified RNA backbones that do not include a phosphorus atom therein have backbones that are formed by short chain alkyl or cycloalkyl internucleoside linkages, mixed heteroatoms and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S, and $CH_2$ component parts.

Representative U.S. Patents that teach the preparation of the above oligonucleosides include, but are not limited to, U.S. Pat. Nos. 5,034,506; 5,166,315; 5,185,444; 5,214,134; 5,216,141; 5,235,033; 5,64,562; 5,264,564; 5,405,938; 5,434,257; 5,466,677; 5,470,967; 5,489,677; 5,541,307; 5,561,225; 5,596,086; 5,602,240; 5,608,046; 5,610,289; 5,618,704; 5,623,070; 5,663,312; 5,633,360; 5,677,437; and 5,677,439, the entire contents of each of which are hereby incorporated herein by reference.

Suitable RNA mimetics are contemplated for use in iRNAs provided herein, in which both the sugar and the internucleoside linkage, i.e., the backbone, of the nucleotide units are replaced with novel groups. The base units are maintained for hybridization with an appropriate nucleic acid target compound. One such oligomeric compound in which an RNA mimetic that has been shown to have excellent hybridization properties is referred to as a peptide nucleic acid (PNA). In PNA compounds, the sugar backbone of an RNA is replaced with an amide containing backbone, in particular an aminoethylglycine backbone. The nucleobases are retained and are bound directly or indirectly to aza nitrogen atoms of the amide portion of the backbone. Representative US patents that teach the preparation of PNA compounds include, but are not limited to, U.S. Pat. Nos. 5,539,082; 5,714,331; and 5,719,262, the entire contents of each of which are hereby incorporated herein by reference.

Additional PNA compounds suitable for use in the iRNAs of the invention are described in, for example, in Nielsen et al., Science, 1991, 254, 1497-1500.

Some embodiments featured in the invention include RNAs with phosphorothioate backbones and oligonucleosides with heteroatom backbones, and in particular —$CH_2$—NH—$CH_2$—, —$CH_2$—N($CH_3$)—O—$CH_2$—[known as a methylene (methylimino) or MMI backbone], —$CH_2$—O—N($CH_3$)—$CH_2$—, —$CH_2$—N($CH_3$)—N($CH_3$)—$CH_2$— and —N($CH_3$)—$CH_2$—$CH_2$— [wherein the native phosphodiester backbone is represented as —O—P—O—$CH_2$—] of the above-referenced U.S. Pat. No. 5,489,677, and the amide backbones of the above-referenced U.S. Pat. No. 5,602,240. In some embodiments, the RNAs featured herein have morpholino backbone structures of the above-referenced U.S. Pat. No. 5,034,506.

Modified RNAs can also contain one or more substituted sugar moieties. The iRNAs, e.g., dsRNAs, featured herein can include one of the following at the 2'-position: OH; F; O-, S-, or N-alkyl; O-, S-, or N-alkenyl; O-, S- or N-alkynyl; or O-alkyl-O-alkyl, wherein the alkyl, alkenyl and alkynyl can be substituted or unsubstituted $C_1$ to $C_{10}$ alkyl or $C_2$ to $C_{10}$ alkenyl and alkynyl. Exemplary suitable modifications include O[($CH_2$)$_n$O]$_m$$CH_3$, O($CH_2$)$_n$O$CH_3$, O($CH_2$)$_n$$NH_2$, O($CH_2$) $CH_3$, O($CH_2$)$_n$O$NH_2$, and O($CH_2$)$_n$ON[($CH_2$) $CH_3$)]2, where n and m are from 1 to about 10. In other embodiments, dsRNAs include one of the following at the 2' position: $C_1$ to $C_{10}$ lower alkyl, substituted lower alkyl, alkaryl, aralkyl, O-alkaryl or O-aralkyl, SH, $SCH_3$, OCN, Cl, Br, CN, CF$_3$, OCF$_3$, SOCH$_3$, SO$_2$CH$_3$, ONO$_2$, NO$_2$, N$_3$, NH$_2$, heterocycloalkyl, heterocycloalkaryl, aminoalkylamino, polyalkylamino, substituted silyl, an RNA cleaving group, a reporter group, an intercalator, a group for improving the pharmacokinetic properties of an iRNA, or a group for improving the pharmacodynamic properties of an iRNA, and other substituents having similar properties. In some embodiments, the modification includes a 2'-methoxyethoxy (2'-O—CH$_2$CH$_2$CH$_3$, also known as 2'-O-(2-methoxyethyl) or 2'-MOE) (Martin et al., *Helv. Chim. Acta*, 1995, 78:486-504) i.e., an alkoxy-alkoxy group. Another exemplary modification is 2'-dimethylaminooxyethoxy, i.e., a O(CH$_2$)$_2$ON (CH$_3$)$_2$ group, also known as 2'-DMAOE, as described in examples herein below, and 2'-dimethylaminoethoxyethoxy (also known in the art as 2'-O-dimethylaminoethoxyethyl or 2'-DMAEOE), i.e., 2'-O—CH$_2$—O—CH$_2$—N(CH$_2$)$_2$. Further exemplary modifications include: 5'-Me-2'-F nucleotides, 5'-Me-2'-OMe nucleotides, 5'-Me-2'-deoxynucleotides, (both R and S isomers in these three families); 2'-alkoxyalkyl; and 2'-NMA (N-methylacetamide).

Other modifications include 2'-methoxy (2'-OCH$_3$), 2'-aminopropoxy (2'-OCH$_2$CH$_2$CH$_2$NH$_2$) and 2'-fluoro (2'-F). Similar modifications can also be made at other positions on the RNA of an iRNA, particularly the 3' position of the sugar on the 3' terminal nucleotide or in 2'-5' linked dsRNAs and the 5' position of 5' terminal nucleotide. iRNAs can also have sugar mimetics such as cyclobutyl moieties in place of the pentofuranosyl sugar. Representative US patents that teach the preparation of such modified sugar structures include, but are not limited to, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; and 5,700,920, certain of which are commonly owned with the instant application. The entire contents of each of the foregoing are hereby incorporated herein by reference.

An iRNA can also include nucleobase (often referred to in the art simply as "base") modifications or substitutions. As used herein, "unmodified" or "natural" nucleobases include the purine bases adenine (A) and guanine (G), and the pyrimidine bases thymine (T), cytosine (C), and uracil (U). Modified nucleobases include other synthetic and natural nucleobases such as deoxy-thymine (dT), 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl anal other 8-substituted adenines and guanines, 5-halo, particularly 5-bromo, 5-trifluoromethyl and other 5-substituted uracils and cytosines, 7-methylguanine and 7-methyladenine, 8-azaguanine and 8-azaadenine, 7-deazaguanine and 7-daazaadenine and 3-deazaguanine and 3-deazaadenine. Further nucleobases include those disclosed in U.S. Pat. No. 3,687,808, those disclosed in Modified Nucleosides in Biochemistry, Biotechnology and Medicine, Herdewijn, P. ed. Wiley-VCH, 2008; those disclosed in The Concise Encyclopedia Of Polymer Science And Engineering, pages 858-859, Kroschwitz, J. L, ed. John Wiley & Sons, 1990, these disclosed by Englisch et al., Angewandte Chemie, International Edition, 1991, 30, 613, and those disclosed by Sanghvi, Y S., Chapter 15, dsRNA Research and Applications, pages 289-302, Crooke, S. T. and Lebleu, B., Ed., CRC Press, 1993. Certain of these nucleobases are particularly useful for increasing the binding affinity of the oligomeric compounds featured in the invention. These include 5-substituted pyrimidines, 6-azapyrimidines and N-2, N-6 and 0-6 substituted purines, including 2-aminopropyladenine, 5-propynyluracil and 5-propynylcytosine. 5-methylcytosine substitutions have been shown to increase nucleic acid duplex stability by 0.6-1.2° C. (Sanghvi, Y. S., Crooke, S. T. and Lebleu, B., Eds., dsRNA Research and Applications, CRC Press, Boca Raton, 1993, pp. 276-278) and are exemplary base substitutions, even more particularly when combined with 2'-O-methoxyethyl sugar modifications.

Representative U.S. Patents that teach the preparation of certain of the above noted modified nucleobases as well as other modified nucleobases include, but are not limited to, the above noted U.S. Pat. Nos. 3,687,808, 4,845,205; 5,130, 30; 5,134,066; 5,175,273; 5,367,066; 5,432,272; 5,457,187; 5,459,255; 5,484,908; 5,502,177; 5,525,711; 5,552,540; 5,587,469; 5,594,121, 5,596,091; 5,614,617; 5,681,941; 5,750,692; 6,015,886; 6,147,200; 6,166,197; 6,222,025; 6,235,887; 6,380,368; 6,528,640; 6,639,062; 6,617,438; 7,045,610; 7,427,672; and 7,495,088, the entire contents of each of which are hereby incorporated herein by reference.

The RNA of an iRNA can also be modified to include one or more locked nucleic acids (LNA). A locked nucleic acid is a nucleotide having a modified ribose moiety in which the ribose moiety comprises an extra bridge connecting the 2' and 4' carbons. This structure effectively "locks" the ribose in the 3'-endo structural conformation. The addition of locked nucleic acids to siRNAs has been shown to increase siRNA stability in serum, and to reduce off-target effects (Elmen, J. et al., (2005) *Nucleic Acids Research* 33(1):439-447; Mook, O R. et al., (2007) *Mol Canc Ther* 6(3):833-843; Grunweller, A. et al., (2003) *Nucleic Acids Research* 31(12): 3185-3193).

In some embodiments, the RNA of an iRNA can also be modified to include one or more bicyclic sugar moieties. A "bicyclic sugar" is a furanosyl ring modified by the bridging of two atoms. A "bicyclic nucleoside" ("BNA") is a nucleoside having a sugar moiety comprising a bridge connecting two carbon atoms of the sugar ring, thereby forming a bicyclic ring system. In certain embodiments, the bridge connects the 4'-carbon and the 2'-carbon of the sugar ring. Thus, in some embodiments an agent of the invention may include one or more locked nucleic acids (LNA). A locked nucleic acid is a nucleotide having a modified ribose moiety in which the ribose moiety comprises an extra bridge connecting the 2' and 4' carbons. In other words, an LNA is a nucleotide comprising a bicyclic sugar moiety comprising a 4'-CH$_2$—O-2' bridge. This structure effectively "locks" the ribose in the 3'-endo structural conformation. The addition of locked nucleic acids to siRNAs has been shown to increase siRNA stability in serum, and to reduce off-target effects (Elmen, J. et al., (2005) *Nucleic Acids Research* 33(1):439-447; Mook, O R. et al., (2007) *Mol Canc Ther* 6(3):833-843; Grunweller, A. et al., (2003) *Nucleic Acids Research* 31(12):3185-3193). Examples of bicyclic nucleosides for use in the polynucleotides of the invention include without limitation nucleosides comprising a bridge between the 4' and the 2' ribosyl ring atoms. In certain embodiments, the antisense polynucleotide agents of the invention include one or more bicyclic nucleosides comprising a 4' to 2' bridge. Examples of such 4' to 2' bridged bicyclic nucleosides, include but are not limited to 4'-(CH$_2$)—O-2' (LNA); 4'-(CH$_2$)—S-2'; 4'-(CH$_2$)$_2$—O-2' (ENA); 4'-CH(CH$_3$)—O-2' (also referred to as "constrained ethyl" or "cEt") and 4'-CH(CH$_2$OCH$_3$)—O-2' (and analogs thereof, see, e.g., U.S. Pat. No. 7,399,845); 4'-C(CH$_3$)(CH$_3$)—O-2' (and analogs thereof; see e.g., U.S. Pat. No. 8,278,283); 4'-CH$_2$—N(OCH$_3$)-2' (and analogs thereof, see e.g., U.S. Pat. No. 8,278,425); 4'-CH$_2$—O—N(CH$_3$)-2' (see, e.g., U.S. Patent Publication No. 2004/0171570); 4'-CH$_2$—N(R)—O-2', wherein R is H, C1-C12 alkyl, or a protecting group (see, e.g., U.S. Pat. No. 7,427,672); 4'-CH$_2$—C(H)(CH$_3$)-2' (see, e.g., Chattopadhyaya et al., J. Org. Chem., 2009, 74, 118-134); and 4'-CH$_2$—C(=CH$_2$)-2' (and analogs thereof, see, e.g., U.S. Pat. No. 8,278,426). The entire contents of each of the foregoing are hereby incorporated herein by reference.

Additional representative U.S. Patents and U.S. Patent Publications that teach the preparation of locked nucleic acid nucleotides include, but are not limited to, the following: U.S. Pat. Nos. 6,268,490; 6,525,191; 6,670,461; 6,770,748; 6,794,499; 6,998,484; 7,053,207; 7,034,133; 7,084,125; 7,399,845; 7,427,672; 7,569,686; 7,741,457; 8,022,193; 8,030,467; 8,278,425; 8,278,426; 8,278,283; US 2008/0039618; and US 2009/0012281, the entire contents of each of which are hereby incorporated herein by reference.

Any of the foregoing bicyclic nucleosides can be prepared having one or more stereochemical sugar configurations including for example α-L-ribofuranose and β-D-ribofuranose (see WO 99/14226).

The RNA of an iRNA can also be modified to include one or more constrained ethyl nucleotides. As used herein, a "constrained ethyl nucleotide" or "cEt" is a locked nucleic acid comprising a bicyclic sugar moiety comprising a 4'-CH(CH$_3$)—O-2' bridge. In one embodiment, a constrained ethyl nucleotide is in the S conformation referred to herein as "S-cEt."

An iRNA of the invention may also include one or more "conformationally restricted nucleotides" ("CRN"). CRN are nucleotide analogs with a linker connecting the C2' and C4' carbons of ribose or the C3 and —C5' carbons of ribose. CRN lock the ribose ring into a stable conformation and increase the hybridization affinity to mRNA. The linker is of sufficient length to place the oxygen in an optimal position for stability and affinity resulting in less ribose ring puckering.

Representative publications that teach the preparation of certain of the above noted CRN include, but are not limited to, U.S. Patent Publication No. 2013/0190383; and PCT publication WO 2013/036868, the entire contents of each of which are hereby incorporated herein by reference.

In some embodiments, an iRNA of the invention comprises one or more monomers that are UNA (unlocked nucleic acid) nucleotides. UNA is unlocked acyclic nucleic acid, wherein any of the bonds of the sugar has been removed, forming an unlocked "sugar" residue. In one example, UNA also encompasses monomer with bonds between C1'-C4' have been removed (i.e. the covalent carbon-oxygen-carbon bond between the C1' and C4' carbons). In another example, the C2'-C3' bond (i.e. the covalent carbon-carbon bond between the C2' and C3' carbons) of the sugar has been removed (see Nuc. Acids Symp. Series, 52, 133-134 (2008) and Fluiter et al., Mol. Biosyst., 2009, 10, 1039 hereby incorporated by reference).

Representative U.S. publications that teach the preparation of UNA include, but are not limited to, U.S. Pat. No. 8,314,227; and U.S. Patent Publication Nos. 2013/0096289; 2013/0011922; and 2011/0313020, the entire contents of each of which are hereby incorporated herein by reference.

Potentially stabilizing modifications to the ends of RNA molecules can include N-(acetylaminocaproyl)-4-hydroxyprolinol (Hyp-C6-NHAc), N-(caproyl-4-hydroxyprolinol (Hyp-C6), N-(acetyl-4-hydroxyprolinol (Hyp-NHAc), thymidine-2'-O-deoxythymidine (ether), N-(aminocaproyl)-4-hydroxyprolinol (Hyp-C6-amino), 2-docosanoyl-uridine-3"-phosphate, inverted base dT(idT) and others. Disclosure of this modification can be found in PCT Publication No. WO 2011/005861.

Other modifications of the nucleotides of an iRNA of the invention include a 5' phosphate or 5' phosphate mimic, e.g., a 5'-terminal phosphate or phosphate mimic on the antisense strand of an iRNA. Suitable phosphate mimics are disclosed in, for example U.S. Patent Publication No. 2012/0157511, the entire contents of which are incorporated herein by reference.

A. Modified iRNAs Comprising Motifs of the Invention

In certain aspects of the invention, the double stranded RNA agents of the invention include agents with chemical modifications as disclosed, for example, in WO2013/075035, the entire contents of each of which are incorporated herein by reference. WO2013/075035 provides motifs of three identical modifications on three consecutive nucleotides into a sense strand or antisense strand of a dsRNAi agent, particularly at or near the cleavage site. In some embodiments, the sense strand and antisense strand of the dsRNAi agent may otherwise be completely modified. The introduction of these motifs interrupts the modification pattern, if present, of the sense or antisense strand. The dsRNAi agent may be optionally conjugated with a GalNAc derivative ligand, for instance on the sense strand.

More specifically, when the sense strand and antisense strand of the double stranded RNA agent are completely modified to have one or more motifs of three identical modifications on three consecutive nucleotides at or near the cleavage site of at least one strand of a dsRNAi agent, the gene silencing activity of the dsRNAi agent was observed.

Accordingly, the invention provides double stranded RNA agents capable of inhibiting the expression of a target gene (i.e., AGT gene) in vivo. The RNAi agent comprises a sense strand and an antisense strand. Each strand of the RNAi agent may be, for example, 17-30 nucleotides in length, 25-30 nucleotides in length, 27-30 nucleotides in length, 19-25 nucleotides in length, 19-23 nucleotides in length, 19-21 nucleotides in length, 21-25 nucleotides in length, or 21-23 nucleotides in length.

The sense strand and antisense strand typically form a duplex double stranded RNA ("dsRNA"), also referred to herein as "dsRNAi agent." The duplex region of a dsRNAi agent may be, for example, the duplex region can be 27-30 nucleotide pairs in length, 19-25 nucleotide pairs in length, 19-23 nucleotide pairs in length, 19-21 nucleotide pairs in length, 21-25 nucleotide pairs in length, or 21-23 nucleotide pairs in length. In another example, the duplex region is selected from 19, 20, 21, 22, 23, 24, 25, 26, and 27 nucleotides in length.

In certain embodiments, the dsRNAi agent may contain one or more overhang regions or capping groups at the 3'-end, 5'-end, or both ends of one or both strands. The overhang can be, independently, 1-6 nucleotides in length, for instance 2-6 nucleotides in length, 1-5 nucleotides in length, 2-5 nucleotides in length, 1-4 nucleotides in length, 2-4 nucleotides in length, 1-3 nucleotides in length, 2-3 nucleotides in length, or 1-2 nucleotides in length. In certain embodiments, the overhang regions can include extended overhang regions as provided above. The overhangs can be the result of one strand being longer than the other, or the result of two strands of the same length being staggered. The overhang can form a mismatch with the target mRNA or it can be complementary to the gene sequences being targeted or can be another sequence. The first and second strands can also be joined, e.g., by additional bases to form a hairpin, or by other non-base linkers.

In certain embodiments, the nucleotides in the overhang region of the dsRNAi agent can each independently be a modified or unmodified nucleotide including, but no limited to 2'-sugar modified, such as, 2'-F, 2'-O-methyl, thymidine (T), 2'-O-methoxyethyl-5-methyluridine (Teo), 2'-O-methoxyethyladenosine (Aeo), 2'-O-methoxyethyl-5-methylcytidine (m5Ceo), and any combinations thereof. For example, TT can be an overhang sequence for either end on either strand. The overhang can form a mismatch with the target mRNA or it can be complementary to the gene sequences being targeted or can be another sequence.

The 5'- or 3'-overhangs at the sense strand, antisense strand, or both strands of the dsRNAi agent may be phosphorylated. In some embodiments, the overhang region(s) contains two nucleotides having a phosphorothioate between the two nucleotides, where the two nucleotides can be the same or different. In some embodiments, the overhang is present at the 3'-end of the sense strand, antisense strand, or both strands. In some embodiments, this 3'-overhang is present in the antisense strand. In some embodiments, this 3'-overhang is present in the sense strand.

The dsRNAi agent may contain only a single overhang, which can strengthen the interference activity of the RNAi, without affecting its overall stability. For example, the single-stranded overhang may be located at the 3'-end of the sense strand or, alternatively, at the 3'-end of the antisense strand. The RNAi may also have a blunt end, located at the 5'-end of the antisense strand (or the 3'-end of the sense strand) or vice versa. Generally, the antisense strand of the dsRNAi agent has a nucleotide overhang at the 3'-end, and the 5'-end is blunt. While not wishing to be bound by theory, the asymmetric blunt end at the 5'-end of the antisense strand and 3'-end overhang of the antisense strand favor the guide strand loading into RISC process.

In certain embodiments, the dsRNAi agent is a double ended bluntmer of 19 nucleotides in length, wherein the sense strand contains at least one motif of three 2'-F modifications on three consecutive nucleotides at positions 7, 8, 9 from the 5' end. The antisense strand contains at least one motif of three 2'-O-methyl modifications on three consecutive nucleotides at positions 11, 12, 13 from the 5' end.

In other embodiments, the dsRNAi agent is a double ended bluntmer of 20 nucleotides in length, wherein the sense strand contains at least one motif of three 2'-F modifications on three consecutive nucleotides at positions 8, 9, 10 from the 5' end. The antisense strand contains at least one motif of three 2'-O-methyl modifications on three consecutive nucleotides at positions 11, 12, 13 from the 5' end.

In yet other embodiments, the dsRNAi agent is a double ended bluntmer of 21 nucleotides in length, wherein the sense strand contains at least one motif of three 2'-F modifications on three consecutive nucleotides at positions 9, 10, 11 from the 5' end. The antisense strand contains at least one motif of three 2'-O-methyl modifications on three consecutive nucleotides at positions 11, 12, 13 from the 5' end.

In certain embodiments, the dsRNAi agent comprises a 21 nucleotide sense strand and a 23 nucleotide antisense strand, wherein the sense strand contains at least one motif of three 2'-F modifications on three consecutive nucleotides at positions 9, 10, 11 from the 5' end; the antisense strand contains at least one motif of three 2'-O-methyl modifications on three consecutive nucleotides at positions 11, 12, 13 from the 5' end, wherein one end of the RNAi agent is blunt, while the other end comprises a 2 nucleotide overhang. Preferably, the 2 nucleotide overhang is at the 3'-end of the antisense strand.

When the 2 nucleotide overhang is at the 3'-end of the antisense strand, there may be two phosphorothioate internucleotide linkages between the terminal three nucleotides, wherein two of the three nucleotides are the overhang nucleotides, and the third nucleotide is a paired nucleotide next to the overhang nucleotide. In one embodiment, the RNAi agent additionally has two phosphorothioate internucleotide linkages between the terminal three nucleotides at both the 5'-end of the sense strand and at the 5'-end of the antisense strand. In certain embodiments, every nucleotide in the sense strand and the antisense strand of the dsRNAi agent, including the nucleotides that are part of the motifs are modified nucleotides. In certain embodiments each residue is independently modified with a 2'-O-methyl or 3'-fluoro, e.g., in an alternating motif Optionally, the dsRNAi agent further comprises a ligand (preferably GalNAc$_3$).

In certain embodiments, the dsRNAi agent comprises a sense and an antisense strand, wherein the sense strand is 25-30 nucleotide residues in length, wherein starting from the 5' terminal nucleotide (position 1) positions 1 to 23 of the first strand comprise at least 8 ribonucleotides; the antisense strand is 36-66 nucleotide residues in length and, starting from the 3' terminal nucleotide, comprises at least 8 ribonucleotides in the positions paired with positions 1-23 of sense strand to form a duplex; wherein at least the 3' terminal nucleotide of antisense strand is unpaired with sense strand, and up to 6 consecutive 3' terminal nucleotides are unpaired with sense strand, thereby forming a 3' single stranded overhang of 1-6 nucleotides; wherein the 5' terminus of antisense strand comprises from 10-30 consecutive nucleotides which are unpaired with sense strand, thereby forming a 10-30 nucleotide single stranded 5' overhang; wherein at least the sense strand 5' terminal and 3' terminal nucleotides are base paired with nucleotides of antisense strand when sense and antisense strands are aligned for maximum complementarity, thereby forming a substantially duplexed region between sense and antisense strands; and antisense strand is sufficiently complementary to a target RNA along at least 19 ribonucleotides of antisense strand length to reduce target gene expression when the double stranded nucleic acid is introduced into a mammalian cell; and wherein the sense strand contains at least one motif of three 2'-F modifications on three consecutive nucleotides, where at least one of the motifs occurs at or near the cleavage site. The antisense strand contains at least one motif of three 2'-O-methyl modifications on three consecutive nucleotides at or near the cleavage site.

In certain embodiments, the dsRNAi agent comprises sense and antisense strands, wherein the dsRNAi agent comprises a first strand having a length which is at least 25 and at most 29 nucleotides and a second strand having a length which is at most 30 nucleotides with at least one motif of three 2'-O-methyl modifications on three consecutive nucleotides at position 11, 12, 13 from the 5' end; wherein the 3' end of the first strand and the 5' end of the second strand form a blunt end and the second strand is 1-4 nucleotides longer at its 3' end than the first strand, wherein the duplex region which is at least 25 nucleotides in length, and the second strand is sufficiently complementary to a target mRNA along at least 19 nucleotide of the second strand length to reduce target gene expression when the RNAi agent is introduced into a mammalian cell, and wherein Dicer cleavage of the dsRNAi agent preferentially results in an siRNA comprising the 3'-end of the second strand, thereby reducing expression of the target gene in the mammal. Optionally, the dsRNAi agent further comprises a ligand.

In certain embodiments, the sense strand of the dsRNAi agent contains at least one motif of three identical modifications on three consecutive nucleotides, where one of the motifs occurs at the cleavage site in the sense strand.

In certain embodiments, the antisense strand of the dsRNAi agent can also contain at least one motif of three identical modifications on three consecutive nucleotides, where one of the motifs occurs at or near the cleavage site in the antisense strand.

For a dsRNAi agent having a duplex region of 19-23 nucleotide in length, the cleavage site of the antisense strand is typically around the 10, 11, and 12 positions from the 5'-end. Thus the motifs of three identical modifications may occur at the 9, 10, 11 positions; the 10, 11, 12 positions; the 11, 12, 13 positions; the 12, 13, 14 positions; or the 13, 14, 15 positions of the antisense strand, the count starting from the first nucleotide from the 5'-end of the antisense strand, or, the count starting from the first paired nucleotide within the duplex region from the 5'-end of the antisense strand. The cleavage site in the antisense strand may also change according to the length of the duplex region of the dsRNAi agent from the 5'-end.

The sense strand of the dsRNAi agent may contain at least one motif of three identical modifications on three consecutive nucleotides at the cleavage site of the strand; and the antisense strand may have at least one motif of three identical modifications on three consecutive nucleotides at or near the cleavage site of the strand. When the sense strand and the antisense strand form a dsRNA duplex, the sense strand and the antisense strand can be so aligned that one motif of the three nucleotides on the sense strand and one motif of the three nucleotides on the antisense strand have at least one nucleotide overlap, i.e., at least one of the three nucleotides of the motif in the sense strand forms a base pair with at least one of the three nucleotides of the motif in the antisense strand. Alternatively, at least two nucleotides may overlap, or all three nucleotides may overlap.

In some embodiments, the sense strand of the dsRNAi agent may contain more than one motif of three identical modifications on three consecutive nucleotides. The first motif may occur at or near the cleavage site of the strand and the other motifs may be a wing modification. The term "wing modification" herein refers to a motif occurring at another portion of the strand that is separated from the motif at or near the cleavage site of the same strand. The wing modification is either adjacent to the first motif or is separated by at least one or more nucleotides. When the motifs are immediately adjacent to each other then the chemistries of the motifs are distinct from each other, and when the motifs are separated by one or more nucleotide than the chemistries can be the same or different. Two or more wing modifications may be present. For instance, when two wing modifications are present, each wing modification may occur at one end relative to the first motif which is at or near cleavage site or on either side of the lead motif.

Like the sense strand, the antisense strand of the dsRNAi agent may contain more than one motifs of three identical modifications on three consecutive nucleotides, with at least one of the motifs occurring at or near the cleavage site of the strand. This antisense strand may also contain one or more wing modifications in an alignment similar to the wing modifications that may be present on the sense strand.

In some embodiments, the wing modification on the sense strand or antisense strand of the dsRNAi agent typically does not include the first one or two terminal nucleotides at the 3'-end, 5'-end, or both ends of the strand.

In other embodiments, the wing modification on the sense strand or antisense strand of the dsRNAi agent typically does not include the first one or two paired nucleotides within the duplex region at the 3'-end, 5'-end, or both ends of the strand.

When the sense strand and the antisense strand of the dsRNAi agent each contain at least one wing modification, the wing modifications may fall on the same end of the duplex region, and have an overlap of one, two, or three nucleotides.

When the sense strand and the antisense strand of the dsRNAi agent each contain at least two wing modifications, the sense strand and the antisense strand can be so aligned that two modifications each from one strand fall on one end of the duplex region, having an overlap of one, two, or three nucleotides; two modifications each from one strand fall on the other end of the duplex region, having an overlap of one, two or three nucleotides; two modifications one strand fall on each side of the lead motif, having an overlap of one, two or three nucleotides in the duplex region.

In some embodiments, every nucleotide in the sense strand and antisense strand of the dsRNAi agent, including the nucleotides that are part of the motifs, may be modified. Each nucleotide may be modified with the same or different modification which can include one or more alteration of one or both of the non-linking phosphate oxygens or of one or more of the linking phosphate oxygens; alteration of a constituent of the ribose sugar, e.g., of the 2'-hydroxyl on the ribose sugar; wholesale replacement of the phosphate moiety with "dephospho" linkers; modification or replacement of a naturally occurring base; and replacement or modification of the ribose-phosphate backbone.

As nucleic acids are polymers of subunits, many of the modifications occur at a position which is repeated within a nucleic acid, e.g., a modification of a base, or a phosphate moiety, or a non-linking O of a phosphate moiety. In some cases the modification will occur at all of the subject positions in the nucleic acid but in many cases it will not. By way of example, a modification may only occur at a 3'- or 5' terminal position, may only occur in a terminal region, e.g., at a position on a terminal nucleotide or in the last 2, 3, 4, 5, or 10 nucleotides of a strand. A modification may occur in a double strand region, a single strand region, or in both. A modification may occur only in the double strand region of an RNA or may only occur in a single strand region of a RNA. For example, a phosphorothioate modification at a non-linking O position may only occur at one or both termini, may only occur in a terminal region, e.g., at a position on a terminal nucleotide or in the last 2, 3, 4, 5, or 10 nucleotides of a strand, or may occur in double strand and single strand regions, particularly at termini. The 5'-end or ends can be phosphorylated.

It may be possible, e.g., to enhance stability, to include particular bases in overhangs, or to include modified nucleotides or nucleotide surrogates, in single strand overhangs, e.g., in a 5'- or 3'-overhang, or in both. For example, it can be desirable to include purine nucleotides in overhangs. In some embodiments all or some of the bases in a 3'- or 5'-overhang may be modified, e.g., with a modification described herein. Modifications can include, e.g., the use of modifications at the 2' position of the ribose sugar with modifications that are known in the art, e.g., the use of deoxyribonucleotides, 2'-deoxy-2'-fluoro (2'-F) or 2'-O-methyl modified instead of the ribosugar of the nucleobase, and modifications in the phosphate group, e.g., phosphorothioate modifications. Overhangs need not be homologous with the target sequence.

In some embodiments, each residue of the sense strand and antisense strand is independently modified with LNA, CRN, cET, UNA, HNA, CeNA, 2'-methoxyethyl, 2'-O-methyl, 2'-O-allyl, 2'-C-allyl, 2'-deoxy, 2'-hydroxyl, or 2'-fluoro. The strands can contain more than one modification. In one embodiment, each residue of the sense strand and antisense strand is independently modified with 2'-O-methyl or 2'-fluoro.

At least two different modifications are typically present on the sense strand and antisense strand. Those two modifications may be the 2'-O-methyl or 2'-fluoro modifications, or others.

In certain embodiments, the $N_a$ or $N_b$ comprise modifications of an alternating pattern. The term "alternating motif" as used herein refers to a motif having one or more modifications, each modification occurring on alternating nucleotides of one strand. The alternating nucleotide may refer to one per every other nucleotide or one per every three nucleotides, or a similar pattern. For example, if A, B and C each represent one type of modification to the nucleotide, the alternating motif can be "ABABABABABAB . . . ," "AAB-BAABBAABB . . . ," "AABAABAABAAB . . . ," "AAA-BAAABAAAB . . . ," "AAABBBAAABBB . . . ," or "ABCABCABCABC . . . ," etc.

The type of modifications contained in the alternating motif may be the same or different. For example, if A, B, C, D each represent one type of modification on the nucleotide, the alternating pattern, i.e., modifications on every other nucleotide, may be the same, but each of the sense strand or antisense strand can be selected from several possibilities of modifications within the alternating motif such as "ABABAB . . . ", "ACACAC . . . " "BDBDBD . . . " or "CDCDCD . . . ," etc.

In some embodiments, the dsRNAi agent of the invention comprises the modification pattern for the alternating motif on the sense strand relative to the modification pattern for the alternating motif on the antisense strand is shifted. The shift may be such that the modified group of nucleotides of the sense strand corresponds to a differently modified group of nucleotides of the antisense strand and vice versa. For example, the sense strand when paired with the antisense strand in the dsRNA duplex, the alternating motif in the sense strand may start with "ABABAB" from 5' to 3' of the strand and the alternating motif in the antisense strand may start with "BABABA" from 5' to 3' of the strand within the duplex region. As another example, the alternating motif in the sense strand may start with "AABBAABB" from 5' to 3' of the strand and the alternating motif in the antisense strand may start with "BBAABBAA" from 5' to 3' of the strand within the duplex region, so that there is a complete or partial shift of the modification patterns between the sense strand and the antisense strand.

In some embodiments, the dsRNAi agent comprises the pattern of the alternating motif of 2'-O-methyl modification and 2'-F modification on the sense strand initially has a shift relative to the pattern of the alternating motif of 2'-O-methyl modification and 2'-F modification on the antisense strand initially, i.e., the 2'-O-methyl modified nucleotide on the sense strand base pairs with a 2'-F modified nucleotide on the antisense strand and vice versa. The 1 position of the sense strand may start with the 2'-F modification, and the 1 position of the antisense strand may start with the 2'-O-methyl modification.

The introduction of one or more motifs of three identical modifications on three consecutive nucleotides to the sense strand or antisense strand interrupts the initial modification pattern present in the sense strand or antisense strand. This interruption of the modification pattern of the sense or antisense strand by introducing one or more motifs of three identical modifications on three consecutive nucleotides to the sense or antisense strand may enhance the gene silencing activity against the target gene.

In some embodiments, when the motif of three identical modifications on three consecutive nucleotides is introduced to any of the strands, the modification of the nucleotide next to the motif is a different modification than the modification of the motif. For example, the portion of the sequence containing the motif is " . . . $N_a$YYY$N_b$ . . . ," where "Y" represents the modification of the motif of three identical modifications on three consecutive nucleotide, and "$N_a$" and "$N_b$" represent a modification to the nucleotide next to the motif "YYY" that is different than the modification of Y, and where $N_a$ and $N_b$ can be the same or different modifications. Alternatively, $N_a$ or $N_b$ may be present or absent when there is a wing modification present.

The iRNA may further comprise at least one phosphorothioate or methylphosphonate internucleotide linkage. The phosphorothioate or methylphosphonate internucleotide linkage modification may occur on any nucleotide of the sense strand, antisense strand, or both strands in any position of the strand. For instance, the internucleotide linkage modification may occur on every nucleotide on the sense strand or antisense strand; each internucleotide linkage modification may occur in an alternating pattern on the sense strand or antisense strand; or the sense strand or antisense strand may contain both internucleotide linkage modifications in an alternating pattern. The alternating pattern of the internucleotide linkage modification on the sense strand may be the same or different from the antisense strand, and the alternating pattern of the internucleotide linkage modification on the sense strand may have a shift relative to the alternating pattern of the internucleotide linkage modification on the antisense strand. In one embodiment, a double-stranded RNAi agent comprises 6-8 phosphorothioate internucleotide linkages. In some embodiments, the antisense strand comprises two phosphorothioate internucleotide linkages at the 5'-end and two phosphorothioate internucleotide linkages at the 3'-end, and the sense strand comprises at least two phosphorothioate internucleotide linkages at either the 5'-end or the 3'-end.

In some embodiments, the dsRNAi agent comprises a phosphorothioate or methylphosphonate internucleotide linkage modification in the overhang region. For example, the overhang region may contain two nucleotides having a phosphorothioate or methylphosphonate internucleotide linkage between the two nucleotides. Internucleotide linkage modifications also may be made to link the overhang nucleotides with the terminal paired nucleotides within the duplex region. For example, at least 2, 3, 4, or all the overhang nucleotides may be linked through phosphorothioate or methylphosphonate internucleotide linkage, and optionally, there may be additional phosphorothioate or methylphosphonate internucleotide linkages linking the overhang nucleotide with a paired nucleotide that is next to the overhang nucleotide. For instance, there may be at least two phosphorothioate internucleotide linkages between the terminal three nucleotides, in which two of the three nucleotides are overhang nucleotides, and the third is a paired nucleotide next to the overhang nucleotide. These terminal three nucleotides may be at the 3'-end of the antisense strand, the 3'-end of the sense strand, the 5'-end of the antisense strand, or the 5' end of the antisense strand.

In some embodiments, the 2-nucleotide overhang is at the 3'-end of the antisense strand, and there are two phosphorothioate internucleotide linkages between the terminal three nucleotides, wherein two of the three nucleotides are the overhang nucleotides, and the third nucleotide is a paired nucleotide next to the overhang nucleotide. Optionally, the dsRNAi agent may additionally have two phosphorothioate internucleotide linkages between the terminal three nucleotides at both the 5'-end of the sense strand and at the 5'-end of the antisense strand.

In one embodiment, the dsRNAi agent comprises mismatch(es) with the target, within the duplex, or combinations thereof. The mismatch may occur in the overhang region or the duplex region. The base pair may be ranked on the basis of their propensity to promote dissociation or melting (e.g., on the free energy of association or dissociation of a particular pairing, the simplest approach is to examine the pairs on an individual pair basis, though next neighbor or similar analysis can also be used). In terms of promoting dissociation: A:U is preferred over G:C; G:U is preferred over G:C; and I:C is preferred over G:C (I=inosine). Mismatches, e.g., non-canonical or other than canonical pairings (as described elsewhere herein) are preferred over canonical (A:T, A:U, G:C) pairings; and pairings which include a universal base are preferred over canonical pairings.

In certain embodiments, the dsRNAi agent comprises at least one of the first 1, 2, 3, 4, or 5 base pairs within the duplex regions from the 5'-end of the antisense strand independently selected from the group of: A:U, G:U, I:C, and mismatched pairs, e.g., non-canonical or other than canonical pairings or pairings which include a universal base, to promote the dissociation of the antisense strand at the 5'-end of the duplex.

In certain embodiments, the nucleotide at the 1 position within the duplex region from the 5'-end in the antisense strand is selected from A, dA, dU, U, and dT. Alternatively, at least one of the first 1, 2, or 3 base pair within the duplex region from the 5'-end of the antisense strand is an AU base pair. For example, the first base pair within the duplex region from the 5'-end of the antisense strand is an AU base pair.

In other embodiments, the nucleotide at the 3'-end of the sense strand is deoxy-thymine (dT) or the nucleotide at the 3'-end of the antisense strand is deoxy-thymine (dT). For example, there is a short sequence of deoxy-thymine nucleotides, for example, two dT nucleotides on the 3'-end of the sense, antisense strand, or both strands.

In certain embodiments, the sense strand sequence may be represented by formula (I):

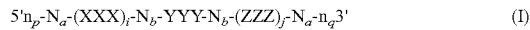 (I)

wherein:
i and j are each independently 0 or 1;
p and q are each independently 0-6;
each $N_a$ independently represents an oligonucleotide sequence comprising 0-25 modified nucleotides, each sequence comprising at least two differently modified nucleotides;
each $N_b$ independently represents an oligonucleotide sequence comprising 0-10 modified nucleotides;
each np and n independently represent an overhang nucleotide;
wherein Nb and Y do not have the same modification; and
XXX, YYY, and ZZZ each independently represent one motif of three identical modifications on three consecutive nucleotides. Preferably YYY is all 2'-F modified nucleotides.

In some embodiments, the $N_a$ or $N_b$ comprises modifications of alternating pattern.

In some embodiments, the YYY motif occurs at or near the cleavage site of the sense strand. For example, when the dsRNAi agent has a duplex region of 17-23 nucleotides in length, the YYY motif can occur at or the vicinity of the cleavage site (e.g.: can occur at positions 6, 7, 8; 7, 8, 9; 8, 9, 10; 9, 10, 11; 10, 11, 12; or 11, 12, 13) of the sense strand, the count starting from the first nucleotide, from the 5'-end; or optionally, the count starting at the first paired nucleotide within the duplex region, from the 5'-end.

In one embodiment, i is 1 and j is 0, or i is 0 and j is 1, or both i and j are 1. The sense strand can therefore be represented by the following formulas:

 (Ib);

 (Ic); or

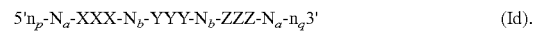 (Id).

When the sense strand is represented by formula (Ib), $N_b$ represents an oligonucleotide sequence comprising 0-10, 0-7, 0-5, 0-4, 0-2, or 0 modified nucleotides. Each $N_a$ independently can represent an oligonucleotide sequence comprising 2-20, 2-15, or 2-10 modified nucleotides.

When the sense strand is represented as formula (Ic), $N_b$ represents an oligonucleotide sequence comprising 0-10, 0-7, 0-10, 0-7, 0-5, 0-4, 0-2, or 0 modified nucleotides. Each $N_a$ can independently represent an oligonucleotide sequence comprising 2-20, 2-15, or 2-10 modified nucleotides.

When the sense strand is represented as formula (Id), each $N_b$ independently represents an oligonucleotide sequence comprising 0-10, 0-7, 0-5, 0-4, 0-2, or 0 modified nucleotides. Preferably, $N_b$ is 0, 1, 2, 3, 4, 5, or 6 Each Na can independently represent an oligonucleotide sequence comprising 2-20, 2-15, or 2-10 modified nucleotides.

Each of X, Y and Z may be the same or different from each other.

In other embodiments, i is 0 and j is 0, and the sense strand may be represented by the formula:

 (Ia).

When the sense strand is represented by formula (Ia), each $N_a$ independently can represent an oligonucleotide sequence comprising 2-20, 2-15, or 2-10 modified nucleotides.

In one embodiment, the antisense strand sequence of the RNAi may be represented by formula (II):

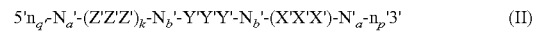 (II)

wherein:
k and l are each independently 0 or 1;
p' and q' are each independently 0-6;
each $N_a'$ independently represents an oligonucleotide sequence comprising 0-25 modified nucleotides, each sequence comprising at least two differently modified nucleotides; each $N_b'$ independently represents an oligonucleotide sequence comprising 0-10 modified nucleotides;
each np' and n' independently represent an overhang nucleotide;
wherein $N_b'$ and Y' do not have the same modification; and
X'X'X', Y'Y'Y', and Z'Z'Z' each independently represent one motif of three identical modifications on three consecutive nucleotides.

In some embodiments, the $N_a'$ or $N_b'$ comprises modifications of alternating pattern.

The Y'Y'Y' motif occurs at or near the cleavage site of the antisense strand. For example, when the dsRNAi agent has a duplex region of 17-23 nucleotides in length, the Y'Y'Y' motif can occur at positions 9, 10, 11; 10, 11, 12; 11, 12, 13; 12, 13, 14; or 13, 14, 15 of the antisense strand, with the count starting from the first nucleotide, from the 5'-end; or optionally, the count starting at the first paired nucleotide within the duplex region, from the 5'-end. Preferably, the Y'Y'Y' motif occurs at positions 11, 12, 13.

In certain embodiments, Y'Y'Y' motif is all 2'-OMe modified nucleotides.

In certain embodiments, k is 1 and is 0, or k is 0 and l is 1, or both k and l are 1.

The antisense strand can therefore be represented by the following formulas:

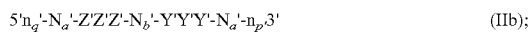  (IIb);

  (Ic); or

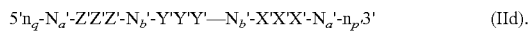  (IId).

When the antisense strand is represented by formula (IIb), $N_b'$ represents an oligonucleotide sequence comprising 0-10, 0-7, 0-10, 0-7, 0-5, 0-4, 0-2, or 0 modified nucleotides. Each $N_a'$ independently represents an oligonucleotide sequence comprising 2-20, 2-15, or 2-10 modified nucleotides.

When the antisense strand is represented as formula (IIc), $N_b'$ represents an oligonucleotide sequence comprising 0-10, 0-7, 0-10, 0-7, 0-5, 0-4, 0-2, or 0 modified nucleotides. Each $N_a'$ independently represents an oligonucleotide sequence comprising 2-20, 2-15, or 2-10 modified nucleotides.

When the antisense strand is represented as formula (IId), each $N_b'$ independently represents an oligonucleotide sequence comprising 0-10, 0-7, 0-10, 0-7, 0-5, 0-4, 0-2, or 0 modified nucleotides. Each $N_a'$ independently represents an oligonucleotide sequence comprising 2-20, 2-15, or 2-10 modified nucleotides. Preferably, $N_b$ is 0, 1, 2, 3, 4, 5, or 6.

In other embodiments, k is 0 and l is 0 and the antisense strand may be represented by the formula:

  (Ia).

When the antisense strand is represented as formula (IIa), each $N_a'$ independently represents an oligonucleotide sequence comprising 2-20, 2-15, or 2-10 modified nucleotides.

Each of X', Y' and Z' may be the same or different from each other.

Each nucleotide of the sense strand and antisense strand may be independently modified with LNA, CRN, UNA, cEt, HNA, CeNA, 2'-methoxyethyl, 2'-O-methyl, 2'-O-allyl, 2'-C-allyl, 2'-hydroxyl, or 2'-fluoro. For example, each nucleotide of the sense strand and antisense strand is independently modified with 2'-O-methyl or 2'-fluoro. Each X, Y, Z, X', Y', and Z', in particular, may represent a 2'-O-methyl modification or a 2'-fluoro modification.

In some embodiments, the sense strand of the dsRNAi agent may contain YYY motif occurring at 9, 10, and 11 positions of the strand when the duplex region is 21 nt, the count starting from the first nucleotide from the 5'-end, or optionally, the count starting at the first paired nucleotide within the duplex region, from the 5'-end; and Y represents 2'-F modification. The sense strand may additionally contain XXX motif or ZZZ motifs as wing modifications at the opposite end of the duplex region; and XXX and ZZZ each independently represents a 2'-OMe modification or 2'-F modification.

In some embodiments the antisense strand may contain Y'Y'Y' motif occurring at positions 11, 12, 13 of the strand, the count starting from the first nucleotide from the 5'-end, or optionally, the count starting at the first paired nucleotide within the duplex region, from the 5'-end; and Y' represents 2'-O-methyl modification. The antisense strand may additionally contain X'X'X' motif or Z'Z'Z' motifs as wing modifications at the opposite end of the duplex region; and X'X'X' and Z'Z'Z' each independently represents a 2'-OMe modification or 2'-F modification.

The sense strand represented by any one of the above formulas (Ia), (Ib), (Ic), and (Id) forms a duplex with a antisense strand being represented by any one of formulas (IIa), (IIb), (IIc), and (IId), respectively.

Accordingly, the dsRNAi agents for use in the methods of the invention may comprise a sense strand and an antisense strand, each strand having 14 to 30 nucleotides, the iRNA duplex represented by formula (III):

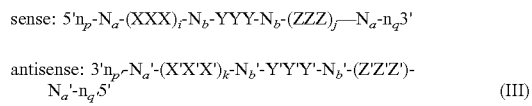  (III)

wherein:

i, j, k, and l are each independently 0 or 1;

p, p', q, and q' are each independently 0-6;

each $N_a$ and $N_a'$ independently represents an oligonucleotide sequence comprising 0-25 modified nucleotides, each sequence comprising at least two differently modified nucleotides;

each $N_b$ and $N_b'$ independently represents an oligonucleotide sequence comprising 0-10 modified nucleotides;

wherein each $n_p'$, $n_p$, $n_q'$, and $n_q$, each of which may or may not be present, independently represents an overhang nucleotide; and XXX, YYY, ZZZ, X'X'X', Y'Y'Y', and Z'Z'Z' each independently represent one motif of three identical modifications on three consecutive nucleotides.

In one embodiment, i is 0 and j is 0; or i is 1 and j is 0; or i is 0 and j is 1; or both i and j are 0; or both i and j are 1. In another embodiment, k is 0 and l is 0; or k is 1 and l is 0; k is 0 and l is 1; or both k and l are 0; or both k and l are 1.

Exemplary combinations of the sense strand and antisense strand forming an iRNA duplex include the formulas below:

  (IIIa)

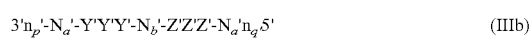  (IIIb)

  (IIIc)

  (IIId)

When the dsRNAi agent is represented by formula (IIIa), each $N_a$ independently represents an oligonucleotide sequence comprising 2-20, 2-15, or 2-10 modified nucleotides.

When the dsRNAi agent is represented by formula (IIIb), each $N_b$ independently represents an oligonucleotide sequence comprising 1-10, 1-7, 1-5, or 1-4 modified nucleotides. Each $N_a$ independently represents an oligonucleotide sequence comprising 2-20, 2-15, or 2-10 modified nucleotides.

When the dsRNAi agent is represented as formula (IIIc), each $N_b$, $N_b'$ independently represents an oligonucleotide sequence comprising 0-10, 0-7, 0-10, 0-7, 0-5, 0-4, 0-2, or 0 modified nucleotides. Each $N_a$ independently represents an oligonucleotide sequence comprising 2-20, 2-15, or 2-10 modified nucleotides.

When the dsRNAi agent is represented as formula (IIId), each $N_b$, $N_b'$ independently represents an oligonucleotide sequence comprising 0-10, 0-7, 0-10, 0-7, 0-5, 0-4, 0-2, or 0 modified nucleotides. Each $N_a$, $N_a'$ independently represents an oligonucleotide sequence comprising 2-20, 2-15, or 2-10 modified nucleotides. Each of $N_a$, $N_a'$, $N_b$, and $N_b'$ independently comprises modifications of alternating pattern.

Each of X, Y, and Z in formulas (III), (IIIa), (IIIb), (IIIc), and (IIId) may be the same or different from each other.

When the dsRNAi agent is represented by formula (III), (IIIa), (IIb), (IIIc), and (IIId), at least one of the Y nucleotides may form a base pair with one of the Y' nucleotides. Alternatively, at least two of the Y nucleotides form base pairs with the corresponding Y' nucleotides; or all three of the Y nucleotides all form base pairs with the corresponding Y' nucleotides.

When the dsRNAi agent is represented by formula (IIb) or (IIId), at least one of the Z nucleotides may form a base pair with one of the Z' nucleotides. Alternatively, at least two of the Z nucleotides form base pairs with the corresponding Z' nucleotides; or all three of the Z nucleotides all form base pairs with the corresponding Z' nucleotides.

When the dsRNAi agent is represented as formula (IIIc) or (IIId), at least one of the X nucleotides may form a base pair with one of the X' nucleotides. Alternatively, at least two of the X nucleotides form base pairs with the corresponding X' nucleotides; or all three of the X nucleotides all form base pairs with the corresponding X' nucleotides.

In certain embodiments, the modification on the Y nucleotide is different than the modification on the Y' nucleotide, the modification on the Z nucleotide is different than the modification on the Z' nucleotide, or the modification on the X nucleotide is different than the modification on the X' nucleotide.

In certain embodiments, when the dsRNAi agent is represented by formula (IId), the $N_a$ modifications are 2'-O-methyl or 2'-fluoro modifications. In other embodiments, when the RNAi agent is represented by formula (IIId), the $N_a$ modifications are 2'-O-methyl or 2'-fluoro modifications and $n_p'>0$ and at least one $n_p'$ is linked to a neighboring nucleotide a via phosphorothioate linkage. In yet other embodiments, when the RNAi agent is represented by formula (IIId), the $N_a$ modifications are 2'-O-methyl or 2'-fluoro modifications, $n_p'>0$ and at least one $n_p'$ is linked to a neighboring nucleotide via phosphorothioate linkage, and the sense strand is conjugated to one or more GaNAc derivatives attached through a bivalent or trivalent branched linker (described below). In other embodiments, when the RNAi agent is represented by formula (IIId), the $N_a$ modifications are 2'-O-methyl or 2'-fluoro modifications, $n_p'>0$ and at least one $n_p'$ is linked to a neighboring nucleotide via phosphorothioate linkage, the sense strand comprises at least one phosphorothioate linkage, and the sense strand is conjugated to one or more GaNAc derivatives attached through a bivalent or trivalent branched linker.

In some embodiments, when the dsRNAi agent is represented by formula (IIa), the $N_a$ modifications are 2'-O-methyl or 2'-fluoro modifications, $n_p'>0$ and at least one $n_p'$ is linked to a neighboring nucleotide via phosphorothioate linkage, the sense strand comprises at least one phosphorothioate linkage, and the sense strand is conjugated to one or more GaNAc derivatives attached through a bivalent or trivalent branched linker.

In some embodiments, the dsRNAi agent is a multimer containing at least two duplexes represented by formula (III), (IIa), (IIb), (IIc), and (IIId), wherein the duplexes are connected by a linker. The linker can be cleavable or non-cleavable. Optionally, the multimer further comprises a ligand. Each of the duplexes can target the same gene or two different genes; or each of the duplexes can target same gene at two different target sites.

In some embodiments, the dsRNAi agent is a multimer containing three, four, five, six, or more duplexes represented by formula (III), (IIa), (IIb), (IIc), and (IIId), wherein the duplexes are connected by a linker. The linker can be cleavable or non-cleavable. Optionally, the multimer further comprises a ligand. Each of the duplexes can target the same gene or two different genes; or each of the duplexes can target same gene at two different target sites.

In one embodiment, two dsRNAi agents represented by at least one of formulas (III), (IIa), (IIb), (IIc), and (IIId) are linked to each other at the 5' end, and one or both of the 3' ends, and are optionally conjugated to a ligand. Each of the agents can target the same gene or two different genes; or each of the agents can target same gene at two different target sites.

In certain embodiments, an RNAi agent of the invention may contain a low number of nucleotides containing a 2'-fluoro modification, e.g., 10 or fewer nucleotides with 2'-fluoro modification. For example, the RNAi agent may contain 10, 9, 8, 7, 6, 5, 4, 3, 2, 1 or 0 nucleotides with a 2'-fluoro modification. In a specific embodiment, the RNAi agent of the invention contains 10 nucleotides with a 2'-fluoro modification, e.g., 4 nucleotides with a 2'-fluoro modification in the sense strand and 6 nucleotides with a 2'-fluoro modification in the antisense strand. In another specific embodiment, the RNAi agent of the invention contains 6 nucleotides with a 2'-fluoro modification, e.g., 4 nucleotides with a 2'-fluoro modification in the sense strand and 2 nucleotides with a 2'-fluoro modification in the antisense strand.

In other embodiments, an RNAi agent of the invention may contain an ultra low number of nucleotides containing a 2'-fluoro modification, e.g., 2 or fewer nucleotides containing a 2'-fluoro modification. For example, the RNAi agent may contain 2, 1 of 0 nucleotides with a 2'-fluoro modification. In a specific embodiment, the RNAi agent may contain 2 nucleotides with a 2'-fluoro modification, e.g., 0 nucleotides with a 2-fluoro modification in the sense strand and 2 nucleotides with a 2'-fluoro modification in the antisense strand.

Various publications describe multimeric iRNAs that can be used in the methods of the invention. Such publications include WO2007/091269, U.S. Pat. No. 7,858,769, WO2010/141511, WO2007/117686, WO2009/014887, and WO2011/031520 the entire contents of each of which are hereby incorporated herein by reference.

As described in more detail below, the iRNA that contains conjugations of one or more carbohydrate moieties to an iRNA can optimize one or more properties of the iRNA. In many cases, the carbohydrate moiety will be attached to a modified subunit of the iRNA. For example, the ribose sugar of one or more ribonucleotide subunits of a iRNA can be replaced with another moiety, e.g., a non-carbohydrate (preferably cyclic) carrier to which is attached a carbohydrate ligand. A ribonucleotide subunit in which the ribose sugar of the subunit has been so replaced is referred to herein as a ribose replacement modification subunit (RRMS). A cyclic carrier may be a carbocyclic ring system, i.e., all ring atoms are carbon atoms, or a heterocyclic ring system, i.e., one or more ring atoms may be a heteroatom, e.g., nitrogen, oxygen, sulfur. The cyclic carrier may be a monocyclic ring system, or may contain two or more rings, e.g. fused rings. The cyclic carrier may be a fully saturated ring system, or it may contain one or more double bonds.

The ligand may be attached to the polynucleotide via a carrier. The carriers include (i) at least one "backbone attachment point," preferably two "backbone attachment points" and (ii) at least one "tethering attachment point." A "backbone attachment point" as used herein refers to a functional group, e.g. a hydroxyl group, or generally, a bond available for, and that is suitable for incorporation of the carrier into the backbone, e.g., the phosphate, or modified phosphate, e.g., sulfur containing, backbone, of a ribonucleic acid. A "tethering attachment point" (TAP) in some embodiments refers to a constituent ring atom of the cyclic carrier, e.g., a carbon atom or a heteroatom (distinct from an atom which provides a backbone attachment point), that connects a selected moiety. The moiety can be, e.g., a carbohydrate, e.g. monosaccharide, disaccharide, trisaccharide, tetrasaccharide, oligosaccharide, or polysaccharide. Optionally, the selected moiety is connected by an intervening tether to the cyclic carrier. Thus, the cyclic carrier will often include a functional group, e.g., an amino group, or generally, provide a bond, that is suitable for incorporation or tethering of another chemical entity, e.g., a ligand to the constituent ring.

The iRNA may be conjugated to a ligand via a carrier, wherein the carrier can be cyclic group or acyclic group; preferably, the cyclic group is selected from pyrrolidinyl, pyrazolinyl, pyrazolidinyl, imidazolinyl, imidazolidinyl, piperidinyl, piperazinyl, [1,3]dioxolane, oxazolidinyl, isoxazolidinyl, morpholinyl, thiazolidinyl, isothiazolidinyl, quinoxalinyl, pyridazinonyl, tetrahydrofuryl, and decalin; preferably, the acyclic group is a serinol backbone or diethanolamine backbone.

In another embodiment of the invention, an iRNA agent comprises a sense strand and an antisense strand, each strand having 14 to 40 nucleotides. The RNAi agent may be represented by formula (L):

In formula (L), B1, B2, B3, B1', B2', B3', and B4' each are independently a nucleotide containing a modification selected from the group consisting of 2'-O-alkyl, 2'-substituted alkoxy, 2'-substituted alkyl, 2'-halo, ENA, and BNA/LNA. In one embodiment, B1, B2, B3, B1', B2', B3', and B4' each contain 2'-OMe modifications. In one embodiment, B1, B2, B3, B1', B2', B3', and B4' each contain 2'-OMe or 2'-F modifications. In one embodiment, at least one of B1, B2, B3, B1', B2', B3', and B4' contain 2'-O—N-methylacetamido (2'-O-NMA) modification.

C1 is a thermally destabilizing nucleotide placed at a site opposite to the seed region of the antisense strand (i.e., at positions 2-8 of the 5'-end of the antisense strand). For example, C1 is at a position of the sense strand that pairs with a nucleotide at positions 2-8 of the 5'-end of the antisense strand. In one example, C1 is at position 15 from the 5'-end of the sense strand. C1 nucleotide bears the thermally destabilizing modification which can include abasic modification; mismatch with the opposing nucleotide in the duplex; and sugar modification such as 2'-deoxy modification or acyclic nucleotide e.g., unlocked nucleic acids (UNA) or glycerol nucleic acid (GNA). In one embodiment, C1 has thermally destabilizing modification selected from the group consisting of: i) mismatch with the opposing nucleotide in the antisense strand; ii) abasic modification selected from the group consisting of:

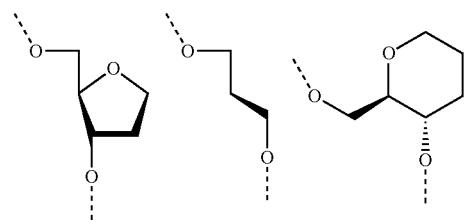

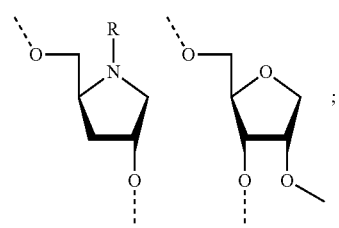

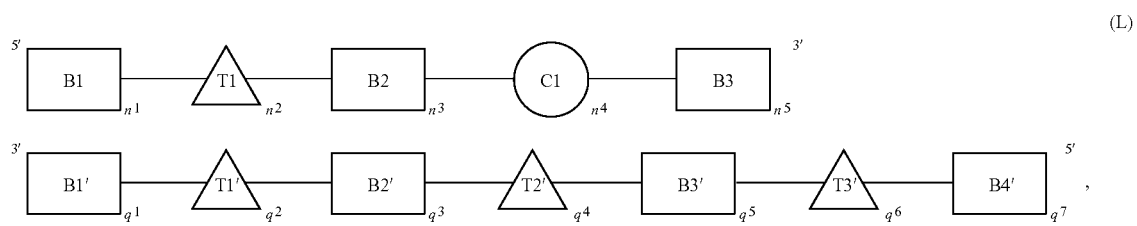

(L)

and iii) sugar modification selected from the group consisting of:

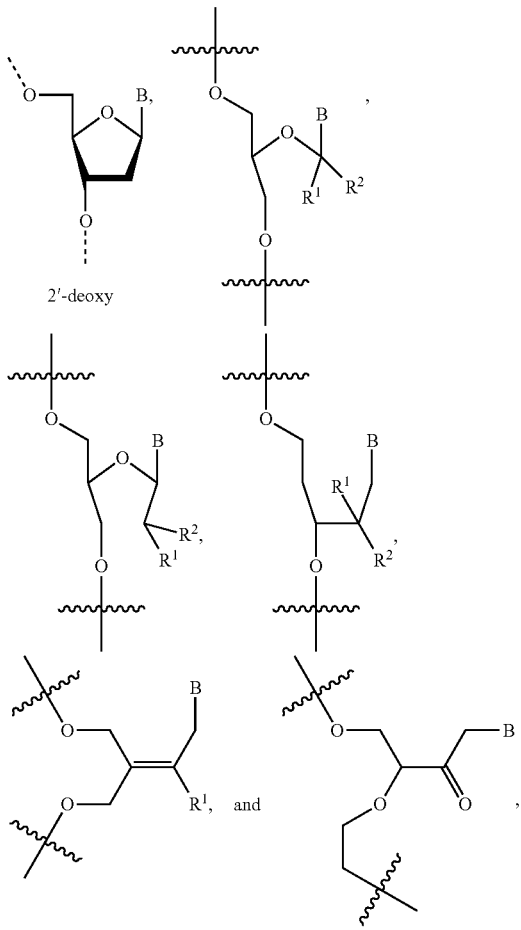

wherein B is a modified or unmodified nucleobase, $R^1$ and $R^2$ independently are H, halogen, $OR_3$, or alkyl; and $R_3$ is H, alkyl, cycloalkyl, aryl, aralkyl, heteroaryl or sugar. In one embodiment, the thermally destabilizing modification in C1 is a mismatch selected from the group consisting of G:G, G:A, G:U, G:T, A:A, A:C, C:C, C:U, C:T, U:U, T:T, and U:T; and optionally, at least one nucleobase in the mismatch pair is a 2'-deoxy nucleobase. In one example, the thermally destabilizing modification in C1 is GNA or

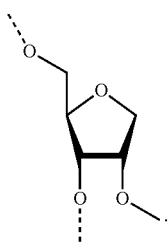

T1, T1', T2', and T3' each independently represent a nucleotide comprising a modification providing the nucleotide a steric bulk that is less or equal to the steric bulk of a 2'-OMe modification. A steric bulk refers to the sum of steric effects of a modification. Methods for determining steric effects of a modification of a nucleotide are known to one skilled in the art. The modification can be at the 2' position of a ribose sugar of the nucleotide, or a modification to a non-ribose nucleotide, acyclic nucleotide, or the backbone of the nucleotide that is similar or equivalent to the 2' position of the ribose sugar, and provides the nucleotide a steric bulk that is less than or equal to the steric bulk of a 2'-OMe modification. For example, T1, T1', T2', and T3' are each independently selected from DNA, RNA, LNA, 2'-F, and 2'-F-5'-methyl. In one embodiment, T1 is DNA. In one embodiment, T1' is DNA, RNA or LNA. In one embodiment, T2' is DNA or RNA. In one embodiment, T3' is DNA or RNA.

$n^1$, $n^3$, and $q^1$ are independently 4 to 15 nucleotides in length.

$n^5$, $q^3$, and $q^7$ are independently 1-6 nucleotide(s) in length.
$n^4$, $q^2$, and $q^6$ are independently 1-3 nucleotide(s) in length; alternatively, $n^4$ is 0.

$q^5$ is independently 0-10 nucleotide(s) in length.

$n^2$ and $q^4$ are independently 0-3 nucleotide(s) in length. Alternatively, $n^4$ is 0-3 nucleotide(s) in length.

In one embodiment, $n^4$ can be 0. In one example, $n^4$ is 0, and $q^2$ and $q^6$ are 1. In another example, $n^4$ is 0, and $q^2$ and $q^6$ are 1, with two phosphorothioate internucleotide linkage modifications within position 1-5 of the sense strand (counting from the 5'-end of the sense strand), and two phosphorothioate internucleotide linkage modifications at positions 1 and 2 and two phosphorothioate internucleotide linkage modifications within positions 18-23 of the antisense strand (counting from the 5'-end of the antisense strand).

In one embodiment, $n^4$, $q^2$, and $q^6$ are each 1.
In one embodiment, $n^2$, $n^4$ $q^2$ 4, and $q^6$ are each 1.
In one embodiment, C1 is at position 14-17 of the 5'-end of the sense strand, when the sense strand is 19-22 nucleotides in length, and $n^4$ is 1. In one embodiment, C1 is at position 15 of the 5'-end of the sense strand In one embodiment, T3' starts at position 2 from the 5' end of the antisense strand. In one example, T3' is at position 2 from the 5' end of the antisense strand and $q^6$ is equal to 1.

In one embodiment, T1' starts at position 14 from the 5' end of the antisense strand. In one example, T1' is at position 14 from the 5' end of the antisense strand and $q^2$ is equal to 1.

In an exemplary embodiment, T3' starts from position 2 from the 5' end of the antisense strand and T1' starts from position 14 from the 5' end of the antisense strand. In one example, T3' starts from position 2 from the 5' end of the antisense strand and $q^6$ is equal to 1 and T1' starts from position 14 from the 5' end of the antisense strand and $q^2$ is equal to 1.

In one embodiment, T1' and T3' are separated by 11 nucleotides in length (i.e. not counting the T1' and T3' nucleotides).

In one embodiment, T1' is at position 14 from the 5' end of the antisense strand. In one example, T1' is at position 14 from the 5' end of the antisense strand and $q^2$ is equal to 1, and the modification at the 2' position or positions in a non-ribose, acyclic or backbone that provide less steric bulk than a 2'-OMe ribose.

In one embodiment, T3' is at position 2 from the 5' end of the antisense strand. In one example, T3' is at position 2 from the 5' end of the antisense strand and $q^6$ is equal to 1, and the modification at the 2' position or positions in a non-ribose, acyclic or backbone that provide less than or equal to steric bulk than a 2'-OMe ribose.

In one embodiment, T1 is at the cleavage site of the sense strand. In one example, T1 is at position 11 from the 5' end of the sense strand, when the sense strand is 19-22 nucleotides in length, and $n^2$ is 1. In an exemplary embodiment, T1 is at the cleavage site of the sense strand at position 11 from the 5' end of the sense strand, when the sense strand is 19-22 nucleotides in length, and $n^2$ is 1, In one embodiment, T2' starts at position 6 from the 5' end of the antisense strand. In one example, T2' is at positions 6-10 from the 5' end of the antisense strand, and $q^4$ is 1.

In an exemplary embodiment, T1 is at the cleavage site of the sense strand, for instance, at position 11 from the 5' end of the sense strand, when the sense strand is 19-22 nucleotides in length, and $n^2$ is 1; T1' is at position 14 from the 5' end of the antisense strand, and $q^2$ is equal to 1, and the modification to T1' is at the 2' position of a ribose sugar or at positions in a non-ribose, acyclic or backbone that provide less steric bulk than a 2'-OMe ribose; T2' is at positions 6-10 from the 5' end of the antisense strand, and $q^4$ is 1; and T3' is at position 2 from the 5' end of the antisense strand, and $q^6$ is equal to 1, and the modification to T3' is at the 2' position or at positions in a non-ribose, acyclic or backbone that provide less than or equal to steric bulk than a 2'-OMe ribose. In one embodiment, T2' starts at position 8 from the 5' end of the antisense strand. In one example, T2' starts at position 8 from the 5' end of the antisense strand, and $q^4$ is 2.

In one embodiment, T2' starts at position 9 from the 5' end of the antisense strand. In one example, T2' is at position 9 from the 5' end of the antisense strand, and $q^4$ is 1.

In one embodiment, B1' is 2'-OMe or 2'-F, $q^1$ is 9, T1' is 2'-F, $q^2$ is 1, B2' is 2'-OMe or 2'-F, $q^3$ is 4, T2' is 2'-F, $q^4$ is 1, B3' is 2'-OMe or 2'-F, $q^5$ is 6, T3' is 2'-F, $q^6$ is 1, B4' is 2'-OMe, and $q^7$ is 1; with two phosphorothioate internucleotide linkage modifications within positions 1-5 of the sense strand (counting from the 5'-end of the sense strand), and two phosphorothioate internucleotide linkage modifications at positions 1 and 2 and two phosphorothioate internucleotide linkage modifications within positions 18-23 of the antisense strand (counting from the 5'-end of the antisense strand).

In one embodiment, $n^4$ is 0, B3 is 2'-OMe, $n^5$ is 3, B1' is 2'-OMe or 2'-F, q is 9, T1' is 2'-F, $q^2$ is 1, B2' is 2'-OMe or 2'-F, $q^3$ is 4, T2' is 2'-F, $q^4$ is 1, B3' is 2'-OMe or 2'-F, $q^5$ is 6, T3' is 2'-F, $q^6$ is 1, B4' is 2'-OMe, and q is 1; with two phosphorothioate internucleotide linkage modifications within positions 1-5 of the sense strand (counting from the 5'-end of the sense strand), and two phosphorothioate internucleotide linkage modifications at positions 1 and 2 and two phosphorothioate internucleotide linkage modifications within positions 18-23 of the antisense strand (counting from the 5'-end of the antisense strand).

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'OMe, $n^5$ is 3, B1' is 2'-OMe or 2'-F, q' is 9, T1' is 2'-F, $q^2$ is 1, B2' is 2'-OMe or 2'-F, $q^3$ is 4, T2' is 2'-F, $q^4$ is 2, B3' is 2'-OMe or 2'-F, $q^5$ is 5, T3' is 2'-F, $q^6$ is 1, B4' is 2'-OMe, and $q^7$ is 1.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'-OMe, $n^5$ is 3, B1' is 2'-OMe or 2'-F, q' is 9, T1' is 2'-F, $q^2$ is 1, B2' is 2'-OMe or 2'-F, $q^3$ is 4, T2' is 2'-F, $q^4$ is 2, B3' is 2'-OMe or 2'-F, $q^5$ is 5, T3' is 2'-F, $q^6$ is 1, B4' is 2'-OMe, and $q^7$ is 1; with two phosphorothioate internucleotide linkage modifications within positions 1-5 of the sense strand (counting from the 5'-end of the sense strand), and two phosphorothioate internucleotide linkage modifications at positions 1 and 2 and two phosphorothioate internucleotide linkage modifications within positions 18-23 of the antisense strand (counting from the 5'-end of the antisense strand).

In one embodiment, B1 is 2'-OMe or 2'-F, $n^1$ is 6, T1 is 2'F, $n^2$ is 3, B2 is 2'-OMe, $n^3$ is 7, $n^4$ is 0, B3 is 2'OMe, $n^5$ is 3, B1' is 2'-OMe or 2'-F, q' is 7, T1' is 2'-F, $q^2$ is 1, B2' is 2'-OMe or 2'-F, $q^3$ is 4, T2' is 2'-F, $q^4$ is 2, B3' is 2'-OMe or 2'-F, $q^5$ is 5, T3' is 2'-F, $q^6$ is 1, B4' is 2'-OMe, and $q^7$ is 1.

In one embodiment, B1 is 2'-OMe or 2'-F, $n^1$ is 6, T1 is 2'F, $n^2$ is 3, B2 is 2'-OMe, $n^3$ is 7, $n^4$ is 0, B3 is 2'-OMe, $n^5$ is 3, B1' is 2'-OMe or 2'-F, q' is 7, T1' is 2'-F, $q^2$ is 1, B2' is 2'-OMe or 2'-F, $q^3$ is 4, T2' is 2'-F, $q^4$ is 2, B3' is 2'-OMe or 2'-F, $q^5$ is 5, T3' is 2'-F, $q^6$ is 1, B4' is 2'-OMe, and $q^7$ is 1; with two phosphorothioate internucleotide linkage modifications within positions 1-5 of the sense strand (counting from the 5'-end of the sense strand), and two phosphorothioate internucleotide linkage modifications at positions 1 and 2 and two phosphorothioate internucleotide linkage modifications within positions 18-23 of the antisense strand (counting from the 5'-end of the antisense strand).

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'-OMe, $n^5$ is 3, B1' is 2'-OMe or 2'-F, q' is 9, T1' is 2'-F, $q^2$ is 1, B2' is 2'-OMe or 2'-F, $q^3$ is 4, T2' is 2'-F, $q^4$ is 1, B3' is 2'-OMe or 2'-F, $q^5$ is 6, T3' is 2'-F, $q^6$ is 1, B4' is 2'-OMe, and $q^7$ is 1.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'-OMe, $n^5$ is 3, B1' is 2'-OMe or 2'-F, q' is 9, T1' is 2'-F, $q^2$ is 1, B2' is 2'-OMe or 2'-F, $q^3$ is 4, T2' is 2'-F, $q^4$ is 1, B3' is 2'-OMe or 2'-F, $q^5$ is 6, T3' is 2'-F, $q^6$ is 1, B4' is 2'-OMe, and $q^7$ is 1; with two phosphorothioate internucleotide linkage modifications within positions 1-5 of the sense strand (counting from the 5'-end of the sense strand), and two phosphorothioate internucleotide linkage modifications at positions 1 and 2 and two phosphorothioate internucleotide linkage modifications within positions 18-23 of the antisense strand (counting from the 5'-end of the antisense strand).

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'OMe, $n^5$ is 3, B1' is 2'-OMe or 2'-F, $q'$ is 9, T1' is 2'-F, $q^2$ is 1, B2' is 2'-OMe or 2'-F, $q^3$ is 5, T2' is 2'-F, $q^4$ is 1, B3' is 2'-OMe or 2'-F, $q^5$ is 5, T3' is 2'-F, $q^6$ is 1, B4' is 2'-OMe, and $q^7$ is 1; optionally with at least 2 additional TT at the 3'-end of the antisense strand.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'-OMe, $n^5$ is 3, B1' is 2'-OMe or 2'-F, $q'$ is 9, T1' is 2'-F, $q^2$ is 1, B2' is 2'-OMe or 2'-F, $q^3$ is 5, T2' is 2'-F, $q^4$ is 1, B3' is 2'-OMe or 2'-F, $q^5$ is 5, T3' is 2'-F, $q^6$ is 1, B4' is 2'-OMe, and $q^7$ is 1; optionally with at least 2 additional TT at the 3'-end of the antisense strand; with two phosphorothioate internucleotide linkage modifications within positions 1-5 of the sense strand (counting from the 5'-end of the sense strand), and two phosphorothioate internucleotide linkage modifications at positions 1 and 2 and two phosphorothioate internucleotide linkage modifications within positions 18-23 of the antisense strand (counting from the 5'-end of the antisense strand).

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'-OMe, $n^5$ is 3, B1' is 2'-OMe or 2'-F, $q^1$ is 9, T1' is 2'-F, $q^2$ is 1, B2' is 2'-OMe or 2'-F, $q^3$ is 4, $q^4$ is 0, B3' is 2'-OMe or 2'-F, $q^5$ is 7, T3' is 2'-F, $q^6$ is 1, B4' is 2'-OMe, and $q^7$ is 1.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'-OMe, $n^5$ is 3, B1' is 2'-OMe or 2'-F, $q^1$ is 9, T1' is 2'-F, $q^2$ is 1, B2' is 2'-OMe or 2'-F, $q^3$ is 4, $q^4$ is 0, B3' is 2'-OMe or 2'-F, $q^5$ is 7, T3' is 2'-F, $q^6$ is 1, B4' is 2'-OMe, and $q^7$ is 1; with two phosphorothioate internucleotide linkage modifications within positions 1-5 of the sense strand (counting from the 5'-end), and two phosphorothioate internucleotide linkage modifications at positions 1 and 2 and two phosphorothioate internucleotide linkage modifications within positions 18-23 of the antisense strand (counting from the 5'-end).

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'OMe, $n^5$ is 3, B1' is 2'-OMe or 2'-F, $q^1$ is 9, T1' is 2'-F, $q^2$ is 1, B2' is 2'-OMe or 2'-F, $q^3$ is 4, T2' is 2'-F, $q^4$ is 2, B3' is 2'-OMe or 2'-F, $q^5$ is 5, T3' is 2'-F, $q^6$ is 1, B4' is 2'-F, and $q^7$ is 1.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'-OMe, $n^5$ is 3, B1' is 2'-OMe or 2'-F, $q^1$ is 9, T1' is 2'-F, $q^2$ is 1, B2' is 2'-OMe or 2'-F, $q^3$ is 4, T2' is 2'-F, $q^4$ is 2, B3' is 2'-OMe or 2'-F, $q^5$ is 5, T3' is 2'-F, $q^6$ is 1, B4' is 2'-F, and $q^7$ is 1; with two phosphorothioate internucleotide linkage modifications within positions 1-5 of the sense strand (counting from the 5'-end of the sense strand), and two phosphorothioate internucleotide linkage modifications at positions 1 and 2 and two phosphorothioate internucleotide linkage modifications within positions 18-23 of the antisense strand (counting from the 5'-end of the antisense strand).

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'-OMe, $n^5$ is 3, B1' is 2'-OMe or 2'-F, $q^1$ is 9, T1' is 2'-F, $q^2$ is 1, B2' is 2'-OMe or 2'-F, $q^3$ is 4, $q^4$ is 0, B3' is 2'-OMe or 2'-F, $q^5$ is 7, T3' is 2'-F, $q^6$ is 1, B4' is 2'-F, and $q^7$ is 1.

In one embodiment, B1 is 2'-OMe or 2'-F, n' is 8, T1 is 2'F, $n^2$ is 3, B2 is 2'-OMe, $n^3$ is 7, $n^4$ is 0, B3 is 2'-OMe, $n^5$ is 3, B1' is 2'-OMe or 2'-F, q' is 9, T1' is 2'-F, $q^2$ is 1, B2' is 2'-OMe or 2'-F, $q^3$ is 4, $q^4$ is 0, B3' is 2'-OMe or 2'-F, $q^5$ is 7, T3' is 2'-F, $q^6$ is 1, B4' is 2'-F, and $q^7$ is 1; with two phosphorothioate internucleotide linkage modifications within positions 1-5 of the sense strand (counting from the 5'-end of the sense strand), and two phosphorothioate internucleotide linkage modifications at positions 1 and 2 and two phosphorothioate internucleotide linkage modifications within positions 18-23 of the antisense strand (counting from the 5'-end of the antisense strand).

The RNAi agent can comprise a phosphorus-containing group at the 5'-end of the sense strand or antisense strand. The 5'-end phosphorus-containing group can be 5'-end phosphate (5'-P), 5'-end phosphorothioate (5'-PS), 5'-end phosphorodithioate (5'-$PS_2$), 5'-end vinylphosphonate (5'-VP), 5'-end methylphosphonate (MePhos), or 5'-deoxy-5'-C-malonyl

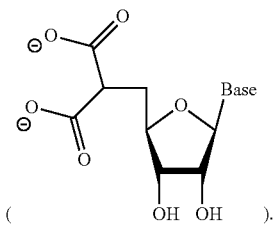

When the 5'-end phosphorus-containing group is 5'-end vinylphosphonate (5'-VP), the 5'-VP can be either 5'-E-VP isomer (i.e., trans-vinylphosphate.

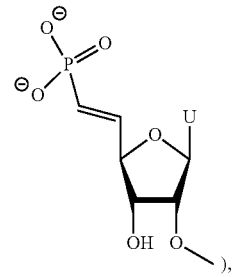

5'-Z-VP isomer (i.e., cis-vinylphosphate,

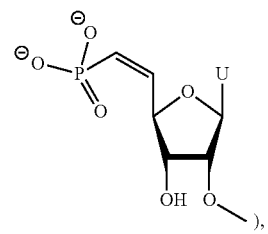

or mixtures thereof.

In one embodiment, the RNAi agent comprises a phosphorus-containing group at the 5'-end of the sense strand. In one embodiment, the RNAi agent comprises a phosphorus-containing group at the 5'-end of the antisense strand.

In one embodiment, the RNAi agent comprises a 5'-P. In one embodiment, the RNAi agent comprises a 5'-P in the antisense strand.

In one embodiment, the RNAi agent comprises a 5'-PS. In one embodiment, the RNAi agent comprises a 5'-PS in the antisense strand.

In one embodiment, the RNAi agent comprises a 5'-VP. In one embodiment, the RNAi agent comprises a 5'-VP in the antisense strand. In one embodiment, the RNAi agent comprises a 5'-E-VP in the antisense strand. In one embodiment, the RNAi agent comprises a 5'-Z-VP in the antisense strand.

In one embodiment, the RNAi agent comprises a 5'-$PS_2$. In one embodiment, the RNAi agent comprises a 5'-$PS_2$ in the antisense strand.

In one embodiment, the RNAi agent comprises a 5'-$PS_2$. In one embodiment, the RNAi agent comprises a 5'-deoxy-5'-C-malonyl in the antisense strand. In one embodiment, B1 is 2'-OMe or 2'-F, is 8, T1 is 2'F, $n^2$ is 3, B2 is 2'-OMe, $n^3$ is 7, $n^4$ is 0, B3 is 2'OMe, $n^5$ is 3, B1' is 2'-OMe or 2'-F, $q^1$ is 9, T1' is 2'-F, $q^2$ is 1, B2' is 2'-OMe or 2'-F, $q^3$ is 4, 53 T2' is 2'-F, $q^4$ is 2, B3' is 2'-OMe or 2'-F, $q^5$ is 5, T3' is 2'-F, $q^6$ is 1, B4' is 2'-OMe, and $q^7$ is 1. The RNAi agent also comprises a 5'-PS.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'OMe, $n^5$ is 3, B1' is 2'-OMe or 2'-F, $q^1$ is 9, T1' is 2'-F, $q^2$ is 1, B2' is 2'-OMe or 2'-F, $q^3$ is 4, T2' is 2'-F, $q^4$ is 2, B3' is 2'-OMe or 2'-F, $q^5$ is 5, T3' is 2'-F, $q^6$ is 1, B4' is 2'-OMe, and $q^7$ is 1. The RNAi agent also comprises a 5'-P.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'OMe, $n^5$ is 3, B1' is 2'-OMe or 2'-F, $q^1$ is 9, T1' is 2'-F, $q^2$ is 1, B2' is 2'-OMe or 2'-F, $q^3$ is 4, T2' is 2'-F, $q^4$ is 2, B3' is 2'-OMe or 2'-F, $q^5$ is 5, T3' is 2'-F, $q^6$ is 1, B4' is 2'-OMe, and $q^7$ is 1. The RNAi agent also comprises a 5'-VP. The 5'-VP may be 5'-E-VP, 5'-Z-VP, or combination thereof.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'OMe, $n^5$ is 3, B1' is 2'-OMe or 2'-F, $q^1$ is 9, T1' is 2'-F, $q^2$ is 1, B2' is 2'-OMe or 2'-F, $q^3$ is 4, T2' is 2'-F, $q^4$ is 2, B3' is 2'-OMe or 2'-F, $q^5$ is 5, T3' is 2'-F, $q^6$ is 1, B4' is 2'-OMe, and $q^7$ is 1. The RNAi agent also comprises a 5'-$PS_2$.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'OMe, $n^5$ is 3, B1' is 2'-OMe or 2'-F, $q^1$ is 9, T1' is 2'-F, $q^2$ is 1, B2' is 2'-OMe or 2'-F, $q^3$ is 4, T2' is 2'-F, $q^4$ is 2, B3' is 2'-OMe or 2'-F, $q^5$ is 5, T3' is 2'-F, $q^6$ is 1, B4' is 2'-OMe, and $q^7$ is 1. The RNAi agent also comprises a 5'-deoxy-5'-C-malonyl.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'-OMe, $n^5$ is 3, B1' is 2'-OMe or 2'-F, $q^1$ is 9, T1' is 2'-F, $q^2$ is 1, B2' is 2'-OMe or 2'-F, $q^3$ is 4, T2' is 2'-F, $q^4$ is 2, B3' is 2'-OMe or 2'-F, $q^5$ is 5, T3' is 2'-F, $q^6$ is 1, B4' is 2'-OMe, and $q^7$ is 1; with two phosphorothioate internucleotide linkage modifications within position 1-5 of the sense strand (counting from the 5'-end of the sense strand), and two phosphorothioate internucleotide linkage modifications at positions 1 and 2 and two phosphorothioate internucleotide linkage modifications within positions 18-23 of the antisense strand (counting from the 5'-end of the antisense strand). The RNAi agent also comprises a 5'-P.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'-OMe, $n^5$ is 3, B1' is 2'-OMe or 2'-F, $q^1$ is 9, T1' is 2'-F, $q^2$ is 1, B2' is 2'-OMe or 2'-F, $q^3$ is 4, T2' is 2'-F, $q^4$ is 2, B3' is 2'-OMe or 2'-F, $q^5$ is 5, T3' is 2'-F, $q^6$ is 1, B4' is 2'-OMe, and $q^7$ is 1; with two phosphorothioate internucleotide linkage modifications within position 1-5 of the sense strand (counting from the 5'-end of the sense strand), and two phosphorothioate internucleotide linkage modifications at positions 1 and 2 and two phosphorothioate internucleotide linkage modifications within positions 18-23 of the antisense strand (counting from the 5'-end of the antisense strand). The RNAi agent also comprises a 5'-PS.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'-OMe, $n^5$ is 3, B1' is 2'-OMe or 2'-F, $q^1$ is 9, T1' is 2'-F, $q^2$ is 1, B2' is 2'-OMe or 2'-F, $q^3$ is 4, T2' is 2'-F, $q^4$ is 2, B3' is 2'-OMe or 2'-F, $q^5$ is 5, T3' is 2'-F, $q^6$ is 1, B4' is 2'-OMe, and $q^7$ is 1; with two phosphorothioate internucleotide linkage modifications within position 1-5 of the sense strand (counting from the 5'-end of the sense strand), and two phosphorothioate internucleotide linkage modifications at positions 1 and 2 and two phosphorothioate internucleotide linkage modifications within positions 18-23 of the antisense strand (counting from the 5'-end of the antisense strand). The RNAi agent also comprises a 5'-VP. The 5'-VP may be 5'-E-VP, 5'-Z-VP, or combination thereof.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'-OMe, $n^5$ is 3, B1' is 2'-OMe or 2'-F, $q^1$ is 9, T1' is 2'-F, $q^2$ is 1, B2' is 2'-OMe or 2'-F, $q^3$ is 4, T2' is 2'-F, $q^4$ is 2, B3' is 2'-OMe or 2'-F, $q^5$ is 5, T3' is 2'-F, $q^6$ is 1, B4' is 2'-OMe, and $q^7$ is 1; with two phosphorothioate internucleotide linkage modifications within position 1-5 of the sense strand (counting from the 5'-end of the sense strand), and two phosphorothioate internucleotide linkage modifications at positions 1 and 2 and two phosphorothioate internucleotide linkage modifications within positions 18-23 of the antisense strand (counting from the 5'-end of the antisense strand). The RNAi agent also comprises a 5'-$PS_2$.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'-OMe, $n^5$ is 3, B1' is 2'-OMe or 2'-F, $q^1$ is 9, T1' is 2'-F, $q^2$ is 1, B2' is 2'-OMe or 2'-F, $q^3$ is 4, T2' is 2'-F, $q^4$ is 2, B3' is 2'-OMe or 2'-F, $q^5$ is 5, T3' is 2'-F, $q^6$ is 1, B4' is 2'-OMe, and $q^7$ is 1; with two phosphorothioate internucleotide linkage modifications within position 1-5 of the sense strand (counting from the 5'-end of the sense strand), and two phosphorothioate internucleotide linkage modifications at positions 1 and 2 and two phosphorothioate internucleotide linkage modifications within positions 18-23 of the antisense strand (counting from the 5'-end of the antisense strand). The RNAi agent also comprises a 5'-deoxy-5'-C-malonyl.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'-OMe, $n^5$ is 3, B1' is 2'-OMe or 2'-F, $q^1$ is 9, T1' is 2'-F, $q^2$ is 1, B2' is 2'-OMe or 2'-F, $q^3$ is 4, $q^4$ is 0, B3' is 2'-OMe or 2'-F, $q^5$ is 7, T3' is 2'-F, $q^6$ is 1, B4' is 2'-OMe, and $q^7$ is 1. The RNAi agent also comprises a 5'-P.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'-OMe, $n^5$ is 3, B1' is 2'-OMe or 2'-F, $q^1$ is 9, T1' is 2'-F, $q^2$ is 1, B2' is 2'-OMe or 2'-F, $q^3$ is 4, $q^4$ is 0, B3' is 2'-OMe or 2'-F, $q^5$ is 7, T3' is 2'-F, $q^6$ is 1, B4' is 2'-OMe, and $q^7$ is 1. The dsRNA agent also comprises a 5'-PS.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'-OMe, $n^5$ is 3, B1' is 2'-OMe or 2'-F, $q^1$ is 9, T1' is 2'-F, $q^2$ is 1, B2' is 2'-OMe or 2'-F, $q^3$ is 4, $q^4$ is 0, B3' is 2'-OMe or 2'-F, $q^5$ is 7, T3' is 2'-F, $q^6$ is 1, B4' is 2'-OMe, and $q^7$ is 1. The RNAi agent also comprises a 5'-VP. The 5'-VP may be 5'-E-VP, 5'-Z-VP, or combination thereof.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'-OMe, $n^5$ is 3, B1' is 2'-OMe or 2'-F, $q^1$ is 9, T1' is 2'-F, $q^2$ is 1, B2' is 2'-OMe or 2'-F, $q^3$ is 4, $q^4$ is 0, B3' is 2'-OMe or 2'-F, $q^5$ is 7, T3' is 2'-F, $q^6$ is 1, B4' is 2'-OMe, and $q^7$ is 1. The RNAi agent also comprises a 5'-$PS_2$.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'-OMe, $n^5$ is 3, B1' is 2'-OMe or 2'-F, $q^1$ is 9, T1' is 2'-F, $q^2$ is 1, B2' is 2'-OMe or 2'-F, $q^3$ is 4, $q^4$ is 0, B3' is 2'-OMe or 2'-F, $q^5$ is 7, T3' is 2'-F, $q^6$ is 1, B4' is 2'-OMe, and $q^7$ is 1. The RNAi agent also comprises a 5'-deoxy-5'-C-malonyl.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'-OMe, $n^5$ is 3, B1' is 2'-OMe or 2'-F, $q^1$ is 9, T1' is 2'-F, $q^2$ is 1, B2' is 2'-OMe or 2'-F, $q^3$ is 4, $q^4$ is 0, B3' is 2'-OMe or 2'-F, $q^5$ is 7, T3' is 2'-F, $q^6$ is 1, B4' is 2'-OMe, and $q^7$ is 1; with two phosphorothioate internucleotide linkage modifications within position 1-5 of the sense strand (counting from the 5'-end), and two phosphorothioate internucleotide linkage modifications at positions 1 and 2 and two phosphorothioate internucleotide linkage modifications within positions 18-23 of the antisense strand (counting from the 5'-end). The RNAi agent also comprises a 5'-P.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'-OMe, $n^5$ is 3, B1' is 2'-OMe or 2'-F, $q^1$ is 9, T1' is 2'-F, $q^2$ is 1, B2' is 2'-OMe or 2'-F, $q^3$ is 4, $q^4$ is 0, B3' is 2'-OMe or 2'-F, $q^5$ is 7, T3' is 2'-F, $q^6$ is 1, B4' is 2'-OMe, and $q^7$ is 1; with two phosphorothioate internucleotide linkage modifications within position 1-5 of the sense strand (counting from the 5'-end), and two phosphorothioate internucleotide linkage modifications at positions 1 and 2 and two phosphorothioate internucleotide linkage modifications within positions 18-23 of the antisense strand (counting from the 5'-end). The RNAi agent also comprises a 5'-PS.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'-OMe, $n^5$ is 3, B1' is 2'-OMe or 2'-F, $q^1$ is 9, T1' is 2'-F, $q^2$ is 1, B2' is 2'-OMe or 2'-F, $q^3$ is 4, $q^4$ is 0, B3' is 2'-OMe or 2'-F, $q^5$ is 7, T3' is 2'-F, $q^6$ is 1, B4' is 2'-OMe, and $q^7$ is 1; with two phosphorothioate internucleotide linkage modifications within position 1-5 of the sense strand (counting from the 5'-end), and two phosphorothioate internucleotide linkage modifications at positions 1 and 2 and two phosphorothioate internucleotide linkage modifications within positions 18-23 of the antisense strand (counting from the 5'-end). The RNAi agent also comprises a 5'-VP. The 5'-VP may be 5'-E-VP, 5'-Z-VP, or combination thereof.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'-OMe, $n^5$ is 3, B1' is 2'-OMe or 2'-F, $q^1$ is 9, T1' is 2'-F, $q^2$ is 1, B2' is 2'-OMe or 2'-F, $q^3$ is 4, $q^4$ is 0, B3' is 2'-OMe or 2'-F, $q^5$ is 7, T3' is 2'-F, $q^6$ is 1, B4' is 2'-OMe, and $q^7$ is 1; with two phosphorothioate internucleotide linkage modifications within position 1-5 of the sense strand (counting from the 5'-end), and two phosphorothioate internucleotide linkage modifications at positions 1 and 2 and two phosphorothioate internucleotide linkage modifications within positions 18-23 of the antisense strand (counting from the 5'-end). The RNAi agent also comprises a 5'-$PS_2$.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'-OMe, $n^5$ is 3, B1' is 2'-OMe or 2'-F, $q^1$ is 9, T1' is 2'-F, $q^2$ is 1, B2' is 2'-OMe or 2'-F, $q^3$ is 4, $q^4$ is 0, B3' is 2'-OMe or 2'-F, $q^5$ is 7, T3' is 2'-F, $q^6$ is 1, B4' is 2'-OMe, and $q^7$ is 1; with two phosphorothioate internucleotide linkage modifications within position 1-5 of the sense strand (counting from the 5'-end), and two phosphorothioate internucleotide linkage modifications at positions 1 and 2 and two phosphorothioate internucleotide linkage modifications within positions 18-23 of the antisense strand (counting from the 5'-end). The RNAi agent also comprises a 5'-deoxy-5'-C-malonyl.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'OMe, $n^5$ is 3, B1' is 2'-OMe or 2'-F, $q^1$ is 9, T1' is 2'-F, $q^2$ is 1, B2' is 2'-OMe or 2'-F, $q^3$ is 4, T2' is 2'-F, $q^4$ is 2, B3' is 2'-OMe or 2'-F, $q^5$ is 5, T3' is 2'-F, $q^6$ is 1, B4' is 2'-F, and $q^7$ is 1. The RNAi agent also comprises a 5'-P.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'OMe, $n^5$ is 3, B1' is 2'-OMe or 2'-F, $q^1$ is 9, T1' is 2'-F, $q^2$ is 1, B2' is 2'-OMe or 2'-F, $q^3$ is 4, T2' is 2'-F, $q^4$ is 2, B3' is 2'-OMe or 2'-F, $q^5$ is 5, T3' is 2'-F, $q^6$ is 1, B4' is 2'-F, and $q^7$ is 1. The RNAi agent also comprises a 5'-PS.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'OMe, $n^5$ is 3, B1' is 2'-OMe or 2'-F, $q^1$ is 9, T1' is 2'-F, $q^2$ is 1, B2' is 2'-OMe or 2'-F, $q^3$ is 4, T2' is 2'-F, $q^4$ is 2, B3' is 2'-OMe or 2'-F, $q^5$ is 5, T3' is 2'-F, $q^6$ is 1, B4' is 2'-F, and $q^7$ is 1. The RNAi agent also comprises a 5'-VP. The 5'-VP may be 5'-E-VP, 5'-Z-VP, or combination thereof.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'OMe, $n^5$ is 3, B1' is 2'-OMe or 2'-F, $q^1$ is 9, T1' is 2'-F, $q^2$ is 1, B2' is 2'-OMe or 2'-F, $q^3$ is 4, T2' is 2'-F, $q^4$ is 2, B3' is 2'-OMe or 2'-F, $q^5$ is 5, T3' is 2'-F, $q^6$ is 1, B4' is 2'-F, and $q^7$ is 1. The dsRNAi RNA agent also comprises a 5'-$PS_2$.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'OMe, $n^5$ is 3, B1' is 2'-OMe or 2'-F, $q^1$ is 9, T1' is 2'-F, $q^2$ is 1, B2' is 2'-OMe or 2'-F, $q^3$ is 4, T2' is 2'-F, $q^4$ is 2, B3' is 2'-OMe or 2'-F, $q^5$ is 5, T3' is 2'-F, $q^6$ is 1, B4' is 2'-F, and $q^7$ is 1. The RNAi agent also comprises a 5'-deoxy-5'-C-malonyl.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'-OMe, $n^5$ is 3, B1' is 2'-OMe or 2'-F, $q^1$ is 9, T1' is 2'-F, $q^2$ is 1, B2' is 2'-OMe or 2'-F, $q^3$ is 4, T2' is 2'-F, $q^4$ is 2, B3' is 2'-OMe or 2'-F, $q^5$ is 5, T3' is 2'-F, $q^6$ is 1, B4' is 2'-F, and $q^7$ is 1; with two phosphorothioate internucleotide linkage modifications within position 1-5 of the sense strand (counting from the 5'-end of the sense strand), and two phosphorothioate internucleotide linkage modifications at positions 1 and 2 and two phosphorothioate internucleotide linkage modifications within positions 18-23 of the antisense strand (counting from the 5'-end of the antisense strand). The RNAi agent also comprises a 5'-P.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'-OMe, $n^5$ is 3, B1' is 2'-OMe or 2'-F, $q^1$ is 9, T1' is 2'-F, $q^2$ is 1, B2' is 2'-OMe or 2'-F, $q^3$ is 4, T2' is 2'-F, $q^4$ is 2, B3' is 2'-OMe or 2'-F, $q^5$ is 5, T3' is 2'-F, $q^6$ is 1, B4' is 2'-F, and $q^7$ is 1; with two phosphorothioate internucleotide linkage modifications within position 1-5 of the sense strand (counting from the 5'-end of the sense strand), and two phosphorothioate internucleotide linkage modifications at positions 1 and 2 and two phosphorothioate internucleotide linkage modifications within positions 18-23 of the antisense strand (counting from the 5'-end of the antisense strand). The RNAi agent also comprises a 5'-PS.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'-OMe, $n^5$ is 3, B1' is 2'-OMe or 2'-F, $q^1$ is 9, T1' is 2'-F, $q^2$ is 1, B2' is 2'-OMe or 2'-F, $q^3$ is 4, T2' is 2'-F, $q^4$ is 2, B3' is 2'-OMe or 2'-F, $q^5$ is 5, T3' is 2'-F, $q^6$ is 1, B4' is 2'-F, and $q^7$ is 1; with two phosphorothioate internucleotide linkage modifications within position 1-5 of the sense strand (counting from the 5'-end of the sense strand), and two phosphorothioate internucleotide linkage modifications at positions 1 and 2 and two phosphorothioate internucleotide linkage modifications within positions 18-23 of the antisense strand (counting from the 5'-end of the antisense strand). The RNAi agent also comprises a 5'-VP. The 5'-VP may be 5'-E-VP, 5'-Z-VP, or combination thereof.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'-OMe, $n^5$ is 3, B1' is 2'-OMe or 2'-F, $q^1$ is 9, T1' is 2'-F, $q^2$ is 1, B2' is 2'-OMe or 2'-F, $q^3$ is 4, T2' is 2'-F, $q^4$ is 2, B3' is 2'-OMe or 2'-F, $q^5$ is 5, T3' is 2'-F, $q^6$ is 1, B4' is 2'-F, and $q^7$ is 1; with two phosphorothioate internucleotide linkage modifications within position 1-5 of the sense strand (counting from the 5'-end of the sense strand), and two phosphorothioate internucleotide linkage modifications at positions 1 and 2 and two phosphorothioate internucleotide linkage modifications within positions 18-23 of the antisense strand (counting from the 5'-end of the antisense strand). The RNAi agent also comprises a 5'-$PS_2$.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'-OMe, $n^5$ is 3, B1' is 2'-OMe or 2'-F, $q^1$ is 9, T1' is 2'-F, $q^2$ is 1, B2' is 2'-OMe or 2'-F, $q^3$ is 4, T2' is 2'-F, $q^4$ is 2, B3' is 2'-OMe or 2'-F, $q^5$ is 5, T3' is 2'-F, $q^6$ is 1, B4' is 2'-F, and $q^7$ is 1; with two phosphorothioate internucleotide linkage modifications within position 1-5 of the sense strand (counting from the 5'-end of the sense strand), and two phosphorothioate internucleotide linkage modifications at positions 1 and 2 and two phosphorothioate internucleotide linkage modifications within positions 18-23 of the antisense strand (counting from the 5'-end of the antisense strand). The RNAi agent also comprises a 5'-deoxy-5'-C-malonyl.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'-OMe, $n^5$ is 3, B1' is 2'-OMe or 2'-F, $q^1$ is 9, T1' is 2'-F, $q^2$ is 1, B2' is 2'-OMe or 2'-F, $q^3$ is 4, $q^4$ is 0, B3' is 2'-OMe or 2'-F, $q^5$ is 7, T3' is 2'-F, $q^6$ is 1, B4' is 2'-F, and $q^7$ is 1. The RNAi agent also comprises a 5'-P.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'-OMe, $n^5$ is 3, B1' is 2'-OMe or 2'-F, $q^1$ is 9, T1' is 2'-F, $q^2$ is 1, B2' is 2'-OMe or 2'-F, $q^3$ is 4, $q^4$ is 0, B3' is 2'-OMe or 2'-F, $q^5$ is 7, T3' is 2'-F, $q^6$ is 1, B4' is 2'-F, and $q^7$ is 1. The RNAi agent also comprises a 5'-PS.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'-OMe, $n^5$ is 3, B1' is 2'-OMe or 2'-F, $q^1$ is 9, T1' is 2'-F, $q^2$ is 1, B2' is 2'-OMe or 2'-F, $q^3$ is 4, $q^4$ is 0, B3' is 2'-OMe or 2'-F, $q^5$ is 7, T3' is 2'-F, $q^6$ is 1, B4' is 2'-F, and $q^7$ is 1. The RNAi agent also comprises a 5'-VP. The 5'-VP may be 5'-E-VP, 5'-Z-VP, or combination thereof.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'-OMe, $n^5$ is 3, B1' is 2'-OMe or 2'-F, $q^1$ is 9, T1' is 2'-F, $q^2$ is 1, B2' is 2'-OMe or 2'-F, $q^3$ is 4, $q^4$ is 0, B3' is 2'-OMe or 2'-F, $q^5$ is 7, T3' is 2'-F, $q^6$ is 1, B4' is 2'-F, and $q^7$ is 1. The RNAi agent also comprises a 5'-PS$_2$.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'-OMe, $n^5$ is 3, B1' is 2'-OMe or 2'-F, $q^1$ is 9, T1' is 2'-F, $q^2$ is 1, B2' is 2'-OMe or 2'-F, $q^3$ is 4, $q^4$ is 0, B3' is 2'-OMe or 2'-F, $q^5$ is 7, T3' is 2'-F, $q^6$ is 1, B4' is 2'-F, and $q^7$ is 1. The RNAi agent also comprises a 5'-deoxy-5'-C-malonyl.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'-OMe, $n^5$ is 3, B1' is 2'-OMe or 2'-F, $q^1$ is 9, T1' is 2'-F, $q^2$ is 1, B2' is 2'-OMe or 2'-F, $q^3$ is 4, $q^4$ is 0, B3' is 2'-OMe or 2'-F, $q^5$ is 7, T3' is 2'-F, $q^6$ is 1, B4' is 2'-F, and $q^7$ is 1; with two phosphorothioate internucleotide linkage modifications within position 1-5 of the sense strand (counting from the 5'-end of the sense strand), and two phosphorothioate internucleotide linkage modifications at positions 1 and 2 and two phosphorothioate internucleotide linkage modifications within positions 18-23 of the antisense strand (counting from the 5'-end of the antisense strand). The RNAi agent also comprises a 5'-P.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'-OMe, $n^5$ is 3, B1' is 2'-OMe or 2'-F, $q^1$ is 9, T1' is 2'-F, $q^2$ is 1, B2' is 2'-OMe or 2'-F, $q^3$ is 4, $q^4$ is 0, B3' is 2'-OMe or 2'-F, $q^5$ is 7, T3' is 2'-F, $q^6$ is 1, B4' is 2'-F, and $q^7$ is 1; with two phosphorothioate internucleotide linkage modifications within position 1-5 of the sense strand (counting from the 5'-end of the sense strand), and two phosphorothioate internucleotide linkage modifications at positions 1 and 2 and two phosphorothioate internucleotide linkage modifications within positions 18-23 of the antisense strand (counting from the 5'-end of the antisense strand). The RNAi agent also comprises a 5'-PS.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'-OMe, $n^5$ is 3, B1' is 2'-OMe or 2'-F, $q^1$ is 9, T1' is 2'-F, $q^2$ is 1, B2' is 2'-OMe or 2'-F, $q^3$ is 4, $q^4$ is 0, B3' is 2'-OMe or 2'-F, $q^5$ is 7, T3' is 2'-F, $q^6$ is 1, B4' is 2'-F, and $q^7$ is 1; with two phosphorothioate internucleotide linkage modifications within position 1-5 of the sense strand (counting from the 5'-end of the sense strand), and two phosphorothioate internucleotide linkage modifications at positions 1 and 2 and two phosphorothioate internucleotide linkage modifications within positions 18-23 of the antisense strand (counting from the 5'-end of the antisense strand). The RNAi agent also comprises a 5'-VP. The 5'-VP may be 5'-E-VP, 5'-Z-VP, or combination thereof.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'-OMe, $n^5$ is 3, B1' is 2'-OMe or 2'-F, $q^1$ is 9, T1' is 2'-F, $q^2$ is 1, B2' is 2'-OMe or 2'-F, $q^3$ is 4, $q^4$ is 0, B3' is 2'-OMe or 2'-F, $q^5$ is 7, T3' is 2'-F, $q^6$ is 1, B4' is 2'-F, and $q^7$ is 1; with two phosphorothioate internucleotide linkage modifications within position 1-5 of the sense strand (counting from the 5'-end of the sense strand), and two phosphorothioate internucleotide linkage modifications at positions 1 and 2 and two phosphorothioate internucleotide linkage modifications within positions 18-23 of the antisense strand (counting from the 5'-end of the antisense strand). The RNAi agent also comprises a 5'-PS$_2$.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'-OMe, $n^5$ is 3, B1' is 2'-OMe or 2'-F, $q^1$ is 9, T1' is 2'-F, $q^2$ is 1, B2' is 2'-OMe or 2'-F, $q^3$ is 4, $q^4$ is 0, B3' is 2'-OMe or 2'-F, $q^5$ is 7, T3' is 2'-F, $q^6$ is 1, B4' is 2'-F, and $q^7$ is 1; with two phosphorothioate internucleotide linkage modifications within position 1-5 of the sense strand (counting from the 5'-end of the sense strand), and two phosphorothioate internucleotide linkage modifications at positions 1 and 2 and two phosphorothioate internucleotide linkage modifications within positions 18-23 of the antisense strand (counting from the 5'-end of the antisense strand). The RNAi agent also comprises a 5'-deoxy-5'-C-malonyl.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'-OMe, $n^5$ is 3, B1' is 2'-OMe or 2'-F, $q^1$ is 9, T1' is 2'-F, $q^2$ is 1, B2' is 2'-OMe or 2'-F, $q^3$ is 4, T2' is 2'-F, $q^4$ is 2, B3' is 2'-OMe or 2'-F, $q^5$ is 5, T3' is 2'-F, $q^6$ is 1, B4' is 2'-OMe, and $q^7$ is 1; with two phosphorothioate internucleotide linkage modifications within position 1-5 of the sense strand (counting from the 5'-end of the sense strand), and two phosphorothioate internucleotide linkage modifications at positions 1 and 2 and two phosphorothioate internucleotide linkage modifications within positions 18-23 of the antisense strand (counting from the 5'-end of the antisense strand). The RNAi agent also comprises a 5'-P and a targeting ligand. In one embodiment, the 5'-P is at the 5'-end of the antisense strand, and the targeting ligand is at the 3'-end of the sense strand.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'-OMe, $n^5$ is 3, B1' is 2'-OMe or 2'-F, $q^1$ is 9, T1' is 2'-F, $q^2$ is 1, B2' is 2'-OMe or 2'-F, $q^3$ is 4, T2' is 2'-F, $q^4$ is 2, B3' is 2'-OMe or 2'-F, $q^5$ is 5, T3' is 2'-F, $q^6$ is 1, B4' is 2'-OMe, and $q^7$ is 1; with two phosphorothioate internucleotide linkage modifications within position 1-5 of the sense strand (counting from the 5'-end of the sense strand), and two phosphorothioate internucleotide linkage modifications at positions 1 and 2 and two phosphorothioate internucleotide linkage modifications within positions 18-23 of the antisense strand (counting from the 5'-end of the antisense strand). The RNAi agent also comprises a 5'-PS and a targeting ligand. In one embodiment, the 5'-PS is at the 5'-end of the antisense strand, and the targeting ligand is at the 3'-end of the sense strand.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'-OMe, $n^5$ is 3, B1' is 2'-OMe or 2'-F, $q^1$ is 9, T1' is 2'-F, $q^2$ is 1, B2' is 2'-OMe or 2'-F, $q^3$ is 4, T2' is 2'-F, $q^4$ is 2, B3' is 2'-OMe or 2'-F, $q^5$ is 5, T3' is 2'-F, $q^6$ is 1, B4' is 2'-OMe, and $q^7$ is 1; with two phosphorothioate internucleotide linkage modifications within position 1-5 of the sense strand (counting from the 5'-end of the sense strand), and two phosphorothioate internucleotide linkage modifications at positions 1 and 2 and two phosphorothioate internucleotide linkage modifications within positions 18-23 of the antisense strand (counting from the 5'-end of the antisense strand). The RNAi agent also comprises a 5'-VP (e.g., a 5'-E-VP, 5'-Z-VP, or combination thereof), and a targeting ligand.

In one embodiment, the 5'-VP is at the 5'-end of the antisense strand, and the targeting ligand is at the 3'-end of the sense strand.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'-OMe, $n^5$ is 3, B1' is 2'-OMe or 2'-F, $q^1$ is 9, T1' is 2'-F, $q^2$ is 1, B2' is 2'-OMe or 2'-F, $q^3$ is 4, T2' is 2'-F, $q^4$ is 2, B3' is 2'-OMe or 2'-F, $q^5$ is 5, T3' is 2'-F, $q^6$ is 1, B4' is 2'-OMe, and $q^7$ is 1; with two phosphorothioate internucleotide linkage modifications within position 1-5 of the sense strand (counting from the 5'-end of the sense strand), and two phosphorothioate internucleotide linkage modifications at positions 1 and 2 and two phosphorothioate internucleotide linkage modifications within positions 18-23 of the antisense strand (counting from the 5'-end of the antisense strand). The RNAi agent also comprises a 5'-PS$_2$ and a targeting ligand. In one embodiment, the 5'-PS$_2$ is at the 5'-end of the antisense strand, and the targeting ligand is at the 3'-end of the sense strand.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'-OMe, $n^5$ is 3, B1' is 2'-OMe or 2'-F, $q^1$ is 9, T1' is 2'-F, $q^2$ is 1, B2' is 2'-OMe or 2'-F, $q^3$ is 4, T2' is 2'-F, $q^4$ is 2, B3' is 2'-OMe or 2'-F, $q^5$ is 5, T3' is 2'-F, $q^6$ is 1, B4' is 2'-OMe, and $q^7$ is 1; with two phosphorothioate internucleotide linkage modifications within position 1-5 of the sense strand (counting from the 5'-end of the sense strand), and two phosphorothioate internucleotide linkage modifications at positions 1 and 2 and two phosphorothioate internucleotide linkage modifications within positions 18-23 of the antisense strand (counting from the 5'-end of the antisense strand). The RNAi agent also comprises a 5'-deoxy-5'-C-malonyl and a targeting ligand. In one embodiment, the 5'-deoxy-5'-C-malonyl is at the 5'-end of the antisense strand, and the targeting ligand is at the 3'-end of the sense strand.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'-OMe, $n^5$ is 3, B1' is 2'-OMe or 2'-F, $q^1$ is 9, T1' is 2'-F, $q^2$ is 1, B2' is 2'-OMe or 2'-F, $q^3$ is 4, $q^4$ is 0, B3' is 2'-OMe or 2'-F, $q^5$ is 7, T3' is 2'-F, $q^6$ is 1, B4' is 2'-OMe, and $q^7$ is 1; with two phosphorothioate internucleotide linkage modifications within position 1-5 of the sense strand (counting from the 5'-end), and two phosphorothioate internucleotide linkage modifications at positions 1 and 2 and two phosphorothioate internucleotide linkage modifications within positions 18-23 of the antisense strand (counting from the 5'-end). The RNAi agent also comprises a 5'-P and a targeting ligand. In one embodiment, the 5'-P is at the 5'-end of the antisense strand, and the targeting ligand is at the 3'-end of the sense strand.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'-OMe, $n^5$ is 3, B1' is 2'-OMe or 2'-F, $q^1$ is 9, T1' is 2'-F, $q^2$ is 1, B2' is 2'-OMe or 2'-F, $q^3$ is 4, $q^4$ is 0, B3' is 2'-OMe or 2'-F, $q^5$ is 7, T3' is 2'-F, $q^6$ is 1, B4' is 2'-OMe, and $q^7$ is 1; with two phosphorothioate internucleotide linkage modifications within position 1-5 of the sense strand (counting from the 5'-end), and two phosphorothioate internucleotide linkage modifications at positions 1 and 2 and two phosphorothioate internucleotide linkage modifications within positions 18-23 of the antisense strand (counting from the 5'-end). The RNAi agent also comprises a 5'-VP (e.g., a 5'-E-VP, 5'-Z-VP, or combination thereof) and a targeting ligand. In one embodiment, the 5'-VP is at the 5'-end of the antisense strand, and the targeting ligand is at the 3'-end of the sense strand.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'-OMe, $n^5$ is 3, B1' is 2'-OMe or 2'-F, $q^1$ is 9, T1' is 2'-F, $q^2$ is 1, B2' is 2'-OMe or 2'-F, $q^3$ is 4, $q^4$ is 0, B3' is 2'-OMe or 2'-F, $q^5$ is 7, T3' is 2'-F, $q^6$ is 1, B4' is 2'-OMe, and $q^7$ is 1; with two phosphorothioate internucleotide linkage modifications within position 1-5 of the sense strand (counting from the 5'-end), and two phosphorothioate internucleotide linkage modifications at positions 1 and 2 and two phosphorothioate internucleotide linkage modifications within positions 18-23 of the antisense strand (counting from the 5'-end). The RNAi agent also comprises a 5'-PS$_2$ and a targeting ligand. In one embodiment, the 5'-PS$_2$ is at the 5'-end of the antisense strand, and the targeting ligand is at the 3'-end of the sense strand.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'-OMe, $n^5$ is 3, B1' is 2'-OMe or 2'-F, $q^1$ is 9, T1' is 2'-F, $q^2$ is 1, B2' is 2'-OMe or 2'-F, $q^3$ is 4, $q^4$ is 0, B3' is 2'-OMe or 2'-F, $q^5$ is 7, T3' is 2'-F, $q^6$ is 1, B4' is 2'-OMe, and $q^7$ is 1; with two phosphorothioate internucleotide linkage modifications within position 1-5 of the sense strand (counting from the 5'-end), and two phosphorothioate internucleotide linkage modifications at positions 1 and 2 and two phosphorothioate internucleotide linkage modifications within positions 18-23 of the antisense strand (counting from the 5'-end). The RNAi agent also comprises a 5'-deoxy-5'-C-malonyl and a targeting ligand. In one embodiment, the 5'-deoxy-5'-C-malonyl is at the 5'-end of the antisense strand, and the targeting ligand is at the 3'-end of the sense strand.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'-OMe, $n^5$ is 3, B1' is 2'-OMe or 2'-F, $q^1$ is 9, T1' is 2'-F, $q^2$ is 1, B2' is 2'-OMe or 2'-F, $q^3$ is 4, T2' is 2'-F, $q^4$ is 2, B3' is 2'-OMe or 2'-F, $q^5$ is 5, T3' is 2'-F, $q^6$ is 1, B4' is 2'-F, and $q^7$ is 1; with two phosphorothioate internucleotide linkage modifications within position 1-5 of the sense strand (counting from the 5'-end of the sense strand), and two phosphorothioate internucleotide linkage modifications at positions 1 and 2 and two phosphorothioate internucleotide linkage modifications within positions 18-23 of the antisense strand (counting from the 5'-end of the antisense strand). The RNAi agent also comprises a 5'-P and a targeting ligand. In one embodiment, the 5'-P is at the 5'-end of the antisense strand, and the targeting ligand is at the 3'-end of the sense strand.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'-OMe, $n^5$ is 3, B1' is 2'-OMe or 2'-F, $q^1$ is 9, T1' is 2'-F, $q^2$ is 1, B2' is 2'-OMe or 2'-F, $q^3$ is 4, T2' is 2'-F, $q^4$ is 2, B3' is 2'-OMe or 2'-F, $q^5$ is 5, T3' is 2'-F, $q^6$ is 1, B4' is 2'-F, and $q^7$ is 1; with two phosphorothioate internucleotide linkage modifications within position 1-5 of the sense strand (counting from the 5'-end of the sense strand), and two phosphorothioate internucleotide linkage modifications at positions 1 and 2 and two phosphorothioate internucleotide linkage modifications within positions 18-23 of the antisense strand (counting from the 5'-end of the antisense strand). The RNAi agent also comprises a 5'-PS and a targeting ligand. In one embodiment, the 5'-PS is at the 5'-end of the antisense strand, and the targeting ligand is at the 3'-end of the sense strand.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'-OMe, $n^5$ is 3, B1' is 2'-OMe or 2'-F, $q^1$ is 9, T1' is 2'-F, $q^2$ is 1, B2' is 2'-OMe or 2'-F, $q^3$ is 4, T2' is 2'-F, $q^4$ is 2, B3' is 2'-OMe or 2'-F, $q^5$ is 5, T3' is 2'-F, $q^6$ is 1, B4' is 2'-F, and $q^7$ is 1; with two phosphorothioate internucleotide linkage modifications within position 1-5 of the sense strand (counting from the 5'-end of the sense strand), and two phosphorothioate internucleotide linkage modifications at positions 1 and 2 and two phosphorothioate internucleotide linkage modifications within positions 18-23 of the antisense strand (counting from the 5'-end of the antisense strand). The RNAi agent also comprises a 5'-VP (e.g., a 5'-E-VP, 5'-Z-VP, or combination thereof) and a targeting ligand. In one embodiment, the 5'-VP is at the 5'-end of the antisense strand, and the targeting ligand is at the 3'-end of the sense strand.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'-OMe, $n^5$ is 3, B1' is 2'-OMe or 2'-F, $q^1$ is 9, T1' is 2'-F, $q^2$ is 1, B2' is 2'-OMe or 2'-F, $q^3$ is 4, T2' is 2'-F, $q^4$ is 2, B3' is 2'-OMe or 2'-F, $q^5$ is 5, T3' is 2'-F, $q^6$ is 1, B4' is 2'-F, and $q^7$ is 1; with two phosphorothioate internucleotide linkage modifications within position 1-5 of the sense strand (counting from the 5'-end of the sense strand), and two phosphorothioate internucleotide linkage modifications at positions 1 and 2 and two phosphorothioate internucleotide linkage modifications within positions 18-23 of the antisense strand (counting from the 5'-end of the antisense strand). The RNAi agent also comprises a 5'-PS$_2$ and a targeting ligand. In one embodiment, the 5'-PS$_2$ is at the 5'-end of the antisense strand, and the targeting ligand is at the 3'-end of the sense strand.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'-OMe, $n^5$ is 3, B1' is 2'-OMe or 2'-F, $q^1$ is 9, T1' is 2'-F, $q^2$ is 1, B2' is 2'-OMe or 2'-F, $q^3$ is 4, T2' is 2'-F, $q^4$ is 2, B3' is 2'-OMe or 2'-F, $q^5$ is 5, T3' is 2'-F, $q^6$ is 1, B4' is 2'-F, and $q^7$ is 1; with two phosphorothioate internucleotide linkage modifications within position 1-5 of the sense strand (counting from the 5'-end of the sense strand), and two phosphorothioate internucleotide linkage modifications at positions 1 and 2 and two phosphorothioate internucleotide linkage modifications within positions 18-23 of the antisense strand (counting from the 5'-end of the antisense strand). The RNAi agent also comprises a 5'-deoxy-5'-C-malonyl and a targeting ligand. In one embodiment, the 5'-deoxy-5'-C-malonyl is at the 5'-end of the antisense strand, and the targeting ligand is at the 3'-end of the sense strand.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'-OMe, $n^5$ is 3, B1' is 2'-OMe or 2'-F, $q^1$ is 9, T1' is 2'-F, $q^2$ is 1, B2' is 2'-OMe or 2'-F, $q^3$ is 4, $q^4$ is 0, B3' is 2'-OMe or 2'-F, $q^5$ is 7, T3' is 2'-F, $q^6$ is 1, B4' is 2'-F, and $q^7$ is 1; with two phosphorothioate internucleotide linkage modifications within position 1-5 of the sense strand (counting from the 5'-end of the sense strand), and two phosphorothioate internucleotide linkage modifications at positions 1 and 2 and two phosphorothioate internucleotide linkage modifications within positions 18-23 of the antisense strand (counting from the 5'-end of the antisense strand). The RNAi agent also comprises a 5'-P and a targeting ligand. In one embodiment, the 5'-P is at the 5'-end of the antisense strand, and the targeting ligand is at the 3'-end of the sense strand.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'-OMe, $n^5$ is 3, B1' is 2'-OMe or 2'-F, $q^1$ is 9, T1' is 2'-F, $q^2$ is 1, B2' is 2'-OMe or 2'-F, $q^3$ is 4, $q^4$ is 0, B3' is 2'-OMe or 2'-F, $q^5$ is 7, T3' is 2'-F, $q^6$ is 1, B4' is 2'-F, and $q^7$ is 1; with two phosphorothioate internucleotide linkage modifications within position 1-5 of the sense strand (counting from the 5'-end of the sense strand), and two phosphorothioate internucleotide linkage modifications at positions 1 and 2 and two phosphorothioate internucleotide linkage modifications within positions 18-23 of the antisense strand (counting from the 5'-end of the antisense strand). The RNAi agent also comprises a 5'-PS and a targeting ligand. In one embodiment, the 5'-PS is at the 5'-end of the antisense strand, and the targeting ligand is at the 3'-end of the sense strand.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'-OMe, $n^5$ is 3, B1' is 2'-OMe or 2'-F, $q^1$ is 9, T1' is 2'-F, $q^2$ is 1, B2' is 2'-OMe or 2'-F, $q^3$ is 4, $q^4$ is 0, B3' is 2'-OMe or 2'-F, $q^5$ is 7, T3' is 2'-F, $q^6$ is 1, B4' is 2'-F, and $q^7$ is 1; with two phosphorothioate internucleotide linkage modifications within position 1-5 of the sense strand (counting from the 5'-end of the sense strand), and two phosphorothioate internucleotide linkage modifications at positions 1 and 2 and two phosphorothioate internucleotide linkage modifications within positions 18-23 of the antisense strand (counting from the 5'-end of the antisense strand). The RNAi agent also comprises a 5'-VP (e.g., a 5'-E-VP, 5'-Z-VP, or combination thereof) and a targeting ligand. In one embodiment, the 5'-VP is at the 5'-end of the antisense strand, and the targeting ligand is at the 3'-end of the sense strand.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'-OMe, $n^5$ is 3, B1' is 2'-OMe or 2'-F, $q^1$ is 9, T1' is 2'-F, $q^2$ is 1, B2' is 2'-OMe or 2'-F, $q^3$ is 4, $q^4$ is 0, B3' is 2'-OMe or 2'-F, $q^5$ is 7, T3' is 2'-F, $q^6$ is 1, B4' is 2'-F, and $q^7$ is 1; with two phosphorothioate internucleotide linkage modifications within position 1-5 of the sense strand (counting from the 5'-end of the sense strand), and two phosphorothioate internucleotide linkage modifications at positions 1 and 2 and two phosphorothioate internucleotide linkage modifications within positions 18-23 of the antisense strand (counting from the 5'-end of the antisense strand). The RNAi agent also comprises a 5'-PS$_2$ and a targeting ligand. In one embodiment, the 5'-PS$_2$ is at the 5'-end of the antisense strand, and the targeting ligand is at the 3'-end of the sense strand.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'-OMe, $n^5$ is 3, B1' is 2'-OMe or 2'-F, $q^1$ is 9, T1' is 2'-F, $q^2$ is 1, B2' is 2'-OMe or 2'-F, $q^3$ is 4, $q^4$ is 0, B3' is 2'-OMe or 2'-F, $q^5$ is 7, T3' is 2'-F, $q^6$ is 1, B4' is 2'-F, and $q^7$ is 1; with two phosphorothioate internucleotide linkage modifications within position 1-5 of the sense strand (counting from the 5'-end of the sense strand), and two phosphorothioate internucleotide linkage modifications at positions 1 and 2 and two phosphorothioate internucleotide linkage modifications within positions 18-23 of the antisense strand (counting from the 5'-end of the antisense strand). The RNAi agent also comprises a 5'-deoxy-5'-C-malonyl and a targeting ligand. In one embodiment, the 5'-deoxy-5'-C-malonyl is at the 5'-end of the antisense strand, and the targeting ligand is at the 3'-end of the sense strand.

In a particular embodiment, an RNAi agent of the present invention comprises:
(a) a sense strand having:
   (i) a length of 21 nucleotides;
   (ii) an ASGPR ligand attached to the 3'-end, wherein said ASGPR ligand comprises three GalNAc derivatives attached through a trivalent branched linker; and
   (iii) 2'-F modifications at positions 1, 3, 5, 7, 9 to 11, 13, 17, 19, and 21, and 2'-OMe modifications at positions 2, 4, 6, 8, 12, 14 to 16, 18, and 20 (counting from the 5' end); and
(b) an antisense strand having:
   (i) a length of 23 nucleotides;
   (ii) 2'-OMe modifications at positions 1, 3, 5, 9, 11 to 13, 15, 17, 19, 21, and 23, and 2'F modifications at positions 2, 4, 6 to 8, 10, 14, 16, 18, 20, and 22 (counting from the 5' end); and
   (iii) phosphorothioate internucleotide linkages between nucleotide positions 21 and 22, and between nucleotide positions 22 and 23 (counting from the 5' end);
wherein the dsRNA agents have a two nucleotide overhang at the 3'-end of the antisense strand, and a blunt end at the 5'-end of the antisense strand.

In another particular embodiment, an RNAi agent of the present invention comprises:
(a) a sense strand having:
   (i) a length of 21 nucleotides;
   (ii) an ASGPR ligand attached to the 3'-end, wherein said ASGPR ligand comprises three GalNAc derivatives attached through a trivalent branched linker;
   (iii) 2'-F modifications at positions 1, 3, 5, 7, 9 to 11, 13, 15, 17, 19, and 21, and 2'-OMe modifications at positions 2, 4, 6, 8, 12, 14, 16, 18, and 20 (counting from the 5' end); and
   (iv) phosphorothioate internucleotide linkages between nucleotide positions 1 and 2, and between nucleotide positions 2 and 3 (counting from the 5' end); and
(b) an antisense strand having:
   (i) a length of 23 nucleotides;
   (ii) 2'-OMe modifications at positions 1, 3, 5, 7, 9, 11 to 13, 15, 17, 19, and 21 to 23, and 2'F modifications at positions 2, 4, 6, 8, 10, 14, 16, 18, and 20 (counting from the 5' end); and
   (iii) phosphorothioate internucleotide linkages between nucleotide positions 1 and 2, between nucleotide positions 2 and 3, between nucleotide positions 21 and 22, and between nucleotide positions 22 and 23 (counting from the 5' end);
wherein the RNAi agents have a two nucleotide overhang at the 3'-end of the antisense strand, and a blunt end at the 5'-end of the antisense strand.

In another particular embodiment, a RNAi agent of the present invention comprises:
(a) a sense strand having:
   (i) a length of 21 nucleotides;
   (ii) an ASGPR ligand attached to the 3'-end, wherein said ASGPR ligand comprises three GalNAc derivatives attached through a trivalent branched linker;
   (iii) 2'-OMe modifications at positions 1 to 6, 8, 10, and 12 to 21, 2'-F modifications at positions 7, and 9, and a deoxy-nucleotide (e.g. dT) at position 11 (counting from the 5' end); and
   (iv) phosphorothioate internucleotide linkages between nucleotide positions 1 and 2, and between nucleotide positions 2 and 3 (counting from the 5' end); and
(b) an antisense strand having:
   (i) a length of 23 nucleotides;
   (ii) 2'-OMe modifications at positions 1, 3, 7, 9, 11, 13, 15, 17, and 19 to 23, and 2'-F modifications at positions 2, 4 to 6, 8, 10, 12, 14, 16, and 18 (counting from the 5' end); and
   (iii) phosphorothioate internucleotide linkages between nucleotide positions 1 and 2, between nucleotide positions 2 and 3, between nucleotide positions 21 and 22, and between nucleotide positions 22 and 23 (counting from the 5' end);
wherein the RNAi agents have a two nucleotide overhang at the 3'-end of the antisense strand, and a blunt end at the 5'-end of the antisense strand.

In another particular embodiment, a RNAi agent of the present invention comprises:
(a) a sense strand having:
   (i) a length of 21 nucleotides;
   (ii) an ASGPR ligand attached to the 3'-end, wherein said ASGPR ligand comprises three GalNAc derivatives attached through a trivalent branched linker;
   (iii) 2'-OMe modifications at positions 1 to 6, 8, 10, 12, 14, and 16 to 21, and 2'-F modifications at positions 7, 9, 11, 13, and 15; and
   (iv) phosphorothioate internucleotide linkages between nucleotide positions 1 and 2, and between nucleotide positions 2 and 3 (counting from the 5' end); and
(b) an antisense strand having:
   (i) a length of 23 nucleotides;
   (ii) 2'-OMe modifications at positions 1, 5, 7, 9, 11, 13, 15, 17, 19, and 21 to 23, and 2'-F modifications at positions 2 to 4, 6, 8, 10, 12, 14, 16, 18, and 20 (counting from the 5' end); and
   (iii) phosphorothioate internucleotide linkages between nucleotide positions 1 and 2, between nucleotide positions 2 and 3, between nucleotide positions 21 and 22, and between nucleotide positions 22 and 23 (counting from the 5' end);
wherein the RNAi agents have a two nucleotide overhang at the 3'-end of the antisense strand, and a blunt end at the 5'-end of the antisense strand.

In another particular embodiment, a RNAi agent of the present invention comprises:
(a) a sense strand having:
   (i) a length of 21 nucleotides;
   (ii) an ASGPR ligand attached to the 3'-end, wherein said ASGPR ligand comprises three GalNAc derivatives attached through a trivalent branched linker;
   (iii) 2'-OMe modifications at positions 1 to 9, and 12 to 21, and 2'-F modifications at positions 10, and 11; and
   (iv) phosphorothioate internucleotide linkages between nucleotide positions 1 and 2, and between nucleotide positions 2 and 3 (counting from the 5' end); and (b) an antisense strand having:
  (i) a length of 23 nucleotides;
  (ii) 2'-OMe modifications at positions 1, 3, 5, 7, 9, 11 to 13, 15, 17, 19, and 21 to 23, and 2'-F modifications at positions 2, 4, 6, 8, 10, 14, 16, 18, and 20 (counting from the 5' end); and
  (iii) phosphorothioate internucleotide linkages between nucleotide positions 1 and 2, between nucleotide positions 2 and 3, between nucleotide positions 21 and 22, and between nucleotide positions 22 and 23 (counting from the 5' end);
wherein the RNAi agents have a two nucleotide overhang at the 3'-end of the antisense strand, and a blunt end at the 5'-end of the antisense strand.

In another particular embodiment, a RNAi agent of the present invention comprises:
(a) a sense strand having:
  (i) a length of 21 nucleotides;
  (ii) an ASGPR ligand attached to the 3'-end, wherein said ASGPR ligand comprises three GalNAc derivatives attached through a trivalent branched linker;
  (iii) 2'-F modifications at positions 1, 3, 5, 7, 9 to 11, and 13, and 2'-OMe modifications at positions 2, 4, 6, 8, 12, and 14 to 21; and
  (iv) phosphorothioate internucleotide linkages between nucleotide positions 1 and 2, and between nucleotide positions 2 and 3 (counting from the 5' end); and
(b) an antisense strand having:
  (i) a length of 23 nucleotides;
  (ii) 2'-OMe modifications at positions 1, 3, 5 to 7, 9, 11 to 13, 15, 17 to 19, and 21 to 23, and 2'-F modifications at positions 2, 4, 8, 10, 14, 16, and 20 (counting from the 5' end); and
  (iii) phosphorothioate internucleotide linkages between nucleotide positions 1 and 2, between nucleotide positions 2 and 3, between nucleotide positions 21 and 22, and between nucleotide positions 22 and 23 (counting from the 5' end);
wherein the RNAi agents have a two nucleotide overhang at the 3'-end of the antisense strand, and a blunt end at the 5'-end of the antisense strand.

In another particular embodiment, a RNAi agent of the present invention comprises:
(a) a sense strand having:
  (i) a length of 21 nucleotides;
  (ii) an ASGPR ligand attached to the 3'-end, wherein said ASGPR ligand comprises three GalNAc derivatives attached through a trivalent branched linker;
  (iii) 2'-OMe modifications at positions 1, 2, 4, 6, 8, 12, 14, 15, 17, and 19 to 21, and 2'-F modifications at positions 3, 5, 7, 9 to 11, 13, 16, and 18; and
  (iv) phosphorothioate internucleotide linkages between nucleotide positions 1 and 2, and between nucleotide positions 2 and 3 (counting from the 5' end); and
(b) an antisense strand having:
  (i) a length of 25 nucleotides;
  (ii) 2'-OMe modifications at positions 1, 4, 6, 7, 9, 11 to 13, 15, 17, and 19 to 23, 2'-F modifications at positions 2, 3, 5, 8, 10, 14, 16, and 18, and desoxynucleotides (e.g. dT) at positions 24 and 25 (counting from the 5' end); and
  (iii) phosphorothioate internucleotide linkages between nucleotide positions 1 and 2, between nucleotide positions 2 and 3, between nucleotide positions 21 and 22, and between nucleotide positions 22 and 23 (counting from the 5' end);
wherein the RNAi agents have a four nucleotide overhang at the 3'-end of the antisense strand, and a blunt end at the 5'-end of the antisense strand.

In another particular embodiment, a RNAi agent of the present invention comprises:
(a) a sense strand having:
  (i) a length of 21 nucleotides;
  (ii) an ASGPR ligand attached to the 3'-end, wherein said ASGPR ligand comprises three GalNAc derivatives attached through a trivalent branched linker;
  (iii) 2'-OMe modifications at positions 1 to 6, 8, and 12 to 21, and 2'-F modifications at positions 7, and 9 to 11; and
  (iv) phosphorothioate internucleotide linkages between nucleotide positions 1 and 2, and between nucleotide positions 2 and 3 (counting from the 5' end); and
(b) an antisense strand having:
  (i) a length of 23 nucleotides;
  (ii) 2'-OMe modifications at positions 1, 3 to 5, 7, 8, 10 to 13, 15, and 17 to 23, and 2'-F modifications at positions 2, 6, 9, 14, and 16 (counting from the 5' end); and
  (iii) phosphorothioate internucleotide linkages between nucleotide positions 1 and 2, between nucleotide positions 2 and 3, between nucleotide positions 21 and 22, and between nucleotide positions 22 and 23 (counting from the 5' end);
wherein the RNAi agents have a two nucleotide overhang at the 3'-end of the antisense strand, and a blunt end at the 5'-end of the antisense strand.

In another particular embodiment, a RNAi agent of the present invention comprises:
(a) a sense strand having:
  (i) a length of 21 nucleotides;
  (ii) an ASGPR ligand attached to the 3'-end, wherein said ASGPR ligand comprises three GalNAc derivatives attached through a trivalent branched linker;
  (iii) 2'-OMe modifications at positions 1 to 6, 8, and 12 to 21, and 2'-F modifications at positions 7, and 9 to 11; and
  (iv) phosphorothioate internucleotide linkages between nucleotide positions 1 and 2, and between nucleotide positions 2 and 3 (counting from the 5' end); and
(b) an antisense strand having:
  (i) a length of 23 nucleotides;
  (ii) 2'-OMe modifications at positions 1, 3 to 5, 7, 10 to 13, 15, and 17 to 23, and 2'-F modifications at positions 2, 6, 8, 9, 14, and 16 (counting from the 5' end); and
  (iii) phosphorothioate internucleotide linkages between nucleotide positions 1 and 2, between nucleotide positions 2 and 3, between nucleotide positions 21 and 22, and between nucleotide positions 22 and 23 (counting from the 5' end);
wherein the RNAi agents have a two nucleotide overhang at the 3'-end of the antisense strand, and a blunt end at the 5'-end of the antisense strand.

In another particular embodiment, a RNAi agent of the present invention comprises:
(a) a sense strand having:
  (i) a length of 19 nucleotides;
  (ii) an ASGPR ligand attached to the 3'-end, wherein said ASGPR ligand comprises three GalNAc derivatives attached through a trivalent branched linker;
  (iii) 2'-OMe modifications at positions 1 to 4, 6, and 10 to 19, and 2'-F modifications at positions 5, and 7 to 9; and (iv) phosphorothioate internucleotide linkages between nucleotide positions 1 and 2, and between nucleotide positions 2 and 3 (counting from the 5' end); and
(b) an antisense strand having:
(i) a length of 21 nucleotides;
(ii) 2'-OMe modifications at positions 1, 3 to 5, 7, 10 to 13, 15, and 17 to 21, and 2'-F modifications at positions 2, 6, 8, 9, 14, and 16 (counting from the 5' end); and
(iii) phosphorothioate internucleotide linkages between nucleotide positions 1 and 2, between nucleotide positions 2 and 3, between nucleotide positions 19 and 20, and between nucleotide positions 20 and 21 (counting from the 5' end);

wherein the RNAi agents have a two nucleotide overhang at the 3'-end of the antisense strand, and a blunt end at the 5'-end of the antisense strand.

In certain embodiments, the iRNA for use in the methods of the invention is an agent selected from agents listed in Table 3, Table 5, or Table 6. These agents may further comprise a ligand.

III. iRNAs Conjugated to Ligands

Another modification of the RNA of an iRNA of the invention involves chemically linking to the iRNA one or more ligands, moieties or conjugates that enhance the activity, cellular distribution, or cellular uptake of the iRNA e.g., into a cell. Such moieties include but are not limited to lipid moieties such as a cholesterol moiety (Letsinger et al., *Proc. Natl. Acad. Sci. USA,* 1989, 86: 6553-6556). In other embodiments, the ligand is cholic acid (Manoharan et al., *Biorg. Med. Chem. Let.,* 1994, 4:1053-1060), a thioether, e.g., beryl-S-tritylthiol (Manoharan et al., *Ann. N. Y. Acad. Sci.,* 1992, 660:306-309; Manoharan et al., *Biorg. Med. Chem. Let.,* 1993, 3:2765-2770), a thiocholesterol (Oberhauser et al., *Nucl. Acids Res.,* 1992, 20:533-538), an aliphatic chain, e.g., dodecandiol or undecyl residues (Saison-Behmoaras et al., *EMBO J,* 1991, 10:1111-1118; Kabanov et al., *FEBS Lett.,* 1990, 259:327-330; Svinarchuk et al., *Biochimie,* 1993, 75:49-54), aphospholipid, e.g., di-hexadecyl-rac-glycerol or triethyl-ammonium 1,2-di-O-hexadecyl-rac-glycero-3-phosphonate (Manoharan et al., *Tetrahedron Lett.,* 1995, 36:3651-3654; Shea et al., *Nucl. Acids Res.,* 1990, 18:3777-3783), a polyamine or a polyethylene glycol chain (Manoharan et al., *Nucleosides & Nucleotides,* 1995, 14:969-973), or adamantane acetic acid (Manoharan et al., *Tetrahedron Lett.,* 1995, 36:3651-3654), a palmityl moiety (Mishra et al., *Biochim. Biophys. Acta,* 1995, 1264:229-237), or an octadecylamine or hexylamino-carbonyloxycholesterol moiety (Crooke et al., *J. Pharmacol. Exp. Ther.,* 1996, 277:923-937).

In certain embodiments, a ligand alters the distribution, targeting, or lifetime of an iRNA agent into which it is incorporated. In preferred embodiments a ligand provides an enhanced affinity for a selected target, e.g., molecule, cell or cell type, compartment, e.g., a cellular or organ compartment, tissue, organ or region of the body, as, e.g., compared to a species absent such a ligand. Preferred ligands do not take part in duplex pairing in a duplexed nucleic acid.

Ligands can include a naturally occurring substance, such as a protein (e.g., human serum albumin (HSA), low-density lipoprotein (LDL), or globulin); carbohydrate (e.g., a dextran, pullulan, chitin, chitosan, inulin, cyclodextrin, N-acetylglucosamine, N-acetylgalactosamine, or hyaluronic acid); or a lipid. The ligand can also be a recombinant or synthetic molecule, such as a synthetic polymer, e.g., a synthetic polyamino acid. Examples of polyamino acids include polyamino acid is a polylysine (PLL), poly L-aspartic acid, poly L-glutamic acid, styrene-maleic acid anhydride copolymer, poly(L-lactide-co-glycolied) copolymer, divinyl ether-maleic anhydride copolymer, N-(2-hydroxypropyl)methacrylamide copolymer (HMPA), polyethylene glycol (PEG), polyvinyl alcohol (PVA), polyurethane, poly (2-ethylacryllic acid), N-isopropylacrylamide polymers, or polyphosphazine. Example of polyamines include: polyethylenimine, polylysine (PLL), spermine, spermidine, polyamine, pseudopeptide-polyamine, peptidomimetic polyamine, dendrimer polyamine, arginine, amidine, protamine, cationic lipid, cationic porphyrin, quaternary salt of a polyamine, or an alpha helical peptide.

Ligands can also include targeting groups, e.g., a cell or tissue targeting agent, e.g., a lectin, glycoprotein, lipid or protein, e.g., an antibody, that binds to a specified cell type such as a kidney cell. A targeting group can be a thyrotropin, melanotropin, lectin, glycoprotein, surfactant protein A, Mucin carbohydrate, multivalent lactose, multivalent galactose, N-acetyl-galactosamine, N-acetyl-glucosamine multivalent mannose, multivalent fucose, glycosylated polyaminoacids, multivalent galactose, transferrin, bisphosphonate, polyglutamate, polyaspartate, a lipid, cholesterol, a steroid, bile acid, folate, vitamin B12, vitamin A, biotin, or an RGD peptide or RGD peptide mimetic. In certain embodiments, the ligand is a multivalent galactose, e.g., an N-acetyl-galactosamine.

Other examples of ligands include dyes, intercalating agents (e.g. acridines), cross-linkers (e.g. psoralene, mitomycin C), porphyrins (TPPC4, texaphyrin, Sapphyrin), polycyclic aromatic hydrocarbons (e.g., phenazine, dihydrophenazine), artificial endonucleases (e.g. EDTA), lipophilic molecules, e.g., cholesterol, cholic acid, adamantane acetic acid, 1-pyrene butyric acid, dihydrotestosterone, 1,3-Bis-O (hexadecyl)glycerol, geranyloxyhexyl group, hexadecylglycerol, bomeol, menthol, 1,3-propanediol, heptadecyl group, palmitic acid, myristic acid, O3-(oleoyl) lithocholic acid, O3-(oleoyl)cholenic acid, dimethoxytrityl, or phenoxazine) and peptide conjugates (e.g., antennapedia peptide, Tat peptide), alkylating agents, phosphate, amino, mercapto, PEG (e.g., PEG-40K), MPEG, [MPEG]$_2$, polyamino, alkyl, substituted alkyl, radiolabeled markers, enzymes, haptens (e.g. biotin), transport/absorption facilitators (e.g., aspirin, vitamin E, folic acid), synthetic ribonucleases (e.g., imidazole, bisimidazole, histamine, imidazole clusters, acridine-imidazole conjugates, Eu3+ complexes of tetraazamacrocycles), dinitrophenyl, HRP, or AP.

Ligands can be proteins, e.g., glycoproteins, or peptides, e.g., molecules having a specific affinity for a co-ligand, or antibodies e.g., an antibody, that binds to a specified cell type such as a hepatic cell. Ligands can also include hormones and hormone receptors. They can also include non-peptidic species, such as lipids, lectins, carbohydrates, vitamins, cofactors, multivalent lactose, multivalent galactose, N-acetyl-galactosamine, N-acetyl-glucosamine multivalent mannose, or multivalent fucose. The ligand can be, for example, a lipopolysaccharide, an activator of p38 MAP kinase, or an activator of NF-κB.

The ligand can be a substance, e.g., a drug, which can increase the uptake of the iRNA agent into the cell, for example, by disrupting the cell's cytoskeleton, e.g., by disrupting the cell's microtubules, microfilaments, or intermediate filaments. The drug can be, for example, taxol, vincristine, vinblastine, cytochalasin, nocodazole, japlakinolide, latrunculin A, phalloidin, swinholide A, indanocine, or myoservin.

In some embodiments, a ligand attached to an iRNA as described herein acts as a pharmacokinetic modulator (PK modulator). PK modulators include lipophiles, bile acids, steroids, phospholipid analogues, peptides, protein binding agents, PEG, vitamins, etc. Exemplary PK modulators include, but are not limited to, cholesterol, fatty acids, cholic acid, lithocholic acid, dialkylglycerides, diacylglyceride, phospholipids, sphingolipids, naproxen, ibuprofen, vitamin E, biotin. Oligonucleotides that comprise a number of phosphorothioate linkages are also known to bind to serum protein, thus short oligonucleotides, e.g., oligonucleotides of about 5 bases, 10 bases, 15 bases, or 20 bases, comprising multiple of phosphorothioate linkages in the backbone are also amenable to the present invention as ligands (e.g. as PK modulating ligands). In addition, aptamers that bind serum components (e.g. serum proteins) are also suitable for use as PK modulating ligands in the embodiments described herein.

Ligand-conjugated iRNAs of the invention may be synthesized by the use of an oligonucleotide that bears a pendant reactive functionality, such as that derived from the attachment of a linking molecule onto the oligonucleotide (described below). This reactive oligonucleotide may be reacted directly with commercially-available ligands, ligands that are synthesized bearing any of a variety of protecting groups, or ligands that have a linking moiety attached thereto.

The oligonucleotides used in the conjugates of the present invention may be conveniently and routinely made through the well-known technique of solid-phase synthesis. Equipment for such synthesis is sold by several vendors including, for example, Applied Biosystems® (Foster City, Calif.). Any other methods for such synthesis known in the art may additionally or alternatively be employed. It is also known to use similar techniques to prepare other oligonucleotides, such as the phosphorothioates and alkylated derivatives.

In the ligand-conjugated iRNAs and ligand-molecule bearing sequence-specific linked nucleosides of the present invention, the oligonucleotides and oligonucleosides may be assembled on a suitable DNA synthesizer utilizing standard nucleotide or nucleoside precursors, or nucleotide or nucleoside conjugate precursors that already bear the linking moiety, ligand-nucleotide or nucleoside-conjugate precursors that already bear the ligand molecule, or non-nucleoside ligand-bearing building blocks.

When using nucleotide-conjugate precursors that already bear a linking moiety, the synthesis of the sequence-specific linked nucleosides is typically completed, and the ligand molecule is then reacted with the linking moiety to form the ligand-conjugated oligonucleotide. In some embodiments, the oligonucleotides or linked nucleosides of the present invention are synthesized by an automated synthesizer using phosphoramidites derived from ligand-nucleoside conjugates in addition to the standard phosphoramidites and non-standard phosphoramidites that are commercially available and routinely used in oligonucleotide synthesis.

A. Lipid Conjugates

In certain embodiments, the ligand or conjugate is a lipid or lipid-based molecule. Such a lipid or lipid-based molecule preferably binds a serum protein, e.g., human serum albumin (HSA). An HSA binding ligand allows for distribution of the conjugate to a target tissue, e.g., a non-kidney target tissue of the body. For example, the target tissue can be the liver, including parenchymal cells of the liver. Other molecules that can bind HSA can also be used as ligands. For example, naproxen or aspirin can be used. A lipid or lipid-based ligand can (a) increase resistance to degradation of the conjugate, (b) increase targeting or transport into a target cell or cell membrane, or (c) can be used to adjust binding to a serum protein, e.g., HSA.

A lipid based ligand can be used to inhibit, e.g., control the binding of the conjugate to a target tissue. For example, a lipid or lipid-based ligand that binds to HSA more strongly will be less likely to be targeted to the kidney and therefore less likely to be cleared from the body. A lipid or lipid-based ligand that binds to HSA less strongly can be used to target the conjugate to the kidney.

In certain embodiments, the lipid based ligand binds HSA. Preferably, it binds HSA with a sufficient affinity such that the conjugate will be preferably distributed to a non-kidney tissue. However, it is preferred that the affinity not be so strong that the HSA-ligand binding cannot be reversed.

In other embodiments, the lipid based ligand binds HSA weakly or not at all, such that the conjugate will be preferably distributed to the kidney. Other moieties that target to kidney cells can also be used in place of, or in addition to, the lipid based ligand.

In another aspect, the ligand is a moiety, e.g., a vitamin, which is taken up by a target cell, e.g., a proliferating cell. These are particularly useful for treating disorders characterized by unwanted cell proliferation, e.g., of the malignant or non-malignant type, e.g., cancer cells. Exemplary vitamins include vitamin A, E, and K. Other exemplary vitamins include are B vitamin, e.g., folic acid, B12, riboflavin, biotin, pyridoxal or other vitamins or nutrients taken up by target cells such as liver cells. Also included are HSA and low density lipoprotein (LDL).

B. Cell Permeation Agents

In another aspect, the ligand is a cell-permeation agent, preferably a helical cell-permeation agent. Preferably, the agent is amphipathic. An exemplary agent is a peptide such as tat or antennopedia. If the agent is a peptide, it can be modified, including a peptidylmimetic, invertomers, non-peptide or pseudo-peptide linkages, and use of D-amino acids. The helical agent is preferably an alpha-helical agent, which preferably has a lipophilic and a lipophobic phase.

The ligand can be a peptide or peptidomimetic. A peptidomimetic (also referred to herein as an oligopeptidomimetic) is a molecule capable of folding into a defined three-dimensional structure similar to a natural peptide. The attachment of peptide and peptidomimetics to iRNA agents can affect pharmacokinetic distribution of the iRNA, such as by enhancing cellular recognition and absorption. The peptide or peptidomimetic moiety can be about 5-50 amino acids long, e.g., about 5, 10, 15, 20, 25, 30, 35, 40, 45, or 50 amino acids long.

A peptide or peptidomimetic can be, for example, a cell permeation peptide, cationic peptide, amphipathic peptide, or hydrophobic peptide (e.g., consisting primarily of Tyr, Trp, or Phe). The peptide moiety can be a dendrimer peptide, constrained peptide or crosslinked peptide. In another alternative, the peptide moiety can include a hydrophobic membrane translocation sequence (MTS). An exemplary hydrophobic MTS-containing peptide is RFGF having the amino acid sequence AAVALLPAVLLALLAP (SEQ ID NO: 15). An RFGF analogue (e.g., amino acid sequence AALLPVL-LAAP (SEQ ID NO:16) containing a hydrophobic MTS can also be a targeting moiety. The peptide moiety can be a "delivery" peptide, which can carry large polar molecules including peptides, oligonucleotides, and protein across cell membranes. For example, sequences from the HIV Tat protein (GRKKRRQRRRPPQ (SEQ ID NO:17) and the Drosophila Antennapedia protein (RQIKIWFQ-NRRMKWKK (SEQ ID NO:18) have been found to be capable of functioning as delivery peptides. A peptide or peptidomimetic can be encoded by a random sequence of DNA, such as a peptide identified from a phage-display library, or one-bead-one-compound (OBOC) combinatorial library (Lam et al., Nature, 354:82-84, 1991). Examples of a peptide or peptidomimetic tethered to a dsRNA agent via an incorporated monomer unit for cell targeting purposes is an arginine-glycine-aspartic acid (RGD)-peptide, or RGD mimic. A peptide moiety can range in length from about 5 amino acids to about 40 amino acids. The peptide moieties can have a structural modification, such as to increase stability or direct conformational properties. Any of the structural modifications described below can be utilized.

An RGD peptide for use in the compositions and methods of the invention may be linear or cyclic, and may be modified, e.g., glycosylated or methylated, to facilitate targeting to a specific tissue(s). RGD-containing peptides and peptidiomimemtics may include D-amino acids, as well as synthetic RGD mimics. In addition to RGD, one can use other moieties that target the integrin ligand. Preferred conjugates of this ligand target PECAM-1 or VEGF.

A "cell permeation peptide" is capable of permeating a cell, e.g., a microbial cell, such as a bacterial or fungal cell, or a mammalian cell, such as a human cell. A microbial cell-permeating peptide can be, for example, an α-helical linear peptide (e.g., LL-37 or Ceropin P1), a disulfide bond-containing peptide (e.g., α-defensin, β-defensin or bactenecin), or a peptide containing only one or two dominating amino acids (e.g., PR-39 or indolicidin). A cell permeation peptide can also include a nuclear localization signal (NLS). For example, a cell permeation peptide can be a bipartite amphipathic peptide, such as MPG, which is derived from the fusion peptide domain of HIV-1 gp41 and the NLS of SV40 large T antigen (Simeoni et al., Nucl. Acids Res. 31:2717-2724, 2003).

C. Carbohydrate Conjugates

In some embodiments of the compositions and methods of the invention, an iRNA further comprises a carbohydrate. The carbohydrate conjugated iRNA is advantageous for the in vivo delivery of nucleic acids, as well as compositions suitable for in vivo therapeutic use, as described herein. As used herein, "carbohydrate" refers to a compound which is either a carbohydrate per se made up of one or more monosaccharide units having at least 6 carbon atoms (which can be linear, branched or cyclic) with an oxygen, nitrogen or sulfur atom bonded to each carbon atom; or a compound having as a part thereof a carbohydrate moiety made up of one or more monosaccharide units each having at least six carbon atoms (which can be linear, branched or cyclic), with an oxygen, nitrogen or sulfur atom bonded to each carbon atom. Representative carbohydrates include the sugars (mono-, di-, tri-, and oligosaccharides containing from about 4, 5, 6, 7, 8, or 9 monosaccharide units), and polysaccharides such as starches, glycogen, cellulose and polysaccharide gums. Specific monosaccharides include C5 and above (e.g., C5, C6, C7, or C8) sugars; di- and trisaccharides include sugars having two or three monosaccharide units (e.g., C5, C6, C7, or C8).

In certain embodiments, a carbohydrate conjugate for use in the compositions and methods of the invention is a monosaccharide.

In one embodiment, a carbohydrate conjugate for use in the compositions and methods of the invention is selected from the group consisting of:

Formula II

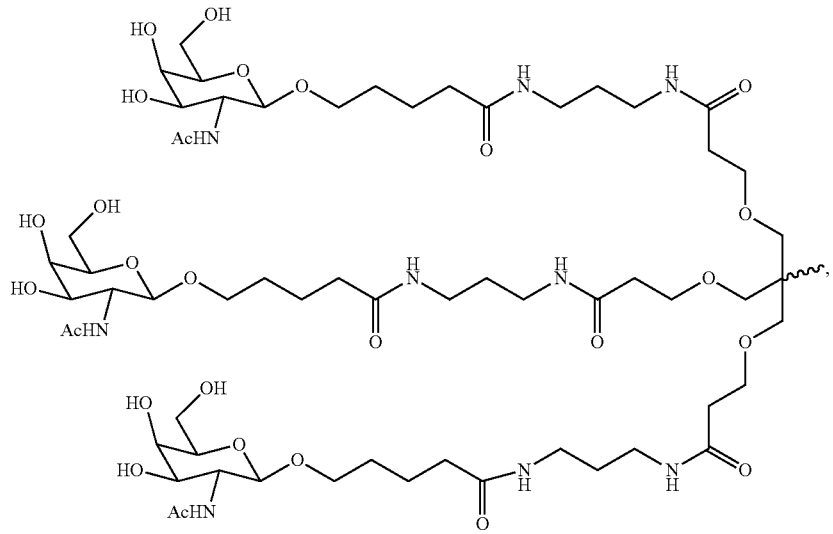

Formula III
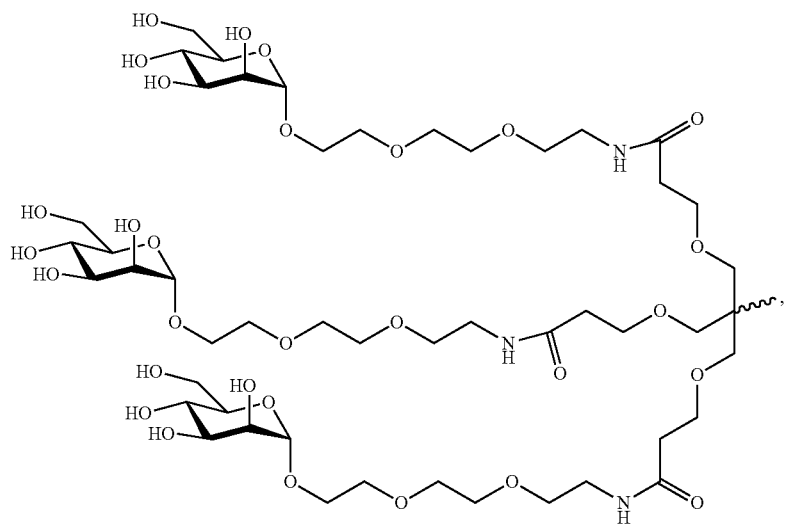
Formula IV
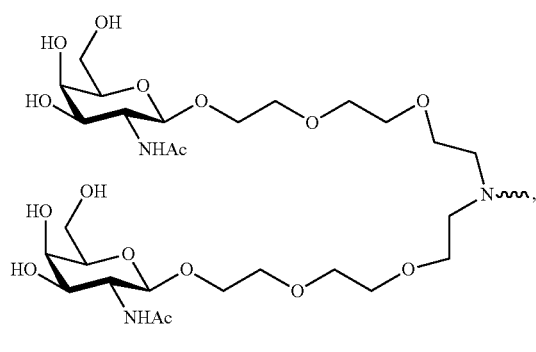
Formula V
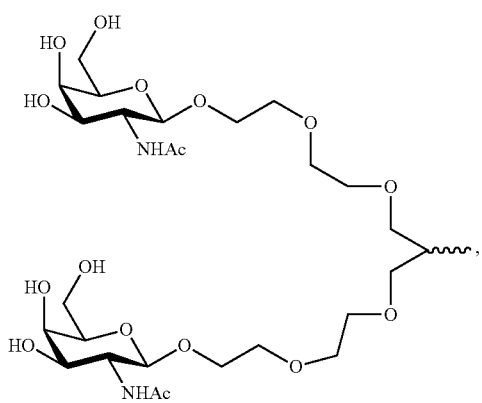
Formula VI
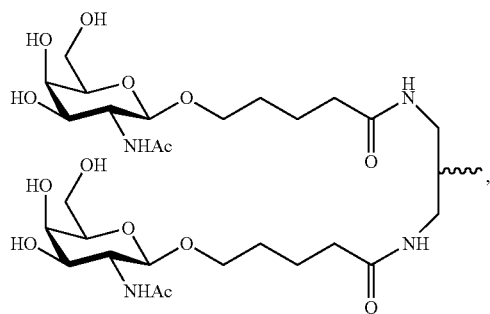
Formula VII
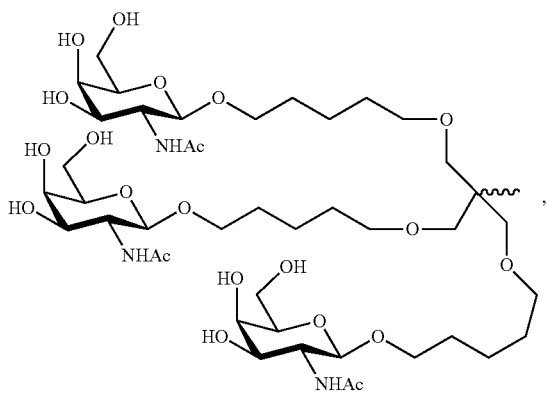
Formula VIII
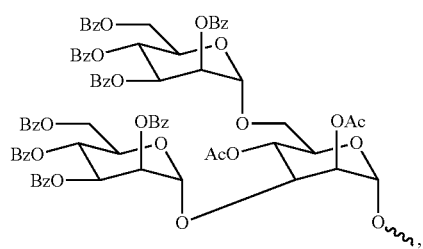

Formula IX
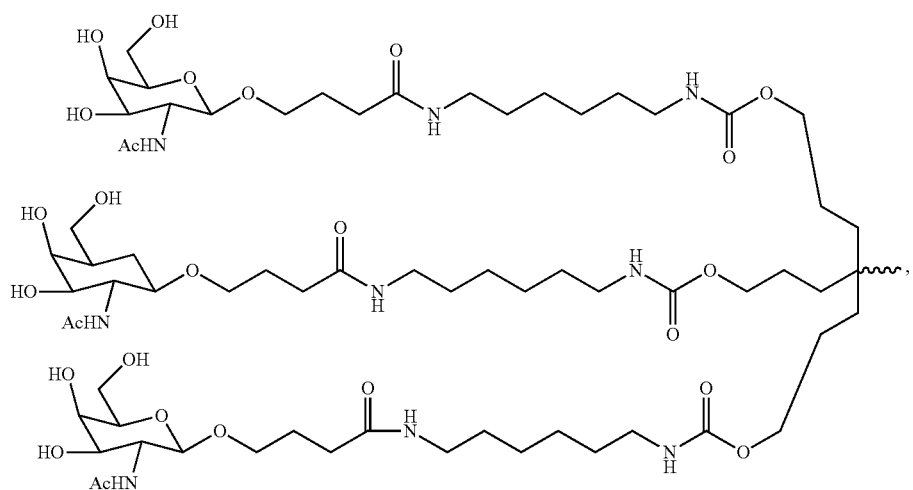
Formula X
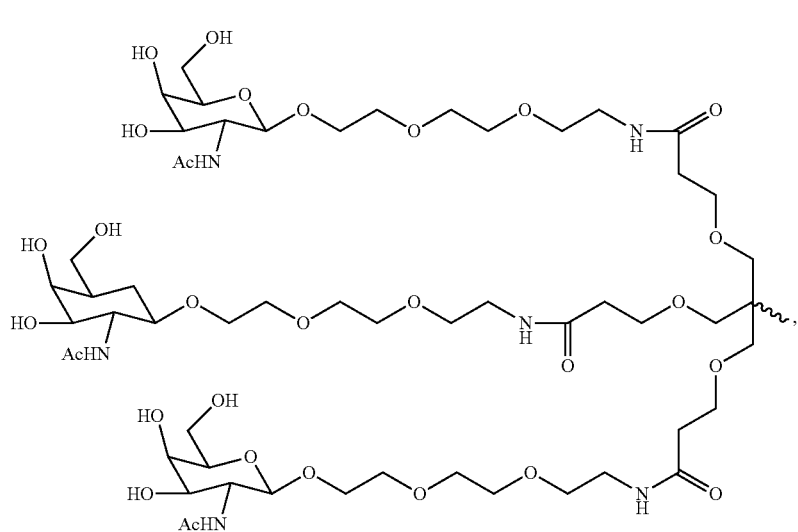
Formula XI
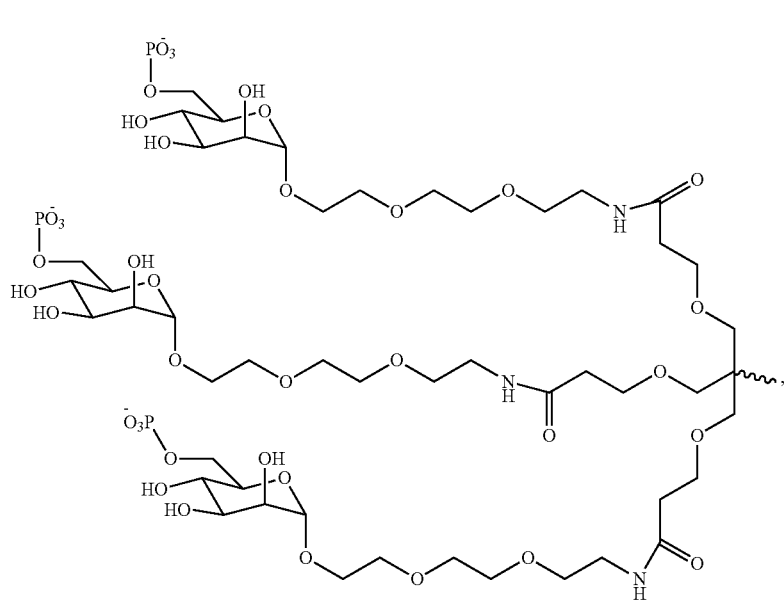

-continued
Formula XII
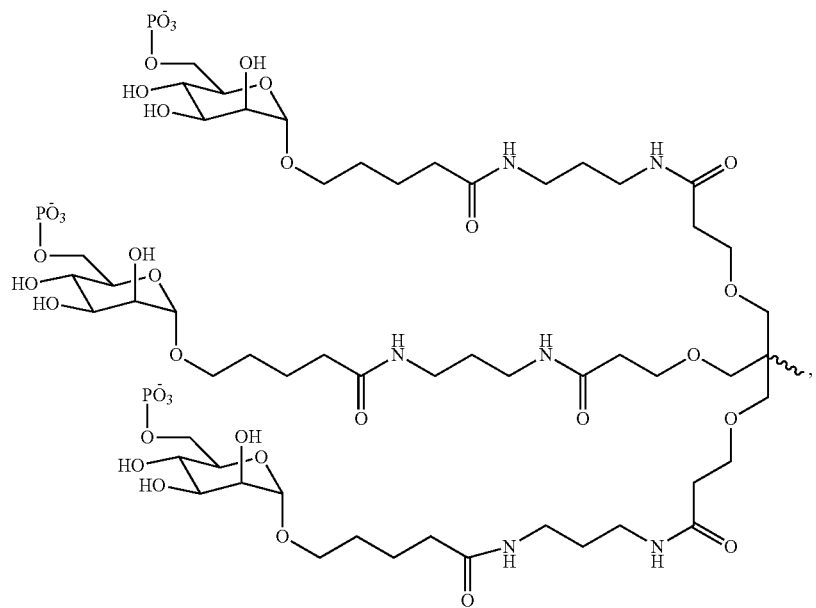
Formula XIII
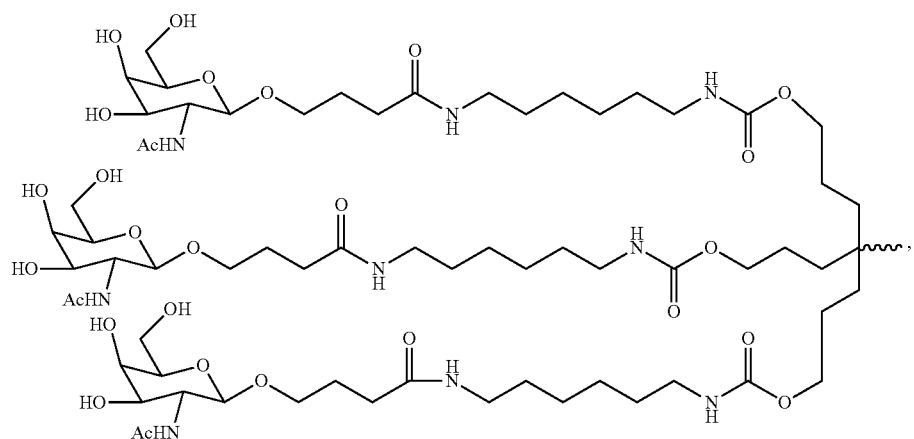
Formula XIV
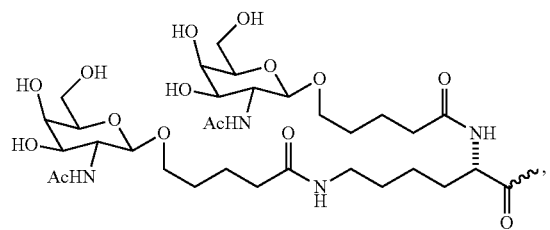
Formula XV
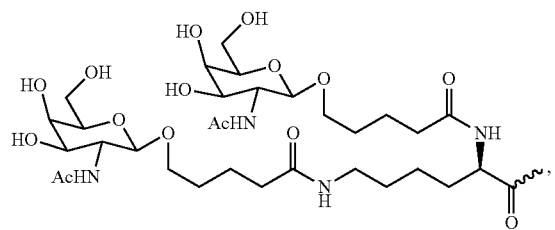
Formula XVI
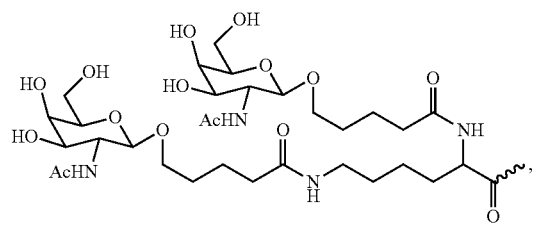
Formula XVII
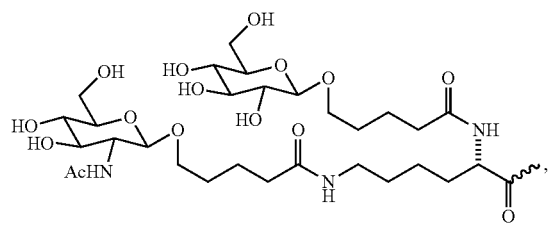

-continued
Formula XVIII
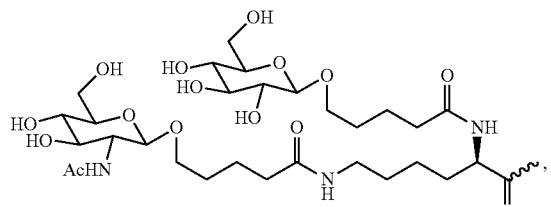
Formula XIX
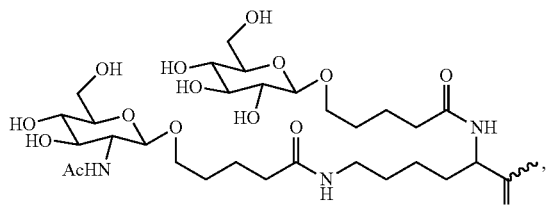
Formula XX
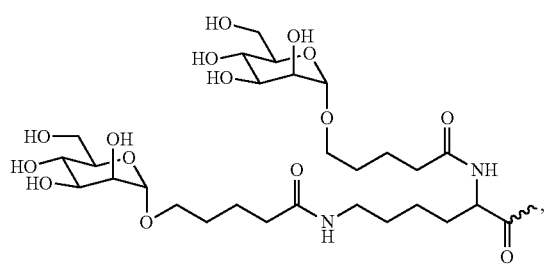
Formula XXI
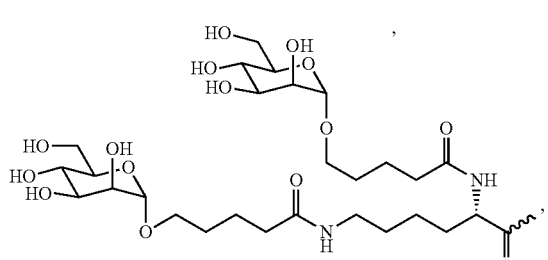
Formula XXII
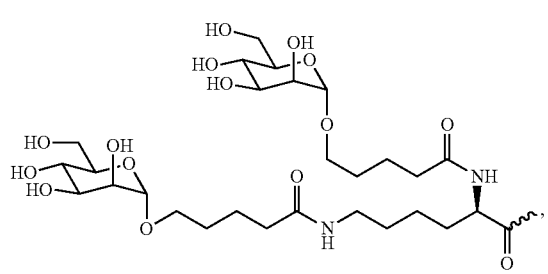
Formula XXIII
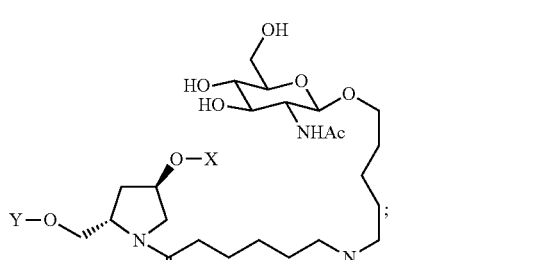
(Formula XXIV)
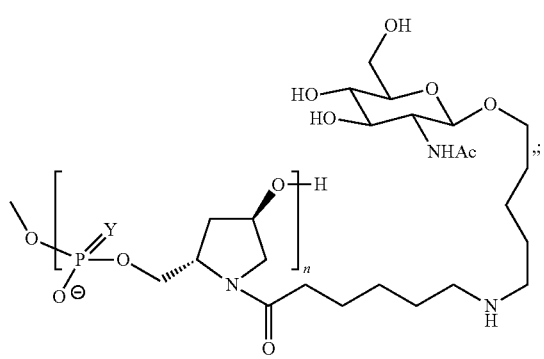
(Formula XXV)
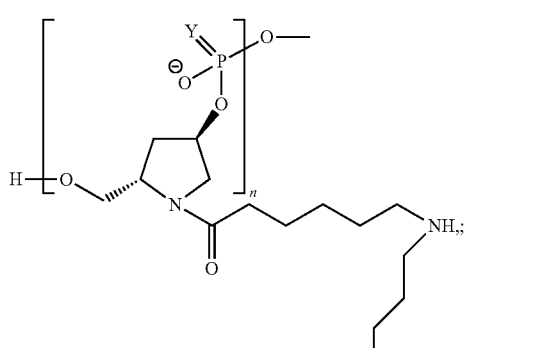
wherein Y is O or S and n is 3-6
wherein Y is O or S and n is 3-6
Formula XXVI
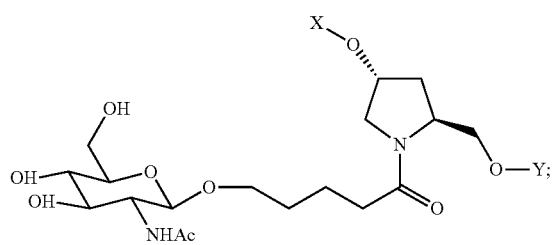

(Formula XXVII)
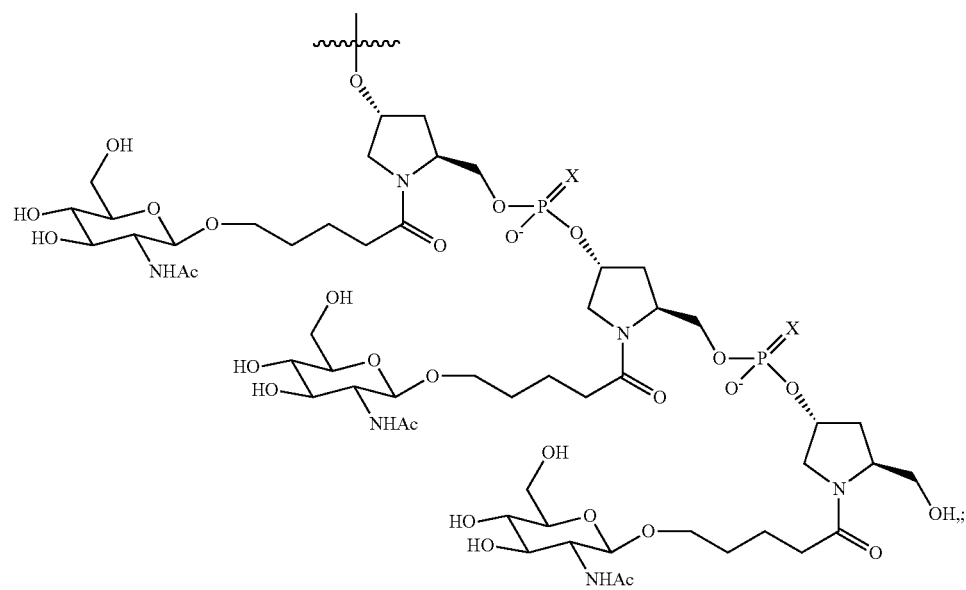
wherein X is O or S
Formula XXVII
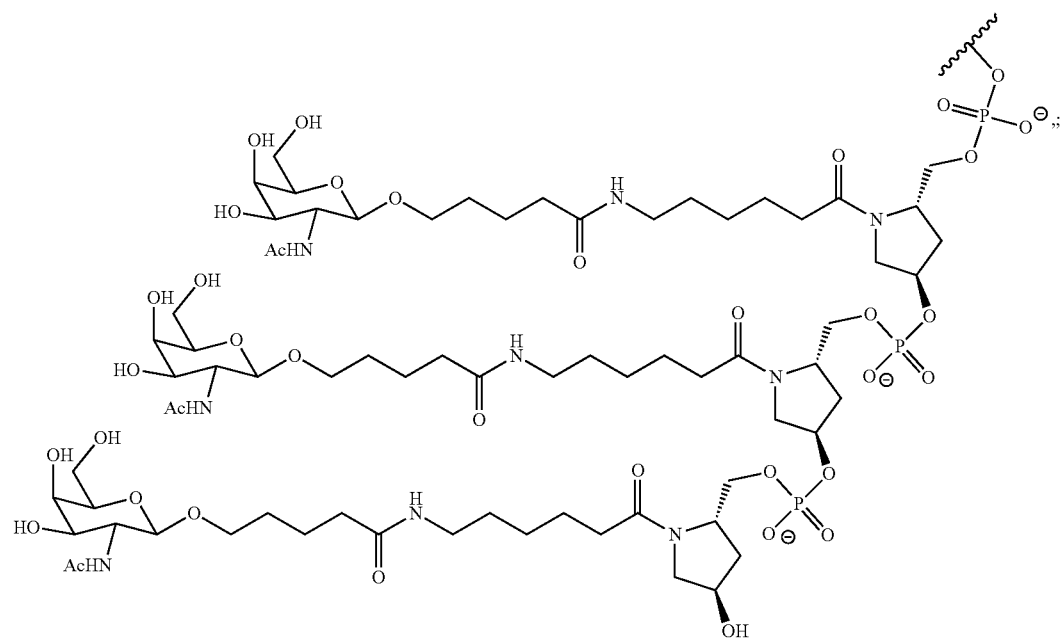

Formula XXIX
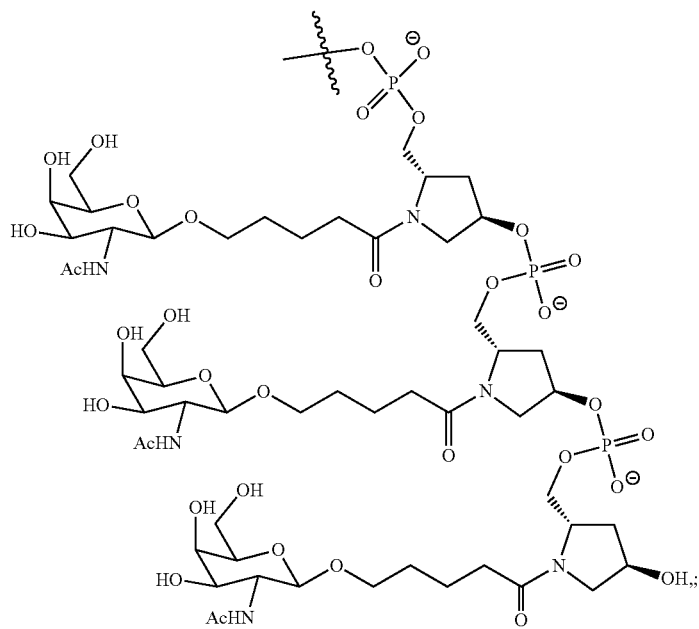
Formula XXX
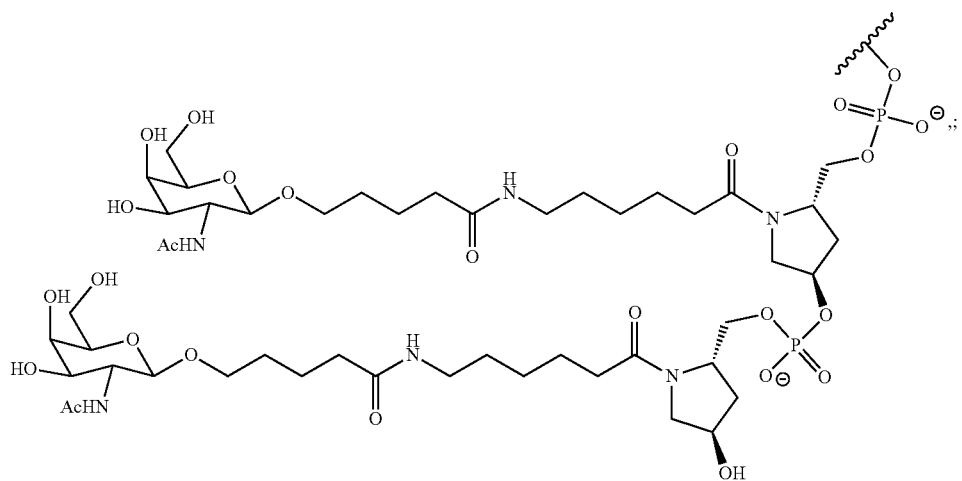
Formula XXXI
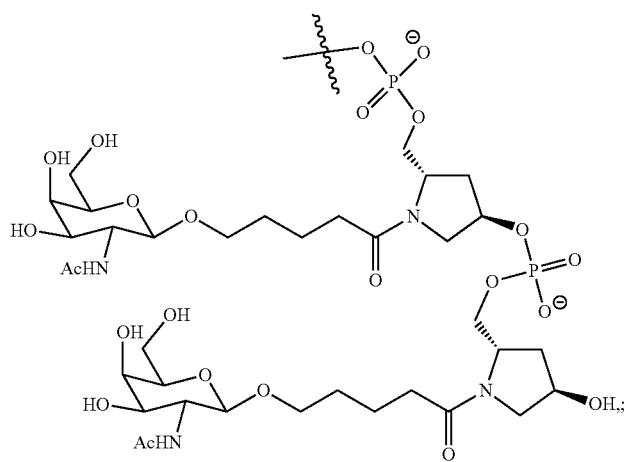

Formula XXXII
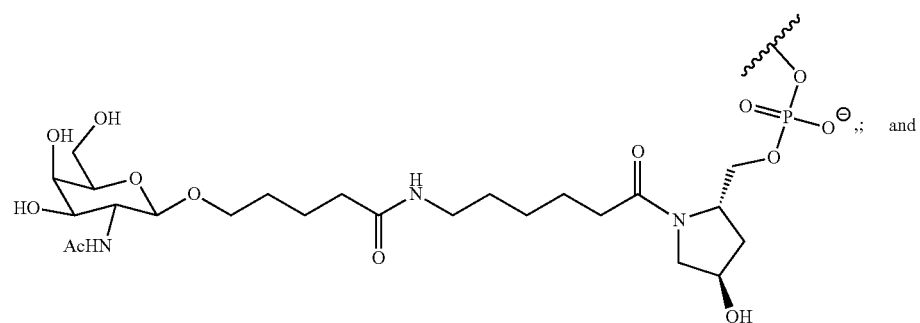
Formula XXXIII
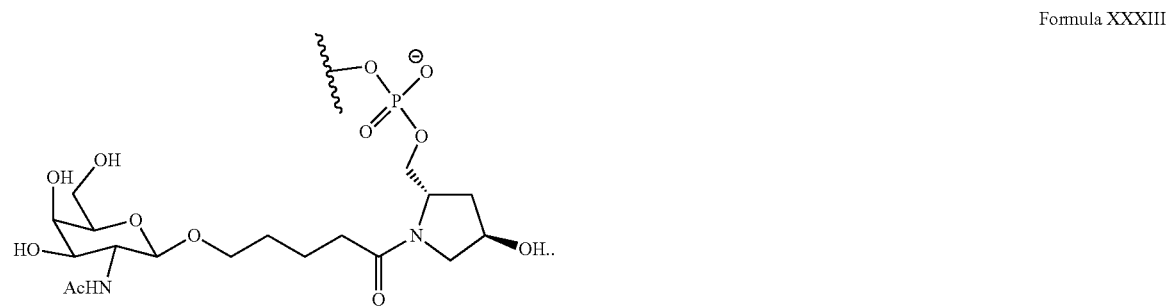
Formula XXXIV
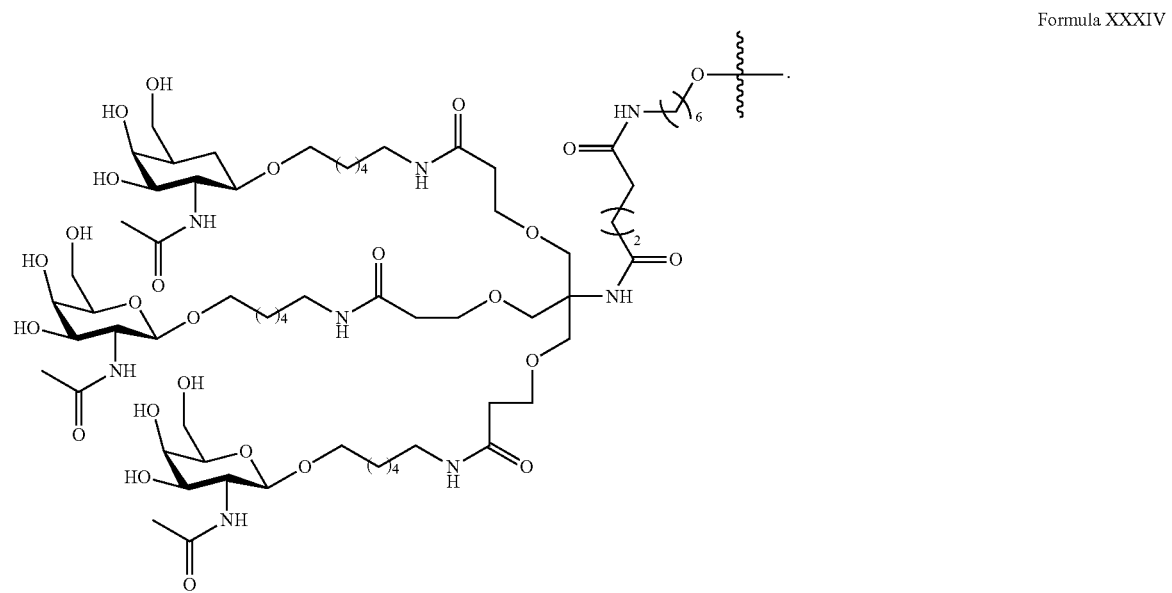

In another embodiment, a carbohydrate conjugate for use in the compositions and methods of the invention is a monosaccharide. In one embodiment, the monosaccharide is an N-acetylgalactosamine, such as
Formula II
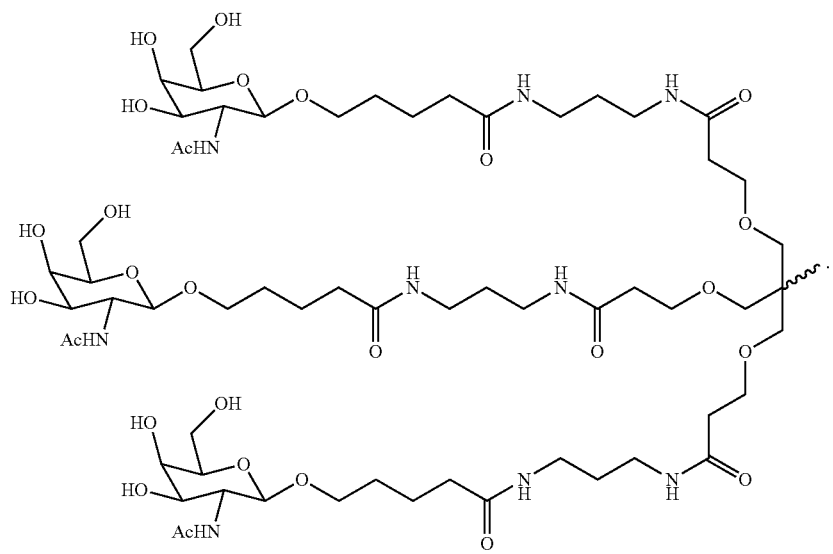 [SMILES: CC(=O)NC1C(OCCCCC(=O)NCCCNC(=O)CCOCC(C)(COCCC(=O)NCCCNC(=O)CCCCOC2OC(CO)C(O)C(O)C2NC(C)=O)COCCC(=O)NCCCNC(=O)CCCCOC2OC(CO)C(O)C(O)C2NC(C)=O)OC(CO)C(O)C1O]
Another representative carbohydrate conjugate for use in the embodiments described herein includes, but is not limited to,

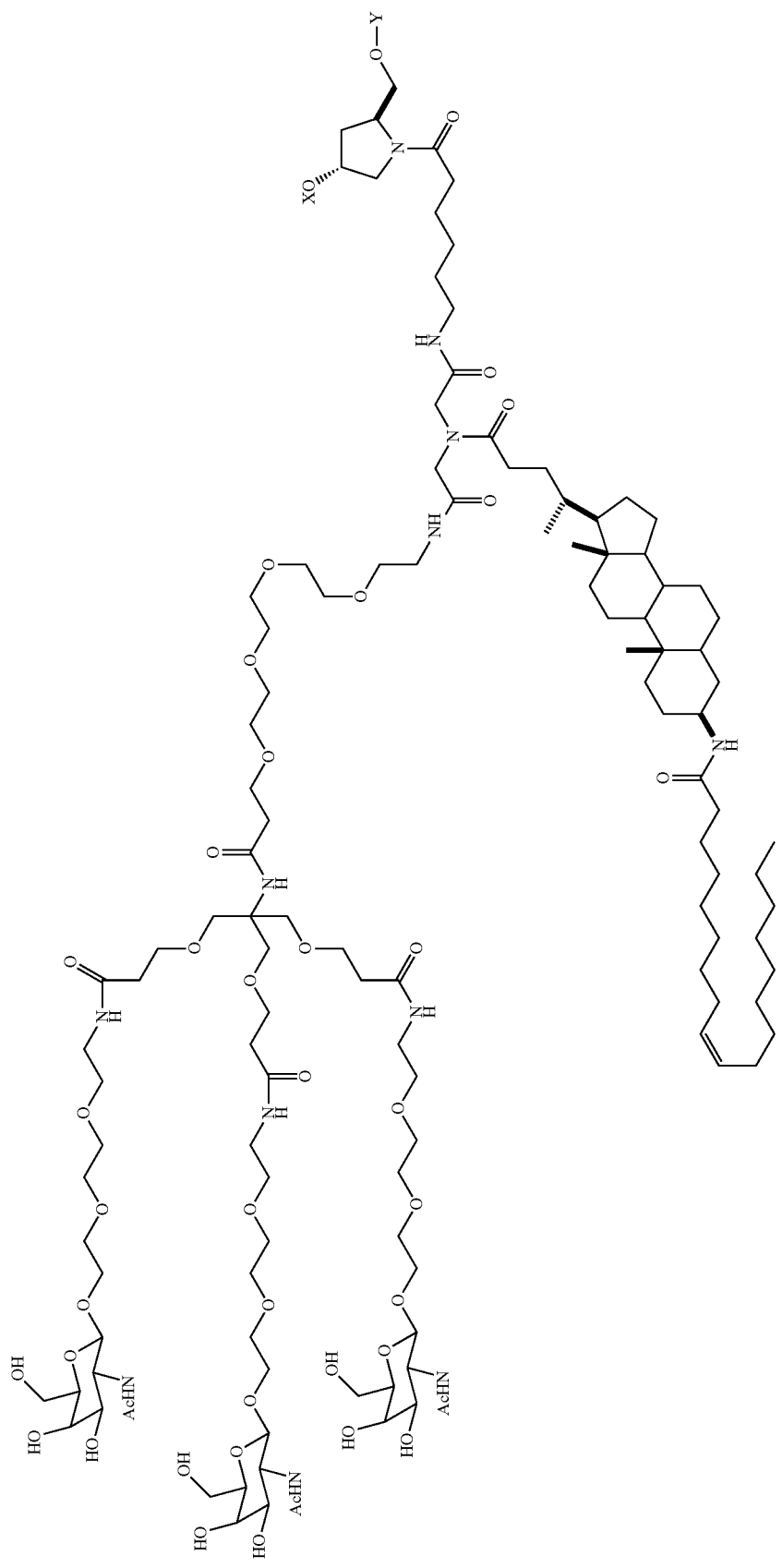

when one of X or Y is an oligonucleotide, the other is a hydrogen.

In certain embodiments of the invention, the GalNAc or GalNAc derivative is attached to an iRNA agent of the invention via a monovalent linker. In some embodiments, the GaNAc or GaNAc derivative is attached to an iRNA agent of the invention via a bivalent linker. In yet other embodiments of the invention, the GalNAc or GalNAc derivative is attached to an iRNA agent of the invention via a trivalent linker.

In one embodiment, the double stranded RNAi agents of the invention comprise one GaNAc or GalNAc derivative attached to the iRNA agent, e.g., the 5' end of the sense strand of a dsRNA agent, or the 5' end of one or both sense strands of a dual targeting RNAi agent as described herein.

In another embodiment, the double stranded RNAi agents of the invention comprise a plurality (e.g., 2, 3, 4, 5, or 6) GaNAc or GaNAc derivatives, each independently attached to a plurality of nucleotides of the double stranded RNAi agent through a plurality of monovalent linkers.

In some embodiments, for example, when the two strands of an iRNA agent of the invention are part of one larger molecule connected by an uninterrupted chain of nucleotides between the 3'-end of one strand and the 5'-end of the respective other strand forming a hairpin loop comprising, a plurality of unpaired nucleotides, each unpaired nucleotide within the hairpin loop may independently comprise a GalNAc or GalNAc derivative attached via a monovalent linker.

In some embodiments, the carbohydrate conjugate further comprises one or more additional ligands as described above, such as, but not limited to, a PK modulator or a cell permeation peptide.

Additional carbohydrate conjugates and linkers suitable for use in the present invention include those described in PCT Publication Nos. WO 2014/179620 and WO 2014/179627, the entire contents of each of which are incorporated herein by reference.

D. Linkers

In some embodiments, the conjugate or ligand described herein can be attached to an iRNA oligonucleotide with various linkers that can be cleavable or non-cleavable.

The term "linker" or "linking group" means an organic moiety that connects two parts of a compound, e.g., covalently attaches two parts of a compound. Linkers typically comprise a direct bond or an atom such as oxygen or sulfur, a unit such as NR8, C(O), C(O)NH, SO, $SO_2$, $SO_2$NH or a chain of atoms, such as, but not limited to, substituted or unsubstituted alkyl, substituted or unsubstituted alkenyl, substituted or unsubstituted alkynyl, arylalkyl, arylalkenyl, arylalkynyl, heteroarylalkyl, heteroarylalkenyl, heteroarylalkynyl, heterocyclylalkyl, heterocyclylalkenyl, heterocyclylalkynyl, aryl, heteroaryl, heterocyclyl, cycloalkyl, cycloalkenyl, alkylarylalkyl, alkylarylalkenyl, alkylarylalkynyl, alkenylarylalkyl, alkenylarylalkenyl, alkenylarylalkynyl, alkynylarylalkyl, alkynylarylalkenyl, alkynylarylalkynyl, alkylheteroarylalkyl, alkylheteroarylalkenyl, alkylheteroarylalkynyl, alkenylheteroarylalkyl, alkenylheteroarylalkenyl, alkenylheteroarylalkynyl, alkynylheteroarylalkyl, alkynylheteroarylalkenyl, alkynylheteroarylalkynyl, alkylheterocyclylalkyl, alkylheterocyclylalkenyl, alkylhererocyclylalkynyl, alkenylheterocyclylalkyl, alkenylheterocyclylalkenyl, alkenylheterocyclylalkynyl, alkynylheterocyclylalkyl, alkynylheterocyclylalkenyl, alkynylheterocyclylalkynyl, alkylaryl, alkenylaryl, alkynylaryl, alkylheteroaryl, alkenylheteroaryl, alkynylhereroaryl, which one or more methylenes can be interrupted or terminated by O, S, S(O), $SO_2$, N(R8), C(O), substituted or unsubstituted aryl, substituted or unsubstituted heteroaryl, or substituted or unsubstituted heterocyclic; where R8 is hydrogen, acyl, aliphatic, or substituted aliphatic. In one embodiment, the linker is about 1-24 atoms, 2-24, 3-24, 4-24, 5-24, 6-24, 6-18, 7-18, 8-18, 7-17, 8-17, 6-16, 7-17, or 8-16 atoms.

A cleavable linking group is one which is sufficiently stable outside the cell, but which upon entry into a target cell is cleaved to release the two parts the linker is holding together. In a preferred embodiment, the cleavable linking group is cleaved at least about 10 times, 20, times, 30 times, 40 times, 50 times, 60 times, 70 times, 80 times, 90 times, or more, or at least 100 times faster in a target cell or under a first reference condition (which can, e.g., be selected to mimic or represent intracellular conditions) than in the blood of a subject, or under a second reference condition (which can, e.g., be selected to mimic or represent conditions found in the blood or serum).

Cleavable linking groups are susceptible to cleavage agents, e.g., pH, redox potential, or the presence of degradative molecules. Generally, cleavage agents are more prevalent or found at higher levels or activities inside cells than in serum or blood. Examples of such degradative agents include: redox agents which are selected for particular substrates or which have no substrate specificity, including, e.g., oxidative or reductive enzymes or reductive agents such as mercaptans, present in cells, that can degrade a redox cleavable linking group by reduction; esterases; endosomes or agents that can create an acidic environment, e.g., those that result in a pH of five or lower; enzymes that can hydrolyze or degrade an acid cleavable linking group by acting as a general acid, peptidases (which can be substrate specific), and phosphatases.

A cleavable linkage group, such as a disulfide bond can be susceptible to pH. The pH of human serum is 7.4, while the average intracellular pH is slightly lower, ranging from about 7.1-7.3. Endosomes have a more acidic pH, in the range of 5.5-6.0, and lysosomes have an even more acidic pH at around 5.0. Some linkers will have a cleavable linking group that is cleaved at a preferred pH, thereby releasing a cationic lipid from the ligand inside the cell, or into the desired compartment of the cell.

A linker can include a cleavable linking group that is cleavable by a particular enzyme. The type of cleavable linking group incorporated into a linker can depend on the cell to be targeted. For example, a liver-targeting ligand can be linked to a cationic lipid through a linker that includes an ester group. Liver cells are rich in esterases, and therefore the linker will be cleaved more efficiently in liver cells than in cell types that are not esterase-rich. Other cell-types rich in esterases include cells of the lung, renal cortex, and testis.

Linkers that contain peptide bonds can be used when targeting cell types rich in peptidases, such as liver cells and synoviocytes.

In general, the suitability of a candidate cleavable linking group can be evaluated by testing the ability of a degradative agent (or condition) to cleave the candidate linking group. It will also be desirable to also test the candidate cleavable linking group for the ability to resist cleavage in the blood or when in contact with other non-target tissue. Thus, one can determine the relative susceptibility to cleavage between a first and a second condition, where the first is selected to be indicative of cleavage in a target cell and the second is selected to be indicative of cleavage in other tissues or biological fluids, e.g., blood or serum. The evaluations can be carried out in cell free systems, in cells, in cell culture, in organ or tissue culture, or in whole animals. It can be useful to make initial evaluations in cell-free or culture conditions and to confirm by further evaluations in whole animals. In preferred embodiments, useful candidate compounds are cleaved at least about 2, 4, 10, 20, 30, 40, 50, 60, 70, 80, 90, or 100 times faster in the cell (or under in vitro conditions selected to mimic intracellular conditions) as compared to blood or serum (or under in vitro conditions selected to mimic extracellular conditions).

i. Redox Cleavable Linking Groups

In certain embodiments, a cleavable linking group is a redox cleavable linking group that is cleaved upon reduction or oxidation. An example of reductively cleavable linking group is a disulphide linking group (—S—S—). To determine if a candidate cleavable linking group is a suitable "reductively cleavable linking group," or for example is suitable for use with a particular iRNA moiety and particular targeting agent one can look to methods described herein. For example, a candidate can be evaluated by incubation with dithiothreitol (DTT), or other reducing agent using reagents know in the art, which mimic the rate of cleavage which would be observed in a cell, e.g., a target cell. The candidates can also be evaluated under conditions which are selected to mimic blood or serum conditions. In one, candidate compounds are cleaved by at most about 10% in the blood. In other embodiments, useful candidate compounds are degraded at least about 2, 4, 10, 20, 30, 40, 50, 60, 70, 80, 90, or about 100 times faster in the cell (or under in vitro conditions selected to mimic intracellular conditions) as compared to blood (or under in vitro conditions selected to mimic extracellular conditions). The rate of cleavage of candidate compounds can be determined using standard enzyme kinetics assays under conditions chosen to mimic intracellular media and compared to conditions chosen to mimic extracellular media.

ii. Phosphate-Based Cleavable Linking Groups

In other embodiments, a cleavable linker comprises a phosphate-based cleavable linking group. A phosphate-based cleavable linking group is cleaved by agents that degrade or hydrolyze the phosphate group. An example of an agent that cleaves phosphate groups in cells are enzymes such as phosphatases in cells. Examples of phosphate-based linking groups are —O—P(O)(ORk)-O—, —O—P(S)(ORk)-O—, —O—P(S)(SRk)-O—, —S—P(O)(ORk)-O—, —O—P(O)(ORk)-S—, —S—P(O)(ORk)-S—, —O—P(S)(ORk)-S—, —S—P(S)(ORk)-O—, —O—P(O)(Rk)-O—, —O—P(S)(Rk)-O—, —S—P(O)(Rk)-O—, —S—P(S)(Rk)-O—, —S—P(O)(Rk)-S—, —O—P(S)(Rk)-S—. Preferred embodiments are —O—P(O)(OH)—O—, —O—P(S)(OH)—O—, —O—P(S)(SH)—O—, —S—P(O)(OH)—O—, —O—P(O)(OH)—S—, —S—P(O)(OH)—S—, —O—P(S)(OH)—S—, —S—P(S)(OH)—O—, —O—P(O)(H)—O—, —O—P(S)(H)—O—, —S—P(O)(H)—O—, —S—P(S)(H)—O—, —S—P(O)(H)—S—, and —O—P(S)(H)—S—. A preferred embodiment is —O—P(O)(OH)—O—. These candidates can be evaluated using methods analogous to those described above.

iii. Acid Cleavable Linking Groups

In other embodiments, a cleavable linker comprises an acid cleavable linking group. An acid cleavable linking group is a linking group that is cleaved under acidic conditions. In preferred embodiments acid cleavable linking groups are cleaved in an acidic environment with a pH of about 6.5 or lower (e.g., about 6.0, 5.5, 5.0, or lower), or by agents such as enzymes that can act as a general acid. In a cell, specific low pH organelles, such as endosomes and lysosomes can provide a cleaving environment for acid cleavable linking groups. Examples of acid cleavable linking groups include but are not limited to hydrazones, esters, and esters of amino acids. Acid cleavable groups can have the general formula —C=NN—, C(O)O, or —OC(O). A preferred embodiment is when the carbon attached to the oxygen of the ester (the alkoxy group) is an aryl group, substituted alkyl group, or tertiary alkyl group such as dimethyl pentyl or t-butyl. These candidates can be evaluated using methods analogous to those described above.

iv. Ester-Based Linking Groups

In other embodiments, a cleavable linker comprises an ester-based cleavable linking group. An ester-based cleavable linking group is cleaved by enzymes such as esterases and amidases in cells. Examples of ester-based cleavable linking groups include, but are not limited to, esters of alkylene, alkenylene and alkynylene groups. Ester cleavable linking groups have the general formula —C(O)O—, or —OC(O)—. These candidates can be evaluated using methods analogous to those described above.

v. Peptide-Based Cleaving Groups

In yet other embodiments, a cleavable linker comprises a peptide-based cleavable linking group. A peptide-based cleavable linking group is cleaved by enzymes such as peptidases and proteases in cells. Peptide-based cleavable linking groups are peptide bonds formed between amino acids to yield oligopeptides (e.g., dipeptides, tripeptides etc.) and polypeptides. Peptide-based cleavable groups do not include the amide group (—C(O)NH—). The amide group can be formed between any alkylene, alkenylene or alkynelene. A peptide bond is a special type of amide bond formed between amino acids to yield peptides and proteins. The peptide based cleavage group is generally limited to the peptide bond (i.e., the amide bond) formed between amino acids yielding peptides and proteins and does not include the entire amide functional group. Peptide-based cleavable linking groups have the general formula —NHCHRAC(O)NHCHRBC(O)—, where RA and RB are the R groups of the two adjacent amino acids. These candidates can be evaluated using methods analogous to those described above.

In some embodiments, an iRNA of the invention is conjugated to a carbohydrate through a linker. Non-limiting examples of iRNA carbohydrate conjugates with linkers of the compositions and methods of the invention include but are not limited to

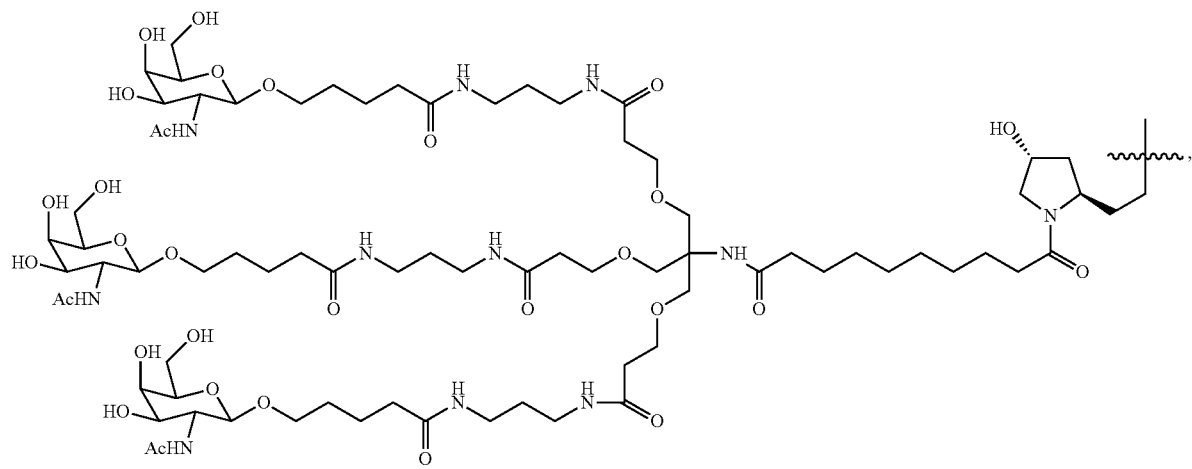
(Formula XXXVII)
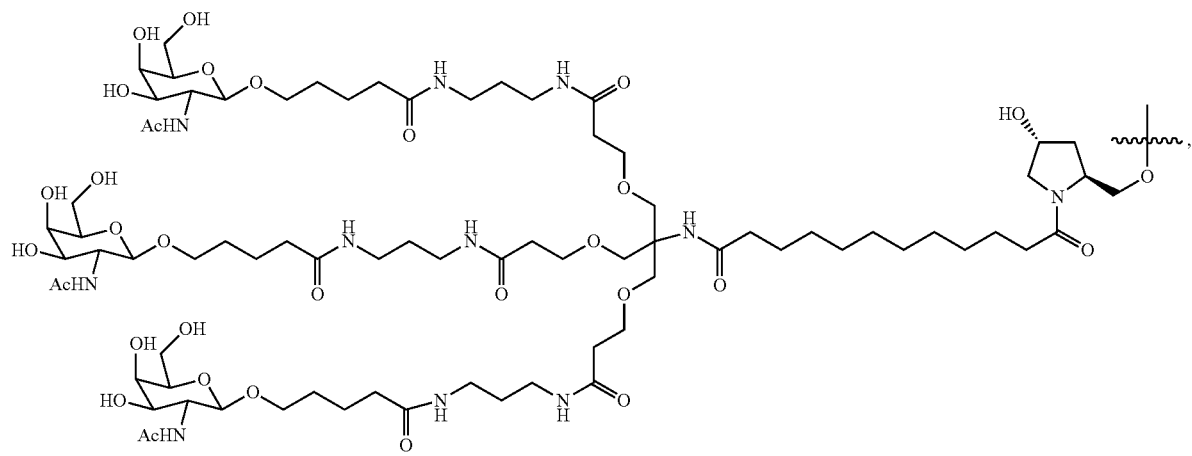
(Formula XXXVIII)
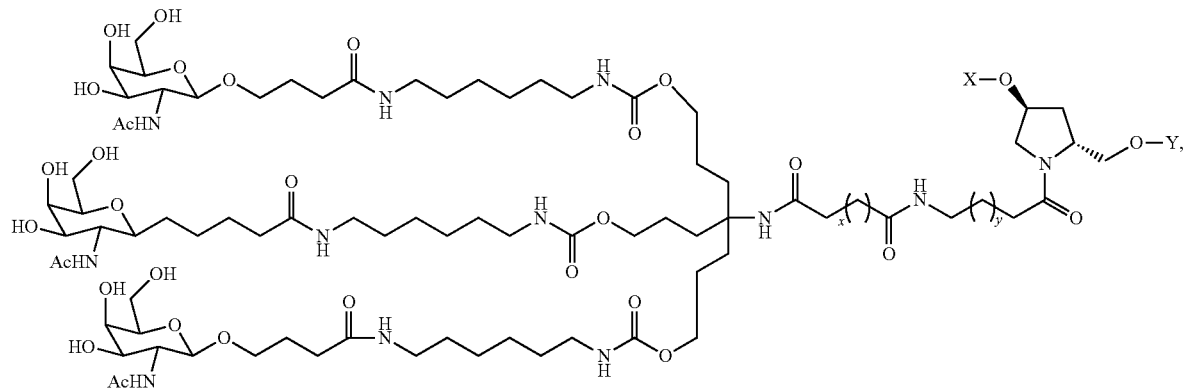
(Formula XXXIX)
x = 1-30
y = 1-15

-continued
(Formula XL)
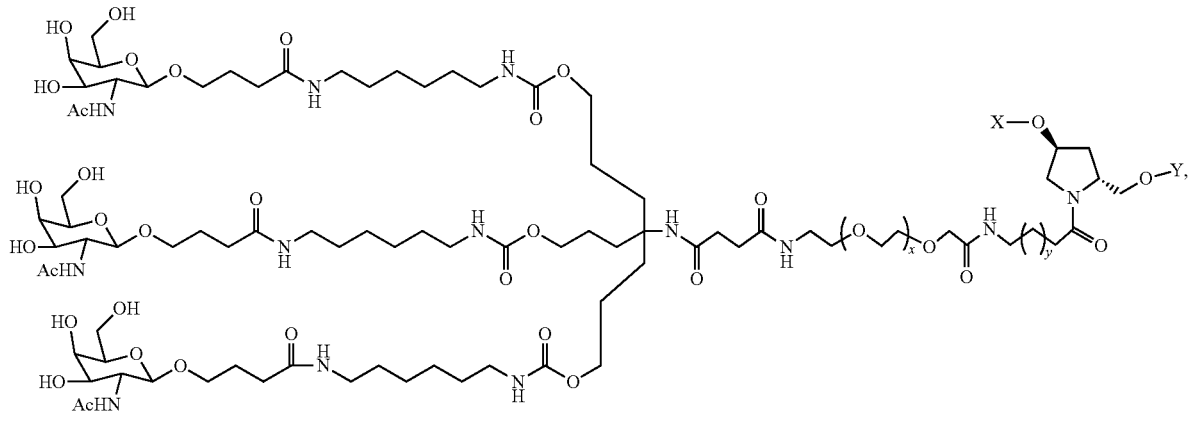
x = 1-30
y = 1-15
(Formula XLI)
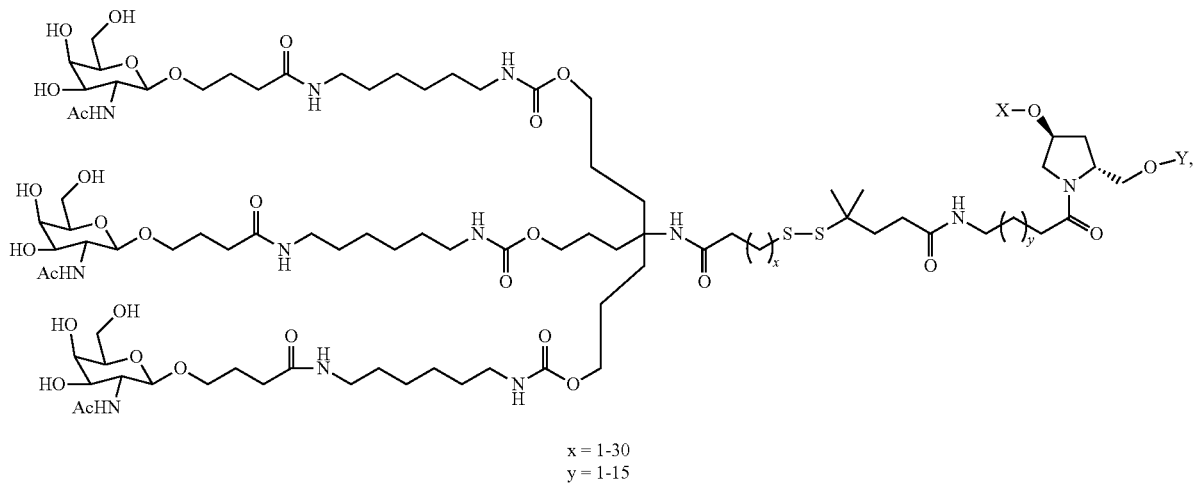
x = 1-30
y = 1-15
(Formula XLII)
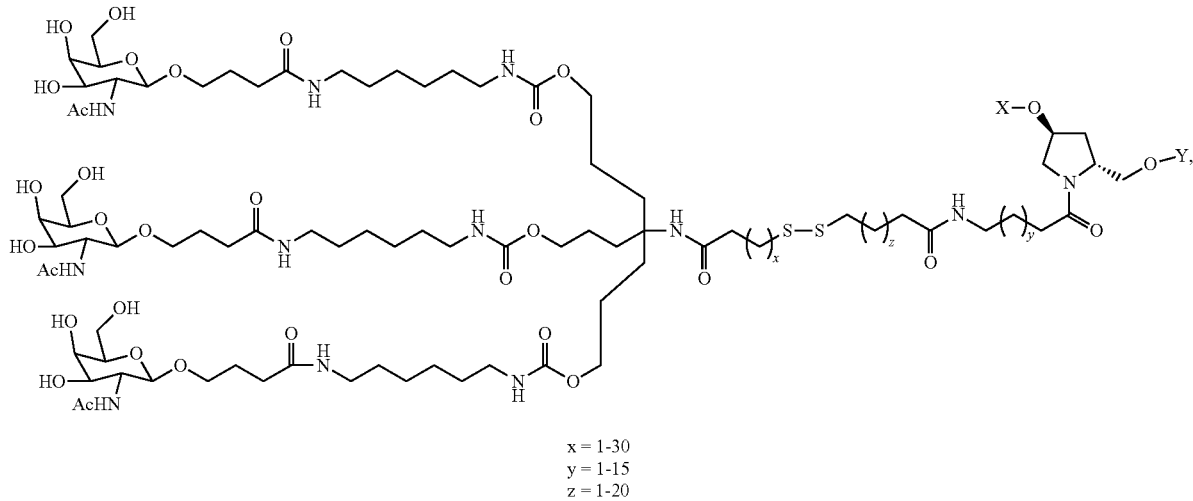
x = 1-30
y = 1-15
z = 1-20

(Formula XLIII)

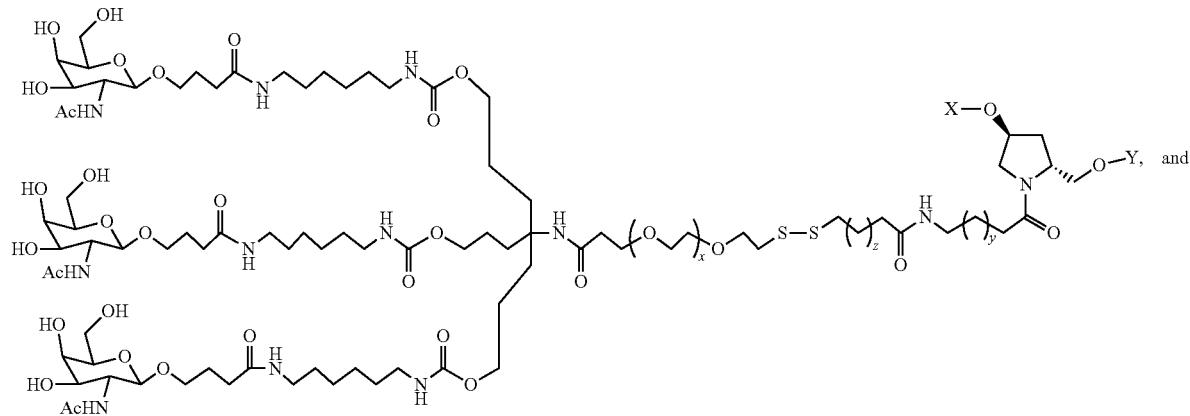

x = 1-30
y = 1-15
z = 1-20

(Formula XLIV)

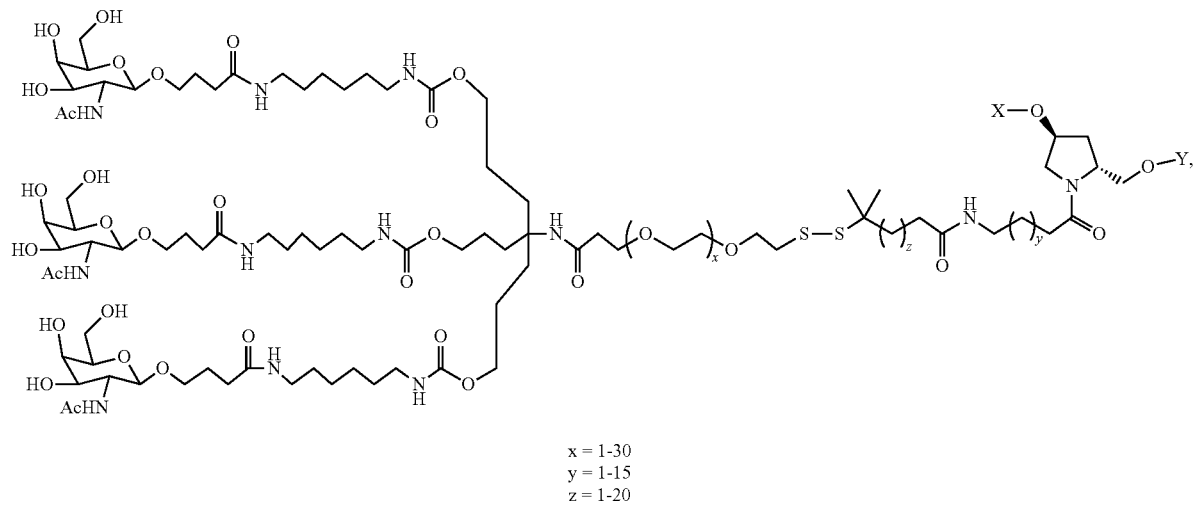

x = 1-30
y = 1-15
z = 1-20 when one of X or Y is an oligonucleotide, the other is a hydrogen.

In certain embodiments of the compositions and methods of the invention, a ligand is one or more "GalNAc" (N-acetylgalactosamine) derivatives attached through a bivalent or trivalent branched linker.

In one embodiment, a dsRNA of the invention is conjugated to a bivalent or trivalent branched linker selected from the group of structures shown in any of formula (XLV)-(XLVI):

Formula XXXXV

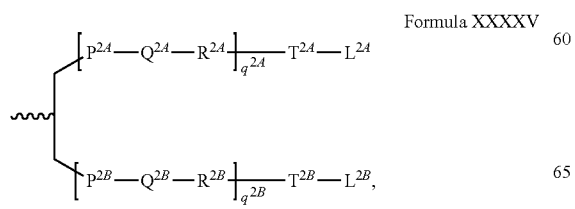

Formula XLVI

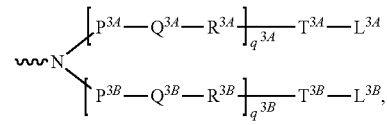

Formula XLVII

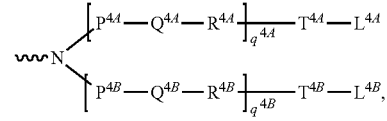

Formula XLVIII

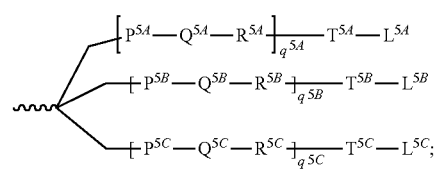

wherein:

q2A, q2B, q3A, q3B, q4A, q4B, q5A, q5B and q5C represent independently for each occurrence 0-20 and wherein the repeating unit can be the same or different;

$P^{2A}$, $P^{2B}$, $P^{3A}$, $P^{3B}$, $P^{4A}$, $P^{4B}$, $P^{5A}$, $P^{5B}$, $P^{5C}$, $T^{2A}$, $T^{2B}$, $T^{3A}$, $T^{3B}$, $T^{4A}$, $T^{4B}$, $T^{4A}$, $T^{5B}$, $T^{5C}$ are each independently for each occurrence absent, CO, NH, O, S, OC(O), NHC(O), $CH_2$, $CH_2NH$ or $CH_2O$;

$Q^{2A}$, $Q^{2B}$, $Q^{3A}$, $Q^{3B}$, $Q^{4A}$, $Q^{4B}$, $Q^{5A}$, $Q^{5B}$, $Q^{5C}$ are independently for each occurrence absent, alkylene, substituted alkylene wherein one or more methylenes can be interrupted or terminated by one or more of O, S, S(O), $SO_2$, $N(R^N)$, C(R')=C(R''), C≡C or C(O);

$R^{2A}$, $R^{2B}$, $R^{3A}$, $R^{3B}$, $R^{4A}$, $R^{4B}$, $R^{5A}$, $R^{5B}$, $R^{5C}$ are each independently for each occurrence absent, NH, O, S, $CH_2$, C(O)O, C(O)NH, $NHCH(R^a)C(O)$, $—C(O)—CH(R^a)—NH—$, CO, CH=N—O,

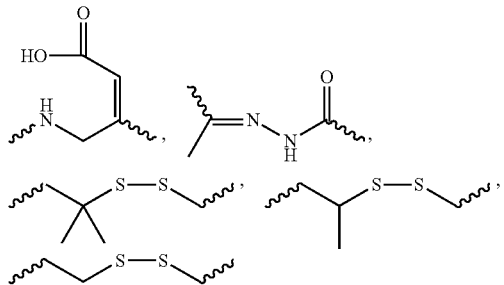

or heterocyclyl; $L^{2A}$, $L^{2B}$, $L^{3A}$, $L^{3B}$, $L^{4A}$, $L^{4B}$, $L^{5A}$, $L^{5B}$ and $L^{5C}$ represent the ligand; i.e. each independently for each occurrence a monosaccharide (such as GaNAc), disaccharide, trisaccharide, tetrasaccharide, oligosaccharide, or polysaccharide; and $R^a$ is H or amino acid side chain. Trivalent conjugating GalNAc derivatives are particularly useful for use with RNAi agents for inhibiting the expression of a target gene, such as those of formula (XLIX):

Formula XLIX

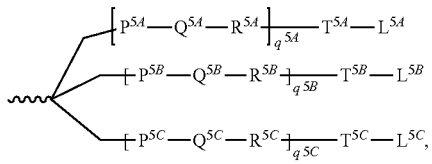

wherein $L^{5A}$, $L^{5B}$ and $L^{5C}$ represent a monosaccharide, such as GalNAc derivative.

Examples of suitable bivalent and trivalent branched linker groups conjugating GaNAc derivatives include, but are not limited to, the structures recited above as formulas II, VII, XI, X, and XIII.

Representative U.S. Patents that teach the preparation of RNA conjugates include, but are not limited to, U.S. Pat. Nos. 4,828,979; 4,948,882; 5,218,105; 5,525,465; 5,541, 313; 5,545,730; 5,552,538; 5,578,717; 5,580,731; 5,591, 584; 5,109,124; 5,118,802; 5,138,045; 5,414,077; 5,486, 603; 5,512,439; 5,578,718; 5,608,046; 4,587,044; 4,605, 735; 4,667,025; 4,762,779; 4,789,737; 4,824,941; 4,835, 263; 4,876,335; 4,904,582; 4,958,013; 5,082,830; 5,112, 963; 5,214,136; 5,082,830; 5,112,963; 5,214,136; 5,245, 022; 5,254,469; 5,258,506; 5,262,536; 5,272,250; 5,292, 873; 5,317,098; 5,371,241; 5,391,723; 5,416,203; 5,451, 463; 5,510,475; 5,512,667; 5,514,785; 5,565,552; 5,567, 810; 5,574,142; 5,585,481; 5,587,371; 5,595,726; 5,597, 696; 5,599,923; 5,599,928; 5,688,941; 6,294,664; 6,320, 017; 6,576,752; 6,783,931; 6,900,297; 7,037,646; and 8,106,022, the entire contents of each of which are hereby incorporated herein by reference.

It is not necessary for all positions in a given compound to be uniformly modified, and in fact more than one of the aforementioned modifications can be incorporated in a single compound or even at a single nucleoside within an iRNA. The present invention also includes iRNA compounds that are chimeric compounds.

"Chimeric" iRNA compounds or "chimeras," in the context of this invention, are iRNA compounds, preferably dsRNAi agents, that contain two or more chemically distinct regions, each made up of at least one monomer unit, i.e., a nucleotide in the case of a dsRNA compound. These iRNAs typically contain at least one region wherein the RNA is modified so as to confer upon the iRNA increased resistance to nuclease degradation, increased cellular uptake, or increased binding affinity for the target nucleic acid. An additional region of the iRNA can serve as a substrate for enzymes capable of cleaving RNA:DNA or RNA:RNA hybrids. By way of example, RNase H is a cellular endonuclease which cleaves the RNA strand of an RNA:DNA duplex. Activation of RNase H, therefore, results in cleavage of the RNA target, thereby greatly enhancing the efficiency of iRNA inhibition of gene expression. Consequently, comparable results can often be obtained with shorter iRNAs when chimeric dsRNAs are used, compared to phosphorothioate deoxy dsRNAs hybridizing to the same target region. Cleavage of the RNA target can be routinely detected by gel electrophoresis and, if necessary, associated nucleic acid hybridization techniques known in the art.

In certain instances, the RNA of an iRNA can be modified by a non-ligand group. A number of non-ligand molecules have been conjugated to iRNAs in order to enhance the activity, cellular distribution or cellular uptake of the iRNA, and procedures for performing such conjugations are available in the scientific literature. Such non-ligand moieties have included lipid moieties, such as cholesterol (Kubo, T. et al., Biochem. Biophys. Res. Comm., 2007, 365(1):54-61; Letsinger et al., Proc. Natl. Acad. Sci. USA, 1989, 86:6553), cholic acid (Manoharan et al., Bioorg. Med. Chem. Lett., 1994, 4:1053), athioether, e.g., hexyl-S-tritylthiol (Manoharan et al., Ann. N. Y. Acad. Sci., 1992, 660:306; Manoharan et al., Bioorg. Med. Chem. Let., 1993, 3:2765), a thiocholesterol (Oberhauser et al., Nucl. Acids Res., 1992, 20:533), an aliphatic chain, e.g., dodecandiol or undecyl residues (Saison-Behmoaras et al., EMBO J., 1991, 10:111; Kabanov et al., FEBS Lett., 1990, 259:327; Svinarchuk et al., Biochimie, 1993, 75:49), a phospholipid, e.g., di-hexadecyl-rac-glycerol or triethylammonium 1,2-di-O-hexadecyl-rac-glycero-3-H-phosphonate (Manoharan et al., Tetrahedron Lett., 1995, 36:3651; Shea et al., Nucl. Acids Res., 1990, 18:3777), a polyamine or a polyethylene glycol chain (Manoharan et al., Nucleosides & Nucleotides, 1995, 14:969), or adamantane acetic acid (Manoharan et al., Tetrahedron Lett., 1995, 36:3651), a palmityl moiety (Mishra et al., Biochim. Biophys. Acta, 1995, 1264:229), or an octadecylamine or hexylamino-carbonyl-oxycholesterol moiety (Crooke et al., J Pharmacol. Exp. Ther., 1996, 277:923). Representative United States patents that teach the preparation of such RNA conjugates have been listed above. Typical conjugation protocols involve the synthesis of RNAs bearing an aminolinker at one or more positions of the sequence. The amino group is then reacted with the molecule being conjugated using appropriate coupling or activating reagents. The conjugation reaction can be performed either with the RNA still bound to the solid support or following cleavage of the RNA, in solution phase. Purification of the RNA conjugate by HPLC typically affords the pure conjugate.

IV. Delivery of an iRNA of the Invention

The delivery of an iRNA of the invention to a cell e.g., a cell within a subject, such as a human subject (e.g., a subject in need thereof, such as a subject susceptible to or diagnosed with an AGT associated disorder, e.g., hypertension) can be achieved in a number of different ways. For example, delivery may be performed by contacting a cell with an iRNA of the invention either in vitro or in vivo. In vivo delivery may also be performed directly by administering a composition comprising an iRNA, e.g., a dsRNA, to a subject. Alternatively, in vivo delivery may be performed indirectly by administering one or more vectors that encode and direct the expression of the iRNA. These alternatives are discussed further below.

In general, any method of delivering a nucleic acid molecule (in vitro or in vivo) can be adapted for use with an iRNA of the invention (see e.g., Akhtar S. and Julian R L. (1992) *Trends Cell. Biol.* 2(5):139-144 and WO94/02595, which are incorporated herein by reference in their entireties). For in vivo delivery, factors to consider in order to deliver an iRNA molecule include, for example, biological stability of the delivered molecule, prevention of non-specific effects, and accumulation of the delivered molecule in the target tissue. RNA interference has also shown success with local delivery to the CNS by direct injection (Dorn, G., et al. (2004) *Nucleic Acids* 32:e49; Tan, P H., et al (2005) *Gene Ther.* 12:59-66; Makimura, H., et al (2002) *BMC Neurosci.* 3:18; Shishkina, G T., et al (2004) *Neuroscience* 129:521-528; Thakker, E R., et al (2004) *Proc. Natl. Acad. Sci. U.S.A.* 101:17270-17275; Akaneya, Y., et al (2005) *J Neurophysiol.* 93:594-602). Modification of the RNA or the pharmaceutical carrier can also permit targeting of the iRNA to the target tissue and avoid undesirable off-target effects. iRNA molecules can be modified by chemical conjugation to lipophilic groups such as cholesterol to enhance cellular uptake and prevent degradation. For example, an iRNA directed against ApoB conjugated to a lipophilic cholesterol moiety was injected systemically into mice and resulted in knockdown of apoB mRNA in both the liver and jejunum (Soutschek, J., et al (2004) *Nature* 432:173-178).

In an alternative embodiment, the iRNA can be delivered using drug delivery systems such as a nanoparticle, a dendrimer, a polymer, liposomes, or a cationic delivery system. Positively charged cationic delivery systems facilitate binding of an iRNA molecule (negatively charged) and also enhance interactions at the negatively charged cell membrane to permit efficient uptake of an iRNA by the cell. Cationic lipids, dendrimers, or polymers can either be bound to an iRNA, or induced to form a vesicle or micelle (see e.g., Kim S H, et al (2008) *Journal of Controlled Release* 129(2):107-116) that encases an iRNA. The formation of vesicles or micelles further prevents degradation of the iRNA when administered systemically. Methods for making and administering cationic-iRNA complexes are well within the abilities of one skilled in the art (see e.g., Sorensen, D R, et al (2003) *J. Mol. Biol* 327:761-766; Verma, U N, et al (2003) *Clin. Cancer Res.* 9:1291-1300; Arnold, A S et al (2007) *J. Hypertens.* 25:197-205, which are incorporated herein by reference in their entirety). Some non-limiting examples of drug delivery systems useful for systemic delivery of iRNAs include DOTAP (Sorensen, D R., et al (2003), supra; Verma, U N, et al (2003), supra), "solid nucleic acid lipid particles" (Zimmermann, T S, et al (2006) *Nature* 441:111-114), cardiolipin (Chien, P Y, et al (2005) *Cancer Gene Ther.* 12:321-328; Pal, A, et al (2005) *Int J Oncol.* 26:1087-1091), polyethyleneimine (Bonnet M E, et al (2008) *Pharm. Res.* August 16 Epub ahead of print; Aigner, A. (2006) *J. Biomed. Biotechnol.* 71659), Arg-Gly-Asp (RGD) peptides (Liu, S. (2006) *Mol. Pharm.* 3:472-487), and polyamidoamines (Tomalia, D A, et al (2007) *Biochem. Soc. Trans.* 35:61-67; Yoo, H., et al (1999) *Pharm. Res.* 16:1799-1804). In some embodiments, an iRNA forms a complex with cyclodextrin for systemic administration. Methods for administration and pharmaceutical compositions of iRNAs and cyclodextrins can be found in U.S. Pat. No. 7,427,605, which is herein incorporated by reference in its entirety.

A. Vector Encoded iRNAs of the Invention iRNA targeting the AGT gene can be expressed from transcription units inserted into DNA or RNA vectors (see, e.g., Couture, A, et al., *TIG.* (1996), 12:5-10; Skillern, A, et al., International PCT Publication No. WO 00/22113, Conrad, International PCT Publication No. WO 00/22114, and Conrad, U.S. Pat. No. 6,054,299). Expression can be transient (on the order of hours to weeks) or sustained (weeks to months or longer), depending upon the specific construct used and the target tissue or cell type. These transgenes can be introduced as a linear construct, a circular plasmid, or a viral vector, which can be an integrating or non-integrating vector. The transgene can also be constructed to permit it to be inherited as an extrachromosomal plasmid (Gassmann, et al., *Proc. Natl. Acad. Sci. USA* (1995) 92:1292).

Viral vector systems which can be utilized with the methods and compositions described herein include, but are not limited to, (a) adenovirus vectors; (b) retrovirus vectors, including but not limited to lentiviral vectors, moloney murine leukemia virus, etc.; (c) adeno-associated virus vectors; (d) herpes simplex virus vectors; (e) SV 40 vectors; (f) polyoma virus vectors; (g) papilloma virus vectors; (h) picornavirus vectors; (i) pox virus vectors such as an orthopox, e.g., vaccinia virus vectors or avipox, e.g. canary pox or fowl pox; and (j) a helper-dependent or gutless adenovirus. Replication-defective viruses can also be advantageous. Different vectors will or will not become incorporated into the cells' genome. The constructs can include viral sequences for transfection, if desired. Alternatively, the construct can be incorporated into vectors capable of episomal replication, e.g. EPV and EBV vectors. Constructs for the recombinant expression of an iRNA will generally require regulatory elements, e.g., promoters, enhancers, etc., to ensure the expression of the iRNA in target cells. Other aspects to consider for vectors and constructs are known in the art.

V. Pharmaceutical Compositions of the Invention

The present invention also includes pharmaceutical compositions and formulations which include the iRNAs of the invention. In one embodiment, provided herein are pharmaceutical compositions containing an iRNA, as described herein, and a pharmaceutically acceptable carrier. The pharmaceutical compositions containing the iRNA are useful for preventing or treating an AGT associated disorder, e.g., hypertension. Such pharmaceutical compositions are formulated based on the mode of delivery. One example is compositions that are formulated for systemic administration via parenteral delivery, e.g., by subcutaneous (SC), intramuscular (IM), or intravenous (IV) delivery. The pharmaceutical compositions of the invention may be administered in dosages sufficient to inhibit expression of an AGT gene.

The pharmaceutical compositions of the invention may be administered in dosages sufficient to inhibit expression of an AGT gene. In general, a suitable dose of an iRNA of the invention will be in the range of about 0.001 to about 200.0 milligrams per kilogram body weight of the recipient per day, generally in the range of about 1 to 50 mg per kilogram body weight per day. Typically, a suitable dose of an iRNA of the invention will be in the range of about 0.1 mg/kg to about 5.0 mg/kg, preferably about 0.3 mg/kg and about 3.0 mg/kg. A repeat-dose regimen may include administration of a therapeutic amount of iRNA on a regular basis, such as every month, once every 3-6 months, or once a year. In certain embodiments, the iRNA is administered about once per month to about once per six months.

After an initial treatment regimen, the treatments can be administered on a less frequent basis. Duration of treatment can be determined based on the severity of disease.

In other embodiments, a single dose of the pharmaceutical compositions can be long lasting, such that doses are administered at not more than 1, 2, 3, or 4 month intervals. In some embodiments of the invention, a single dose of the pharmaceutical compositions of the invention is administered about once per month. In other embodiments of the invention, a single dose of the pharmaceutical compositions of the invention is administered quarterly (i.e., about every three months). In other embodiments of the invention, a single dose of the pharmaceutical compositions of the invention is administered twice per year (i.e., about once every six months).

The skilled artisan will appreciate that certain factors can influence the dosage and timing required to effectively treat a subject, including but not limited to mutations present in the subject, previous treatments, the general health or age of the subject, and other diseases present. Moreover, treatment of a subject with a prophylactically or therapeutically effective amount, as appropriate, of a composition can include a single treatment or a series of treatments.

The iRNA can be delivered in a manner to target a particular tissue (e.g., hepatocytes).

Pharmaceutical compositions of the present invention include, but are not limited to, solutions, emulsions, and liposome-containing formulations. These compositions can be generated from a variety of components that include, but are not limited to, preformed liquids, self-emulsifying solids, and self-emulsifying semisolids. Formulations include those that target the liver.

The pharmaceutical formulations of the present invention, which can conveniently be presented in unit dosage form, can be prepared according to conventional techniques well known in the pharmaceutical industry. Such techniques include the step of bringing into association the active ingredients with the pharmaceutical carrier(s) or excipient(s). In general, the formulations are prepared by uniformly and intimately bringing into association the active ingredients with liquid carriers.

A. Additional Formulations
i. Emulsions

The compositions of the present invention can be prepared and formulated as emulsions. Emulsions are typically heterogeneous systems of one liquid dispersed in another in the form of droplets usually exceeding 0.1 μm in diameter (see e.g., Ansel's Pharmaceutical Dosage Forms and Drug Delivery Systems, Allen, L V., Popovich N G., and Ansel H C., 2004, Lippincott Williams & Wilkins (8th ed.), New York, N.Y.; Idson, in Pharmaceutical Dosage Forms, Lieberman, Rieger and Banker (Eds.), 1988, Marcel Dekker, Inc., New York, N.Y., volume 1, p. 199; Rosoff, in Pharmaceutical Dosage Forms, Lieberman, Rieger and Banker (Eds.), 1988, Marcel Dekker, Inc., New York, N.Y., Volume 1, p. 245; Block in Pharmaceutical Dosage Forms, Lieberman, Rieger and Banker (Eds.), 1988, Marcel Dekker, Inc., New York, N.Y., volume 2, p. 335; Higuchi et al., in Remington's Pharmaceutical Sciences, Mack Publishing Co., Easton, Pa., 1985, p. 301). Emulsions are often biphasic systems comprising two immiscible liquid phases intimately mixed and dispersed with each other. In general, emulsions can be of either the water-in-oil (w/o) or the oil-in-water (o/w) variety. When an aqueous phase is finely divided into and dispersed as minute droplets into a bulk oily phase, the resulting composition is called a water-in-oil (w/o) emulsion. Alternatively, when an oily phase is finely divided into and dispersed as minute droplets into a bulk aqueous phase, the resulting composition is called an oil-in-water (o/w) emulsion. Emulsions can contain additional components in addition to the dispersed phases, and the active drug which can be present as a solution either in the aqueous phase, oily phase or itself as a separate phase. Pharmaceutical excipients such as emulsifiers, stabilizers, dyes, and anti-oxidants can also be present in emulsions as needed. Pharmaceutical emulsions can also be multiple emulsions that are comprised of more than two phases such as, for example, in the case of oil-in-water-in-oil (o/w/o) and water-in-oil-in-water (w/o/w) emulsions. Such complex formulations often provide certain advantages that simple binary emulsions do not. Multiple emulsions in which individual oil droplets of an o/w emulsion enclose small water droplets constitute a w/o/w emulsion. Likewise a system of oil droplets enclosed in globules of water stabilized in an oily continuous phase provides an o/w/o emulsion.

Emulsions are characterized by little or no thermodynamic stability. Often, the dispersed or discontinuous phase of the emulsion is well dispersed into the external or continuous phase and maintained in this form through the means of emulsifiers or the viscosity of the formulation. Other means of stabilizing emulsions entail the use of emulsifiers that can be incorporated into either phase of the emulsion. Emulsifiers can broadly be classified into four categories: synthetic surfactants, naturally occurring emulsifiers, absorption bases, and finely dispersed solids (see e.g., Ansel's Pharmaceutical Dosage Forms and Drug Delivery Systems, Allen, L V., Popovich N G., and Ansel H C., 2004, Lippincott Williams & Wilkins (8th ed.), New York, N.Y.; Idson, in Pharmaceutical Dosage Forms, Lieberman, Rieger and Banker (Eds.), 1988, Marcel Dekker, Inc., New York, N.Y., volume 1, p. 199).

Synthetic surfactants, also known as surface active agents, have found wide applicability in the formulation of emulsions and have been reviewed in the literature (see e.g., Ansel's Pharmaceutical Dosage Forms and Drug Delivery Systems, Allen, L V., Popovich N G., and Ansel H C., 2004, Lippincott Williams & Wilkins (8th ed.), New York, N.Y.; Rieger, in Pharmaceutical Dosage Forms, Lieberman, Rieger and Banker (Eds.), 1988, Marcel Dekker, Inc., New York, N.Y., volume 1, p. 285; Idson, in Pharmaceutical Dosage Forms, Lieberman, Rieger and Banker (Eds.), Marcel Dekker, Inc., New York, N.Y., 1988, volume 1, p. 199). Surfactants are typically amphiphilic and comprise a hydrophilic and a hydrophobic portion. The ratio of the hydrophilic to the hydrophobic nature of the surfactant has been termed the hydrophile/lipophile balance (HLB) and is a valuable tool in categorizing and selecting surfactants in the preparation of formulations. Surfactants can be classified into different classes based on the nature of the hydrophilic group: nonionic, anionic, cationic, and amphoteric (see e.g., Ansel's Pharmaceutical Dosage Forms and Drug Delivery Systems, Allen, L V., Popovich N G., and Ansel H C., 2004, Lippincott Williams & Wilkins (8th ed.), New York, N.Y. Rieger, in Pharmaceutical Dosage Forms, Lieberman, Rieger and Banker (Eds.), 1988, Marcel Dekker, Inc., New York, N.Y., volume 1, p. 285).

A large variety of non-emulsifying materials are also included in emulsion formulations and contribute to the properties of emulsions. These include fats, oils, waxes, fatty acids, fatty alcohols, fatty esters, humectants, hydrophilic colloids, preservatives, and antioxidants (Block, in Pharmaceutical Dosage Forms, Lieberman, Rieger and Banker (Eds.), 1988, Marcel Dekker, Inc., New York, N.Y., volume 1, p. 335; Idson, in Pharmaceutical Dosage Forms, Lieberman, Rieger and Banker (Eds.), 1988, Marcel Dekker, Inc., New York, N.Y., volume 1, p. 199).

The application of emulsion formulations via dermatological, oral, and parenteral routes, and methods for their manufacture have been reviewed in the literature (see e.g., Ansel's Pharmaceutical Dosage Forms and Drug Delivery Systems, Allen, L V., Popovich N G., and Ansel H C., 2004, Lippincott Williams & Wilkins (8th ed.), New York, N.Y.; Idson, in Pharmaceutical Dosage Forms, Lieberman, Rieger and Banker (Eds.), 1988, Marcel Dekker, Inc., New York, N.Y., volume 1, p. 199).

ii. Microemulsions

In one embodiment of the present invention, the compositions of iRNAs and nucleic acids are formulated as microemulsions. A microemulsion can be defined as a system of water, oil, and amphiphile which is a single optically isotropic and thermodynamically stable liquid solution (see e.g., Ansel's Pharmaceutical Dosage Forms and Drug Delivery Systems, Allen, L V., Popovich N G., and Ansel H C., 2004, Lippincott Williams & Wilkins (8th ed.), New York, N.Y.; Rosoff, in Pharmaceutical Dosage Forms, Lieberman, Rieger and Banker (Eds.), 1988, Marcel Dekker, Inc., New York, N.Y., volume 1, p. 245). Typically microemulsions are systems that are prepared by first dispersing an oil in an aqueous surfactant solution and then adding a sufficient amount of a fourth component, generally an intermediate chain-length alcohol to form a transparent system. Therefore, microemulsions have also been described as thermodynamically stable, isotropically clear dispersions of two immiscible liquids that are stabilized by interfacial films of surface-active molecules (Leung and Shah, in: Controlled Release of Drugs: Polymers and Aggregate Systems, Rosoff, M., Ed., 1989, VCH Publishers, New York, pages 185-215).

iii. Microparticles

An iRNA of the invention may be incorporated into a particle, e.g., a microparticle. Microparticles can be produced by spray-drying, but may also be produced by other methods including lyophilization, evaporation, fluid bed drying, vacuum drying, or a combination of these techniques.

iv. Penetration Enhancers

In one embodiment, the present invention employs various penetration enhancers to effect the efficient delivery of nucleic acids, particularly iRNAs, to the skin of animals. Most drugs are present in solution in both ionized and nonionized forms. However, usually only lipid soluble or lipophilic drugs readily cross cell membranes. It has been discovered that even non-lipophilic drugs can cross cell membranes if the membrane to be crossed is treated with a penetration enhancer. In addition to aiding the diffusion of non-lipophilic drugs across cell membranes, penetration enhancers also enhance the permeability of lipophilic drugs.

Penetration enhancers can be classified as belonging to one of five broad categories, i.e., surfactants, fatty acids, bile salts, chelating agents, and non-chelating non-surfactants (see e.g., Malmsten, M. Surfactants and polymers in drug delivery, Informa Health Care, New York, N.Y., 2002; Lee et al., Critical Reviews in Therapeutic Drug Carrier Systems, 1991, p. 92). Each of the above mentioned classes of penetration enhancers and their use in manufacture of pharmaceutical compositions and delivery of pharmaceutical agents are well known in the art.

v. Excipients

In contrast to a carrier compound, a "pharmaceutical carrier" or "excipient" is a pharmaceutically acceptable solvent, suspending agent, or any other pharmacologically inert vehicle for delivering one or more nucleic acids to an animal. The excipient can be liquid or solid and is selected, with the planned manner of administration in mind, so as to provide for the desired bulk, consistency, etc., when combined with a nucleic acid and the other components of a given pharmaceutical composition. Such agent are well known in the art.

vi. Other Components

The compositions of the present invention can additionally contain other adjunct components conventionally found in pharmaceutical compositions, at their art-established usage levels. Thus, for example, the compositions can contain additional, compatible, pharmaceutically-active materials such as, for example, antipruritics, astringents, local anesthetics or anti-inflammatory agents, or can contain additional materials useful in physically formulating various dosage forms of the compositions of the present invention, such as dyes, flavoring agents, preservatives, antioxidants, opacifiers, thickening agents and stabilizers. However, such materials, when added, should not unduly interfere with the biological activities of the components of the compositions of the present invention. The formulations can be sterilized and, if desired, mixed with auxiliary agents, e.g., lubricants, preservatives, stabilizers, wetting agents, emulsifiers, salts for influencing osmotic pressure, buffers, colorings, flavorings, or aromatic substances, and the like which do not deleteriously interact with the nucleic acid(s) of the formulation.

Aqueous suspensions can contain substances which increase the viscosity of the suspension including, for example, sodium carboxymethylcellulose, sorbitol, or dextran. The suspension can also contain stabilizers.

In some embodiments, pharmaceutical compositions featured in the invention include (a) one or more iRNA and (b) one or more agents which function by a non-iRNA mechanism and which are useful in treating an AGT associated disorder, e.g., hypertension.

Toxicity and prophylactic efficacy of such compounds can be determined by standard pharmaceutical procedures in cell cultures or experimental animals, e.g., for determining the LD50 (the dose lethal to 50% of the population) and the ED50 (the dose prophylactically effective in 50% of the population). The dose ratio between toxic and therapeutic effects is the therapeutic index and it can be expressed as the ratio LD50/ED50. Compounds that exhibit high therapeutic indices are preferred.

The data obtained from cell culture assays and animal studies can be used in formulating a range of dosage for use in humans. The dosage of compositions featured herein in the invention lies generally within a range of circulating concentrations that include the ED50, preferably an ED80 or ED90, with little or no toxicity. The dosage can vary within this range depending upon the dosage form employed and the route of administration utilized. For any compound used in the methods featured in the invention, the prophylactically effective dose can be estimated initially from cell culture assays. A dose can be formulated in animal models to achieve a circulating plasma concentration range of the compound or, when appropriate, of the polypeptide product of a target sequence (e.g., achieving a decreased concentration of the polypeptide) that includes the IC50 (i.e., the concentration of the test compound which achieves a half-maximal inhibition of symptoms) or higher levels of inhibition as determined in cell culture. Such information can be used to more accurately determine useful doses in humans. Levels in plasma can be measured, for example, by high performance liquid chromatography.

In addition to their administration, as discussed above, the iRNAs featured in the invention can be administered in combination with other known agents used for the prevention or treatment of an AGT associated disorder, e.g., hypertension. In any event, the administering physician can adjust the amount and timing of iRNA administration on the basis of results observed using standard measures of efficacy known in the art or described herein.

VI. Methods for Inhibiting AGT Expression

The present invention also provides methods of inhibiting expression of an AGT gene in a cell. The methods include contacting a cell with an RNAi agent, e.g., double stranded RNA agent, in an amount effective to inhibit expression of AGT in the cell, thereby inhibiting expression of AGT in the cell.

Contacting of a cell with an iRNA, e.g., a double stranded RNA agent, may be done in vitro or in vivo. Contacting a cell in vivo with the iRNA includes contacting a cell or group of cells within a subject, e.g., a human subject, with the iRNA. Combinations of in vitro and in vivo methods of contacting a cell are also possible. Contacting a cell may be direct or indirect, as discussed above. Furthermore, contacting a cell may be accomplished via a targeting ligand, including any ligand described herein or known in the art. In preferred embodiments, the targeting ligand is a carbohydrate moiety, e.g., a GalNAc$_3$ ligand, or any other ligand that directs the RNAi agent to a site of interest.

The term "inhibiting," as used herein, is used interchangeably with "reducing," "silencing," "downregulating", "suppressing", and other similar terms, and includes any level of inhibition.

The phrase "inhibiting expression of an AGT" is intended to refer to inhibition of expression of any AGT gene (such as, e.g., a mouse AGT gene, a rat AGT gene, a monkey AGT gene, or a human AGT gene) as well as variants or mutants of an AGTgene. Thus, the AGT gene may be a wild-type AGT gene, a mutant AGT gene, or a transgenic AGT gene in the context of a genetically manipulated cell, group of cells, or organism.

"Inhibiting expression of an AGT gene" includes any level of inhibition of an AGT gene, e.g., at least partial suppression of the expression of an AGT gene. The expression of the AGT gene may be assessed based on the level, or the change in the level, of any variable associated with AGT gene expression, e.g., AGT mRNA level or AGT protein level. This level may be assessed in an individual cell or in a group of cells, including, for example, a sample derived from a subject. It is understood that AGT is expressed predominantly in the liver, but also in the brain, gall bladder, heart, and kidney, and is present in circulation.

Inhibition may be assessed by a decrease in an absolute or relative level of one or more variables that are associated with AGT expression compared with a control level. The control level may be any type of control level that is utilized in the art, e.g., a pre-dose baseline level, or a level determined from a similar subject, cell, or sample that is untreated or treated with a control (such as, e.g., buffer only control or inactive agent control).

In some embodiments of the methods of the invention, expression of an AGT gene is inhibited by at least 50%, 55%, 60%, 65%, 70%, 75%, 80%, 85%, 90%, or 95%, or to below the level of detection of the assay. In preferred embodiments, expression of an AGT gene is inhibited by at least 70%. It is further understood that inhibition of AGT expression in certain tissues, e.g., in liver, without a significant inhibition of expression in other tissues, e.g., brain, may be desirable. In preferred embodiments, expression level is determined using the assay method provided in Example 2 with a 10 nM siRNA concentration in the appropriate species matched cell line.

In certain embodiments, inhibition of expression in vivo is determined by knockdown of the human gene in a rodent expressing the human gene, e.g., an AAV-infected mouse expressing the human target gene (i.e., AGT), e.g., when administered a single dose at 3 mg/kg at the nadir of RNA expression. Knockdown of expression of an endogenous gene in a model animal system can also be determined, e.g., after administration of a single dose at 3 mg/kg at the nadir of RNA expression. Such systems are useful when the nucleic acid sequence of the human gene and the model animal gene are sufficiently close such that the human iRNA provides effective knockdown of the model animal gene. RNA expression in liver is determined using the PCR methods provided in Example 2.

Inhibition of the expression of an AGT gene may be manifested by a reduction of the amount of mRNA expressed by a first cell or group of cells (such cells may be present, for example, in a sample derived from a subject) in which an AGT gene is transcribed and which has or have been treated (e.g., by contacting the cell or cells with an iRNA of the invention, or by administering an iRNA of the invention to a subject in which the cells are or were present) such that the expression of an AGT gene is inhibited, as compared to a second cell or group of cells substantially identical to the first cell or group of cells but which has not or have not been so treated (control cell(s) not treated with an iRNA or not treated with an iRNA targeted to the gene of interest). In preferred embodiments, the inhibition is assessed by the method provided in Example 2 using a 10 nM siRNA concentration in the species matched cell line and expressing the level of mRNA in treated cells as a percentage of the level of mRNA in control cells, using the following formula:

$$\frac{(mRNA \text{ in control cells}) - (mRNA \text{ in treated cells})}{(mRNA \text{ in control cells})} \cdot 100\%$$

In other embodiments, inhibition of the expression of an AGT gene may be assessed in terms of a reduction of a parameter that is functionally linked to AGT gene expression, e.g., AGT protein level in blood or serum from a subject. AGT gene silencing may be determined in any cell expressing AGT, either endogenous or heterologous from an expression construct, and by any assay known in the art.

Inhibition of the expression of an AGT protein may be manifested by a reduction in the level of the AGT protein that is expressed by a cell or group of cells or in a subject sample (e.g., the level of protein in a blood sample derived from a subject). As explained above, for the assessment of mRNA suppression, the inhibition of protein expression levels in a treated cell or group of cells may similarly be expressed as a percentage of the level of protein in a control cell or group of cells, or the change in the level of protein in a subject sample, e.g., blood or serum derived therefrom.

A control cell, a group of cells, or subject sample that may be used to assess the inhibition of the expression of an AGT gene includes a cell, group of cells, or subject sample that has not yet been contacted with an RNAi agent of the invention. For example, the control cell, group of cells, or subject sample may be derived from an individual subject (e.g., a human or animal subject) prior to treatment of the subject with an RNAi agent or an appropriately matched population control.

The level of AGT mRNA that is expressed by a cell or group of cells may be determined using any method known in the art for assessing mRNA expression. In one embodiment, the level of expression of AGT in a sample is determined by detecting a transcribed polynucleotide, or portion thereof, e.g., mRNA of the AGT gene. RNA may be extracted from cells using RNA extraction techniques including, for example, using acid phenol/guanidine isothiocyanate extraction (RNAzol B; Biogenesis), RNeasy™ RNA preparation kits (Qiagen®) or PAXgene™ (PreAnalytix™, Switzerland). Typical assay formats utilizing ribonucleic acid hybridization include nuclear run-on assays, RT-PCR, RNase protection assays, northern blotting, in situ hybridization, and microarray analysis.

In some embodiments, the level of expression of AGT is determined using a nucleic acid probe. The term "probe", as used herein, refers to any molecule that is capable of selectively binding to a specific AGT. Probes can be synthesized by one of skill in the art, or derived from appropriate biological preparations. Probes may be specifically designed to be labeled. Examples of molecules that can be utilized as probes include, but are not limited to, RNA, DNA, proteins, antibodies, and organic molecules.

Isolated mRNA can be used in hybridization or amplification assays that include, but are not limited to, Southern or northern analyses, polymerase chain reaction (PCR) analyses and probe arrays. One method for the determination of mRNA levels involves contacting the isolated mRNA with a nucleic acid molecule (probe) that can hybridize to AGT mRNA. In one embodiment, the mRNA is immobilized on a solid surface and contacted with a probe, for example by running the isolated mRNA on an agarose gel and transferring the mRNA from the gel to a membrane, such as nitrocellulose. In an alternative embodiment, the probe(s) are immobilized on a solid surface and the mRNA is contacted with the probe(s), for example, in an Affymetrix® gene chip array. A skilled artisan can readily adapt known mRNA detection methods for use in determining the level of AGT mRNA.

An alternative method for determining the level of expression of AGT in a sample involves the process of nucleic acid amplification or reverse transcriptase (to prepare cDNA) of for example mRNA in the sample, e.g., by RT-PCR (the experimental embodiment set forth in Mullis, 1987, U.S. Pat. No. 4,683,202), ligase chain reaction (Barany (1991) Proc. Nat. Acad. Sci. USA 88:189-193), self sustained sequence replication (Guatelli et al. (1990) Proc. Nat. Acad. Sci. USA 87:1874-1878), transcriptional amplification system (Kwoh et al. (1989) Proc. Nat. Acad. Sci. USA 86:1173-1177), Q-Beta Replicase (Lizardi et al. (1988) Bio/Technology 6:1197), rolling circle replication (Lizardi et al., U.S. Pat. No. 5,854,033) or any other nucleic acid amplification method, followed by the detection of the amplified molecules using techniques well known to those of skill in the art. These detection schemes are especially useful for the detection of nucleic acid molecules if such molecules are present in very low numbers. In particular aspects of the invention, the level of expression of AGT is determined by quantitative fluorogenic RT-PCR (i.e., the TaqMan™ System). In preferred embodiments, expression level is determined by the method provided in Example 2 using a 10 nM siRNA concentration in the species matched cell line.

The expression levels of AGT mRNA may be monitored using a membrane blot (such as used in hybridization analysis such as northern, Southern, dot, and the like), or microwells, sample tubes, gels, beads or fibers (or any solid support comprising bound nucleic acids). See U.S. Pat. Nos. 5,770,722, 5,874,219, 5,744,305, 5,677,195 and 5,445,934, which are incorporated herein by reference. The determination of AGT expression level may also comprise using nucleic acid probes in solution.

In preferred embodiments, the level of mRNA expression is assessed using branched DNA (bDNA) assays or real time PCR (qPCR). The use of these methods is described and exemplified in the Examples presented herein. In preferred embodiments, expression level is determined by the method provided in Example 2 using a 10 nM siRNA concentration in the species matched cell line.

The level of AGT protein expression may be determined using any method known in the art for the measurement of protein levels. Such methods include, for example, electrophoresis, capillary electrophoresis, high performance liquid chromatography (HPLC), thin layer chromatography (TLC), hyperdiffusion chromatography, fluid or gel precipitin reactions, absorption spectroscopy, a colorimetric assays, spectrophotometric assays, flow cytometry, immunodiffusion (single or double), immunoelectrophoresis, western blotting, radioimmunoassay (RIA), enzyme-linked immunosorbent assays (ELISAs), immunofluorescent assays, electrochemiluminescence assays, and the like.

In some embodiments, the efficacy of the methods of the invention are assessed by a decrease in AGT mRNA or protein level (e.g., in a liver biopsy).

In some embodiments of the methods of the invention, the iRNA is administered to a subject such that the iRNA is delivered to a specific site within the subject. The inhibition of expression of AGT may be assessed using measurements of the level or change in the level of AGT mRNA or agt protein in a sample derived from fluid or tissue from the specific site within the subject (e.g., liver or blood).

As used herein, the terms detecting or determining a level of an analyte are understood to mean performing the steps to determine if a material, e.g., protein, RNA, is present. As used herein, methods of detecting or determining include detection or determination of an analyte level that is below the level of detection for the method used.

VII. Prohylactic and Treatment Methods of the Invention

The present invention also provides methods of using an iRNA of the invention or a composition containing an iRNA of the invention to inhibit expression of AGT, thereby preventing or treating a an AGT associated disorder, e.g., high blood pressure, e.g., hypertension.

In the methods of the invention the cell may be contacted with the siRNA in vitro or in vivo, i.e., the cell may be within a subject.

A cell suitable for treatment using the methods of the invention may be any cell that expresses an AGT gene, e.g., a liver cell, a brain cell, a gall bladder cell, a heart cell, or a kidney cell, but preferably a liver cell. A cell suitable for use in the methods of the invention may be a mammalian cell, e.g., a primate cell (such as a human cell, including human cell in a chimeric non-human animal, or a non-human primate cell, e.g., a monkey cell or a chimpanzee cell), or a non-primate cell. In certain embodiments, the cell is a human cell, e.g., a human liver cell. In the methods of the invention, AGT expression is inhibited in the cell by at least 50, 55, 60, 65, 70, 75, 80, 85, 90, or 95, or to a level below the level of detection of the assay.

The in vivo methods of the invention may include administering to a subject a composition containing an iRNA, where the iRNA includes a nucleotide sequence that is complementary to at least a part of an RNA transcript of the AGT gene of the mammal to which the RNAi agent is to be administered. The composition can be administered by any means known in the art including, but not limited to oral, intraperitoneal, or parenteral routes, including intracranial (e.g., intraventricular, intraparenchymal, and intrathecal), intravenous, intramuscular, subcutaneous, transdermal, airway (aerosol), nasal, rectal, and topical (including buccal and sublingual) administration. In certain embodiments, the compositions are administered by intravenous infusion or injection. In certain embodiments, the compositions are administered by subcutaneous injection. In certain embodiments, the compositions are administered by intramuscular injection.

In one aspect, the present invention also provides methods for inhibiting the expression of an AGTgene in a mammal. The methods include administering to the mammal a composition comprising a dsRNA that targets an AGT gene in a cell of the mammal and maintaining the mammal for a time sufficient to obtain degradation of the mRNA transcript of the AGT gene, thereby inhibiting expression of the AGT gene in the cell. Reduction in gene expression can be assessed by any methods known in the art and by methods, e.g. qRT-PCR, described herein, e.g., in Example 2. Reduction in protein production can be assessed by any methods known it the art, e.g. ELISA. In certain embodiments, a puncture liver biopsy sample serves as the tissue material for monitoring the reduction in the AGT gene or protein expression. In other embodiments, a blood sample serves as the subject sample for monitoring the reduction in the agt protein expression.

The present invention further provides methods of treatment in a subject in need thereof, e.g., a subject diagnosed with a hypertension.

The present invention further provides methods of prophylaxis in a subject in need thereof. The treatment methods of the invention include administering an iRNA of the invention to a subject, e.g., a subject that would benefit from a reduction of AGT expression, in a prophylactically effective amount of an iRNA targeting an AGT gene or a pharmaceutical composition comprising an iRNA targeting an AGT gene.

An iRNA of the invention may be administered as a "free iRNA." A free iRNA is administered in the absence of a pharmaceutical composition. The naked iRNA may be in a suitable buffer solution. The buffer solution may comprise acetate, citrate, prolamine, carbonate, or phosphate, or any combination thereof. In one embodiment, the buffer solution is phosphate buffered saline (PBS). The pH and osmolarity of the buffer solution containing the iRNA can be adjusted such that it is suitable for administering to a subject.

Alternatively, an iRNA of the invention may be administered as a pharmaceutical composition, such as a dsRNA liposomal formulation.

Subjects that would benefit from an inhibition of AGT gene expression are subjects susceptible to or diagnosed with hypertension.

In an embodiment, the method includes administering a composition featured herein such that expression of the target AGT gene is decreased, such as for about 1, 2, 3, 4, 5, 6, 1-6, 1-3, or 3-6 months per dose. In certain embodiments, the composition is administered once every 3-6 months.

Preferably, the iRNAs useful for the methods and compositions featured herein specifically target RNAs (primary or processed) of the target AGT gene. Compositions and methods for inhibiting the expression of these genes using iRNAs can be prepared and performed as described herein.

Administration of the iRNA according to the methods of the invention may result prevention or treatment of an AGT associated disorder disorder, e.g., high blood pressure, e.g., hypertension. Diagnostic criteria for various types of high blood pressure are provided below.

Subjects can be administered a therapeutic amount of iRNA, such as about 0.01 mg/kg to about 200 mg/kg.

The iRNA is preferably administered subcutaneously, i.e., by subcutaneous injection. One or more injections may be used to deliver the desired dose of iRNA to a subject. The injections may be repeated over a period of time.

The administration may be repeated on a regular basis. In certain embodiments, after an initial treatment regimen, the treatments can be administered on a less frequent basis. A repeat-dose regimen may include administration of a therapeutic amount of iRNA on a regular basis, such as once per month to once a year. In certain embodiments, the iRNA is administered about once per month to about once every three months, or about once every three months to about once every six months.

VIII. Diagnostic Criteria, Risk Factors, and Treatments for Hypertension

Recently practice guidelines for prevention and treatment of hypertension were revised. Extensive reports were published by Reboussin et al. (Systematic Review for the 2017 ACC/AHA/AAPA/ABC/ACPM/AGS/APhA/ASH/ASPC/NMA/PCNA Guideline for the Prevention, Detection, Evaluation, and Management of High Blood Pressure in Adults: A Report of the American College of Cardiology/American Heart Association Task Force on Clinical Practice Guidelines. J Am Coll Cardiol. 2017 Nov. 7. pii: S0735-1097(17)41517-8. doi: 10.1016/j.jacc.2017.11.004.) and Whelton et al. (2017 ACC/AHA/AAPA/ABC/ACPM/AGS/APhA/ASH/ASPC/NMA/PCNA Guideline for the Prevention, Detection, Evaluation, and Management of High Blood Pressure in Adults: A Report of the American College of Cardiology/American Heart Association Task Force on Clinical Practice Guidelines. J Am Coll Cardiol. 2017 Nov. 7. pii: S0735-1097(17)41519-1. doi: 10.1016/j.jacc.2017.11.006). Some highlights of the new Guidelines are provided below. However, the Guidelines should be understood as providing the knowledge of those of skill in the art regarding diagnostic and monitoring criteria and treatment for hypertension at the time of filing of this application and are incorporated herein by reference.

A. Diagnostic Criteria

Although a continuous association exists between higher blood pressure and increased cardiovascular disease risk, it is useful to categorize blood pressure levels for clinical and public health decision making. Blood pressure can be categorized into 4 levels on the basis of average blood pressure measured in a healthcare setting (office pressures): normal, elevated, and stage 1 or 2 hypertension as shown in the table below (from Whelton et al., 2017).

| Blood Pressure Category | Systolic Blood Pressure | | Diastolic Blood Pressure |
|---|---|---|---|
| Normal | <120 mm Hg | and | <80 mm Hg |
| Elevated | 120-129 mm Hg | and | <80 mm Hg |
| Hypertension* | | | |
| Stage 1 | 130-139 mm Hg | or | 80-89 mm Hg |
| Stage 2 | ≥140 mm Hg | or | ≥90 mm Hg |

*Individuals with systolic blood pressure and diastolic blood pressure in 2 categories should be designated to the higher blood pressure category.

Blood pressure indicates blood pressure based on an average of >2 careful readings obtained on ≥2 occasions. Best practices for obtaining careful blood pressure readings are detailed in Whelton et al., 2017 and are known in the art.

This categorization differs from that previously recommended in the JNC 7 report (Chobanian et al; the National High Blood Pressure Education Program Coordinating Committee. Seventh Report of the Joint National Committee on Prevention, Detection, Evaluation, and Treatment of High Blood Pressure. Hypertension. 2003; 42:1206-52) with stage 1 hypertension now defined as a systolic blood pressure (SBP) of 130-139 or a diastolic blood pressure (DBP) of 80-89 mm Hg, and with stage 2 hypertension in the present document corresponding to stages 1 and 2 in the JNC 7 report. The rationale for this categorization is based on observational data related to the association between SBP/DBP and cardiovascular disease risk, randomized clinical trials of lifestyle modification to lower blood pressure, and randomized clinical trials of treatment with antihypertensive medication to prevent cardiovascular disease.

The increased risk of cardiovascular disease among adults with stage 2 hypertension is well established. An increasing number of individual studies and meta-analyses of observational data have reported a gradient of progressively higher cardiovascular disease risk going from normal blood pressure to elevated blood pressure and stage 1 hypertension. In many of these meta-analyses, the hazard ratios for coronary heart disease and stroke were between 1.1 and 1.5 for the comparison of SBP/DBP of 120-129/80-84 mm Hg versus <120/80 mm Hg and between 1.5 and 2.0 for the comparison of SBP/DBP of 130-139/85-89 mm Hg versus <120/80 mm Hg. This risk gradient was consistent across subgroups defined by sex and race/ethnicity. The relative increase in cardiovascular disease risk associated with higher blood pressure was attenuated but still present among older adults.

Lifestyle modification and pharmacological antihypertensive treatment are recommended for individuals with elevated blood pressure and stages 1 and 2 hypertension. Clinical benefit can be obtained by a reduction of the stage of elevated blood pressure, even if blood pressure is not normalized by a treatment.

B. Risk Factors

Hypertension is a complex disease that results from a combination of factors including, but not limited to, genetics, lifestyle, diet, and secondary risk factors. Hypertension can also be associated with pregnancy. It is understood that due to the complex nature of hypertension, it is understood that multiple interventions may be required for treatment of hypertension. Moreover, non-pharmacological interventions, including modification of diet and lifestyle, can be useful for the prevention and treatment of hypertension. Further, an intervention may provide a clinical benefit without fully normalizing blood pressure in an individual.

1. Genetic Risk Factors

Several monogenic forms of hypertension have been identified, such as glucocorticoid-remediable aldosteronism, Liddle's syndrome, Gordon's syndrome, and others in which single-gene mutations fully explain the pathophysiology of hypertension, these disorders are rare. The current tabulation of known genetic variants contributing to blood pressure and hypertension includes more than 25 rare mutations and 120 single nucleotide polymorphisms. However, although genetic factors may contribute to hypertension in some individuals, it is estimated that genetic variation accounts for only about 3.5% of blood pressure variability.

2. Diet and Alcohol Consumption

Common environmental and lifestyle risk factors leading to hypertension include poor diet, insufficient physical activity, and excess alcohol consumption. These factors can lead to a person to become overweight or obese, further increasing the likelihood of developing or exacerbating hypertension. Elevated blood pressure is even more strongly correlated with increased waist-to-hip ratio or other measures of central fat distribution. Obesity at a young age and ongoing obesity is strongly correlated with hypertension later in life. Achieving a normal weight can reduce the risk of developing high blood pressure to that of a person who has never been obese.

Intake of sodium, potassium, magnesium, and calcium can also have a significant effect on blood pressure. Sodium intake is positively correlated with blood pressure and accounts for much of the age-related increase in blood pressure. Certain groups are more sensitive to increased sodium consumption than others including black and older adults (≥65 years old), and those with a higher level of blood pressure or comorbidities such as chronic kidney disease, diabetes mellitus, or metabolic syndrome. In aggregate, these groups constitute more than half of all US adults. Salt sensitivity may be a marker for increased cardiovascular disease and all-cause mortality, independent of blood pressure. Currently, techniques for recognition of salt sensitivity are impractical in a clinical setting. Therefore, salt sensitivity is best considered as a group characteristic.

Potassium intake is inversely related to blood pressure and stroke, and a higher level of potassium seems to blunt the effect of sodium on blood pressure. A lower sodium-potassium ratio is associated with a lower blood pressure than that noted for corresponding levels of sodium or potassium on their own. A similar observation has been made for risk of cardiovascular disease.

Alcohol consumption has long been associated with high blood pressure. In the US, it has been estimated that alcohol consumption accounts for about 10% of the population burden of hypertension, with the burden being greater in men than women.

It is understood that changes in diet or alcohol consumption can be an aspect of prevention or treatment of hypertension.

3. Physical Activity

There is a well-established inverse correlation between physical activity/physical fitness and blood pressure levels. Even modest levels of physical activity have been demonstrated to be beneficial in decreasing hypertension.

It is understood that an increase in physical activity can be an aspect of prevention or treatment of hypertension.

4. Secondary Risk Factors

Secondary hypertension can underlie severe elevation of blood pressure, pharmacologically resistant hypertension, sudden onset of hypertension, increased blood pressure in patients with hypertension previously controlled on drug therapy, onset of diastolic hypertension in older adults, and target organ damage disproportionate to the duration or severity of the hypertension. Although secondary hypertension should be suspected in younger patients (<30 years of age) with elevated blood pressure, it is not uncommon for primary hypertension to manifest at a younger age, especially in blacks, and some forms of secondary hypertension, such as renovascular disease, are more common at older age (≥65 years of age). Many of the causes of secondary hypertension are strongly associated with clinical findings or groups of findings that suggest a specific disorder. In such cases, treatment of the underlying condition may resolve the findings of elevated blood pressure without administering agents typically used for the treatment of hypertension.

5. Pregnancy

Pregnancy is a risk factor for high blood pressure, and high blood pressure during pregnancy is a risk factor for cardiovascular disease and hypertension later in life. A Report on pregnancy associated hypertension was published in 2013 by the American College of Obstetrics and Gynecology (ACOG) (American College of Obstetricians and Gynecologists, Task Force on Hypertension in Pregnancy. Hypertension in pregnancy. Report of the American College of Obstetricians and Gynecologists' Task Force on Hypertension in Pregnancy. Obstet Gynecol. 2013; 122:1122-31). Some highlights of the Report are provided below. However, the Report should be understood as providing the knowledge of those of skill in the art regarding diagnostic and monitoring criteria and treatment for hypertension in pregnancy at the time of filing of this application and are incorporated herein by reference.'

The diagnostic criteria for preeclampsia are provided in the table below (from Table 1 of the ACOG report, 2013).

| | |
|---|---|
| Blood Pressure | ≥140 mm Hg diastolic or ≥90 mm Hg diastolic on two occasions at least 4 hours apart after 20 weeks of gestation in a woman with a previously normal blood pressure |
| | ≥160 mm Hg systolic or ≥110 mm Hg diastolic, hypertension can be confirmed within a short interval (minutes) to facilitate timely antihypertensive therapy and |
| Proteinurea | ≥300 mg per 24-hour urine collection (or this amount extrapolated for a timed collection) Or Protein/ creatinine ratio ≥0.3 (each measured as mg/dL) |
| Or in the absence of proteinurea, new onset of hypertension with the new onset of an of the following: | |
| Thrombocytopenia | Platelet count ≤100,000/microliter |
| Renal insufficiency | Serum creatinine concentration ≥1.1 mg/dL or a doubling of the serum creatinine concentration in the absence of other renal disease |
| Impaired liver function | Elevated blood concentrations if liver transaminases to twice normal concentration |
| Pulmonary edema | |
| Cerebral or visual symptoms | |

Blood Pressure management during pregnancy is complicated by the fact that many commonly used antihypertensive agents, including ACE inhibitors and ARBs, are contraindicated during pregnancy because of potential harm to the fetus. The goal of antihypertensive treatment during pregnancy includes prevention of severe hypertension and the possibility of prolonging gestation to allow the fetus more time to mature before delivery. A review of treatment for pregnancy-associated severe hypertension found insufficient evidence to recommend specific agents; rather, clinician experience was recommended in this setting (Duley L, Meher S, Jones L. Drugs for treatment of very high blood pressure during pregnancy. Cochrane Database Syst Rev. 2013; 7:CD001449).

C. Treatments

Treatment of high blood pressure is complex as it is frequently present with other comorbidities, often including reduced renal function, for which the subject may also be undergoing treatment. Clinicians managing adults with high blood pressure should focus on overall patient health, with a particular emphasis on reducing the risk of future adverse cardiovascular disease outcomes. All patient risk factors need to be managed in an integrated fashion with a comprehensive set of nonpharmacological and pharmacological strategies. As patient blood pressure and risk of future cardiovascular disease events increase, blood pressure management should be intensified.

Whereas treatment of high blood pressure with blood pressure-lowering medications on the basis of blood pressure level alone is considered cost effective, use of a combination of absolute cardiovascular disease risk and blood pressure level to guide such treatment is more efficient and cost effective at reducing risk of cardiovascular disease than is use of blood pressure level alone. Many patients started on a single agent will subsequently require ≥2 drugs from different pharmacological classes to reach their blood pressure goals. Knowledge of the pharmacological mechanisms of action of each agent is important. Drug regimens with complementary activity, where a second antihypertensive agent is used to block compensatory responses to the initial agent or affect a different pressor mechanism, can result in additive lowering of blood pressure. For example, thiazide diuretics may stimulate the renin-angiotensin-aldosterone system. By adding an ACE inhibitor or ARB to the thiazide, an additive blood pressure lowering effect may be obtained. Use of combination therapy may also improve adherence. Several 2- and 3-fixed-dose drug combinations of antihypertensive drug therapy are available, with complementary mechanisms of action among the components.

Table 18 from Whelton et al. 2017 listing oral antihypertensive drugs is provided below. Classes of therapeutic agents for the treatment of high blood pressure and drugs that fall within those classes are provided. Dose ranges, frequencies, and comments are also provided.

| Class | Drug | Usual Dose, Range (mg/d)* | Daily Frequency | Comments |
|---|---|---|---|---|
| | | Primary agents | | |
| Thiazide or thiazide-type diuretics | Chlorthalidone<br>Hydro-chlorothiazide<br>Indapamide<br>Metolazone | 12.5-25<br>25-50<br><br>1.25-2.5<br>2.5-10 | 1<br>1<br><br>1<br>1 | Chlorthalidone is preferred on the basis of prolonged half-life and proven trial reduction of CVD. Monitor for hyponatremia and hypokalemia, uric acid and calcium levels. Use with caution in patients with history of acute gout unless patient is on uric acid-lowering therapy. |
| ACE inhibitors | Benazepril<br>Captopril<br>Enalapril<br>Fosinopril<br>Lisinopril<br>Moexipril<br>Perindopril<br>Quinapril<br>Ramipril<br>Trandolapril | 10-40<br>12.5-150<br>5-40<br>10-40<br>10-40<br>7.5-30<br>4-16<br>10-80<br>2.5-10<br>1-4 | 1 or 2<br>2 or 3<br>1 or 2<br>1<br>1<br>1 or 2<br>1<br>1 or 2<br>1 or 2<br>1 | Do not use in combination with ARBs or direct renin inhibitor There is an increased risk of hyperkalemia, especially in patents with CKD or in those on K$^+$ supplements or K$^+$-sparing drugs. There is a risk of acute renal failure in patients with severe bilateral renal artery stenosis. Do no use if patient has history of angioedema with ACE inhibitors. Avoid in pregnancy. |
| ARBs | Azilsartan<br>Candesartan<br>Eprosartan<br>Irbesartan<br>Losartan<br>Olmesartan<br>Telmisartan<br>Valsartan | 40-80<br>8-32<br>600-800<br>150-300<br>50-100<br>20-40<br>20-80<br>80-320 | 1<br>1<br>1 or 2<br>1<br>1 or 2<br>1<br>1<br>1 | Do not use in combination with ACE inhibitors or direct renin inhibitors. There is an increased risk of hyperkalemia in CKD or in those on K$^+$ supplements or K$^+$-sparing drugs. There is a risk of acute renal failure in patients with severe bilateral renal artery stenosis. Do not use if patient has history of angioedema with ARBs. Patients with a history of angioedema with an ACE inhibitor can receive an ARB beginning 6 weeks after ACE inhibitor is discontinued. Avoid in pregnancy. |
| CCB-dihydropyridines | Amlodipine<br>Felodipine<br>Isradipine<br>Nicardipine SR<br>Nifedipine LA<br>Nisoldipine | 2.5-10<br>5-10<br>5-10<br>5-20<br>60-120<br>30-90 | 1<br>1<br>2<br>1<br>1<br>1 | Avoid use in patients with HFrEF; amlodipine or felodipine may be used if required They are associated with dose-related pedal edema, which is more common in women than men. |
| CCB-nondihydropyridines | Diltiazem SR<br>Diltiazem ER<br>Verapamil IR<br>Verapamil SR<br>Verapamil-delayed onset ER (various forms) | 180-360<br>120-480<br>40-80<br>120-480<br>100-480 | 2<br>1<br>3<br>1 or 2<br>1 (in the evening) | Avoid routine use with beta blockers because of increased risk of bradycardia and heart block. Do not use in patients with HFrEF. There are drug interactions with diltiazem and verapamil (CYP3A4 major substrate and moderate inhibitor). |
| | | Secondary agents | | |
| Diuretics-loop | Bumetanide<br>Furosemide<br>Torsemide | 0.5-4<br>20-80<br>5-10 | 2<br>2<br>1 | There are preferred diuretics in patients with symptomatic HF. They are preferred over thiazides in |

-continued

| Class | Drug | Usual Dose, Range (mg/d)* | Daily Frequency | Comments |
|---|---|---|---|---|
| Diuretics-potassium sparing | Amiloride | 5-10 | 1 or 2 | patients with moderate-to-severe CKD (e.g., GFR <30 mL/min). These are monotherapy agents and minimally effective antihypertensive agents. |
| | Triamterene | 50-100 | 1 or 2 | Combination therapy of potassium-sparing diuretic with a thiazide can be considered in patients with hypokalemia on thiazide monotherapy. Avoid in patients with significant CKD (e.g. GFR <45 mL/min). |
| Diuretics-aldosterone antagonists | Eplerenone | 50-100 | 12 | These are preferred agents in primary aldosteronism and resistant hypertension. Spironolactone is associated with greater risk of gynecomastia and impotence as compared with eplerenone. This is common add-on therapy in resistant hypertension. Avoid use with K$^+$ supplements, other K$^+$-sparing diuretics, or significant renal dysfunction. Eplerenone often requires twice-daily dosing for adequate BP lowering. |
| | Spironolactone | 25-100 | 1 | |
| Beta blockers-cardioselective | Atenolol | 25-100 | 12 | Beta blockers are not recommended as first-line agents unless the patient has IHD or HF. These are preferred in patients with broncho spastic airway disease requiring a beta blocker. Bisoprolol and metoprolol succinate are preferred in patients with HFrEF. Avoid abrupt cessation. |
| | Betaxolol | 5-20 | 1 | |
| | Bisoprolol | 2.5-10 | 1 | |
| | Metoprolol tartrate | 100-400 | 2 | |
| | Metoprolol succinate | 50-200 | 1 | |
| Beta blockers-cardioselective and vasodilatory | Nebivolol | 5-40 | 1 | Nebivolol induces nitric oxide-inducesd vasodilation. Avoid abrupt cessation. |
| Beta blockers-noncardioselective | Nadolol | 40-120 | 1 | Avoid in patients with reactive airiways disease. Avoid abrupt cessation. |
| | Propanolol IR | 160-480 | 2 | |
| | Propanolol LA | 80-320 | 1 | |
| Beta blockers-intrinsic sympathomimetic activity | Acebutolol | 200-800 | 1 | Generally avoid, especially in patients with IHD or HF. Avoid abrupt cessation. |
| | Carteolol | 2.5-10 | 1 | |
| | Penbutolol | 10-40 | 1 | |
| | Pindolol | 10-60 | 2 | |
| Beta blockers-combined alpha-and beta receptor | Carvediol | 12.5-50 | 2 | Carvedilol is preferred in patients with HFrEF. Avoid abrupt cessation. |
| | Carvedilol phosphate | 20-80 | 1 | |
| | Labetalol | 200-800 | 2 | |
| Direct renin inhibitor | Aliskiren | 150-300 | 1 | Do not use in combination with ACE inhibitors or ARBs. Aliskiren is very long acting. There is an increased risk of hyperkalemina in CKD or in those on K$^+$ supplements or K$^+$-sparing drugs. |

-continued

| Class | Drug | Usual Dose, Range (mg/d)* | Daily Frequency | Comments |
|---|---|---|---|---|
| | | | | Aliskiren may cause acute renal failure in patients with severe bilateral renal artery stenosis. Avoid in pregnacy. |
| Alpha-1-blockers | Doxazosin | 1-8 | 1 | These are associated with orthostatic hypotension, especially in older adults. They may be considered as second-line agent in patients with concominant BPH. |
| | Prazosin | 2-20 | 2 or 3 | |
| | Terazosin | 1-20 | 1 or 2 | |
| Central alpha-agonist and other centrally acting drugs | Clonidine oral | 0.1-0.8 | 2 | These are generally reserved as last-line because of significant CNS adverse effects, especially in older adults. Avoid abrupt discontinuation of clonidine, which may induce hypertensive crisis; clonidine must be tapered to avoid rebound hypertension. |
| | Clonidine patch | 0.1-0.3 | 1 weekly | |
| | Methyldopa | 250-1000 | 2 | |
| | Guanfacine | 0.5-2 | 1 | |
| Direct vasodilators | Hydrazine | 250-200 | 2 or 3 | These are associated with sodium and water retention and reflex tachycardia; use with a diuretic and beta blocker. Hydralazine is associated with drug-induced lupus-like syndrome at higher doses. Minoxidil is associated with hirsutism and required a loop diurestic. Minoxidil can induce pericardial effusion. |
| | Minoxidil | 5-100 | 1-3 | |

*Dosages may vary from those listed in the FDA approved labeling (available at htttps://dailymed.nlm.nih.gov/dailymed/). ACE indicates angiotensin-converting enzyme; ARB, angiotensin receptor blocker; BP, blood pressure; BPH, benign prostatic hyperplasia; CCB, calcium channel blocker; CKD, chronic kidney disease; CNS, central nervous system; CVD, cardiovascular disease; ER, extended release; GFR, glomerular filtration rate; HF, heart failure; HFrEF, heart failure with reduced ejection fraction; IHD, ischemic heart disease; IR, immediate release; LA, long-acting; and SR, sustained release. From, Chobanian et al. (2003) The JNC 7 Report. JAMA 289(19):2560.

This invention is further illustrated by the following examples which should not be construed as limiting. The entire contents of all references, patents and published patent applications cited throughout this application, as well as the Sequence Listing, are hereby incorporated herein by reference.

EXAMPLES

Example 1. iRNA Synthesis

Source of Reagents

Where the source of a reagent is not specifically given herein, such reagent can be obtained 20 from any supplier of reagents for molecular biology at a quality/purity standard for application in molecular biology.

siRNA Design

A set of siRNAs targeting the human AGT gene (human: NCBI refseqID NM_000029.3; NCBI GeneID: 183) was designed using custom R and Python scripts. The human NM_000029 REFSEQ mRNA, version 3, has a length of 2587 bases.

A detailed list of the unmodified AGT sense and antisense strand nucleotide sequences is shown in Table 3. A detailed list of the modified AGT sense and antisense strand nucleotide sequences is shown in Table 5.

siRNA Synthesis siRNAs were synthesized and annealed using routine methods known in the art.

Example 2. In Vitro Screening Methods

Cell Culture and 384-Well Transfections

Hep3b cells (ATCC, Manassas, Va.) were grown to near confluence at 37° C. in an atmosphere of 5% $CO_2$ in Eagle's Minimum Essential Medium (Gibco) supplemented with 10% FBS (ATCC) before being released from the plate by trypsinization.

Transfection was performed by adding 4.9 µl of Opti-MEM plus 0.1 µl of Lipofectamine RNAiMax per well (Invitrogen, Carlsbad Calif. cat #13778-150) to 5 µl of each siRNA duplex to an individual well in a 384-well plate. The mixture was then incubated at room temperature for 20 minutes. Fifty µl of complete growth media containing 5,000 Hep3b cells were then added to the siRNA mixture. Cells were incubated for 24 hours prior to RNA purification. Single dose experiments were performed at 10 nM and 0.1 nM final duplex concentration, and dose response experiments were performed using an eight-point six-fold serial dilution over the range of 10 nM to 37.5 fM.

Additional dsRNA agents targeting an AGT mRNA are described in PCT Publication No. WO 2015/179724, the entire contents of which are incorporated herein by reference.

Total RNA Isolation Using DYNABEADS mRNA Isolation Kit (Invitrogen™, Part #: 610-12)

Cells were lysed in 75 µl of Lysis/Binding Buffer containing 3 uL of beads per well and mixed for 10 minutes on an electrostatic shaker. The washing steps were automated on a Biotek EL406, using a magnetic plate support. Beads were washed (in 90 µL) once in Buffer A, once in Buffer B, and twice in Buffer E, with aspiration steps in between. Following a final aspiration, complete 10 µL RT mixture was added to each well, as described below.

cDNA Synthesis Using ABI High Capacity cDNA Reverse Transcription Kit (Applied Biosystems, Foster City, Calif., Cat #4368813):

A master mix of 1 ul 10× Buffer, 0.4 µl 25×dNTPs, 1 µl Random primers, 0.5 µl Reverse Transcriptase, 0.5 µl RNase inhibitor and 6.6 µl of H$_2$O per reaction were added per well. Plates were sealed, agitated for 10 minutes on an electrostatic shaker, and then incubated at 37 degrees C. for 2 hours. Following this, the plates were agitated at 80 degrees C. for 8 minutes.

Real Time PCR:

Two µl of cDNA were added to a master mix containing 0.5 µl of human GAPDH TaqMan Probe (4326317E), 0.5 µl human AGT (Hs00174854 ml), 2 µl nuclease-free water and 5 µl Lightcycler 480 probe master mix (Roche Cat #04887301001) per well in a 384 well plates (Roche cat #04887301001). Real time PCR was done in a LightCycler480 Real Time PCR system (Roche).

To calculate relative fold change, data were analyzed using the ΔΔCt method and normalized to assays performed with cells transfected with 10 nM AD-1955, or mock transfected cells. IC$_{50}$s were calculated using a 4 parameter fit model using XLFit and normalized to cells transfected with AD-1955 or mock-transfected. The sense and antisense sequences of AD-1955 are: sense: cuuAcGcuGAGuAcuucGAdTsdT (SEQ ID NO:19) and antisense UCGAAGuA-CUcAGCGuAAGdTsdT (SEQ ID NO: 20). Results from the screening are shown in Table 4.

TABLE 2

Abbreviations of nucleotide monomers used in nucleic acid sequence representation. It will be understood that these monomers, when present in an oligonucleotide, are mutually linked by 5'-3'-phosphodiester bonds.

| Abbreviation | Nucleotide(s) |
|---|---|
| A | Adenosine-3'-phosphate |
| Ab | beta-L-adenosine-3'-phosphate |
| Abs | beta-L-adenosine-3'-phosphorothioate |
| Af | 2'-fluoroadenosine-3'-phosphate |
| Afs | 2'-fluoroadenosine-3'-phosphorothioate |
| As | adenosine-3'-phosphorothioate |
| C | cytidine-3'-phosphate |
| Cb | beta-L-cytidine-3'-phosphate |
| Cbs | beta-L-cytidine-3'-phosphorothioate |
| Cf | 2'-fluorocytidine-3'-phosphate |
| Cfs | 2'-fluorocytidine-3'-phosphorothioate |
| Cs | cytidine-3'-phosphorothioate |
| G | guanosine-3'-phosphate |
| Gb | beta-L-guanosine-3'-phosphate |
| Gbs | beta-L-guanosine-3'-phosphorothioate |
| Gf | 2'-fluoroguanosine-3'-phosphate |
| Gfs | 2'-fluoroguanosine-3'-phosphorothioate |
| Gs | guanosine-3'-phosphorothioate |
| T | 5'-me thyluri dine-3'-phosphate |
| Tf | 2'-fluoro-5-methyluridine-3'-phosphate |

TABLE 2-continued

Abbreviations of nucleotide monomers used in nucleic acid sequence representation. It will be understood that these monomers, when present in an oligonucleotide, are mutually linked by 5'-3'-phosphodiester bonds.

| Abbreviation | Nucleotide(s) |
|---|---|
| Tfs | 2'-fluoro-5-methyluridine-3'-phosphorothioate |
| Ts | 5-methyluridine-3'-phosphorothioate |
| U | Uridine-3'-phosphate |
| Uf | 2'-fluorouridine-3'-phosphate |
| Ufs | 2'-fluorouridine-3'-phosphorothioate |
| Us | uridine-3'-phosphorothioate |
| N | any nucleotide, modified or unmodified |
| a | 2'-O-methyladenosine-3'-phosphate |
| as | 2'-O-methyladenosine-3'-phosphorothioate |
| c | 2'-O-methylcytidine-3'-phosphate |
| cs | 2'-O-methylcytidine-3'-phosphorothioate |
| g | 2'-O-methylguanosine-3'-phosphate |
| gs | 2'-O-methylguanosine-3'-phosphorothioate |
| t | 2'-O-methyl-5-methyluridine-3'-phosphate |
| ts | 2'-O-methyl-5-methyluridine-3'-phosphorothioate |
| u | 2'-O-methyluridine-3'-phosphate |
| us | 2'-O-methyluridine-3'-phosphorothioate |
| s | phosphorothioate linkage |
| L96 | N-[tris(GalNAc-alkyl)-amidodecanoyl)]-4-hydroxyprolinol (Hyp-(GalNAc-alkyl)3) |
| Y34 | 2-hydroxymethyl-tetrahydrofurane-4-methoxy-3-phosphate (abasic 2'-OMe furanose) |
| Y44 | inverted abasic DNA (2-hydroxymethyl-tetrahydrofurane-5-phosphate) |
| (Agn) | Adenosine-glycol nucleic acid (GNA) |
| (Cgn) | Cytidine-glycol nucleic acid (GNA) |
| (Ggn) | Guanosine-glycol nucleic acid (GNA) |
| (Tgn) | Thymidine-glycol nucleic acid (GNA) S-Isomer |
| P | Phosphate |
| VP | Vinyl-phosphate |
| (Aam) | 2'-O-(N-methylacetamide)adenosine-3'-phosphate |
| (Aams) | 2'-O-(N-methylacetamide)adenosine-3'-phosphorothioate |
| (Gam) | 2'-O-(N-methylacetamide)guanosine-3'-phosphate |
| (Gams) | 2'-O-(N-methylacetamide)guanosine-3'-phosphorothioate |
| (Tam) | 2'-O-(N-methylacetamide)thymidine-3'-phosphate |
| (Tams) | 2'-O-(N-methylace tamide)thymidine-3'-phosphorothioate |
| dA | 2'-deoxyadenosine-3'-phosphate |
| dAs | 2'-deoxyadenosine-3'-phosphorothioate |
| dC | 2'-deoxycytidine-3'-phosphate |
| dCs | 2'-deoxycytidine-3'-phosphorothioate |
| dG | 2'-deoxyguanosine-3'-phosphate |
| dGs | 2'-deoxyguanosine-3'-phosphorothioate |
| dT | 2'-deoxythymidine-3'-phosphate |
| dTs | 2'-deoxythymidine-3'-phosphorothioate |
| dU | 2'-deoxyuridine |
| dUs | 2'-deoxyuridine-3'-phosphorothioate |
| (Aeo) | 2'-O-methoxyethyladenosine-3'-phosphate |
| (Aeos) | 2'-O-methoxyethyladenosine-3'-phosphorothioate |
| (Geo) | 2'-O-methoxyethylguanosine-3'-phosphate |
| (Geos) | 2'-O-methoxyethylguanosine-3'-phosphorothioate |
| (Teo) | 2'-O-methoxyethyl-5-methyluridine-3'-phosphate |
| (Teos) | 2'-O-methoxyethyl-5-methyluridine-3'-phosphorothioate |
| (m5Ceo) | 2'-O-methoxyethyl-5-methylcytidine-3'-phosphate |
| (m5Ceos) | 2'-O-methoxyethyl-5-methylcytidine-3'-phosphorothioate |
| (A3m) | 3'-O-methyladeno sine-2'-phosphate |
| (A3mx) | 3'-O-methyl-xylofuranosyladeno sine-2'-phosphate |
| (G3m) | 3'-O-methylguanosine-2'-phosphate |
| (G3mx) | 3'-O-methyl-xylofuranosylguanosine-2'-phosphate |
| (C3m) | 3'-O-methylcytidine-2'-phosphate |
| (C3mx) | 3'-O-methyl-xylofuranosylcytidine-2'-phosphate |
| (U3m) | 3'-O-methyluridine-2'-phosphate |
| U3mx) | 3'-O-methyl-xylofuranosyluridine-2'-phosphate |
| (m5Cam) | 2'-O-(N-methylace tamide)-5-methylcytidine-3'-phosphate |
| (m5Cams) | 2'-O-(N-methylace tamide)-5-methylcytidine-3'-phosphorothioate |
| (Chd) | 2'-O-hexadecyl-cytidine-3'-phosphate |
| (Chds) | 2'-O-hexadecyl-cytidine-3'-phosphorothioate |
| (Uhd) | 2'-O-hexadecyl-uridine-3'-phosphate |
| (Uhds) | 2'-O-hexadecyl-uridine-3'-phosphorothioate |
| (pshe) | Hydroxyethylphosphorothioate |

TABLE 3

Unmodified Sense and Antisense Strand Sequences of AGT dsRNA Agents

| Duplex Name | Sense Oligo Name | Sense Sequence 5' to 3' | SEQ ID NO: | Range in NM_000029.3 | Antisense Oligo Name | Antisense Sequence 5' to 3' | SEQ ID NO: | Range in NM_000029.3 |
|---|---|---|---|---|---|---|---|---|
| AD-84704 | A-168477 | CACAAUGAGAGUACCUGUGAA | 21 | 644-664 | A-168478 | UUCACAGGUACUCUCAUUGUGGA | 205 | 642-664 |
| AD-84705 | A-168479 | GUCUCCCACCUUUUCUUCUAA | 22 | 2076-2096 | A-168480 | UUAGAAGAAAAGGUGGGAGACUG | 206 | 2074-2096 |
| AD-84706 | A-168481 | ACUUUCCAGCAAAACUCCCUA | 23 | 1586-1606 | A-168482 | UAGGGAGUUUUGCUGGAAAGUGA | 207 | 1584-1606 |
| AD-84707 | A-168483 | CCUCAACUGGAUGAAGAAACU | 24 | 1603-1623 | A-168484 | AGUUUCUUCAUCCAGUUGAGGGA | 208 | 1601-1623 |
| AD-84708 | A-168485 | CUGUUUGCUGUGUAUGAUCAA | 25 | 1889-1909 | A-168486 | UUGAUCAUACACAGCAAACAGGA | 209 | 1887-1909 |
| AD-84709 | A-168487 | UUUGCUGUGUAUGAUCAAAGA | 26 | 1892-1912 | A-168488 | UCUUUGAUCAUACACAGCAAACA | 210 | 1890-1912 |
| AD-84710 | A-168489 | CCGACCAGCUUGUUUGUGAAA | 27 | 2283-2303 | A-168490 | UUUCACAAACAAGCUGGUCGGUU | 211 | 2281-2303 |
| AD-84711 | A-168491 | UCCAACCGACCAGCUUGUUUA | 28 | 2278-2298 | A-168492 | UAAACAAGCUGGUCGGUUGGAAU | 212 | 2276-2298 |
| AD-84712 | A-168493 | CCAUUCCUGUUUGCUGUGUAU | 29 | 1883-1903 | A-168494 | AUACACAGCAAACAGGAAUGGGC | 213 | 1881-1903 |
| AD-84713 | A-168495 | CACCUUUUCUUCUAAUGAGUA | 30 | 2082-2102 | A-168496 | UACUCAUUAGAAGAAAAGGUGGG | 214 | 2080-2102 |
| AD-84714 | A-168497 | GUUUGCUGUGUAUGAUCAAAA | 31 | 1891-1911 | A-168498 | UUUUGAUCAUACACAGCAAACAG | 215 | 1889-1911 |
| AD-84715 | A-168499 | GCUGAGAAGAUUGACAGGUUA | 32 | 1250-1270 | A-168500 | UAACCUGUCAAUCUUCUCAGCAG | 216 | 1248-1270 |
| AD-84716 | A-168501 | UUCCAGCAAAACUCCCUCAAA | 33 | 1589-1609 | A-168502 | UUUGAGGGAGUUUUGCUGGAAAG | 217 | 1587-1609 |
| AD-84717 | A-168503 | UGCUGAGAAGAUUGACAGGUU | 34 | 1249-1269 | A-168504 | AACCUGUCAAUCUUCUCAGCAGC | 218 | 1247-1269 |
| AD-84718 | A-168505 | UCUCACUUUCCAGCAAAACUA | 35 | 1582-1602 | A-168506 | UAGUUUUGCUGGAAAGUGAGACC | 219 | 1580-1602 |
| AD-84719 | A-168507 | UCCACAAUGAGAGUACCUGUA | 36 | 642-662 | A-168508 | UACAGGUACUCUCAUUGUGGAUG | 220 | 640-662 |
| AD-84720 | A-168509 | CCACCUCGUCAUCCACAAUGA | 37 | 631-651 | A-168510 | UCAUUGUGGAUGACGAGGUGGAA | 221 | 629-651 |
| AD-84721 | A-168511 | UCACUUUCCAGCAAAACUCCA | 38 | 1584-1604 | A-168512 | UGGAGUUUUGCUGGAAAGUGAGA | 222 | 1582-1604 |
| AD-84722 | A-168513 | UCCCUCAACUGGAUGAAGAAA | 39 | 1601-1621 | A-168514 | UUUCUUCAUCCAGUUGAGGGAGU | 223 | 1599-1621 |
| AD-84723 | A-168515 | GAGAGUACCUGUGAGCAGCUA | 40 | 650-670 | A-168516 | UAGCUGCUCACAGGUACUCUCAU | 224 | 648-670 |
| AD-84724 | A-168517 | AGAAUUCCAACCGACCAGCUU | 41 | 2273-2293 | A-168518 | AAGCUGGUCGGUUGGAAUUCUUU | 225 | 2271-2293 |
| AD-84725 | A-168519 | CAUUCCUGUUUGCUGUGUAUA | 42 | 1884-1904 | A-168520 | UAUACACAGCAAACAGGAAUGGG | 226 | 1882-1904 |
| AD-84726 | A-168521 | GAAUUCCAACCGACCAGCUUA | 43 | 2274-2294 | A-168522 | UAAGCUGGUCGGUUGGAAUUCUU | 227 | 2272-2294 |
| AD-84727 | A-168523 | CAUCCACAAUGAGAGUACCUA | 44 | 640-660 | A-168524 | UAGGUACUCUCAUUGUGGAUGAC | 228 | 638-660 |
| AD-84728 | A-168525 | CCCAUUCCUGUUUGCUGUGUA | 45 | 1882-1902 | A-168526 | UACACAGCAAACAGGAAUGGGCG | 229 | 1880-1902 |
| AD-84729 | A-168527 | CUGGGUUUAUUUUAGAGAAUA | 46 | 2202-2222 | A-168528 | UAUUCUCUAAAAUAAACCCAGCA | 230 | 2200-2222 |
| AD-84730 | A-168529 | GCUGGGUUUAUUUUAGAGAAU | 47 | 2201-2221 | A-168530 | AUUCUCUAAAAUAAACCCAGCAA | 231 | 2199-2221 |
| AD-84731 | A-168531 | AUGGCAUGCACAGUGAGCUAU | 48 | 861-881 | A-168532 | AUAGCUCACUGUGCAUGCCAUAU | 232 | 859-881 |
| AD-84732 | A-168533 | GAGAGAGCCCACAGAGUCUAA | 49 | 1816-1836 | A-168534 | UUAGACUCUGUGGGCUCUCUCUC | 233 | 1814-1836 |
| AD-84733 | A-168535 | GCAAGAACCAGUGUUUAGCGA | 50 | 2234-2254 | A-168536 | UCGCUAAACACUGGUUCUUGCCU | 234 | 2232-2254 |
| AD-84734 | A-168537 | CCAGCAAAACUCCCUCAACUA | 51 | 1591-1611 | A-168538 | UAGUUGAGGGAGUUUUGCUGGAA | 235 | 1589-1611 |
| AD-84735 | A-168539 | CACCUCGUCAUCCACAAUGAA | 52 | 632-652 | A-168540 | UUCAUUGUGGAUGACGAGGUGGA | 236 | 630-652 |
| AD-84736 | A-168541 | CGUCAUCCACAAUGAGAGUAA | 53 | 637-657 | A-168542 | UUACUCUCAUUGUGGAUGACGAG | 237 | 635-657 |
| AD-84737 | A-168543 | CUCCCACGCUCUCUGGACUUA | 54 | 1211-1231 | A-168544 | UAAGUCCAGAGAGCGUGGGAGGA | 238 | 1209-1231 |
| AD-84738 | A-168545 | AACUCCCUCAACUGGAUGAAA | 55 | 1598-1618 | A-168546 | UUUCAUCCAGUUGAGGGAGUUUU | 239 | 1596-1618 |
| AD-84739 | A-168547 | UGAAGAUUGACAGGUUCAU | 56 | 1252-1272 | A-168548 | AUGAACCUGUCAAUCUUCUCAGC | 240 | 1250-1272 |
| AD-84740 | A-168549 | CCUCGUCAUCCACAAUGAGAA | 57 | 634-654 | A-168550 | UUCUCAUUGUGGAUGACGAGGUG | 241 | 632-654 |

TABLE 3-continued

Unmodified Sense and Antisense Strand Sequences of AGT dsRNA Agents

| Duplex Name | Sense Oligo Name | Sense Sequence 5' to 3' | SEQ ID NO: | Range in NM_000029.3 | Antisense Oligo Name | Antisense Sequence 5' to 3' | SEQ ID NO: | Range in NM_000029.3 |
|---|---|---|---|---|---|---|---|---|
| AD-84741 | A-168551 | GAGAAGAUUGACAGGUUCAUA | 58 | 1253-1273 | A-168552 | UAUGAACCUGUCAAUCUUCUCAG | 242 | 1251-1273 |
| AD-84742 | A-168553 | CUUCUUGGGCUUCCGUAUAUA | 59 | 841-861 | A-168554 | UAUAUACGGAAGCCCAAGAAGUU | 243 | 839-861 |
| AD-84743 | A-168555 | UCCACCUCGUCAUCCACAAUA | 60 | 630-650 | A-168556 | UAUUGUGGAUGACGAGGUGGAAG | 244 | 628-650 |
| AD-84744 | A-168557 | AGAUUGACAGGUUCAUGCAGA | 61 | 1257-1277 | A-168558 | UCUGCAUGAACCUGUCAAUCUUC | 245 | 1255-1277 |
| AD-84745 | A-168559 | CUCCCUCAACUGGAUGAAGAA | 62 | 1600-1620 | A-168560 | UUCUUCAUCCAGUUGAGGGAGUU | 246 | 1598-1620 |
| AD-84746 | A-168561 | AAUGAGAGUACCUGUGAGCAA | 63 | 647-667 | A-168562 | UUGCUCACAGGUACUCUCAUUGU | 247 | 645-667 |
| AD-85431 | A-168469 | CCACCUUUUCUUCUAAUGAGU | 64 | 2081-2101 | A-170464 | ACUCAUUAGAAGAAAAGGUGGGA | 248 | 2079-2101 |
| AD-85432 | A-168471 | CGACCAGCUUGUUUGUGAAAA | 65 | 2284-2304 | A-170465 | UUUUCACAAACAAGCUGGUCGGU | 249 | 2282-2304 |
| AD-85433 | A-168473 | ACCUUUUCUUCUAAUGAGUCA | 66 | 2083-2103 | A-170466 | UGACUCAUUAGAAGAAAAGGUGG | 250 | 2081-2103 |
| AD-85434 | A-168475 | GUCAUCCACAAUGAGAGUACA | 67 | 638-658 | A-170467 | UGUACUCUCAUUGUGGAUGACGA | 251 | 636-658 |
| AD-85435 | A-168477 | CACAAUGAGAGUACCUGUGAA | 68 | 644-664 | A-170468 | UUCACAGGUACUCUCAUUGUGGA | 252 | 642-664 |
| AD-85436 | A-168479 | GUCUCCCACCUUUUCUUCUAA | 69 | 2076-2096 | A-170469 | UUAGAAGAAAAGGUGGGAGACUG | 253 | 2074-2096 |
| AD-85437 | A-168481 | ACUUUCCAGCAAAACUCCCUA | 70 | 1586-1606 | A-170470 | UAGGGAGUUUUGCUGGAAAGUGA | 254 | 1584-1606 |
| AD-85438 | A-168483 | CCUCAACUGGAUGAAGAAACU | 71 | 1603-1623 | A-170471 | AGUUUCUUCAUCCAGUUGAGGGA | 255 | 1601-1623 |
| AD-85439 | A-168485 | CUGUUUGCUGUGUAUGAUCAA | 72 | 1889-1909 | A-170472 | UUGAUCAUACACAGCAAACAGGA | 256 | 1887-1909 |
| AD-85440 | A-168487 | UUUGCUGUGUAUGAUCAAAGA | 73 | 1892-1912 | A-170473 | UCUUUGAUCAUACACAGCAAACA | 257 | 1890-1912 |
| AD-85441 | A-168489 | CCGACCAGCUUGUUUGUGAAA | 74 | 2283-2303 | A-170474 | UUUCACAAACAAGCUGGUCGGUU | 258 | 2281-2303 |
| AD-85442 | A-168491 | UCCAACCGACCAGCUUGUUUA | 75 | 2278-2298 | A-170475 | UAAACAAGCUGGUCGGUUGGAAU | 259 | 2276-2298 |
| AD-85443 | A-168493 | CCAUUCCGUUUGCUGUGUAU | 76 | 1883-1903 | A-170476 | AUACACAGCAAACAGGAAUGGGC | 260 | 1881-1903 |
| AD-85444 | A-168495 | CACCUUUUCUUCUAAUGAGUA | 77 | 2082-2102 | A-170477 | UACUCAUUAGAAGAAAAGGUGGG | 261 | 2080-2102 |
| AD-85445 | A-168497 | GUUUGCUGUGUAUGAUCAAA | 78 | 1891-1911 | A-170478 | UUUGAUCAUACACAGCAAACAG | 262 | 1889-1911 |
| AD-85446 | A-168499 | GCUGAGAAGAUUGACAGGUUA | 79 | 1250-1270 | A-170479 | UAACCUGUCAAUCUUCUCAGCAG | 263 | 1248-1270 |
| AD-85447 | A-168501 | UUCCAGCAAAACUCCCUCAAA | 80 | 1589-1609 | A-170480 | UUUGAGGGAGUUUUGCUGGAAAG | 264 | 1587-1609 |
| AD-85448 | A-168503 | UGCUGAGAAGAUUGACAGGUU | 81 | 1249-1269 | A-170481 | AACCUGUCAAUCUUCUCAGCAGC | 265 | 1247-1269 |
| AD-85449 | A-168505 | UCUCACUUUCCAGCAAAACUA | 82 | 1582-1602 | A-170482 | UAGUUUUGCUGGAAAGUGAGACC | 266 | 1580-1602 |
| AD-85450 | A-168507 | UCCACAAUGAGAGUACCUGUA | 83 | 642-662 | A-170483 | UACAGGUACUCUCAUUGUGGAUG | 267 | 640-662 |
| AD-85451 | A-168509 | CCACCUCGUCAUCCACAAUGA | 84 | 631-651 | A-170484 | UCAUUGUGGAUGACGAGGUGGAA | 268 | 629-651 |
| AD-85452 | A-168511 | UCACUUUCCAGCAAAACUCCA | 85 | 1584-1604 | A-170485 | UGGAGUUUUGCUGGAAAGUGAGA | 269 | 1582-1604 |
| AD-85453 | A-168513 | UCCCUCAACUGGAUGAAGAAA | 86 | 1601-1621 | A-170486 | UUUCUUCAUCCAGUUGAGGGAGU | 270 | 1599-1621 |
| AD-85454 | A-168515 | GAGAGUACCUGUGAGCAGCUA | 87 | 650-670 | A-170487 | UAGCUGCUCACAGGUACUCUCAU | 271 | 648-670 |
| AD-85455 | A-168517 | AGAAUUCCAACCGACCAGCUU | 88 | 2273-2293 | A-170488 | AAGCUGGUCGGUUGGAAUUCUUU | 272 | 2271-2293 |
| AD-85456 | A-168519 | CAUUCCUGUUUGCUGUGUAUA | 89 | 1884-1904 | A-170489 | UAUACACAGCAAACAGGAAUGGG | 273 | 1882-1904 |
| AD-85457 | A-168521 | GAAUUCCAACCGACCAGCUUA | 90 | 2274-2294 | A-170490 | UAAGCUGGUCGGUUGGAAUUCUU | 274 | 2272-2294 |
| AD-85458 | A-168523 | CAUCCACAAUGAGAGUACCUA | 91 | 640-660 | A-170491 | UAGGUACUCUCAUUGUGGAUGAC | 275 | 638-660 |
| AD-85459 | A-168525 | CCCAUUCCUGUUUGCUGUGUA | 92 | 1882-1902 | A-170492 | UACACAGCAAACAGGAAUGGGCG | 276 | 1880-1902 |
| AD-85460 | A-168527 | CUGGGUUUAUUUUAGAGAAUA | 93 | 2202-2222 | A-170493 | UAUUCUCUAAAAUAAACCCAGCA | 277 | 2200-2222 |
| AD-85461 | A-168529 | GCUGGGUUUAUUUUAGAGAAU | 94 | 2201-2221 | A-170494 | AUUCUCUAAAAUAAACCCAGCAA | 278 | 2199-2221 |

TABLE 3-continued

Unmodified Sense and Antisense Strand Sequences of AGT dsRNA Agents

| Duplex Name | Sense Oligo Name | Sense Sequence 5' to 3' | SEQ ID NO: | Range in NM_000029.3 | Antisense Oligo Name | Antisense Sequence 5' to 3' | SEQ ID NO: | Range in NM_000029.3 |
|---|---|---|---|---|---|---|---|---|
| AD-85462 | A-168531 | AUGGCAUGCACAGUGAGCUAU | 95 | 861-881 | A-170495 | AUAGCUCACUGUGCAUGCCAUAU | 279 | 859-881 |
| AD-85463 | A-168533 | GAGAGAGCCCACAGAGUCUAA | 96 | 1816-1836 | A-170496 | UUAGACUCUGUGGGCUCUCUCUC | 280 | 1814-1836 |
| AD-85464 | A-168535 | GCAAGAACCAGUGUUUAGCGA | 97 | 2234-2254 | A-170497 | UCGCUAAACACUGGUUCUUGCCU | 281 | 2232-2254 |
| AD-85465 | A-168537 | CCAGCAAAACUCCCUCAACUA | 98 | 1591-1611 | A-170498 | UAGUUGAGGGAGUUUUGCUGGAA | 282 | 1589-1611 |
| AD-85466 | A-168539 | CACCUCGUCAUCCACAAUGAA | 99 | 632-652 | A-170499 | UUCAUUGUGGAUGACGAGGUGGA | 283 | 630-652 |
| AD-85467 | A-168541 | CGUCAUCCACAAUGAGAGUAA | 100 | 637-657 | A-170500 | UUACUCUCAUUGUGGAUGACGAG | 284 | 635-657 |
| AD-85468 | A-168543 | CUCCCACGCUCUCUGGACUUA | 101 | 1211-1231 | A-170501 | UAAGUCCAGAGAGCGUGGGAGGA | 285 | 1209-1231 |
| AD-85469 | A-168545 | AACUCCCUCAACUGGAUGAAA | 102 | 1598-1618 | A-170502 | UUUCAUCCAGUUGAGGGAGUUUU | 286 | 1596-1618 |
| AD-85470 | A-168547 | UGAAGAUUGACAGGUUCAU | 103 | 1252-1272 | A-170503 | AUGAACCUGUCAAUCUUCUCAGC | 287 | 1250-1272 |
| AD-85471 | A-168549 | CCUCGUCAUCCACAAUGAGAA | 104 | 634-654 | A-170504 | UUCUCAUUGUGGAUGACGAGGUG | 288 | 632-654 |
| AD-85472 | A-168551 | GAGAAGAUUGACAGGUUCAUA | 105 | 1253-1273 | A-170505 | UAUGAACCUGUCAAUCUUCUCAG | 289 | 1251-1273 |
| AD-85473 | A-168553 | CUUCUUGGGCUUCCGUAUAUA | 106 | 841-861 | A-170506 | UAUAUACGGAAGCCCAAGAAGUU | 290 | 839-861 |
| AD-85474 | A-168555 | UCCACCUCGUCAUCCACAAUA | 107 | 630-650 | A-170507 | UAUUGUGGAUGACGAGGUGGAAG | 291 | 628-650 |
| AD-85475 | A-168557 | AGAUUGACAGGUUCAUGCAGA | 108 | 1257-1277 | A-170508 | UCUGCAUGAACCUGUCAAUCUUC | 292 | 1255-1277 |
| AD-85476 | A-168559 | CUCCCUCAACUGGAUGAAGAA | 109 | 1600-1620 | A-170509 | UUCUUCAUCCAGUUGAGGGAGUU | 293 | 1598-1620 |
| AD-85477 | A-168561 | AAUGAGAGUACCUGUGAGCAA | 110 | 647-667 | A-170510 | UUGCUCACAGGUACUCUCAUUGU | 294 | 645-667 |
| AD-85478 | A-168469 | CCACCUUUUCUUCUAAUGAGU | 111 | 2081-2101 | A-170511 | ACUCAUUAGAAGAAAAGGUGGGA | 295 | 2079-2101 |
| AD-85479 | A-168471 | CGACCAGCUUGUUUGUGAAAA | 112 | 2284-2304 | A-170512 | UUUUCACAAACAAGCUGGUCGGU | 296 | 2282-2304 |
| AD-85480 | A-168473 | ACCUUUUCUUCUAAUGAGUCA | 113 | 2083-2103 | A-170513 | UGACUCAUUAGAAGAAAAGGUGG | 297 | 2081-2103 |
| AD-85481 | A-168475 | GUCAUCCACAAUGAGAGUACA | 114 | 638-658 | A-170514 | UGUACUCUCAUUGUGGAUGACGA | 298 | 636-658 |
| AD-85482 | A-168477 | CACAAUGAGAGUACCUGUGAA | 115 | 644-664 | A-170515 | UUCACAGGUACUCUCAUUGUGGA | 299 | 642-664 |
| AD-85483 | A-168479 | GUCUCCCACCUUUUCUUCUAA | 116 | 2076-2096 | A-170516 | UUAGAAGAAAAGGUGGGAGACUG | 300 | 2074-2096 |
| AD-85484 | A-168481 | ACUUUCCAGCAAAACUCCCUA | 117 | 1586-1606 | A-170517 | UAGGGAGUUUUGCUGGAAAGUGA | 301 | 1584-1606 |
| AD-85485 | A-168483 | CCUCAACUGGAUGAAGAAACU | 118 | 1603-1623 | A-170518 | AGUUUCUUCAUCCAGUUGAGGGA | 302 | 1601-1623 |
| AD-85486 | A-168485 | CUGUUUGCUGUGUAUGAUCAA | 119 | 1889-1909 | A-170519 | UUGAUCAUACACAGCAAACAGGA | 303 | 1887-1909 |
| AD-85487 | A-168487 | UUUGCUGUGUAUGAUCAAAGA | 120 | 1892-1912 | A-170520 | UCUUUGAUCAUACACAGCAAACA | 304 | 1890-1912 |
| AD-85488 | A-168489 | CCGACCAGCUUGUUUGUGAAA | 121 | 2283-2303 | A-170521 | UUUCACAAACAAGCUGGUCGGUU | 305 | 2281-2303 |
| AD-85489 | A-168491 | UCCAACCGACCAGCUUGUUUA | 122 | 2278-2298 | A-170522 | UAAACAAGCUGGUCGGUUGGAAU | 306 | 2276-2298 |
| AD-85490 | A-168493 | CCAUUCCUGUUUGCUGUGUAU | 123 | 1883-1903 | A-170523 | AUACACAGCAAACAGGAAUGGGC | 307 | 1881-1903 |
| AD-85491 | A-168495 | CACCUUUUCUUCUAAUGAGUA | 124 | 2082-2102 | A-170524 | UACUCAUUAGAAGAAAAGGUGGG | 308 | 2080-2102 |
| AD-85492 | A-168497 | GUUUGCUGUGUAUGAUCAAAA | 125 | 1891-1911 | A-170525 | UUUUGAUCAUACACAGCAAACAG | 309 | 1889-1911 |
| AD-85493 | A-168499 | GCUGAGAAGAUUGACAGGUUA | 126 | 1250-1270 | A-170526 | UAACCUGUCAAUCUUCUCAGCAG | 310 | 1248-1270 |
| AD-85494 | A-168501 | UUCCAGCAAAACUCCCUCAAA | 127 | 1589-1609 | A-170527 | UUUGAGGGAGUUUUGCUGGAAAG | 311 | 1587-1609 |
| AD-85495 | A-168503 | UGCUGAGAAGAUUGACAGGUU | 128 | 1249-1269 | A-170528 | AACCUGUCAAUCUUCUCAGCAGC | 312 | 1247-1269 |
| AD-85496 | A-168505 | UCUCACUUUCCAGCAAAACUA | 129 | 1582-1602 | A-170529 | UAGUUUUGCUGGAAAGUGAGACC | 313 | 1580-1602 |
| AD-85497 | A-168507 | UCCACAAUGAGAGUACCUGUA | 130 | 642-662 | A-170530 | UACAGGUACUCUCAUUGUGGAUG | 314 | 640-662 |
| AD-85498 | A-168509 | CCACCUCGUCAUCCACAAUGA | 131 | 631-651 | A-170531 | UCAUUGUGGAUGACGAGGUGGAA | 315 | 629-651 |

TABLE 3-continued

Unmodified Sense and Antisense Strand Sequences of AGT dsRNA Agents

| Duplex Name | Sense Oligo Name | Sense Sequence 5' to 3' | SEQ ID NO: | Range in NM_000029.3 | Antisense Oligo Name | Antisense Sequence 5' to 3' | SEQ ID NO: | Range in NM_000029.3 |
|---|---|---|---|---|---|---|---|---|
| AD-85499 | A-168511 | UCACUUUCCAGCAAAACUCCA | 132 | 1584-1604 | A-170532 | UGGAGUUUUGCUGGAAAGUGAGA | 316 | 1582-1604 |
| AD-85500 | A-168513 | UCCCUCAACUGGAUGAAGAAA | 133 | 1601-1621 | A-170533 | UUUCUUCAUCCAGUUGAGGGAGU | 317 | 1599-1621 |
| AD-85501 | A-168515 | GAGAGUACCUGUGAGCAGCUA | 134 | 650-670 | A-170534 | UAGCUGCUCACAGGUACUCUCAU | 318 | 648-670 |
| AD-85502 | A-168517 | AGAAUUCCAACCGACCAGCUU | 135 | 2273-2293 | A-170535 | AAGCUGGUCGGUUGGAAUUCUUU | 319 | 2271-2293 |
| AD-85503 | A-168519 | CAUUCCUGUUUGCUGUGUAUA | 136 | 1884-1904 | A-170536 | UAUACACAGCAAACAGGAAUGGG | 320 | 1882-1904 |
| AD-85504 | A-168521 | GAAUUCCAACCGACCAGCUUA | 137 | 2274-2294 | A-170537 | UAAGCUGGUCGGUUGGAAUUCUU | 321 | 2272-2294 |
| AD-85505 | A-168523 | CAUCCACAAUGAGAGUACCUA | 138 | 640-660 | A-170538 | UAGGUACUCUCAUUGUGGAUGAC | 322 | 638-660 |
| AD-85506 | A-168525 | CCCAUUCCUGUUUGCUGUGUA | 139 | 1882-1902 | A-170539 | UACACAGCAAACAGGAAUGGGCG | 323 | 1880-1902 |
| AD-85507 | A-168527 | CUGGGUUUAUUUUAGAGAAUA | 140 | 2202-2222 | A-170540 | UAUUCUCUAAAAUAAACCCAGCA | 324 | 2200-2222 |
| AD-85508 | A-168529 | GCUGGGUUUAUUUUAGAGAAU | 141 | 2201-2221 | A-170541 | AUUCUCUAAAAUAAACCCAGCAA | 325 | 2199-2221 |
| AD-85509 | A-168531 | AUGGCAUGCACAGUGAGCUAU | 142 | 861-881 | A-170542 | AUAGCUCACUGUGCAUGCCAUAU | 326 | 859-881 |
| AD-85510 | A-168533 | GAGAGAGCCCACAGAGUCUAA | 143 | 1816-1836 | A-170543 | UUAGACUCUGUGGGCUCUCUCUC | 327 | 1814-1836 |
| AD-85511 | A-168535 | GCAAGAACCAGUGUUUAGCGA | 144 | 2234-2254 | A-170544 | UCGCUAAACACUGGUUCUUGCCU | 328 | 2232-2254 |
| AD-85512 | A-168537 | CCAGCAAAACUCCCUCAACUA | 145 | 1591-1611 | A-170545 | UAGUUGAGGGAGUUUUGCUGGAA | 329 | 1589-1611 |
| AD-85513 | A-168539 | CACCUCGUCAUCCACAAUGAA | 146 | 632-652 | A-170546 | UUCAUUGUGGAUGACGAGGUGGA | 330 | 630-652 |
| AD-85514 | A-168541 | CGUCAUCCACAAUGAGAGUAA | 147 | 637-657 | A-170547 | UUACUCUCAUUGUGGAUGACGAG | 331 | 635-657 |
| AD-85515 | A-168543 | CUCCCACGCUCUCUGGACUUA | 148 | 1211-1231 | A-170548 | UAAGUCCAGAGAGCGUGGGAGGA | 332 | 1209-1231 |
| AD-85516 | A-168545 | AACUCCCUCAACUGGAUGAAA | 149 | 1598-1618 | A-170549 | UUUCAUCCAGUUGAGGGAGUUUU | 333 | 1596-1618 |
| AD-85517 | A-168547 | UGAGAAGAUUGACAGGUUCAU | 150 | 1252-1272 | A-170550 | AUGAACCUGUCAAUCUUCUCAGC | 334 | 1250-1272 |
| AD-85518 | A-168549 | CCUCGUCAUCCACAAUGAGAA | 151 | 634-654 | A-170551 | UUCUCAUUGUGGAUGACGAGGUG | 335 | 632-654 |
| AD-85519 | A-168551 | GAGAAGAUUGACAGGUUCAUA | 152 | 1253-1273 | A-170552 | UAUGAACCUGUCAAUCUUCUCAG | 336 | 1251-1273 |
| AD-85520 | A-168553 | CUUCUUGGGCUUCCGUAUAUA | 153 | 841-861 | A-170553 | UAUAUACGGAAGCCCAAGAAGUU | 337 | 839-861 |
| AD-85521 | A-168555 | UCCACCUCGUCAUCCACAAUA | 154 | 630-650 | A-170554 | UAUUGUGGAUGACGAGGUGGAAG | 338 | 628-650 |
| AD-85522 | A-168557 | AGAUUGACAGGUUCAUGCAGA | 155 | 1257-1277 | A-170555 | UCUGCAUGAACCUGUCAAUCUUC | 339 | 1255-1277 |
| AD-85523 | A-168559 | CUCCCUCAACUGGAUGAAGAA | 156 | 1600-1620 | A-170556 | UUCUUCAUCCAGUUGAGGGAGUU | 340 | 1598-1620 |
| AD-85524 | A-168561 | AAUGAGAGUACCUGUGAGCAA | 157 | 647-667 | A-170557 | UUGCUCACAGGUACUCUCAUUGU | 341 | 645-667 |
| AD-85619 | A-168469 | CCACCUUUUCUUCUAAUGAGU | 158 | 2081-2101 | A-170558 | ACUCAUUAGAAGAAAAGGUGGGA | 342 | 2079-2101 |
| AD-85620 | A-168471 | CGACCAGCUUGUUUGUGAAAA | 159 | 2284-2304 | A-170559 | UUUUCACAAACAAGCUGGUCGGU | 343 | 2282-2304 |
| AD-85621 | A-168473 | ACCUUUUCUUCUAAUGAGUCA | 160 | 2083-2103 | A-170560 | UGACUCAUUAGAAGAAAAGGUGG | 344 | 2081-2103 |
| AD-85622 | A-168475 | GUCAUCCACAAUGAGAGUACA | 161 | 638-658 | A-170561 | UGUACUCUCAUUGUGGAUGACGA | 345 | 636-658 |
| AD-85623 | A-168477 | CACAAUGAGAGUACCUGUGAA | 162 | 644-664 | A-170562 | UUCACAGGUACUCUCAUUGUGGA | 346 | 642-664 |
| AD-85624 | A-168479 | GUCUCCACCUUUUCUUCUAA | 163 | 2076-2096 | A-170563 | UUAGAAGAAAAGGUGGGAGACUG | 347 | 2074-2096 |
| AD-85625 | A-168481 | ACUUUCCAGCAAAACUCCCUA | 164 | 1586-1606 | A-170564 | UAGGGAGUUUUGCUGGAAAGUGA | 348 | 1584-1606 |
| AD-85626 | A-168483 | CCUACAACUGGAUGAAGAACU | 165 | 1603-1623 | A-170565 | AGUUCUUCAUCCAGUUGAGGGA | 349 | 1601-1623 |
| AD-85627 | A-168485 | CUGUUUGCUGUGUAUGAUCAA | 166 | 1889-1909 | A-170566 | UUGAUCAUACACAGCAAACAGGA | 350 | 1887-1909 |
| AD-85628 | A-168487 | UUUGCUGUGUAUGAUCAAAGA | 167 | 1892-1912 | A-170567 | UCUUUGAUCAUACACAGCAAACA | 351 | 1890-1912 |
| AD-85629 | A-168489 | CCGACCAGCUUGUUUGUGAAA | 168 | 2283-2303 | A-170568 | UUUCACAAACAAGCUGGUCGGUU | 352 | 2281-2303 |

TABLE 3-continued

Unmodified Sense and Antisense Strand Sequences of AGT dsRNA Agents

| Duplex Name | Sense Oligo Name | Sense Sequence 5' to 3' | SEQ ID NO: | Range in NM_000029.3 | Antisense Oligo Name | Antisense Sequence 5' to 3' | SEQ ID NO: | Range in NM_000029.3 |
|---|---|---|---|---|---|---|---|---|
| AD-85630 | A-168491 | UCCAACCGACCAGCUUGUUUA | 169 | 2278-2298 | A-170569 | UAAACAAGCUGGUCGGUUGGAAU | 353 | 2276-2298 |
| AD-85631 | A-168493 | CCAUUCCUGUUUGCUGUGUAU | 170 | 1883-1903 | A-170570 | AUACACAGCAAACAGGAAUGGGC | 354 | 1881-1903 |
| AD-85632 | A-168495 | CACCUUUUCUUCUAAUGAGUA | 171 | 2082-2102 | A-170571 | UACUCAUUAGAAGAAAAGGUGGG | 355 | 2080-2102 |
| AD-85633 | A-168497 | GUUUGCUGUGUAUGAUCAAAA | 172 | 1891-1911 | A-170572 | UUUUGAUCAUACACAGCAAACAG | 356 | 1889-1911 |
| AD-85634 | A-168499 | GCUGAGAAGAUUGACAGGUUA | 173 | 1250-1270 | A-170573 | UAACCUGUCAAUCUUCUCAGCAG | 357 | 1248-1270 |
| AD-85635 | A-168501 | UUCCAGCAAAACUCCCUCAAA | 174 | 1589-1609 | A-170574 | UUUGAGGGAGUUUUGCUGGAAAG | 358 | 1587-1609 |
| AD-85636 | A-168503 | UGCUGAGAAGAUUGACAGGUU | 175 | 1249-1269 | A-170575 | AACCUGUCAAUCUUCUCAGCAGC | 359 | 1247-1269 |
| AD-85637 | A-168505 | UCUCACUUUCCAGCAAAACUA | 176 | 1582-1602 | A-170576 | UAGUUUUGCUGGAAAGUGAGACC | 360 | 1580-1602 |
| AD-85638 | A-168507 | UCCACAAUGAGAGUACCUGUA | 177 | 642-662 | A-170577 | UACAGGUACUCUCAUUGUGGAUG | 361 | 640-662 |
| AD-85639 | A-168509 | CCACCUCGUCAUCCACAAUGA | 178 | 631-651 | A-170578 | UCAUUGUGGAUGACGAGGUGGAA | 362 | 629-651 |
| AD-85640 | A-168511 | UCACUUUCCAGCAAAACUCCA | 179 | 1584-1604 | A-170579 | UGGAGUUUUGCUGGAAAGUGAGA | 363 | 1582-1604 |
| AD-85641 | A-168513 | UCCCUCAACUGGAUGAAGAAA | 180 | 1601-1621 | A-170580 | UUUCUUCAUCCAGUUGAGGGAGU | 364 | 1599-1621 |
| AD-85642 | A-168515 | GAGAGUACCUGUGAGCAGCUA | 181 | 650-670 | A-170581 | UAGCUGCUCACAGGUACUCUCAU | 365 | 648-670 |
| AD-85643 | A-168517 | AGAAUUCCAACCGACCAGCUU | 182 | 2273-2293 | A-170582 | AAGCUGGUCGGUUGGAAUUCUUU | 366 | 2271-2293 |
| AD-85644 | A-168519 | CAUUCCUGUUUGCUGUGUAUA | 183 | 1884-1904 | A-170583 | UAUACACAGCAAACAGGAAUGGG | 367 | 1882-1904 |
| AD-85645 | A-168521 | GAAUUCCAACCGACCAGCUUA | 184 | 2274-2294 | A-170584 | UAAGCUGGUCGGUUGGAAUUCUU | 368 | 2272-2294 |
| AD-85646 | A-168523 | CAUCCACAAUGAGAGUACCUA | 185 | 640-660 | A-170585 | UAGGUACUCUCAUUGUGGAUGAC | 369 | 638-660 |
| AD-85647 | A-168525 | CCCAUUCCUGUUUGCUGUGUA | 186 | 1882-1902 | A-170586 | UACACAGCAAACAGGAAUGGGCG | 370 | 1880-1902 |
| AD-85648 | A-168527 | CUGGGUUUAUUUUAGAGAAUA | 187 | 2202-2222 | A-170587 | UAUUCUAAAAUAAACCCAGCA | 371 | 2200-2222 |
| AD-85649 | A-168529 | GCUGGGUUUAUUUUAGAGAAU | 188 | 2201-2221 | A-170588 | AUUCUCUAAAAUAAACCCAGCAA | 372 | 2199-2221 |
| AD-85650 | A-168531 | AUGGCAUGCACAGUGAGCUAU | 189 | 861-881 | A-170589 | AUAGCUCACUGUGCAUGCCAUAU | 373 | 859-881 |
| AD-85651 | A-168533 | GAGAGAGCCCACAGAGUCUAA | 190 | 1816-1836 | A-170590 | UUAGACUCUGUGGGCUCUCUCUC | 374 | 1814-1836 |
| AD-85652 | A-168535 | GCAAGAACCAGUGUUUAGCGA | 191 | 2234-2254 | A-170591 | UCGCUAAACACUGGUUCUUGCCU | 375 | 2232-2254 |
| AD-85653 | A-168537 | CCAGCAAAACUCCCUCAACUA | 192 | 1591-1611 | A-170592 | UAGUUGAGGGAGUUUUGCUGGAA | 376 | 1589-1611 |
| AD-85654 | A-168539 | CACCUCGUCAUCCACAAUGAA | 193 | 632-652 | A-170593 | UUCAUUGUGGAUGACGAGGUGGA | 377 | 630-652 |
| AD-85655 | A-168541 | CGUCAUCCACAAUGAGAGUAA | 194 | 637-657 | A-170594 | UUACUCUCAUUGUGGAUGACGAG | 378 | 635-657 |
| AD-85656 | A-168543 | CUCCCACGCUCUCUGGACUUA | 195 | 1211-1231 | A-170595 | UAAGUCCAGAGAGCGUGGGAGGA | 379 | 1209-1231 |
| AD-85657 | A-168545 | AACUCCCUCAACUGGAUGAAA | 196 | 1598-1618 | A-170596 | UUUCAUCCAGUUGAGGGAGUUUU | 380 | 1596-1618 |
| AD-85658 | A-168547 | UGAGAAGAUUGACAGGUUCAU | 197 | 1252-1272 | A-170597 | AUGAACCUGUCAAUCUUCUCAGC | 381 | 1250-1272 |
| AD-85659 | A-168549 | CCUCGUCAUCCACAAUGAGAA | 198 | 634-654 | A-170598 | UUCUCAUUGUGGAUGACGAGGUG | 382 | 632-654 |
| AD-85660 | A-168551 | GAGAAGAUUGACAGGUUCAUA | 199 | 1253-1273 | A-170599 | UAUGAACCUGUCAAUCUUCUCAG | 383 | 1251-1273 |
| AD-85661 | A-168553 | CUUCUGGGCUUCCGUAUAUA | 200 | 841-861 | A-170600 | UAUAUACGGAAGCCCAAGAAGUU | 384 | 839-861 |
| AD-85662 | A-168555 | UCCACCUCGUCAUCCACAAUA | 201 | 630-650 | A-170601 | UAUUGUGGAUGACGAGGUGGAAG | 385 | 628-650 |
| AD-85663 | A-168557 | AGAUUGACAGGUUCAUGCAGA | 202 | 1257-1277 | A-170602 | UCUGCAUGAACCUGUCAAUCUUC | 386 | 1255-1277 |
| AD-85664 | A-168559 | CUCCCUCAACUGGAUGAAGAA | 203 | 1600-1620 | A-170603 | UUCUUCAUCCAGUUGAGGGAGU | 387 | 1598-1620 |
| AD-85665 | A-168561 | AAUGAGAGUACCUGUGAGCAA | 204 | 647-667 | A-170604 | UUGCUCACAGGUACUCUCAUUGU | 388 | 645-667 |

TABLE 4

AGT Single 10 nM and 0.1 nM Dose Screen in Hep3B cells

| Duplex ID | 10 nM Avg. | 10 nM SD | 0.1 nM Avg. | 0.1 nM SD |
|---|---|---|---|---|
| AD-67327 | 6.2 | 1.5 | 30.1 | 5.9 |
| AD-84700 | 14.5 | 5.7 | 127.9 | 53.6 |
| AD-84701 | 8.7 | 6.5 | 59.7 | 5.5 |
| AD-84702 | 11.4 | 4.2 | 95.1 | 14.6 |
| AD-84703 | 6.7 | 4.2 | 36.7 | 2.4 |
| AD-84704 | 7.2 | 4.3 | 54.9 | 5.5 |
| AD-84705 | 7.8 | 2.3 | 52.7 | 10.3 |
| AD-84706 | 6.3 | 4.3 | 65.0 | 13.0 |
| AD-84707 | 10.2 | 9.2 | 52.2 | 2.6 |
| AD-84708 | 10.1 | 4.1 | 98.7 | 24.6 |
| AD-84709 | 19.0 | 4.3 | 102.7 | 18.5 |
| AD-84710 | 11.3 | 7.9 | 65.9 | 19.0 |
| AD-84711 | 10.4 | 6.5 | 66.5 | 13.8 |
| AD-84712 | 7.5 | 6.4 | 66.4 | 13.9 |
| AD-84713 | 9.7 | 5.9 | 66.4 | 5.6 |
| AD-84714 | 13.7 | 2.0 | 89.0 | 28.9 |
| AD-84715 | 7.7 | 5.3 | 59.0 | 2.7 |
| AD-84716 | 7.4 | 2.4 | 45.9 | 15.0 |
| AD-84717 | 14.6 | 4.2 | 102.9 | 15.8 |
| AD-84718 | 6.8 | 0.7 | 66.9 | 8.3 |
| AD-84719 | 21.1 | 4.0 | 92.5 | 19.6 |
| AD-84720 | 11.3 | 0.4 | 96.0 | 22.1 |
| AD-84721 | 14.7 | 5.2 | 88.4 | 12.7 |
| AD-84722 | 35.9 | 14.8 | 106.6 | 21.2 |
| AD-84723 | 13.4 | 6.5 | 83.7 | 25.9 |
| AD-84724 | 20.8 | 6.7 | 108.0 | 17.6 |
| AD-84725 | 17.4 | 1.2 | 100.5 | 22.3 |
| AD-84726 | 9.7 | 0.6 | 73.1 | 9.0 |
| AD-84727 | 16.5 | 5.0 | 102.4 | 20.5 |
| AD-84728 | 17.6 | 2.6 | 103.6 | 12.8 |
| AD-84729 | 11.6 | 3.4 | 78.9 | 16.1 |
| AD-84730 | 11.2 | 1.5 | 77.6 | 8.7 |
| AD-84731 | 11.4 | 2.9 | 80.4 | 15.9 |
| AD-84732 | 26.9 | 2.6 | 88.2 | 19.5 |
| AD-84733 | 21.4 | 2.2 | 101.5 | 13.9 |
| AD-84734 | 20.4 | 1.9 | 92.8 | 20.5 |
| AD-84735 | 11.4 | 1.9 | 85.0 | 6.0 |
| AD-84736 | 8.4 | 2.5 | 68.0 | 20.7 |
| AD-84737 | 22.9 | 4.0 | 80.0 | 13.1 |
| AD-84738 | 16.0 | 1.8 | 98.3 | 29.5 |
| AD-84739 | 6.6 | 2.1 | 40.5 | 6.8 |
| AD-84740 | 10.2 | 1.8 | 78.9 | 32.7 |
| AD-84741 | 6.3 | 1.0 | 37.0 | 9.7 |
| AD-84742 | 14.1 | 2.0 | 86.9 | 7.4 |
| AD-84743 | 80.9 | 9.9 | 97.3 | 16.5 |
| AD-84744 | 23.1 | 5.8 | 93.4 | 18.9 |
| AD-84745 | 27.8 | 5.0 | 79.2 | 25.3 |
| AD-84746 | 7.5 | 1.2 | 48.0 | 14.4 |
| AD-85431 | 12.3 | 3.9 | 61.8 | 29.6 |
| AD-85432 | 10.1 | 6.6 | 50.5 | 19.8 |
| AD-85433 | 11.5 | 4.0 | 61.4 | 25.4 |
| AD-85434 | 5.8 | 2.5 | 37.2 | 20.4 |
| AD-85435 | 7.3 | 1.8 | 44.9 | 17.8 |
| AD-85436 | 8.2 | 4.9 | 35.2 | 12.8 |
| AD-85437 | 7.2 | 6.3 | 30.4 | 18.6 |
| AD-85438 | 10.4 | 7.5 | 41.8 | 18.1 |
| AD-85439 | 15.4 | 3.8 | 62.1 | 25.9 |
| AD-85440 | 26.1 | 5.1 | 85.5 | 34.7 |
| AD-85441 | 9.9 | 7.4 | 50.6 | 19.3 |
| AD-85442 | 8.4 | 5.2 | 52.4 | 20.4 |
| AD-85443 | 11.5 | 12.9 | 59.0 | 25.0 |
| AD-85444 | 8.4 | 4.4 | 48.6 | 24.9 |
| AD-85445 | 21.7 | 6.8 | 63.2 | 36.1 |
| AD-85446 | 14.7 | 11.5 | 59.0 | 27.5 |
| AD-85447 | 8.4 | 2.9 | 52.8 | 15.5 |
| AD-85448 | 12.6 | 4.0 | 89.5 | 25.2 |
| AD-85449 | 8.3 | 1.5 | 72.7 | 14.2 |
| AD-85450 | 35.3 | 6.3 | 91.4 | 30.0 |
| AD-85451 | 17.7 | 2.3 | 80.7 | 20.8 |
| AD-85452 | 21.5 | 5.2 | 73.3 | 27.4 |
| AD-85453 | 60.5 | 32.6 | 69.0 | 33.9 |
| AD-85454 | 21.8 | 8.6 | 63.2 | 23.6 |
| AD-85455 | 34.0 | 12.4 | 88.8 | 23.4 |
| AD-85456 | 21.6 | 1.4 | 91.9 | 18.1 |
| AD-85457 | 12.1 | 2.6 | 85.6 | 28.0 |
| AD-85458 | 29.8 | 7.1 | 98.1 | 25.4 |
| AD-85459 | 23.8 | 2.0 | 101.2 | 34.7 |
| AD-85460 | 9.9 | 1.8 | 69.0 | 12.7 |
| AD-85461 | 11.0 | 3.7 | 60.1 | 13.4 |
| AD-85462 | 25.7 | 4.1 | 78.5 | 6.8 |
| AD-85463 | 56.6 | 13.1 | 89.7 | 20.5 |
| AD-85464 | 21.8 | 6.3 | 99.8 | 34.4 |
| AD-85465 | 25.2 | 6.2 | 99.2 | 24.6 |
| AD-85466 | 35.3 | 8.4 | 104.2 | 31.5 |
| AD-85467 | 12.7 | 2.7 | 82.2 | 8.4 |
| AD-85468 | 30.9 | 6.5 | 93.0 | 31.2 |
| AD-85469 | 44.7 | 8.0 | 82.1 | 13.4 |
| AD-85470 | 7.9 | 4.6 | 66.7 | 11.2 |
| AD-85471 | 15.8 | 3.7 | 95.3 | 14.0 |
| AD-85472 | 9.3 | 3.3 | 71.3 | 15.1 |
| AD-85473 | 21.5 | 3.9 | 102.2 | 22.4 |
| AD-85474 | 100.2 | 24.5 | 110.4 | 21.9 |
| AD-85475 | 28.7 | 8.6 | 105.2 | 31.1 |
| AD-85476 | 35.5 | 10.2 | 81.4 | 13.1 |
| AD-85477 | 10.1 | 2.2 | 76.9 | 30.6 |
| AD-85478 | 15.1 | 1.9 | 94.6 | 27.5 |
| AD-85479 | 18.7 | 5.8 | 92.1 | 26.6 |
| AD-85480 | 11.8 | 4.1 | 68.8 | 16.7 |
| AD-85481 | 5.3 | 1.1 | 32.9 | 8.7 |
| AD-85482 | 7.1 | 3.4 | 52.7 | 11.5 |
| AD-85483 | 7.9 | 3.0 | 61.1 | 15.3 |
| AD-85484 | 11.5 | 3.3 | 84.6 | 8.8 |
| AD-85485 | 11.6 | 5.5 | 58.9 | 19.7 |
| AD-85486 | 25.3 | 6.2 | 94.8 | 21.4 |
| AD-85487 | 40.5 | 10.2 | 101.0 | 24.4 |
| AD-85488 | 32.8 | 7.4 | 97.6 | 24.2 |
| AD-85489 | 12.8 | 4.0 | 87.2 | 20.9 |
| AD-85490 | 7.6 | 0.8 | 78.5 | 20.2 |
| AD-85491 | 12.5 | 4.5 | 92.3 | 19.0 |
| AD-85492 | 89.7 | 17.7 | 112.3 | 20.2 |
| AD-85493 | 6.3 | 2.6 | 51.0 | 14.5 |
| AD-85494 | 11.0 | 2.4 | 79.8 | 24.0 |
| AD-85495 | 10.4 | 2.8 | 70.1 | 23.2 |
| AD-85496 | 6.8 | 2.2 | 55.0 | 20.8 |
| AD-85497 | 72.4 | 18.6 | 108.5 | 36.5 |
| AD-85498 | 7.3 | 2.3 | 85.3 | 26.5 |
| AD-85499 | 94.7 | 6.8 | 104.2 | 24.5 |
| AD-85500 | 63.1 | 21.9 | 98.4 | 21.4 |
| AD-85501 | 38.3 | 12.3 | 129.0 | 47.3 |
| AD-85502 | 27.2 | 8.3 | 92.0 | 21.9 |
| AD-85503 | 36.2 | 11.5 | 108.3 | 25.4 |
| AD-85504 | 9.2 | 3.7 | 56.1 | 9.4 |
| AD-85505 | 50.3 | 12.2 | 111.6 | 15.5 |
| AD-85506 | 40.8 | 8.7 | 109.4 | 31.6 |
| AD-85507 | 7.7 | 2.2 | 64.3 | 22.6 |
| AD-85508 | 82.0 | 21.9 | 100.9 | 29.0 |
| AD-85509 | 20.9 | 5.5 | 101.5 | 23.0 |
| AD-85510 | 104.0 | 28.6 | 90.1 | 42.0 |
| AD-85511 | 14.1 | 2.6 | 84.2 | 9.3 |
| AD-85512 | 50.6 | 14.7 | 98.5 | 30.7 |
| AD-85513 | 35.0 | 9.0 | 78.5 | 24.4 |
| AD-85514 | 13.0 | 0.9 | 80.3 | 27.9 |
| AD-85515 | 69.1 | 5.7 | 72.5 | 35.1 |
| AD-85516 | 54.0 | 16.1 | 88.4 | 38.9 |
| AD-85517 | 7.4 | 1.3 | 47.9 | 7.0 |
| AD-85518 | 12.0 | 4.6 | 79.4 | 42.4 |
| AD-85519 | 8.9 | 2.5 | 54.6 | 6.2 |
| AD-85520 | 10.9 | 3.0 | 81.3 | 19.1 |
| AD-85521 | 79.1 | 15.6 | 108.4 | 35.4 |
| AD-85522 | 51.3 | 10.1 | 114.7 | 27.9 |
| AD-85523 | 23.6 | 2.9 | 91.3 | 26.6 |
| AD-85524 | 9.9 | 2.8 | 46.9 | 10.8 |
| AD-85619 | 20.7 | 1.0 | 114.4 | 53.5 |
| AD-85620 | 20.0 | 5.8 | 96.8 | 25.7 |
| AD-85621 | 8.9 | 6.9 | 80.4 | 20.3 |
| AD-85622 | 6.4 | 3.7 | 50.2 | 12.9 |
| AD-85623 | 7.6 | 6.0 | 38.0 | 4.6 |
| AD-85624 | 9.2 | 3.7 | 81.0 | 15.9 |

TABLE 4-continued

AGT Single 10 nM and 0.1 nM Dose Screen in Hep3B cells

| Duplex ID | 10 nM Avg. | 10 nM SD | 0.1 nM Avg. | 0.1 nM SD |
|---|---|---|---|---|
| AD-85625 | 6.0 | 2.4 | 58.9 | 8.7 |
| AD-85626 | 7.6 | 6.3 | 43.8 | 3.9 |
| AD-85627 | 25.5 | 8.3 | 103.0 | 20.0 |
| AD-85628 | 39.0 | 7.3 | 114.5 | 19.9 |
| AD-85629 | 23.6 | 18.5 | 86.1 | 14.8 |
| AD-85630 | 17.2 | 15.9 | 83.0 | 22.5 |
| AD-85631 | 10.1 | 6.2 | 79.0 | 18.2 |
| AD-85632 | 10.2 | 4.3 | 67.5 | 10.8 |
| AD-85633 | 42.1 | 19.9 | 95.1 | 4.5 |
| AD-85634 | 7.5 | 2.9 | 54.6 | 11.7 |
| AD-85635 | 8.2 | 2.6 | 53.5 | 24.0 |
| AD-85636 | 11.4 | 2.2 | 96.0 | 23.7 |
| AD-85637 | 9.9 | 5.9 | 58.2 | 17.0 |
| AD-85638 | 53.1 | 6.2 | 112 | 31.1 |
| AD-85639 | 13.7 | 2.1 | 96.9 | 19.6 |
| AD-85640 | 72.8 | 11.7 | 106.9 | 7.2 |
| AD-85641 | 47.2 | 19.8 | 89.6 | 9.5 |
| AD-85642 | 15.3 | 3.5 | 86.7 | 24.5 |
| AD-85643 | 35.4 | 12.9 | 494.9 | 779.7 |
| AD-85644 | 79.0 | 7.2 | 110.6 | 23.5 |
| AD-85645 | 7.8 | 1.2 | 63.6 | 13.1 |
| AD-85646 | 33.6 | 8.6 | 105.6 | 28.1 |
| AD-85647 | 19.4 | 3.1 | 102.3 | 9.7 |
| AD-85648 | 49.0 | 6.6 | 106.0 | 10.7 |
| AD-85649 | 18.5 | 2.9 | 82.4 | 10.1 |
| AD-85650 | 69.4 | 19.0 | 87.2 | 15.6 |
| AD-85651 | 90.4 | 17.3 | 106.9 | 31.9 |
| AD-85652 | 31.3 | 8.5 | 90.0 | 37.7 |
| AD-85653 | 47.6 | 2.8 | 104.1 | 20.6 |
| AD-85654 | 66.7 | 3.7 | 97.5 | 17.8 |
| AD-85655 | 10.4 | 0.8 | 55.4 | 6.9 |
| AD-85656 | 96.7 | 4.3 | 98.6 | 23.4 |
| AD-85657 | 83.6 | 3.3 | 86.6 | 31.4 |
| AD-85658 | 7.6 | 1.8 | 65.4 | 9.2 |
| AD-85659 | 14.1 | 4.2 | 76.0 | 33.0 |
| AD-85660 | 40.9 | 6.5 | 95.8 | 24.0 |
| AD-85661 | 63.6 | 10.4 | 93.0 | 34.1 |
| AD-85662 | 83.4 | 11.5 | 87.3 | 17.2 |
| AD-85663 | 23.0 | 5.3 | 79.1 | 30.8 |
| AD-85664 | 44.8 | 2.9 | 112.2 | 19.9 |
| AD-85665 | 13.5 | 2.5 | 81.0 | 25.4 |

TABLE 5

Modified Sense and Antisense Strand Sequences of hAGT dsRNA Agents

| Duplex Name | Modified Sense Sequence 5' to 3' | SEQ ID NO: | Modified Antisense Sequence 5' to 3' | SEQ ID NO: | mRNA target sequence 5' to 3' | SEQ ID NO: |
|---|---|---|---|---|---|---|
| AD-84704 | csascaauGfaGfAfGfuaccugugaaL96 | 389 | usUfscacAfgGfUfacucUfcAfuuguggsgsa | 573 | UCCACAAUGAGAGUACCUGUGAG | 757 |
| AD-84705 | gsuscuccCfaCfCfUfuuucuucuaaL96 | 390 | usUfsagaAfgAfAfaaggUfgGfgagacsusg | 574 | CAGUCCCCACCUUUCUUCUAA | 758 |
| AD-84706 | ascsuuuccCfaGfCfAfaaacucccuaL96 | 391 | usAfsgggAfgUfUfuugcUfgGfaaagusgsa | 575 | UCACUUUCCAGCAAAACUCCCUC | 759 |
| AD-84707 | cscsucaaCfuGfGfAfugaagaaacuL96 | 392 | asGfsuuuCfuUfCfauccAfgUfugaggsgsa | 576 | UCCCCAACUGGAUGAAGAAACU | 760 |
| AD-84708 | csusguuuGfcUfGfUfguaugaucaaL96 | 393 | usUfsgauCfaUfAfcacaGfcAfaacagsgsa | 577 | UCCUGUUUGCUGUGUAUGAUCAA | 761 |
| AD-84709 | ususugcuGfuGfUfAfugaucaaagaL96 | 394 | usCfsuuuGfaUfCfauacAfcAfgcaaascsa | 578 | UGUUUGCUGUGUAUGAUCAAAGC | 762 |
| AD-84710 | cscsgaccAfgCfUfUfguuugugaaaL96 | 395 | usUfsucaCfaAfAfcaagCfuGfgucggsgsu | 579 | AACCGACCAGCUUGUUUGUGAAA | 763 |
| AD-84711 | uscscaacCfuGfCfCfagcuuguuugL96 | 396 | usAfsaacAfaGfCfuggucUfgGfuuggaasasu | 580 | AUUCCAGCAAAACUCCCUCUAA (AUUCCAACCGACCAGCUUGUUUG) | 764 |
| AD-84712 | cscsauucCfuGfUfUfugcuguguauL96 | 397 | asUfsacaCfaGfCfaaacAfgGfaauggsgsc | 581 | GCCCAUUCCUGUUUGCUGUGUAU | 765 |
| AD-84713 | csasccuuUfcUfCfUfcuaaugaguoL96 | 398 | usAfscucAfuUfAfagaaAfaAfaggugsgsg | 582 | CCCACCUUUCUUCUAAUGAGUC | 766 |
| AD-84714 | gsusugcUfgUfGfUfaugaucaaaaL96 | 399 | usUfsuugAfuCfAfuacaCfaGfcaaacasag | 583 | CUGUUUGCUGUGUAUGAUCAAAG | 767 |
| AD-84715 | gscsugagAfaGfAfUfugacagguaL96 | 400 | usAfsaccUfgUfCfaaucUfuCfucagcsasg | 584 | CUGCUGAGAAGAUUGACAGGUUC | 768 |
| AD-84716 | ususccagCfaAfAfAfcucccucaaaL96 | 401 | usUfsgaGfgGfAfguuuUfgCfuggaasasg | 585 | CUUUCCAGCAAAACUCCCUCAAC | 769 |
| AD-84717 | usgscugaGfaAfGfAfuugacagguuL96 | 402 | asAfsccugCftuCfAfaucuUfcUfcagcasgsc | 586 | GCUGCUGAGAAGAUUGACAGGUU | 770 |
| AD-84718 | uscscucacUfuCfCfagcaaaacucL96 | 403 | usAfsguuuUfugCfCfuggaaAfaGfugagascsc | 587 | GGUUCCACUUUCCAGCAAAACUC | 771 |
| AD-84719 | uscscacaAfuGfAfGfaguaccugaL96 | 404 | usAfscaggUfaCfUfcucuAfuUfguggasusg | 588 | CAUCCACAAUGAGAGUACCUGUG | 772 |
| AD-84720 | uscscaccCfuGfUfCfAfuccacaaugaL96 | 405 | usCfsauuGfuGfGfaugaCftgAfgggasasa | 589 | UUCCACCCUGUCAUCCACAAUGA | 773 |
| AD-84721 | uscscacuUfcCfAfGfcaaaacuccaL96 | 406 | usGfsgagUfuUfUfgcugGfaAfguagasgsa | 590 | UCUCACUUUCCAGCAAAACUCCC | 774 |
| AD-84722 | uscscccucAfcAfCfUfGfgaugaagaaaL96 | 407 | usUfsucuUfcAfUfccagUfgUfagggasgsu | 591 | ACUCCCUCAACUGGAUGAAGAAA | 775 |
| AD-84723 | gsasgaguAfcCfUfGfugagcagcuaL96 | 408 | usAfsgcuGfcUfCfacagGfuAfcucucsasu | 592 | AUGAGAGUACCUGUGAGCAGCUG | 776 |
| AD-84724 | asggsaauUfcCfAfAfCfcgaccaguuL96 | 409 | asAfsgcuGfcuUfGfgauuCfgaaaCfcuuL | 593 | AAAGAUUCCAACCGACCAGCUU | 777 |
| AD-84725 | csasuuccCfuGfUfUfUfgcuguauaL96 | 410 | usAfsuacAfcAfGfcaaaCfaGfgaaugsgsg | 594 | CCCAUUCCUGUUUGCUGUGUAUG | 778 |
| AD-84726 | gsasauucCfaAfCfCfgaccaguuaL96 | 411 | usAfsagcUfgGfUfcgguUfgGfaauucsusu | 595 | AAGAAUUCCAACCGACCAGCUUG | 779 |

TABLE 5-continued

Modified Sense and Antisense Strand Sequences of hAGT dsRNA Agents

| Duplex Name | Modified Sense Sequence 5' to 3' | SEQ ID NO: | Modified Antisense Sequence 5' to 3' | SEQ ID NO: | mRNA target sequence 5' to 3' | SEQ ID NO: |
|---|---|---|---|---|---|---|
| AD-84727 | csasuccaCfaAfUfGfagaguaccuaL96 | 412 | usAfgguAfcUfCfucauUfgUfggaugsasc | 596 | GUCAUCCACAAUGAGAGUACCUG | 780 |
| AD-84728 | cscscauuCfcUfGfUfUfuugcuguguaL96 | 413 | usAfscacAfgCfAfaacaGfgAfaugggcsg | 597 | CGCCCAUUCCUGUUUGCUGUGUA | 781 |
| AD-84729 | csusgggUfuAfUfUfuuagaauauaL96 | 414 | usAfsuucUfcUfAfaaauAfaAfcccagcsa | 598 | UGCUGGGUUUAUUUAGAGAAUG | 782 |
| AD-84730 | gscsugggUfuUfAfUfuuuagaauuL96 | 415 | asUfsucUfcuAfAfaauaAfaCfccagcsasa | 599 | UUGCUGGGUUUAUUUAGAGAAU | 783 |
| AD-84731 | asusggcaUfgCfAfCfaguagcuauL96 | 416 | asUfsagcUfcAfCfugugCfaUfgccauasu | 600 | AUAUGGCAUGCACAGUGAGCUAU | 784 |
| AD-84732 | gsasgagaGfcCfCfAfcagagucuacL96 | 417 | usUfsagaCfuCfUfguggGfcUfcucucsusc | 601 | GAGAGAGCCCACAGAGUCUAC | 785 |
| AD-84733 | gscsaagaAfcCfAfGfGfuguuuagcgaL96 | 418 | usCfsgcuAfaAfCfacugGfuUfcugcscsu | 602 | AGGCAAGAACCAGUGUUUAGCGC | 786 |
| AD-84734 | cscsagcaAfaAfCfUfcccucaacuaL96 | 419 | usAfsgguuGfaGfGfgaguUfuUfcuggsasa | 603 | UUCCAGCAAAACUCCCUCAACUG | 787 |
| AD-84735 | csasccucGfucAfAfCfacaaugaguaL96 | 420 | usUfscauUfgUfGfgaugAfcGfaggugsga | 604 | UCCACCUCGUCAUCCACAAUGAG | 788 |
| AD-84736 | csgsucauCfcAfCfAfaugagacuaL96 | 421 | usUfsacUfucAfUfGfuagagTfgAfugacgsasg | 605 | CUCGUCAUCCACACGUCUGGACUAC | 789 |
| AD-84737 | csgsucauCfgCfUfCfAfaugagaaaL96 | 422 | asUfscucCfuCfAfguugAfgFfagggagsga | 606 | UCCUCCACGUCUCAACUGGAUGAAG | 790 |
| AD-84738 | asasucucCfuuCfAfAfcuggaugaaL96 | 423 | asUfsgaaCfcCfUfgucaaUfcUfuccasgc | 607 | AAAAUCCCUCAACUGGAUGAAG | 791 |
| AD-84739 | usgsagaaGfaUfUfGfacaggucauL96 | 424 | asUfscucAfuUfGfuggaUfGfgaguusu | 608 | GCUGAAGAUUGACAGGUCAU | 792 |
| AD-84740 | cscsucguCfaUfCfCfacaaugaaL96 | 425 | usUfscuuCfaUfCfaguUfgAfcaggsug | 609 | CACCUCGUCAUCCACAAUGAAG | 793 |
| AD-84741 | gsasgaagAfuUfUfGfacaggucaaL96 | 426 | usAfsuaAfcCfUfgucaAfuCfuucucsasg | 610 | CUGAAGAAUUGACAGGUCAUG | 794 |
| AD-84742 | csusucuugGfgGfCfUfCfgauauauaL96 | 427 | usAfsuaAfcGfGfaagcCfcAfagaagsusu | 611 | AACUUGGGCUUCCGUAUAUA | 795 |
| AD-84743 | uscscaccUfcGfUfCfCfaaccacaauL96 | 428 | usAfsuuGfuGfGfAfAfaugacGfaGfgguggaasg | 612 | CUUCCACCUCGUCAUCCACAUG | 796 |
| AD-84744 | asgsauugAfcAfGfGfUfuccaugcaL96 | 429 | usCfsugcAfuGfAfAfaccuGfuCfaaucsusc | 613 | GAAGAUUGACAGGUCAUGCAGG | 797 |
| AD-84745 | csusccccUfcAfAfCfUfGfgaugaagaL96 | 430 | usUfscuuCfaUfCfCfaguUfgAfgggagsusu | 614 | AACUCCCUCAACUGGAUGAAGAA | 798 |
| AD-84746 | asasugagAfgUfAfCfCfugugagcaaL96 | 431 | usUfsgcuCfaCfAfAfgguaCfuCfucauusgsu | 615 | ACAAUGAGAGUACCUGUAGAGU | 799 |
| AD-85431 | cscsaccuUfuUfCfUfUfucaaugaguL96 | 432 | asCfsucauuagagaAfaAfggugsgsa | 616 | UCCCACCUUUCUUCUAAUGAGU | 800 |
| AD-85432 | csgsaccaGfcUfUfGfuuuguguaaaL96 | 433 | usUfsuucacaaacaaGfcUfggucgsgsu | 617 | ACCGACCAGCUUGUUUGUGAAAC | 801 |
| AD-85433 | ascscuuuUfcUfUfCfuaaugagucgL96 | 434 | usGfsacucauuagaaGfaAfaaggusgsg | 618 | CCACCUUUCUUCUAAUGAGUCG | 802 |
| AD-85434 | gsuscaucCfaCfAfAfugagacaL96 | 435 | usGfsuacucucaugUfgFfaugacsgsa | 619 | UCGUCAUCCACAAUGAGAGUACC | 803 |

TABLE 5-continued

Modified Sense and Antisense Strand Sequences of hAGT dsRNA Agents

| Duplex Name | Modified Sense Sequence 5' to 3' | SEQ ID NO: | Modified Antisense Sequence 5' to 3' | SEQ ID NO: | mRNA target sequence 5' to 3' | SEQ ID NO: |
|---|---|---|---|---|---|---|
| AD-85435 | csascaauGfaGfAfGfuaccugugaaL96 | 436 | usUfscacagguacucUfAfuugugsgsa | 620 | UCCACAAUGAGAGUACCUGUGAG | 804 |
| AD-85436 | gsuscuccCfacCfcAfCfUfuuucuuccuaaL96 | 437 | usUfsagaagaaaaggUfGfgagacusug | 621 | CAGUCUCCCACCUUUUCUUCUAA | 805 |
| AD-85437 | ascsuuuccCfaGfCfAfCfAfaaacucccuaL96 | 438 | usAfsgggaguuuugcUfGfaaagusgsa | 622 | UCACUUUCCAGCAAAACUCCCUC | 806 |
| AD-85438 | cscsucaaCfuGfGfAfUfgaagaaacuL96 | 439 | asGfsuuucuucauccAfgUfugaggsgsa | 623 | UCCCUGCAACUGGAUGAAGAAACU | 807 |
| AD-85439 | csusguuuGfcUfGfUfGfUfAfugaugaucaaL96 | 440 | usUfsgaucaucacaGfcAfaacagsgsa | 624 | UCCUGUUGCUGUGUAUGAUCAA | 808 |
| AD-85440 | ususugcuGfuGfUfAfugaucaaagaL96 | 441 | uscCfsuuugaucauacAfcAfgcaaascsa | 625 | UGUUUGCUGUAUGAUCAAAGC | 809 |
| AD-85441 | cscsgaccAfgCfUfUfgguuugugaaL96 | 442 | usUfsucacaaacaagCfuGfgucggsusu | 626 | AACCGACCAGCUUGUUUGUGAAA | 810 |
| AD-85442 | uscscaacCfgAfCfCfagcuuguuuaL96 | 443 | usAfsaacaagcugguCfgGfuuggasasu | 627 | AUUCCACCGACCAGCUUGUUUG | 811 |
| AD-85443 | cscsauucCfuGfUfUfugcuguguauL96 | 444 | asUfsacacagcaaacAfgGfaauggsgsc | 628 | GCCCAUUCCUGUUGCUGUGUAU | 812 |
| AD-85444 | csasccuuUfcCfUfCfuaaugagauL96 | 445 | usAfscuauuagaagAfaAfaggugsgsg | 629 | CCCACCUUUCUUCUAAUGAGAUC | 813 |
| AD-85445 | gsusuugcUfgUfGfUfAfugaucaaaL96 | 446 | usUfsuugaucauacaCfaGfcaaacsasg | 630 | CUGUUUGCUGUGUAUGAUCAAAG | 814 |
| AD-85446 | gscsugagaAfaGfAfUfugacagguuaL96 | 447 | usAfsaccugucaaucUfuCfucagcsasg | 631 | CUGCUGAGAAGAUUGACAGGUUC | 815 |
| AD-85447 | ususccagCfaAfAfAfcuccccuaaL96 | 448 | usUfsugagggaguuuUfgCfuggaasasg | 632 | CUUUCCAGCAAAACUCCCCUAAC | 816 |
| AD-85448 | usgscugaGfaAfGfAfUfugacagguuL96 | 449 | asAfscugucaaucuUfcUfcagcasgsc | 633 | GCUGCUGAGAAGAUUGACAGGUU | 817 |
| AD-85449 | uscscuucacUfuUfCfCfagcaaacuaL96 | 450 | usAfsguuuugcuggaAfaGfugagascsc | 634 | GGUCCACUUUCCAGCAAAACUC | 818 |
| AD-85450 | uscscacaAfuGfAfGfaguaccugauL96 | 451 | usAfscagguacucuAfuUfuggagasug | 635 | CAUCCACAAUGAGAGUACCUGUG | 819 |
| AD-85451 | cscsacccUfgUfCfCfAfuccacaaugaL96 | 452 | usCfsaauguggaugaCfgAfgguggsasa | 636 | UUCCACCGUCCAUCCACAUGA | 820 |
| AD-85452 | uscsacuuUfcCfAfGfCfaaaacucaL96 | 453 | usGfsgaguuuugcugGfaAfagugasgsa | 637 | UCUCACUUUCCAGCAAAACUCCC | 821 |
| AD-85453 | uscscucaCfaCfUfGfGfaugaagaaaL96 | 454 | usUfsucuucauccagUfuGfagggasgsu | 638 | ACUCCCUCAACUGGAUGAAGAAA | 822 |
| AD-85454 | gsasgaguAfcCfUfGfugagcagcuaL96 | 455 | usAfsgcugcucacagGfuAfcucucsasu | 639 | AUGAGAGUACCUGUGAGCAGCUG | 823 |
| AD-85455 | asgsaauuCfcAfAfCfcgaccuuL96 | 456 | asAfsgcuggucgguuGfaAfauucususu | 640 | AAAGAAUUCCAACCGACCAGCUU | 824 |
| AD-85456 | cscsauucCfuGfUfUfugcuguauaL96 | 457 | usAfsuacacagcaaaCfaGfgaaugsgsg | 641 | CCCAUUCCUGUUGCUGUGUAUG | 825 |
| AD-85457 | gsasauucCfaAfCfCfgaccagcuuL96 | 458 | usAfsagcuggucgguUfgGfaauucsusu | 642 | AAGAAUUCCAACCGACCAGCUUG | 826 |
| AD-85458 | csasuccaCfaAfUfGfagaguaccuaL96 | 459 | usAfsgguacucuauUfGfgaugasasc | 643 | GUCAUCCACAAUGAGAGUACCUG | 827 |

TABLE 5-continued

Modified Sense and Antisense Strand Sequences of hAGT dsRNA Agents

| Duplex Name | Modified Sense Sequence 5' to 3' | SEQ ID NO: | Modified Antisense Sequence 5' to 3' | SEQ ID NO: | mRNA target sequence 5' to 3' | SEQ ID NO: |
|---|---|---|---|---|---|---|
| AD-85459 | cscscauuCfcUfGfUfuugcugugua aL96 | 460 | usAfscacagcaaacaGfgAfaugggscsg | 644 | CGCCCAUUCCUGUUGCUGUGUA | 828 |
| AD-85460 | csusgggUfuAfUfUfuuuagagaaua UL96 | 461 | usAfsuucucuaaaauAfaAfcccagscsa | 645 | UGCUGGGUUUAUUUAGAGAAUG | 829 |
| AD-85461 | gscsuggGfUfuAfAfUfuuuagagaau uL96 | 462 | asUfsucucuaaaauaAfaCfcccagcsasa | 646 | UUGCUGGGUUUAUUUAGAGAAU | 830 |
| AD-85462 | asusggcaUfgCfAfCfagugagcuau L96 | 463 | asUfsagcucacugugCfaUfgccauasasu | 647 | AUAUGGCAUGCACAGUGAGCUAU | 831 |
| AD-85463 | gsasgagaGfcCfCfcAfcagagucua aL96 | 464 | usUfsagacucuguggGfcUfcucucsusc | 648 | GAGAGAGAGCCCACAGAGUCUAC | 832 |
| AD-85464 | gscsaagaAfcCfAfGfuguuuagcga L96 | 465 | usCfsgcuaaacacugGfuUfcuugcscsu | 649 | AGGCAAGAACCAGUGUUUAGCGC | 833 |
| AD-85465 | cscsagcaAfaAfCfUfcccucaacua L96 | 466 | usAfsguuggggaguUfuUfgcuggsasa | 650 | UCCAGCAAAACUCCCCUCAACUG | 834 |
| AD-85466 | csascucGfuCfAfUfcccacaaugaa L96 | 467 | usUfscauuguggaugAfcGfaggusgsa | 651 | UCCACCUGUCAUCCACAAUGAG | 835 |
| AD-85467 | csgsucaucAfCfAfAfaugagagua cL96 | 468 | usAfsacucucauuguGfgAfugacgsasg | 652 | CUCGUCAUCCACAAUGAGAGUAC | 836 |
| AD-85468 | csusccaCfgCfUfCfucuggacuua L96 | 469 | usAfsagucagagagCfgUfgggagsgsa | 653 | UCCUCCCACGCUCUCUGGACUUC | 837 |
| AD-85469 | asasucccCfuCfAfAfcuggaugaa aL96 | 470 | usUfsucauccagugAfgGfaguuususu | 654 | AAAACUCCCAACUGGAUGAAG | 838 |
| AD-85470 | usgsagaaGfaUfUfGfacagguucau L96 | 471 | asUfsgaaccuguuAfcUfucucasgsc | 655 | GCUGAGAAGAUUGACAGGUUCAU | 839 |
| AD-85471 | cscsucgucCfGfUfCfaucaaugaa uL96 | 472 | usUfscucauuguggaUfgAfcgagsusg | 656 | CACCUCGUCAUCCACAAUGAGAG | 840 |
| AD-85472 | gsasgaagAfuUfGfAfcagguucau aL96 | 473 | usAfsugaaccugucaAfuCfuucucsasg | 657 | CUGAGAAGAUUGACAGGUUCAUG | 841 |
| AD-85473 | csusucuuGfgGfCfUfuccguauaua L96 | 474 | usAfsuauacggaagCfcAfagaagsusu | 658 | AACUCUUGGGCUUCCGUAUAUA | 842 |
| AD-85474 | uscsccacCfcGfUfCfauccacauaUL96 | 475 | usAfsuugugaugacGfaGfgugasasg | 659 | CUUCCACCUCGUCAUCCACAAUG | 843 |
| AD-85475 | asgsaaugAfcAfGfGfuucaugcagaL96 | 476 | usCfsugcaugaaccGfuCfaaucusuc | 660 | GAAGAUUGACAGGUUCAUGCAGG | 844 |
| AD-85476 | csusccccCfaAfCfUfGfgaugaagaa aL96 | 477 | usUfscuucaucaguUfgAfgggagsusu | 661 | AACUCCCCAACUGGAUGAAGAA | 845 |
| AD-85477 | asasugagAfgUfAfCfcugugagcaaL96 | 478 | usUfsgcucacagguaCfuCfucauusgsu | 662 | ACAAUGAGAGUACCUGUGAGCAG | 846 |
| AD-85478 | cscsaccuUfuUfCfUfucuaaugaguL96 | 479 | asCfsuca(Tgn)uagaagaAfaAfguggsa | 663 | UCCCACCUUUUCUUCUAAUGAGU | 847 |
| AD-85479 | csgsaccaGfcCfUfGfuuugugaaaL96 | 480 | usUfsuuc(Agn)caaacaGfcUfggucgsgsu | 664 | ACCGACCAGCUGUUUGUGAAAC | 848 |
| AD-85480 | ascscuuuUfcUfUfCfuaaugagucaL96 | 481 | usGfsacu(Cgn)auuagaaGfaAfaaggusgsg | 665 | CCACCUUUUCUUCUAAUGAGUCG | 849 |
| AD-85481 | gsusucauCfcAfCfAfaugagaguacaL96 | 482 | usGfsuac(Tgn)cucauugUfgGfaugacsgsa | 666 | UCGUCAUCCACAAUGAGAGUACC | 850 |
| AD-85482 | csascaauGfaGfAfGfuaccugugaaL96 | 483 | usUfscac(Agn)gguacucUfcAfuugusgsa | 667 | UCCACAAUGAGAGUACCUGUGAG | 851 |

TABLE 5-continued

Modified Sense and Antisense Strand Sequences of hAGT dsRNA Agents

| Duplex Name | Modified Sense Sequence 5' to 3' | SEQ ID NO: | Modified Antisense Sequence 5' to 3' | SEQ ID NO: | mRNA target sequence 5' to 3' | SEQ ID NO: |
|---|---|---|---|---|---|---|
| AD-85483 | gsuscuccCfaCfcUfuuucuucuaaL96 | 484 | usUfsaga(Agn)gaaaagUfgGfgagacsusg | 668 | CAGUCUCCCACCUUUUCUUCUAA | 852 |
| AD-85484 | ascsuuucCfaGfcCfAfaaacucccuaL96 | 485 | usAfsggg(Agn)guuuugcUfgGfaaagusgsa | 669 | UCACUUUCCAGCAAAACUCCCUC | 853 |
| AD-85485 | cscsucaaCfuGfGfAfugaagaacuL96 | 486 | asGfsuuu(Cgn)uucauccAfgUfugaggsgsa | 670 | UCCCUCAACUGGAUGAAGAACU | 854 |
| AD-85486 | csusguuuGfcUfGfUfguauguacaaL96 | 487 | usUfsgau(Cgn)auacacaGfcAfaacagsgsa | 671 | UCCUGUUGCUGUGUAUGAUCAA | 855 |
| AD-85487 | ususugcuGfuGfUfAfugaucaagaL96 | 488 | usCfsuuu(Ggn)aucauaCfcAfgcaaascsa | 672 | UGUUUGCUGUGUAUGAUCAAAGC | 856 |
| AD-85488 | cscsgaccAfgCfUfGfguuugugaaaL96 | 489 | usUfsuca(Cgn)aaacaagCfuGfgucggsusu | 673 | AACCGACCAGCUUGGUUUGUGAAA | 857 |
| AD-85489 | uscscaacCfgAfcCfCfagcuuguuuaL96 | 490 | usAfsaac(Agn)agcugguCfgGfuuggasasu | 674 | AUUCCAACCGACCAGCUUGUUG | 858 |
| AD-85490 | cscsauucCfuGfUfUfugcugugauL96 | 491 | asAfsaca(Cgn)agcaaacAfgGfaaugggsc | 675 | GCCCAUUCCUGUUUGCUGUGUAU | 859 |
| AD-85491 | csascccuuUfcUfCfUfUfcuaaugaguL96 | 492 | uaAfscuc(Agn)uuagaagAfaAfaggusgsg | 676 | CCCACCUUUCUUCUAAUGAGUC | 860 |
| AD-85492 | gsusuugCfuGfUfGfUfaugaucaaL96 | 493 | uaUfsuug(Agn)ucauacaCfaGfcaaacsasg | 677 | CUGUUUGCUGUGAAGAUCAGAGUUC | 861 |
| AD-85493 | gcsugagAfaGfAfUfUfugacagguuaL96 | 494 | usAfsacc(Tgn)gucaauUfuCfucagcsasg | 678 | CUGCUGAGAAGAUUGACAGGUUC | 862 |
| AD-85494 | ususccagGfaAfAfAfcucccucaaL96 | 495 | usUfsuga(Ggn)ggaguuuUfgCfuggaasasg | 679 | CUUUCCAGCAAAACUCCCUCAAC | 863 |
| AD-85495 | usgscugaGfaAfGfAfAfuugacagguuL96 | 496 | asAfsccu(Ggn)ucaaucUfcUfcagcagsc | 680 | GCUGCUGAGAAGAUUGACAGUU | 864 |
| AD-85496 | uscsucaCfuUfCfCfagcaaaacuaL96 | 497 | usAfsguu(Tgn)ugcuggaAfaGfugagascsc | 681 | GGUCCACUUCCAGCAAAACUC | 865 |
| AD-85497 | uscscacaAfuGfAfGfaguaccugauL96 | 498 | usAfscag(Ggn)uacucuCfaUfuguggasusg | 682 | CAUCCACAAUGAGAGUACCUGUG | 866 |
| AD-85498 | cscsaccuCfgUfCfAfuccacaugaL96 | 499 | usCfsauu(Ggn)uggaugaCfgAfgguggasa | 683 | UUCCACCGUCAUCCACAUGA | 867 |
| AD-85499 | uscsaacuUfcCfAfGfGfgaugaagaaL96 | 500 | usGfsgag(Tgn) uuugcugCfgAfaAfagusgsa | 684 | UCUCACUUCCAGCAAAACUCCC | 868 |
| AD-85500 | usccscucAfaCfUfGfGfgaugaagaaL96 | 501 | usUfsucu(Tgn)cauccagUfuGfagggsgsu | 685 | ACUCCCUCAACUGGAUGAAGAA | 869 |
| AD-85501 | gsaagaguAfcCfUfGfGfugagcaguL96 | 502 | usAfsgcu(Ggn)cucacagGfuAfcucucsasu | 686 | AUGAGAGUACCUGGUGAGCAGCUG | 870 |
| AD-85502 | asgsaauCfcAfAfCfcgaccagcuuL96 | 503 | asAfsgcu(Ggn)gucgguuGfgAfauucususu | 687 | AAAGAUUCCAACCGACCAGCUU | 871 |
| AD-85503 | csasuucCfUfGfUfUfgcuguauaL96 | 504 | usAfsuac(Agn)cagcaaaCfaGfaaugssg | 688 | CCCAUUCCUGUUUGCUGUGUAUG | 872 |
| AD-85504 | gsasauccCfaCfCfgaccagcuuL96 | 505 | usAfsagc(Tgn)ggucgguUfgGfaauucsusu | 689 | AAGAUUCCAACCGACCAGCUUG | 873 |
| AD-85505 | csasuccaCfaAfUfGfagaguaccuL96 | 506 | usAfsggu(Ggn)cucucauUfgGfaugsasc | 690 | GUCAUCCACAAUGAGAGUACCUG | 874 |
| AD-85506 | cscscauuCfcUfGfUfuugcugugaL96 | 507 | usAfscac(Agn)gcaaacaGfaAfugggascsg | 691 | CGCCCAUUCCUGUUUGCUGUGUA | 875 |

TABLE 5-continued

Modified Sense and Antisense Strand Sequences of hAGT dsRNA Agents

| Duplex Name | Modified Sense Sequence 5' to 3' | SEQ ID NO: | Modified Antisense Sequence 5' to 3' | SEQ ID NO: | mRNA target sequence 5' to 3' | SEQ ID NO: |
|---|---|---|---|---|---|---|
| AD-85507 | csusgggUfuAfUfUfuuagagauaL96 | 508 | usAfsuuc(Tgn)cuaaaauAfaAfcccagcsca | 692 | UGCUGGGUUUAUUUAGAGAAUG | 876 |
| AD-85508 | gscsugggUfuUfAfUfuuuagagauuL96 | 509 | asUfsucu(Cgn)uaaaauaAfaAfccagcsasa | 693 | UUGCUGGGUUUAUUUAGAGAAU | 877 |
| AD-85509 | asusggcaUfgCfAfCfagugagcuauL96 | 510 | asUfsagc(Tgn)cacugugCfaUfgccausasu | 694 | AUAUGGCAUGCACAGUGAGCUAU | 878 |
| AD-85510 | gsasgagaGfcCfCfAfcagagucucaL96 | 511 | usUfsaga(Cgn)ucugugGfcUfcucucusc | 695 | GAGAGAGAGCCCACAGAGUCUAC | 879 |
| AD-85511 | gscsaagaAfcCfAfGfuguuuagcgaL96 | 512 | usCfsgcu(Agn)aacacugGfuUfcuugcscsu | 696 | AGGCAAGAACCAGUGUUUAGCGC | 880 |
| AD-85512 | cscsagcaAfaAfCfUfcccucaacuaL96 | 513 | usAfsgguu(Ggn)agggaguUfuUfcuggasa | 697 | UUCCAGCAAAACUCCCUCAACUG | 881 |
| AD-85513 | csasccucGfuCfAfUfccacaaugaaL96 | 514 | usUfscau(Tgn)guggaugAfcGfaggugsga | 698 | UCCACCUCGUCAUCCACAAUGAG | 882 |
| AD-85514 | csgsucaucUfcAfCfAfaugagaguaL96 | 515 | usUfsacu(Cgn)ucauuguGfaAfugacgsasg | 699 | CUCGUCAUCCACAAUGAGAGUAC | 883 |
| AD-85515 | csusccacUfgCfUfCfucuggacuuL96 | 516 | usAfsagu(Cgn)cagagagCfgUfgggasgsa | 700 | UCCUCCACGCUCUCUGGACUUC | 884 |
| AD-85516 | asascuccCfuCfAfAfcuggaugaaL96 | 517 | usUfsuca(Tgn)ccaguugAfgGfaguususu | 701 | AAAACUCCCUCAACUGGAUGAAG | 885 |
| AD-85517 | usgsagaaGfaUfUfGfacaggucauL96 | 518 | asUfsgaa(Cgn)cugucaaUfcUfucucagsc | 702 | GCUGAGAAGAUUGACAGGUUCAU | 886 |
| AD-85518 | cscsucguCfaUfCfCfacaaugaaaL96 | 519 | usUfscuc(Agn)uuguggaUfgAfcgaggsug | 703 | CACCUCGUCAUCCACAAUGAGAG | 887 |
| AD-85519 | gsasgaagAfuUfGfAfcagguucaaL96 | 520 | usAfsuga(Agn)ccgucaAfuCfuucucsasg | 704 | CUGAGAAGAUUGACAGGUUCAUG | 888 |
| AD-85520 | csusucuuGfgGfCfUfuccguauauaL96 | 521 | usAfsuau(Agn)cggaagcCfcAfagaagsusu | 705 | AACUUCUUGGGCCUUCCGUAUAUA | 889 |
| AD-85521 | uscscaccUfcGfUfCfauccacaugL96 | 522 | usAfsuug(Tgn)ggaugacCfaGfguggasag | 706 | CUUCCACCUCGUCAUCCACAUG | 890 |
| AD-85522 | asgsauugAfcAfGfGfuucauccagL96 | 523 | usCfsugc(Agn)ugaaccuGfucfaaucsusu | 707 | GAAGAUUGACAGGUUCAUCGAGG | 891 |
| AD-85523 | csuscccuCfaAfCfuGfggaugagaaL96 | 524 | usUfscuu(Cgn)auccaguUfgAfgggagsusu | 708 | AACUCCCUCAACUGGAUGAGAA | 892 |
| AD-85524 | asasugagAfgUfAfCfcugugagcaL96 | 525 | usUfsgcu(Cgn)acagguaCfuCfucauusg | 709 | ACAAUGAGAGUACCUGUGAGCAG | 893 |
| AD-85619 | cscsaccuUfuUfCfUfcuaaugaguL96 | 526 | asCfsucau(Tgn)agaagaAfaAfggugg | 710 | UCCCACCUUUCUCUAAUGAGAU | 894 |
| AD-85620 | csgsaccaGfcUfUfGfuuugaaaaL96 | 527 | usUfsuuca(Cgn)aaacaaGfcUfgucgsg | 711 | ACCGACCAGCUUGUUUGUGAAAC | 895 |
| AD-85621 | asscsuuuUfcUfUfCfuaaugagucL96 | 528 | usGfsacuc(Agn)uuagaaGfaAfaagugsg | 712 | CCACCUUUCUCUAAUGAGUCG | 896 |
| AD-85622 | gsuscaucCfaCfAfAfugagaguacL96 | 529 | usUfsuacu(Cgn)ucauugUfgGfaugacsg | 713 | UCGUCAUCCACAAUGAGAGUACC | 897 |
| AD-85623 | csascaauGfaGfAfGfuaccugugaL96 | 530 | usUfscaca(Ggn)guacucUfcAfuugugsga | 714 | UCCACAAUGAGUACCUGUGAG | 898 |
| AD-85624 | gsuscuccCfaCfCfUfuuucucuaaL96 | 531 | usUfsagaa(Ggn)aaaaggUfgGfgagacsug | 715 | CAGUCUCCCACCUUUCUCUAA | 899 |

TABLE 5-continued

Modified Sense and Antisense Strand Sequences of hAGT dsRNA Agents

| Duplex Name | Modified Sense Sequence 5' to 3' | SEQ ID NO: | Modified Antisense Sequence 5' to 3' | SEQ ID NO: | mRNA target sequence 5' to 3' | SEQ ID NO: |
|---|---|---|---|---|---|---|
| AD-85625 | ascsuuuccCfaGfcCfAfaaacucccuaL96 | 532 | usAfsggga(Ggn)uuuugcUfgGfaaagusgsa | 716 | UCACUUUCCAGCAAAACUCCCUC | 900 |
| AD-85626 | cscsucaaCfuGfGfAfugaagaaacuL96 | 533 | asGfsuuuc(Tgn)ucauccAfgUfugaggsgsa | 717 | UCCCUCAACUGGAUGAAGAAACU | 901 |
| AD-85627 | csusguuuGfcUfGfUfguaugaucaaL96 | 534 | usUfsgauc(Agn)uacacaGfcAfaacagsgsa | 718 | UCCUGUUGCUGUGUAUGAUCAA | 902 |
| AD-85628 | ususugcuGfcUfuGfUfAfugaucaaagaL96 | 535 | uscCfsuuug(Agn)ucauacAfcAfgcaaacsa | 719 | UGUUUGCUGUGUAUGAUCAAAGC | 903 |
| AD-85629 | cscsgaccAfgCfUfUfgguuguugaaaL96 | 536 | usUfsucac(Agn)aacaagCfuGfgucggsusu | 720 | AACCGACCAGCUUGUUGUGAAA | 904 |
| AD-85630 | uscscaacCfgAfCfCfagcuuguuuaL96 | 537 | usUfsuaca(Agn)gcugguCfgGfuuggasasu | 721 | AUUCCAACCGACCAGCUUGUUG | 905 |
| AD-85631 | cscsauccCfuGfUfuCfuaaugacagL96 | 538 | asUfsacac(Agn)gcaaacAfgGfaauggsgsc | 722 | GCCCAUUCCUGUUGCUGUGUAU | 906 |
| AD-85632 | csascuuuUfcuCfUfuCfuaaugauaL96 | 539 | usAfscuca(Tgn)uagaagAfaAfaggugsgsg | 723 | CCCACCUUUCUUCUAAUGACAGUC | 907 |
| AD-85633 | gsusuugcUfgUfGfUfaugaucaaaL96 | 540 | usUfsuuga(Tgn)cauacaCfaGfcaaacsasg | 724 | CUGUUUGCUGUGUAUGAUCAAAG | 908 |
| AD-85634 | gscsugaGfaAfGfAfUfugacagguuaL96 | 541 | usAfsaccu(Ggn)ucaaucUfuCfucagcasag | 725 | CUGCUGAGAAGAUUGACAGGUUC | 909 |
| AD-85635 | ususccagFfaAfAfAfcuccccuaaaL96 | 542 | usUfsugag(Ggn)gaguuuUfgCfuggaasasg | 726 | CUUUCCAGCAAAACUCCCUACAAC | 910 |
| AD-85636 | usgscugaGfaAfGfAfuugacagguuL96 | 543 | asAfsccug(Tgn)caaucUfcUfcagcasgsc | 727 | GCUGCUGAGAAGAUUGACAGGUU | 911 |
| AD-85637 | uscscucacUfuCfCfagcaaaacuaL96 | 544 | usAfsguuu(Tgn)gcuggaAfaAfaUfgagascsc | 728 | GGUCUCACUUUCCAGCAAAACUC | 912 |
| AD-85638 | uscscacaAfuGfAfGfaguaccugaL96 | 545 | usAfscagg(Tgn)acucucAfUfgugasusg | 729 | CAUCCACAAUGAGAGUACCUGUG | 913 |
| AD-85639 | cscsaccuCfgUfCfAfuccacaaugaL96 | 546 | usCfsaaug(Tgn)ggaugaCfgAfggugsasa | 730 | UUCCACCUCGUCAUCCACAAUGA | 914 |
| AD-85640 | uscsacuuUfcCfAfGfCcaaaacuccaL96 | 547 | usGfsagu(Tgn)uugcugGfaAfagugsgsa | 731 | UCUCACUUUCCAGCAAAACUCCC | 915 |
| AD-85641 | uscscccucAfcaCfUfGfGfgaugaagaaaL96 | 548 | usUfsucuu(Cgn)auccagUfuGfagggasgsu | 732 | ACUCCCUCACUGGAUGAAGAAA | 916 |
| AD-85642 | gsasgaguAfcCfUfGfugagcagcuaL96 | 549 | usAfsgcug(Cgn)ucacagGfuAfcucucsasu | 733 | AUGAGAGUACCUGUGAGCAGCUG | 917 |
| AD-85643 | asgsaauuCfcAfAfCfcgaccagcuuL96 | 550 | asAfsgcug(Ggn)ucgguuGfgAfauucususu | 734 | AAAGAAUUCCAACCGACCAGCUU | 918 |
| AD-85644 | csasuuccUfgUfUfGfcguguauaL96 | 551 | usAfsuaca(Ggn)agcaaaCfaGfgaauggsg | 735 | CCCAUUCCUGUUGCUGUGUAUG | 919 |
| AD-85645 | gsasauucCfaAfCfCfgaccagcuaL96 | 552 | usAfsagcu(Ggn)gucgguUfgGfaauucsusu | 736 | AAGAAUUCCAACCGACCAGCUUG | 920 |
| AD-85646 | csasuccaCfaAfUfGfagaguaccaL96 | 553 | usAfsggua(Cgn)ucucuauUfgUfgaugasc | 737 | GUCAUCCACAAUGAGAGUACCUG | 921 |
| AD-85647 | cscscauuCfcUfGfUfuugcuguguaL96 | 554 | usAfscaca(Ggn)caaacaGfgAfaugggscsg | 738 | CGCCCAUUCCUGUUGCUGUGUA | 922 |
| AD-85648 | csusgggUfuAfUfUfuuagagaauaL96 | 555 | usAfsuucu(Cgn)uaaaauUfaAfcccagscsa | 739 | UGCUGGGUUUAUUUAGAGAAUG | 923 |

TABLE 5-continued

Modified Sense and Antisense Strand Sequences of hAGT dsRNA Agents

| Duplex Name | Modified Sense Sequence 5' to 3' | SEQ ID NO: | Modified Antisense Sequence 5' to 3' | SEQ ID NO: | mRNA target sequence 5' to 3' | SEQ ID NO: |
|---|---|---|---|---|---|---|
| AD-85649 | gscsugggUfuUfAfUfuuuagagaauL96 | 556 | asUfsucuc(Tgn)aaaauaAfaCfccagcsasa | 740 | UUGCUGGGUUUAUUUAGAGAAU | 924 |
| AD-85650 | asusggcaUfgCfaCfCfagugagcuauL96 | 557 | asUfsagcu(Cgn)acugugCfaUfgccausasu | 741 | AUAUGGCAUGCACAGUGAGCUAU | 925 |
| AD-85651 | gsasgagaGfcCfCfCfAfcagagucuacL96 | 558 | usUfsagac(Tgn)cuguggGfcUfcucucsusc | 742 | GAGAGAGCCCACAGAGUCUAC | 926 |
| AD-85652 | gscsaagaAfccCfAfGfuguuuagcgaL96 | 559 | usCfsgcua(Agn)acacugGfuUfcuugcscsu | 743 | AGGCAAGAACCAGUGUUUAGCGC | 927 |
| AD-85653 | cscsagcaAfaAfcUfcAfUfcccucaacuaL96 | 560 | usAfsguug(Agn)gggaguUfuUfgcuggsasa | 744 | UUCCAGCAAAACUCCCUCAACUG | 928 |
| AD-85654 | csascccucGfuCfaUfUfcccacaaugaaL96 | 561 | usUfscauu(Ggn)uggaugAfcGfaggugsgsa | 745 | UCCACCUCGUCAUCCACAAUGAG | 929 |
| AD-85655 | csgsucaucCfaCfCfAfaugacgaguaaL96 | 562 | usUfsacuc(Tgn)cauuguGfgAfugacgsasg | 746 | CUCGUCAUCCACAAUGAGUAC | 930 |
| AD-85656 | csuscccaCfgCfUfCfucuggacuaL96 | 563 | usAfsaguc(Cgn)agagagCfgUfgggagsgsa | 747 | UCCUCCACGCUCUCUGGACUUC | 931 |
| AD-85657 | asascucCfuCfAfAfcuggaugaaL96 | 564 | usUfsucau(Cgn)caguugAfgGfgaguususu | 748 | AAAACUCCCUCAACUGGAUGAAG | 932 |
| AD-85658 | usgsagaaGfaUfUfGfacaggucauL96 | 565 | asUfsgaac(Cgn)ugucaaUfcUfucucaagsc | 749 | GCUGAGAAGAUUGACAGGUUCAU | 933 |
| AD-85659 | cscsucguCfaUfCfcAfcaaugagaaL96 | 566 | usUfscuca(Tgn)ugugaUfgAfcgaggsusg | 750 | CACCUCGUCAUCCACAAUGAGAG | 934 |
| AD-85660 | gsasgaagAfuUfGfAfcagguucauaL96 | 567 | usAfsugaa(Cgn)cugucaAfuCfuucucsasg | 751 | CUGAGAAGAUUGACAGGUUCAUG | 935 |
| AD-85661 | csusucuuGfgGfCfUfccguauauaL96 | 568 | usAfsuaua(Cgn)ggaagcCfcAfagaagsusu | 752 | AACUUCUUGGGCUUCCGUAUAUA | 936 |
| AD-85662 | uscscaccUfcGfUfCfauccacauaL96 | 569 | usAfsuugu(Ggn)gaugacGfaGfguggasasg | 753 | CUUCACCUCGUCAUCCACAAUG | 937 |
| AD-85663 | asgsauugAfcAfGfGfuucaugcagaL96 | 570 | usCfsugca(Tgn)gaaccuGfuCfaaucususc | 754 | GAAGAUUGACAGGUUCAUGCAGG | 938 |
| AD-85664 | csusccucUfcAfUfCfUfggaugaagaaL96 | 571 | usUfscuuc(Agn)uccaguUfgAfgggagsusu | 755 | AACUCCCACUGGAUGAAGAA | 939 |
| AD-85665 | asasugagAfgUfAfCfcugugagcagL96 | 572 | usUfsgcuc(Agn)cagguaCfuCfucauusgsu | 756 | ACAAUGAGAGUACCUGUGAGCAG | 940 |

TABLE 6

Additional Modified Sense and Antisense Strand Sequences of hAGT dsRNA Agents

| Duplex Name | Sense Oligo Name | Modified Sense Sequence 5' to 3' | SEQ ID NO: | Range in NM_000029.3 | Antisense Oligo Name | Modified Antisense Sequence | SEQ ID NO: | Range in NM_000029.3 |
|---|---|---|---|---|---|---|---|---|
| AD-126306 | A-168475 | gsuscaucCfaCfAfAfugagaguacaL96 | 941 | 638-658 | A-250785 | usGfsua(Cgn)ucucauugUfgGfaugacsgsa | 951 | 636-658 |
| AD-126307 | A-168477 | csascaauGfaGfAfGfuaccugugaaL96 | 942 | 644-664 | A-250786 | usUfsca(Cgn)agguacucUfcAfuugugsgsa | 952 | 642-664 |
| AD-126308 | A-168479 | gsuscuccCfaCfCfUfuuucuucuaaL96 | 943 | 2076-2096 | A-250787 | usUfsag(Agn)agaaaaggUfgGfgagacsusg | 953 | 2074-2096 |
| AD-126310 | A-168483 | cscsucaaCfuGfGfAfugaagaaacuL96 | 944 | 1603-1623 | A-250789 | asGfsuu(Tgn)cuucauccAfgUfugaggsgsa | 954 | 1601-1623 |
| AD-126343 | A-168549 | cscsucguCfaUfCfCfacaaugagaaL96 | 945 | 634-654 | A-250822 | usUfscu(Cgn)auuguggaUfgAfcgaggsusg | 955 | 632-654 |
| AD-133360 | A-168475 | gsuscaucCfaCfAfAfugagaguacaL96 | 946 | 638-658 | A-264752 | usGfs(Tgn)acucucauugUfgGfaugacsgsa | 956 | 636-658 |
| AD-133361 | A-168475 | gsuscaucCfaCfAfAfugagaguacaL96 | 947 | 638-658 | A-264753 | usGfsu(Agn)cucucauugUfgGfaugacsgsa | 957 | 636-658 |
| AD-133362 | A-168475 | gsuscaucCfaCfAfAfugagaguacaL96 | 948 | 638-658 | A-264754 | usGfsuacuc(Tgn)cauugUfgGfaugacsgsa | 958 | 636-658 |
| AD-133374 | A-168479 | gsuscuccCfaCfCfUfuuucuucuaaL96 | 949 | 2076-2096 | A-264766 | usUfsagaag(Agn)aaaggUfgGfgagacsusg | 959 | 2074-2096 |
| AD-133385 | A-168477 | csascaauGfaGfAfGfuaccugugaaL96 | 950 | 644-664 | A-264777 | usUfsc(Agn)cagguacucUfcAfuugugsgsa | 960 | 642-664 |

Example 3. In Vivo Screening of dsRNA Duplexes in Mice Transduced with AAV Expressing Human AGT To express human angiotensinogen, C57/BL6 mice were first transduced with an AAV (adeno-associated virus) vector expressing the human AGT transcript. After at least two weeks from AAV introduction, blood was obtained from mice for baseline circulating human AGT levels, and animals then received a single 3 mg/kg subcutaneous dose of one of a subset of the dsRNA agents provided in Tables 5 and 6 (N=3 per group). Blood was obtained from animals again at fourteen days post-dose of dsRNA agent. Human AGT levels were quantified using an ELISA specific for human angiotensinogen, according to manufacturer's protocol (IBL America #27412). Data were expressed as percent of baseline value, and presented as mean plus standard deviation. Certain dsRNA duplexes were selected for further analysis.

TABLE 7

AGT Single 3 mg/kg Dose Screen in AAV-human AGT transduced mouse

| DuplexID | Avg | SD |
|---|---|---|
| AD-67327 | 13.2 | 4.5 |
| AD-85110 | 97.0 | 3.6 |
| AD-85117 | 86.7 | 10.8 |
| AD-85118 | 107.2 | 14.2 |
| AD-85434 | 18.4 | 0.6 |
| AD-85435 | 25.7 | 1.7 |
| AD-85438 | 12.6 | 2.7 |
| AD-85446 | 8.4 | 1.0 |
| AD-85481 | 27.0 | 11.5 |
| AD-85482 | 64.2 | 13.0 |
| AD-85482 | 48.5 | 5.9 |
| AD-85483 | 38.9 | 4.6 |
| AD-85485 | 63.6 | 3.0 |
| AD-85493 | 35.7 | 20.5 |
| AD-85496 | 78.5 | 10.3 |
| AD-85517 | 93.8 | 4.6 |
| AD-85524 | 90.4 | 14.7 |
| AD-85622 | 38.1 | 10.6 |
| AD-85623 | 28.0 | 8.4 |
| AD-85625 | 87.6 | 13.7 |
| AD-85626 | 29.9 | 14.0 |
| AD-85634 | 27.7 | 4.5 |
| AD-85635 | 87.1 | 13.5 |
| AD-126306 | 12.4 | 1.4 |
| AD-126307 | 21.6 | 9.0 |
| AD-126308 | 15.7 | 1.8 |
| AD-126310 | 38.3 | 1.1 |
| AD-126343 | 65.5 | 13.4 |
| AD-133360 | 50.6 | 7.5 |
| AD-133361 | 23.2 | 12.4 |
| AD-133362 | 12.2 | 4.1 |
| AD-133374 | 26.2 | 3.3 |
| AD-133385 | 33.8 | 8.7 |

Example 4. In Vivo Screening of dsRNA Duplexes in Cynomolgus Monkeys

Duplexes of interest, identified from the above mouse studies, were evaluated in cynomolgus monkey. Animals (N=3 per group) received a single 3 mg/kg subcutaneous dose of a dsRNA agent (AD-85481, AD-126306, AD-126307, AD-126308, or AD-133362) on day 1. Blood was obtained on days −6, 1, 4, 8, 15, 22, 29, 32, 35, 43, 57, 71, 85, and 99 post-dose. Circulating AGT levels were quantified using an ELISA specific for human angiotensinogen (and cross-reactive with cynomolgus), according to manufacturer's protocol (IBL America #27412). Data were expressed as percent of baseline value, and presented as mean plus/minus standard deviation. The results are shown in FIG. 1A. The apparent differences between AD-85481, AD-126306, and AD-133362 are within the range of typical study-to-study variability in non-human primates.

Dose-response studies were performed to assess the activity of AD-67327 and AD-85481. Although the experiments were performed separately, the methods used were essentially the same and the results are presented together in FIG. 1B. Cynomolgus monkeys received a single 0.3 mg/kg, 1 mg/kg, or 3 mg/kg subcutaneous dose of dsRNA agent on day 1. Blood was obtained on days −6, 1, 8, 15, 22, 29, 36, 43, 50, 57, 64, 71 and 78 post-dose for AD-67327 and on days −6, 1, 4, 8, 15, 22, 29, 32, 35, 43, 57, 71, 85, and 99 post-dose for AD-85481. Circulating AGT levels were quantified using an ELISA specific for human angiotensinogen (and cross-reactive with cynomolgus), according to manufacturer's protocol (IBL America #27412). Data were expressed as percent of baseline value, and presented as mean plus standard deviation. The results are shown in FIG. 1B. These data demonstrate a roughly 3-fold improvement in efficacy and duration for AD-85481 over AD-67327.

Figure 1C:
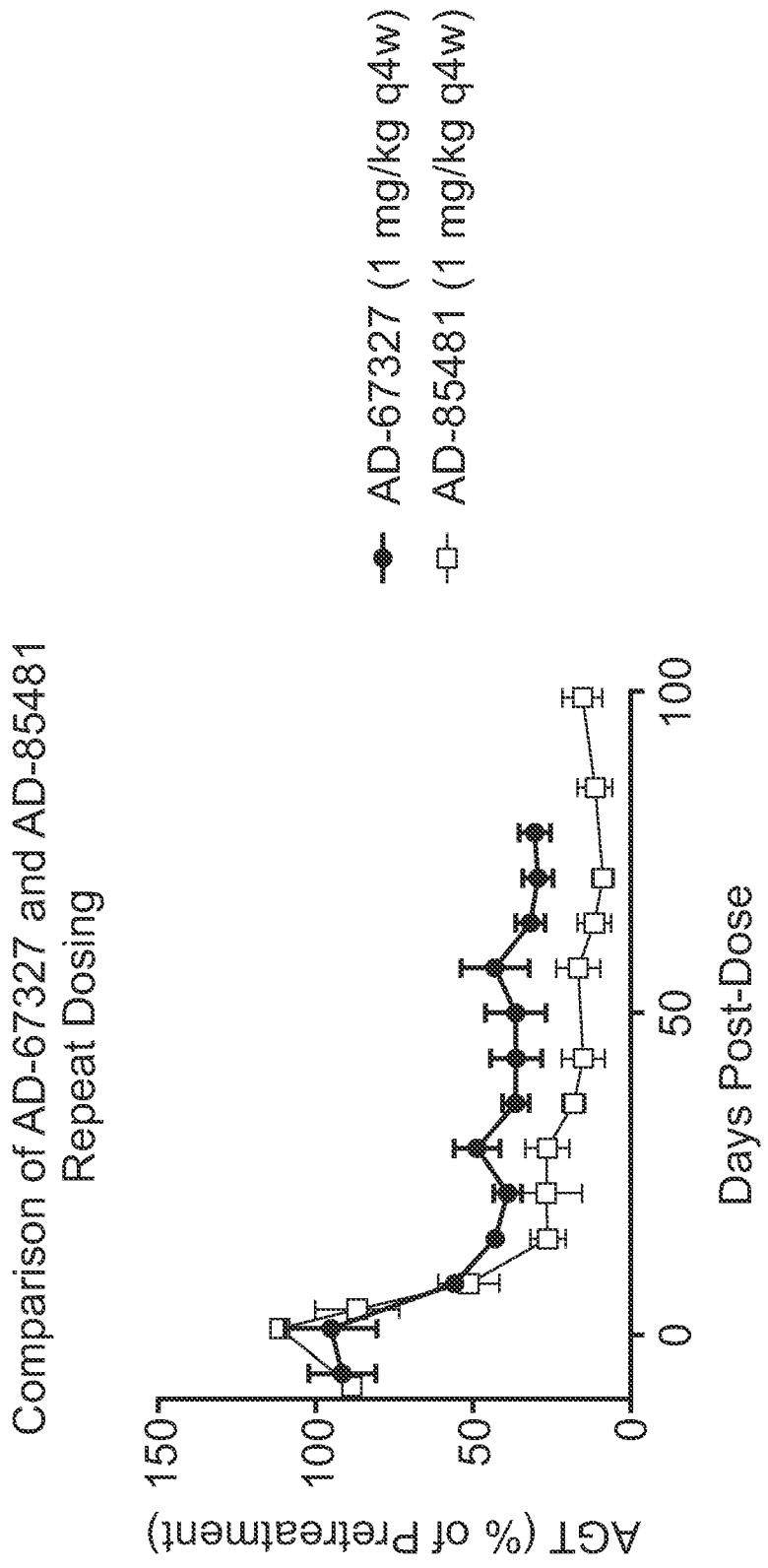
FIG. 1C is a graph showing serum AGT protein levels in cynomolgus monkeys (n=3 per group) administered a 1 mg/kg dose of AD-85481 or AD-67327 once every four weeks for three doses. AGT levels are shown as a percent of AGT level prior to treatment.

Multidose studies were performed to determine the potency and durability of AD-67327 and AD-85481. Although the experiments were performed separately, the methods used were essentially the same and the results are presented together in FIG. 1C. Cynomolgus monkeys were subcutaneously administered a 1 mg/kg dose of AD-67327 or AD-85481 once every four weeks for three weeks (q4w dosing) (days 1, 29, and 57 post first dose). Blood was obtained for evaluation of circulating AGT at days −6, 1, 8, 15, 22, 29, 36, 43, 50, 57, 64, 71 and 78 post first dose of AD-67327 and at days −8, 1, 4, 8, 15, 22, 29, 36, 43, 57, 64, 71, 85, 99 post first dose of AD-85481. These data demonstrate an increase in potency and durability of target silencing by AD-85481 compared to AD-67327.

Example 5. Treatment of Hypertension with an AGT dsRNA in a Spontaneous Hypertensive Rat Model A rat specific dsRNA was designed to test the effect of AGT knockdown in a spontaneously hypertensive rat model. Spontaneously hypertensive rats (N=9 per group) were subcutaneously administered a 10 mg/kg dose of the rat-specific AGT dsRNA once every 2 weeks (10 mg/kg q2w), or daily oral doses of the ARB valsartan (31 mg/kg/day), or daily oral doses of the ACE inhibitor captopril (100 mg/kg/day). Select combinations (the rat specific dsRNA agent plus valsartan or captopril plus valsartan) were also evaluated, dosed as noted above. Mean arterial pressure was measured by telemetry over a 4-week period. After four weeks of treatment, animals were anaesthetized by i.p. pentobarbital injection, and blood collected from the hepatic portal vein for the measurement of plasma AGT, plasma Renin, plasma Angiotensin II, plasma aldosterone, plasma K+, and plasma Renin activity. Heart weights and tibia length (for normalization of heart weights) were also obtained.

Figure 2A:
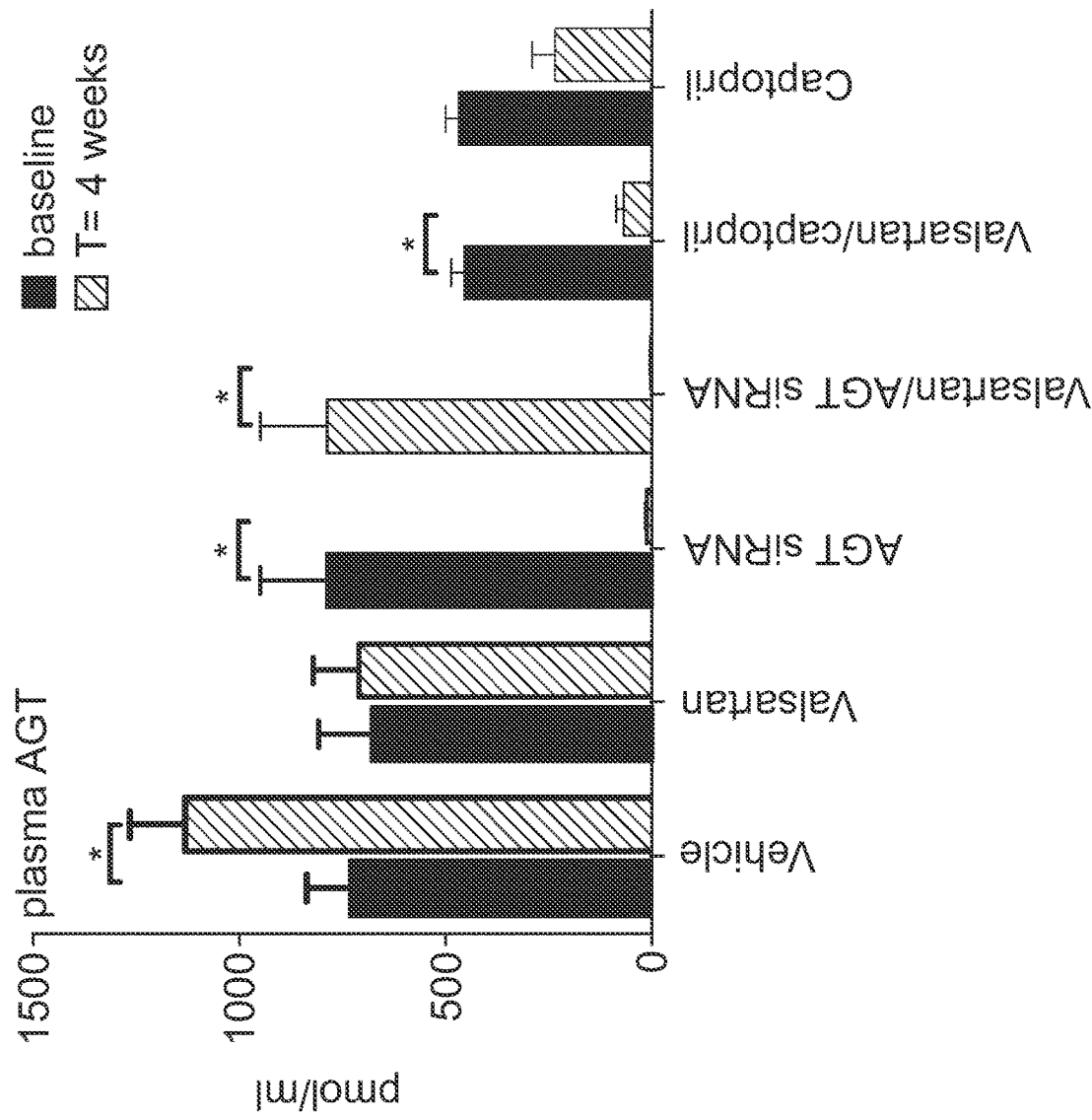
FIGS. 2A-2G show the results of a various parameters in a study of spontaneously hypertensive rats (n=9 per group) treated with a vehicle, valsartan (31 mg/kg/day), a rat specific AGT-siRNA (10 mg/kg q2w), captopril (100 mg/kg/day), valsartan and captopril, or valsartan and AGT-siRNA.
Figure 3:
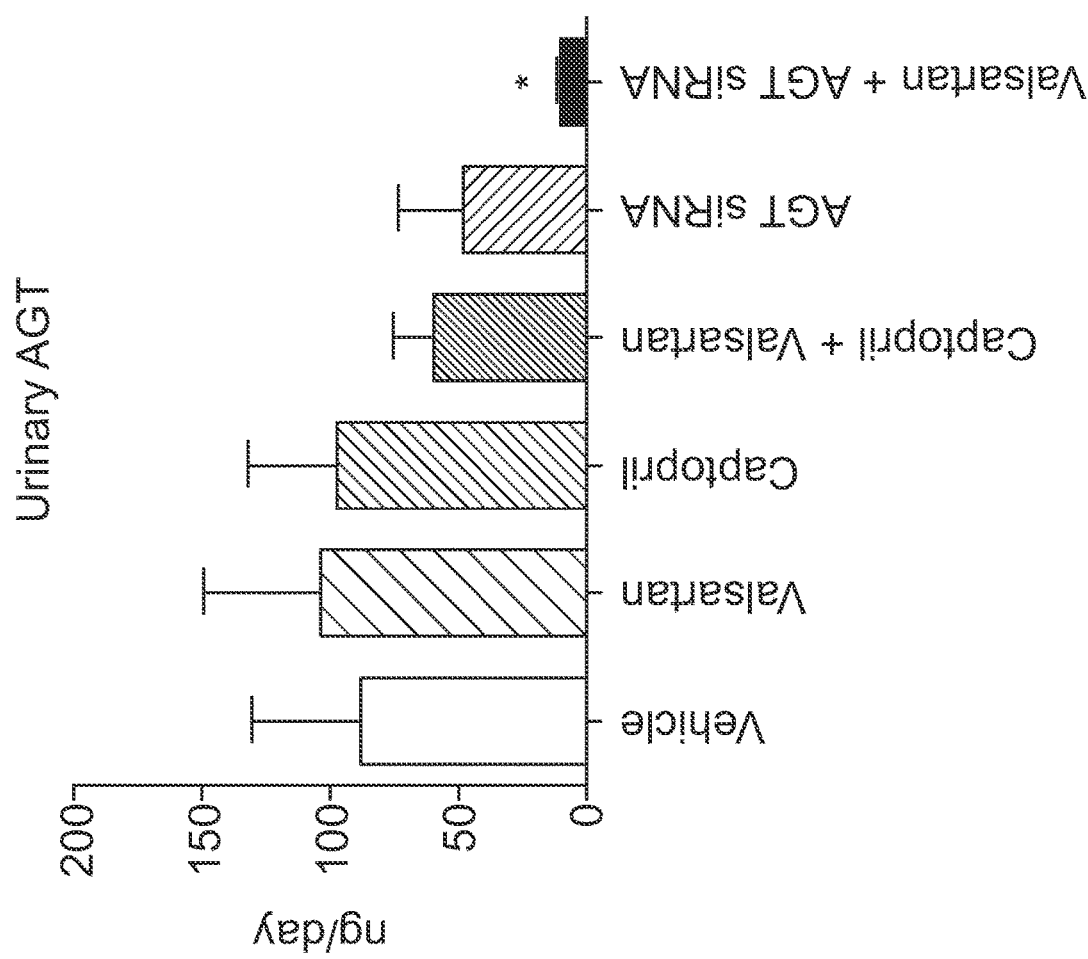
FIG. 3 is a graph showing urine AGT levels in the spontaneously hypertensive rat study.

Treatment with the rat-specific dsRNA agent knocked down plasma AGT levels by over 98% when administered alone or in combination with valsartan relative to pre-treatment levels (FIG. 2A). Treatment with the combination of valsartan and captopril was also demonstrated to significantly decrease serum AGT levels. All treatments increased the level of Renin, with the greatest increase occurring in animals treated with a combination of valsartan and the dsRNA agent, followed by a substantial increase in the dsRNA agent alone-treated group. Only combination treatment with valsartan and the dsRNA agent was found to lower circulating Angiotensin II levels. A trend towards reduced urinary AGT was observed after treatment with the dsRNA agent, suggesting that levels of AGT protein in the kidney are not significantly inhibited by treatment with the dsRNA agent (FIG. 3). Only the combination of valsartan and the dsRNA agent was found to significantly lower urinary AGT. No treatments altered aldosterone levels. Plasma $K^+$ tended to increase in all groups, with significance only being reached in the combination valsartan plus siRNA treatment group.

Figure 2B:
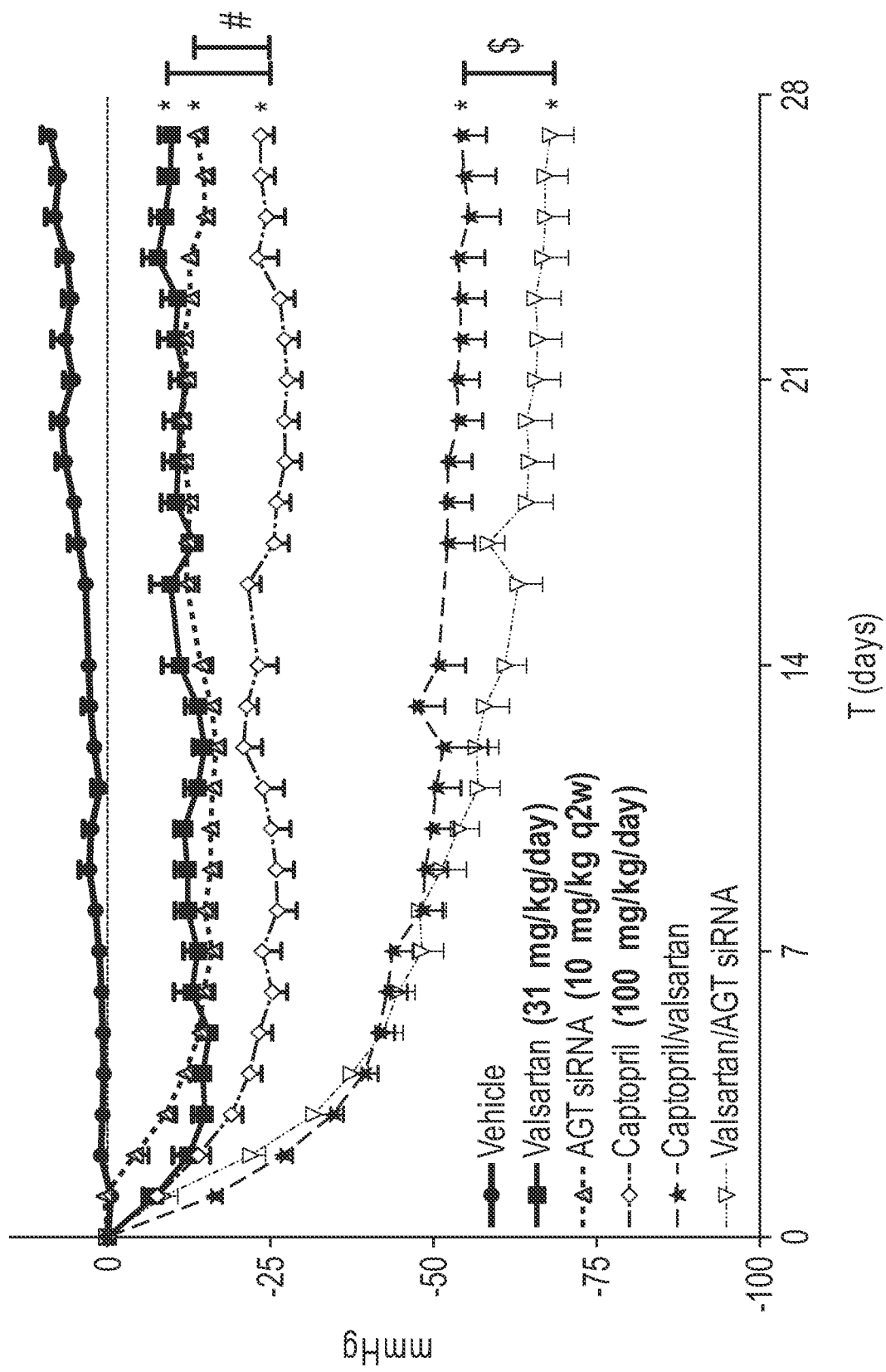

FIG. 2B shows mean arterial pressure levels measured by telemetry throughout the experiment and graphed relative to starting blood pressure levels. Each of the treatments caused a statistically significant decrease in blood pressure as compared to untreated animals. Statistical comparisons ($p<0.05$) are noted relative to baseline (#) or valsartan plus captopril ($). Treatment with valsaratan plus the rat-specific dsRNA agent was significantly better than treatment with captopril plus valsartan in lowering mean arterial pressure.

Figure 2C:
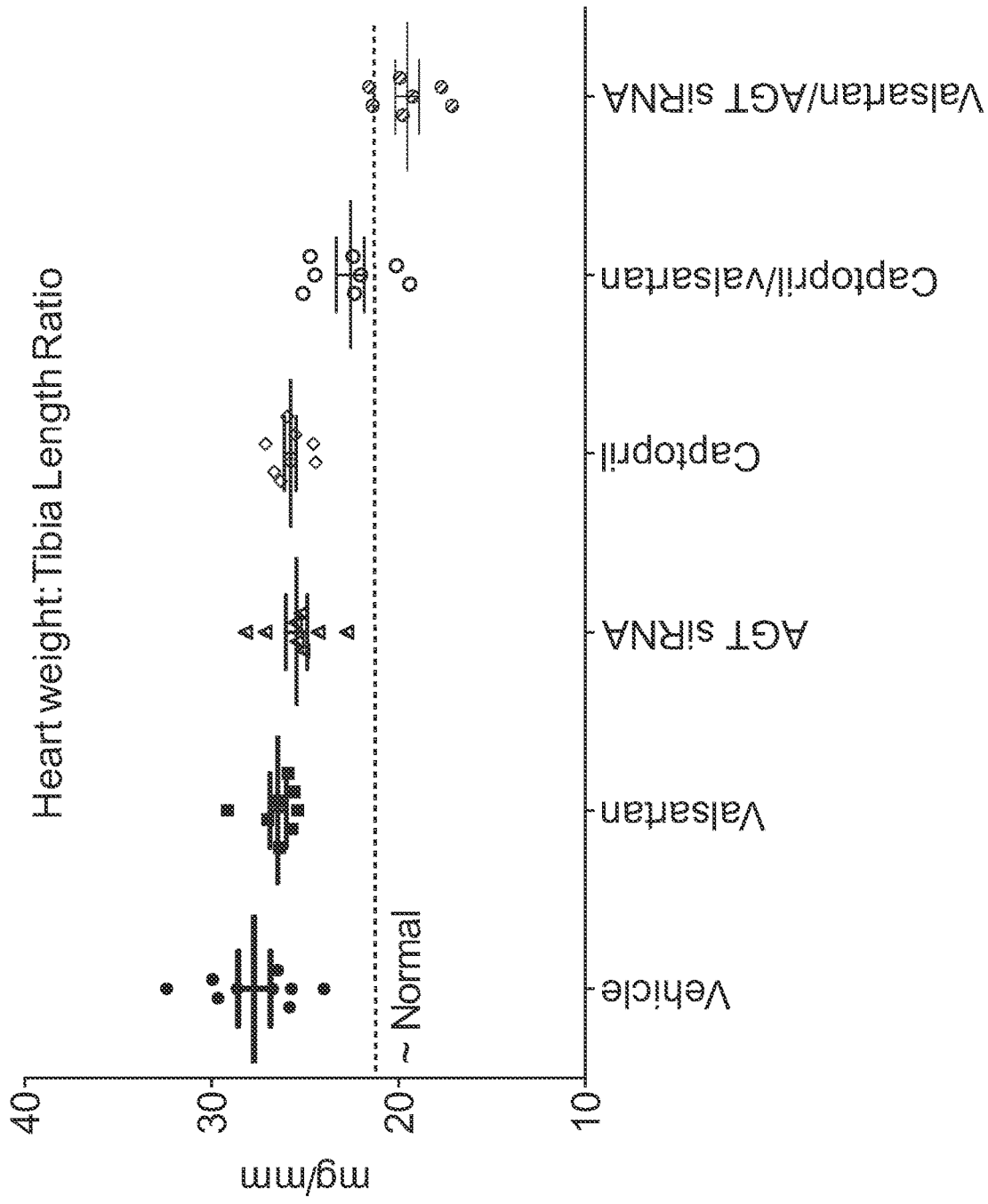

FIG. 2C shows heart weights normalized to tibial lengths to provide a measure of cardiac hypertrophy. Treatment with both valsartan plus captopril and valsartan plus the dsRNA agent were effective at reducing cardiac hypertrophy relative to control ($p<0.05$), with valsartan plus the dsRNA agent also reducing cardiac hypertrophy relative to valsartan plus captopril ($p<0.05$). FIG. 2E depicts the same data as a scatterplot of heart weight to tibial length versus MAP. A linear relationship between cardiac hypertrophy and MAP is observed, with valsartan plus the dsRNA agent providing the greatest reduction in cardiac hypertrophy. Cardiomyocyte size was reduced relative to vehicle by all groups except valsartan (FIG. 2F), while NT-proBNP was reduced in the captopril plus valsartan group and a trend to reduction was observed in the valsartan plus dsRNA group (FIG. 2G).

Figure 2D:
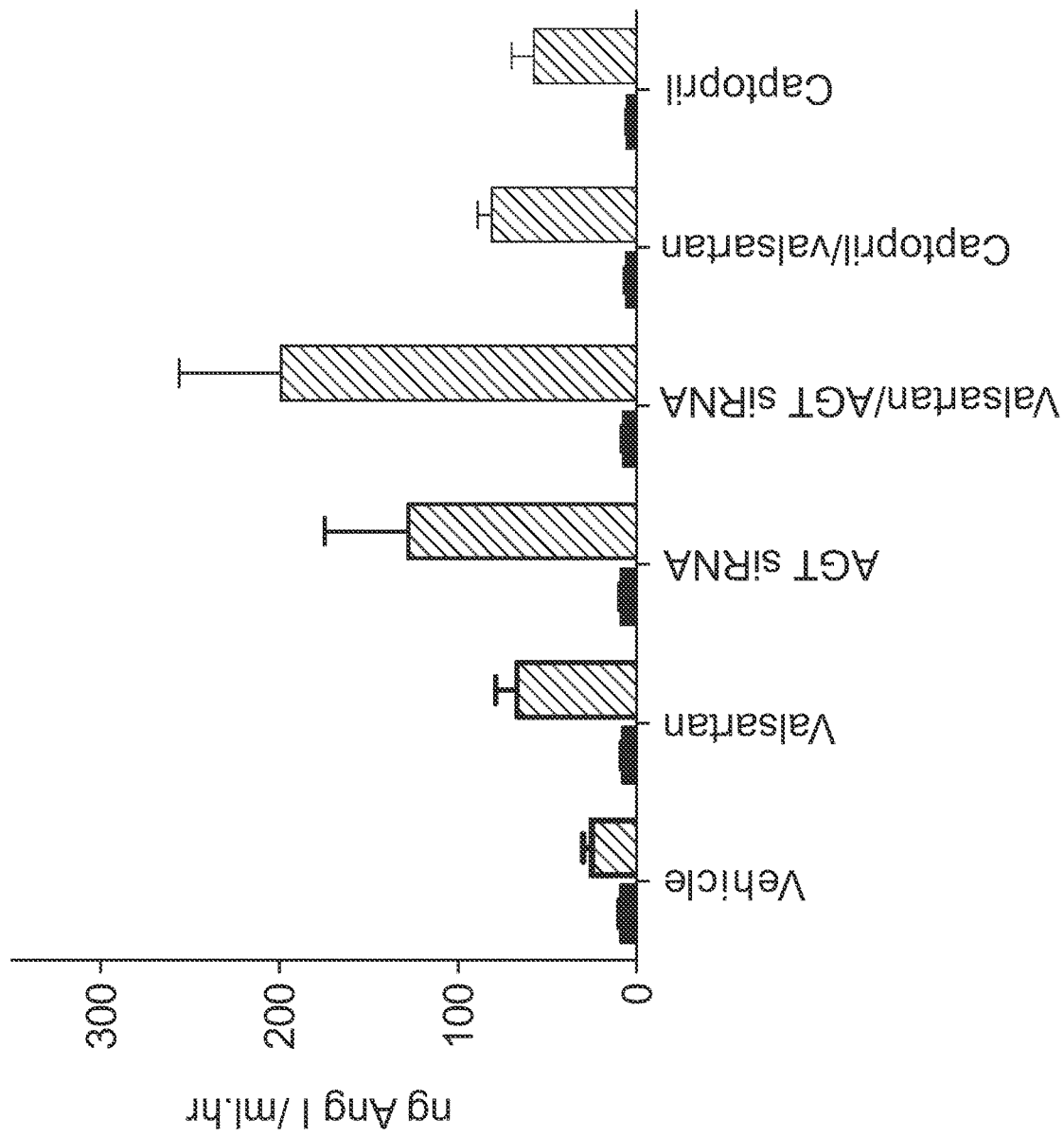
Figure 2G:
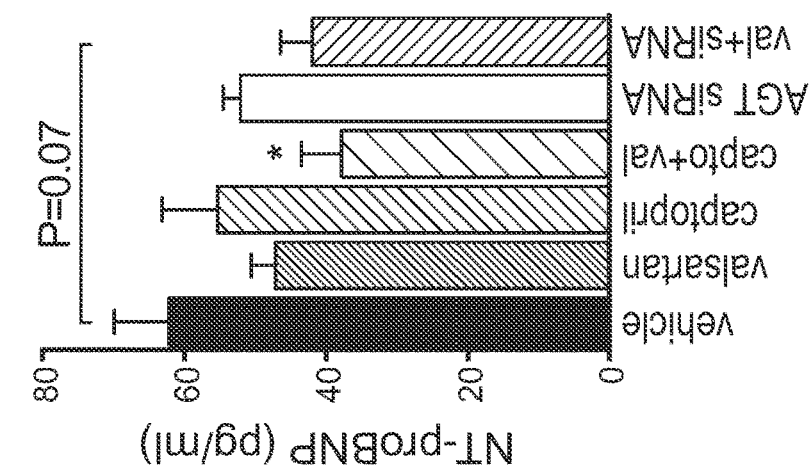
Figure 2F:
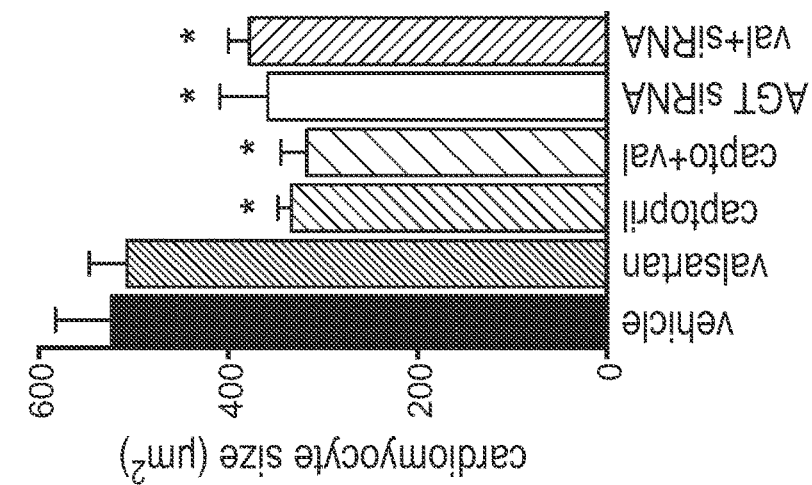
Figure 2E:
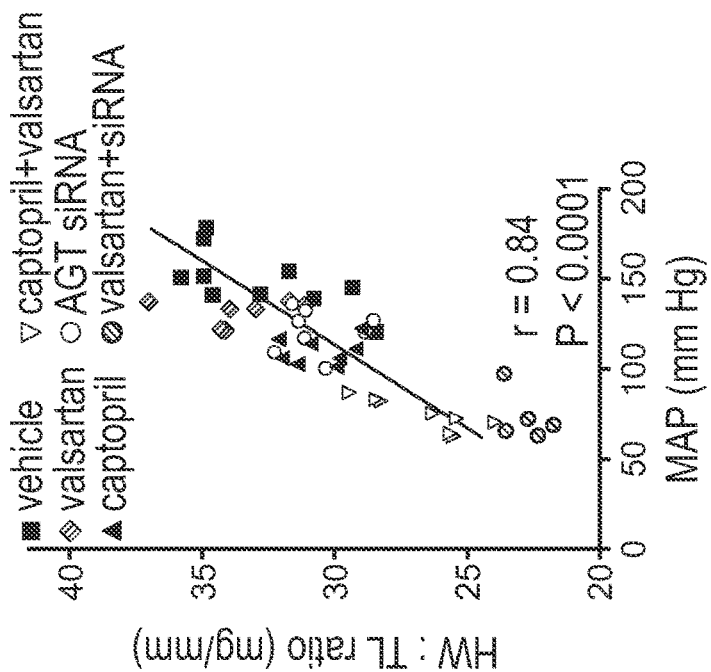

FIG. 2D shows relative Renin activity at level at 4 weeks relative to baseline. Plasma Renin activity (PRA), which reflects reduced angiotensin signaling, indicates a clear increase in PRA with the dsRNA agent treatment ($p<0.05$ relative to both baseline and control group, for both the dsRNA agent alone and valsartan plus siRNA). The PRA assay measures Renin activity by quantifying the amount of Angiotensin I produced by Renin in a blood sample, in the presence of excess angiotensinogen. These data demonstrate a reduction in Angiotensin II signaling following that treatment with AGT-dsRNA agent, and that the effect is enhanced by co-treatment with valsartan. Due to upregulation, circulating angiotensin II remains intact even when AGT levels are almost completely knocked down. These data demonstrate that AGT-dsRNA agent causes a similar antihypertensive effect as valsartan and captopril. Without being bound by theory, it is proposed that only when combining dsRNA agent plus valsartan do angiotensin II levels collapse, resulting in a synergistic decrease in blood pressure.

Figures 4A, 4B, 4C:
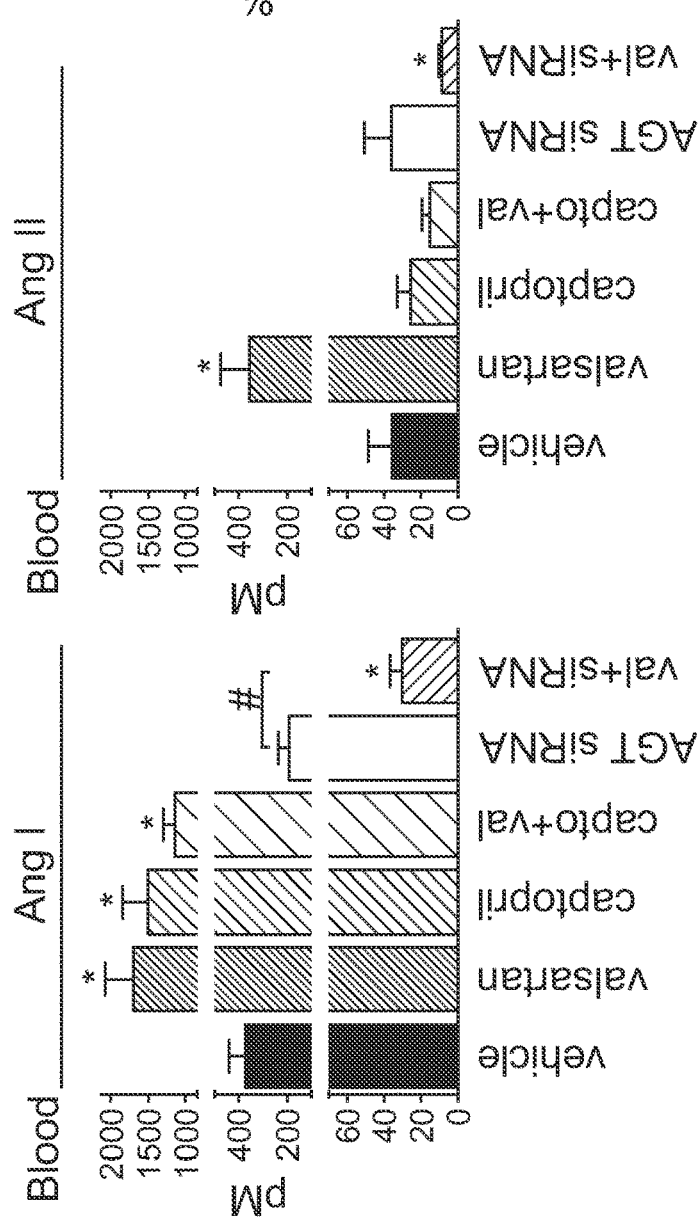
FIG. 4A is a graph showing the level of blood Ang I in the spontaneous hypertensive rat study.
FIG. 4B is a graph showing the level of blood Ang II in the spontaneous hypertensive rat study.
FIG. 4C is a graph showing the ratio of blood Ang II to blood Ang I in the spontaneous hypertensive rat study.

The effect of various treatments on blood and renal AngI and AngII levels was investigated after four weeks of treatment. FIGS. 4A-4C show that treatment with valsartan and captopril, either alone or in combination, significantly increased blood levels of AngI as compared to vehicle control (FIG. 4A). The dsRNA agent alone did not significantly alter blood levels of AngI, but the combination of valsartan with the dsRNA agent significantly decreased blood AngI as compared to vehicle control and treatment with the dsRNA agent alone. Valsartan alone was found to significantly increase blood AngII as compared to vehicle control (FIG. 4B). Combination of valsartan with the dsRNA agent was found to significantly decrease blood AngII as compared to vehicle control. These changes resulted in a significant decrease in the ratio of AngII/AngI in the captopril and captopril+valsartan treated animals. The data for captopril and valsartan and consistent with their mechanisms of action, while the data for the dsRNA alone indicates little effect on AngIII in the blood.

Figure 5A:
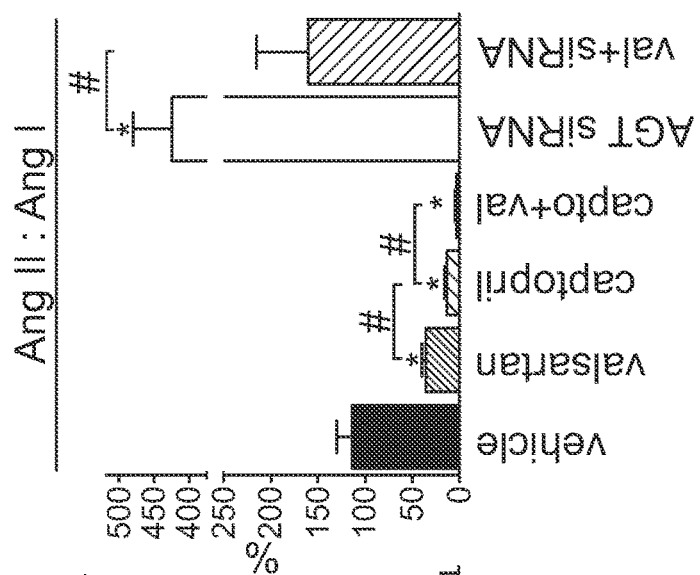
FIG. 5A is a graph showing the level of renal Ang I in the spontaneous hypertensive rat study.
Figure 5B:
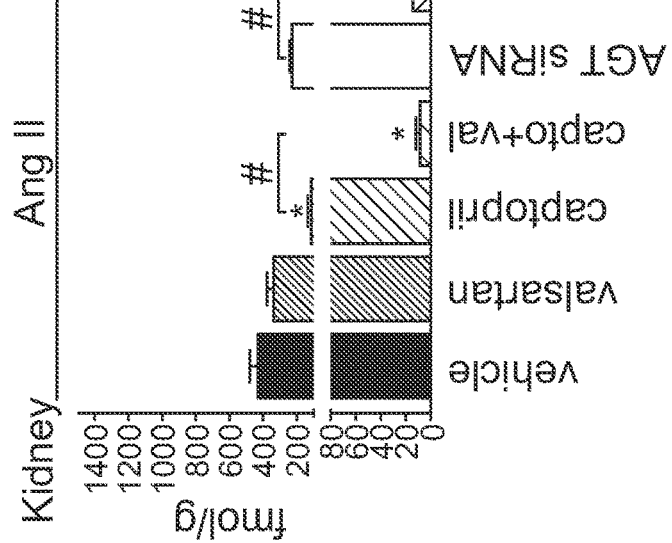
FIG. 5B is a graph showing the level of renal Ang II in the spontaneous hypertensive rat study.
Figure 5C:
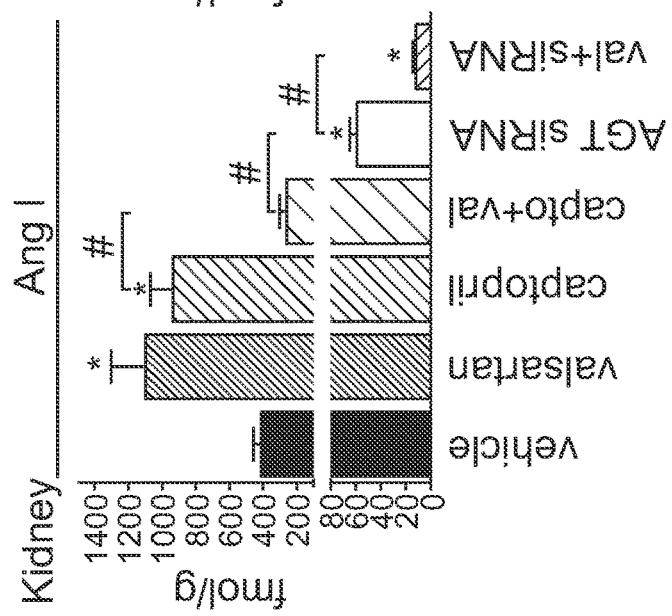
FIG. 5C is a graph showing the ratio of renal Ang II to renal Ang I in the spontaneous hypertensive rat study.

FIGS. 5A-5C show that the dsRNA agent reduced renal AngI without apparent effect on renal AngII, resulting in an upregulated renal AngIII ratio. FIG. 5A shows that each valsartan and captopril significantly increased renal AngI, while the combination of the agents did not have a significant effect on the level of AngI. Renal AngI was significantly decreased by the dsRNA agent and the combination of the dsRNA agent with valsartan. Moreover, the combination treatment significantly reduced renal AngI level as compared to treatment with the dsRNA agent alone. FIG. 5B shows no significant change in renal AngII after treatment with any of the monotherapies except captoril, i.e., valsartan or the dsRNA agent alone. However, the combination of captopril and valsartan and the combination of valsartan and the dsRNA agent were demonstrated to significantly reduce renal Ang II. The data for captopril and valsartan are consistent with their mechanisms of action, while the data for the dsRNA alone indicates little apparent effect on AngII in the kidneys. The renal AngII/AngI ratio increased by 4-fold after administration of the AGT dsRNA agent alone (FIG. 5C). Conversely, a decrease of over 70% in the Ang II/Ang I ratio was seen after treatment with valsartan, captopril, and the combination of valsartan+captopril. No significant change in the ratio of AngII/AngI was observed after treatment with the valsartan+AGT dsRNA agent. The increase in renal AngII was demonstrated to not be a result of alterations in renal angiotensin receptor levels or ACE mRNA expression in renal cortex or medulla. FIGS. 6A-6C show no significant changes in AT1a receptor, AT1b receptor, or ACE mRNA level in kidney under any treatment conditions except one. Treatment with captopril caused a significant increase in AT1b receptor level in kidney medulla. The effect of the treatment regimens on kidney function was also assessed. No changes in glomerular filtration rate (GFR), natriuresis, and albuminuria were observed. This indicates that these treatments did not impair kidney function.

Figure 7:
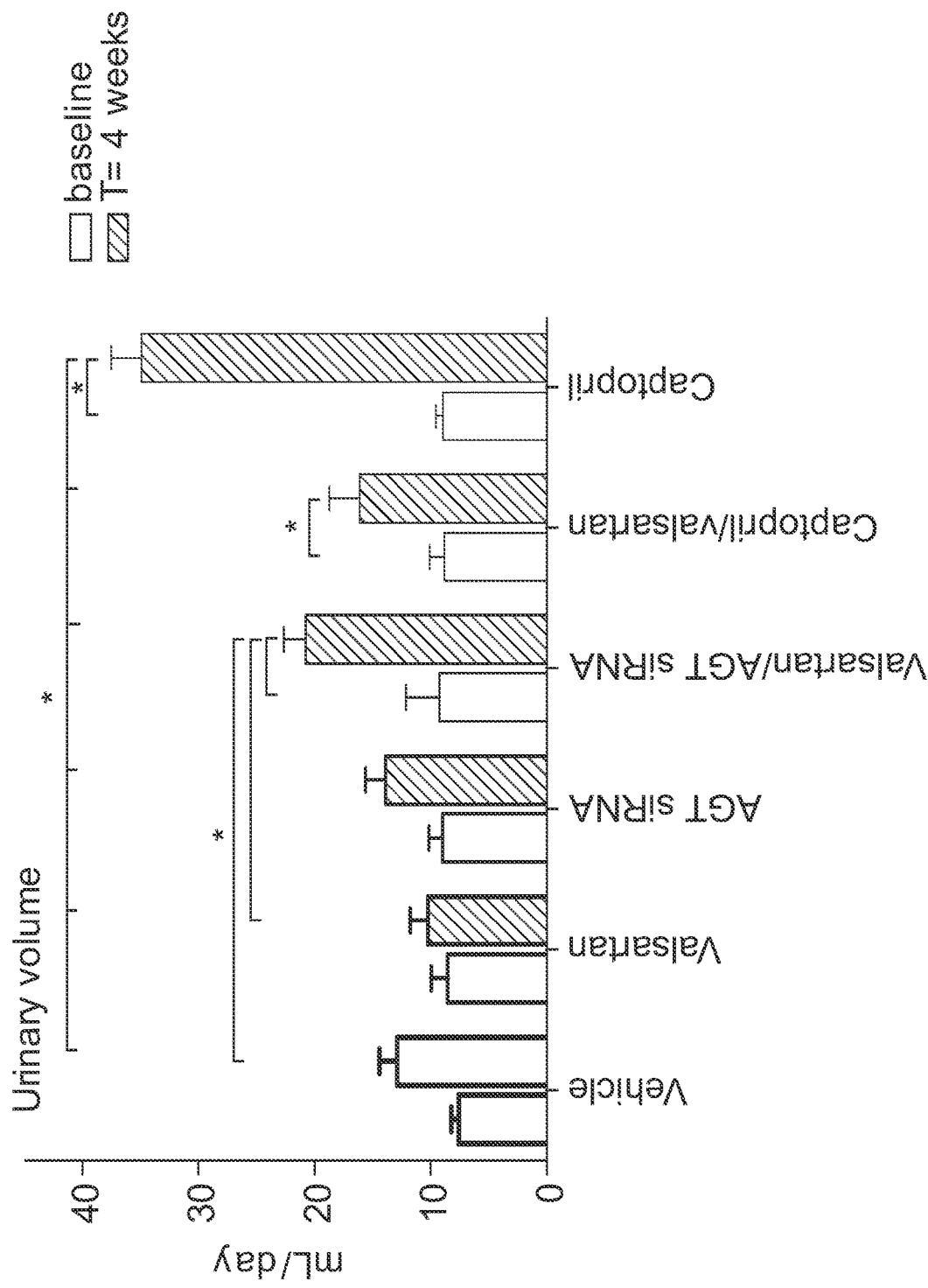
FIG. 7 is a graph showing urinary volume at baseline and at 4 weeks after the start of treatment in the spontaneous rat hypertensive study.

Urinary volume and urinary sodium were monitored during the experiment. Treatment with valsartan+dsRNA agent, valsartan+captopril, and captopril alone caused a significant increase in urinary volume within groups between baseline and 4 weeks (FIG. 7). Comparison of urinary volume across groups at 4 weeks showed a significant increase in urinary output in captopril treated animals as compared to all other groups. Treatment with valsartan+ dsRNA agent resulted in a significant increase in urinary output at 4 weeks as compared to treatment with valsartan alone or vehicle. No significant changes in urinary sodium were observed across or within groups during the experiment.

These data demonstrate that the reduced renal Ang III ratio during both ACEi and ARB confirms that renal ACE generates Ang II, and that tissue Ang II represents ATR-internalized Ang II (van Esch et al., *Cardiovasc Res* 2010 86(3):401-409). Further, the lowering of renal Ang I after liver-targeted AGT siRNA treatment demonstrates that renal Ang generation depends on hepatic AGT. Although, urinary AGT is partly kidney-derived, this renal AGT does not contribute to renal Ang generation, as has been suggested before (Matsusaka et al., *JASN* 2012 23: 1181-1189). The increased renal Ang III ratio after AGT dsRNA treatment, allowing renal Ang II levels to remain intact, is suggestive for enhanced Ang II internalization, albeit in the absence of AT1b receptor upregulation. In agreement with this concept, additive ARB exposure virtually abolished renal Ang II.

Treatment with the liver-specific AGT dsRNA agent synergistically lowers arterial pressure when combined with existing RAS blockers and lowers renal Ang production, without apparent negative effects on renal function.

Example 6. Treatment of Hypertension with an AGT dsRNA in a High Salt Rat Model

The deoxycorticosterone acetate (DOCA)-salt rat model is a well established model for hypertension in the context of high salt levels, and is considered a model of neurogenic hypertension due to the effect on central and peripheral nervous systems (Basting T & Lazartigues E, Cur Hypertension Rep 2017).

Upon arrival, Sprague-Dawley rats are allowed to acclimatize for 7 days. Subsequently, telemetry transmitters are implanted intra-abdominally, in the abdominal aorta, in the rats under isoflurane anaesthesia. The rats are allowed to recover from this procedure for 10 days. From then onwards, blood pressure, heart rate, and other indicators of hypertension are measured by telemetry over a 7-week time period. During the first 4 weeks, animals are subcutaneoulsy implanted with a 200 mg DOCA pellet and receive 0.9% salt in the drinking water (ad libitum) on a chronic basis to induce hypertension. After this period during which hypertension begins, a 3-week treatment period is initiated. Rats are treated with 1) vehicle;
2) valsartan, 31 mg/kg/day added to drinking water;
3) an AGT dsRNA agent, 10 mg/kg once every two weeks, subcutaneously;
4) spironolactone, 50 mg/kg/day, subcutaneously; a combination of an AGT dsRNA agent, 10 mg/kg once every two weeks, subcutaneously, and valsartan, 31 mg/kg/day added to drinking water;
5) an AGT dsRNA agent, 10 mg/kg once every two weeks, subcutaneously, and spironolactone, 50 mg/kg/day, subcutaneously;
6) valsartan, 31 mg/kg/day added to drinking water, and spironolactone, 50 mg/kg/day, subcutaneously; or
7) an AGT dsRNA agent, 30 mg/kg once every two weeks, subcutaneously. In addition, one group of rats that do not receive DOCA and salt in the drinking water serves as controls to evaluate the effect of the treatments to normalize blood pressure.

Example 7. Treatment of Obesity with an AGT dsRNA Agent in a High Fat Fed Mouse Model of Diet Induced Obesity (DIO)

Sixteen-week old high fat fed (HFF) obese mice (diet-induced obesity (DIO)) and normal-weight control animals were purchased and kept on their respective high fat diet (60% of calories as fat) or normal chow. After acclimatization, animals were divided into four groups: Normal weight+ PBS; Normal weight+AGT dsRNA; DIO+PBS; and DIO+ AGT dsRNA (n=5/group). Animals received 10 mg/kg mouse-specific dsRNA or PBS every other week for 12 weeks starting at week 0. Animals were weighed and blood obtained biweekly. Serum AGT levels were determined by ELISA. A fasting glucose tolerance test was performed predose, at 6 weeks post-first dose, and at twelve weeks post-first dose. Organ weights were determined at study end.

Administration of the AGT dsRNA agent was effective at silencing AGT in both the high fat and normal chow animals with sustained knockdown of about 93% across AGT dsRNA agent treatment groups starting at the first time point, two weeks after the first administration of the dsRNA agent.

Figure 8A:
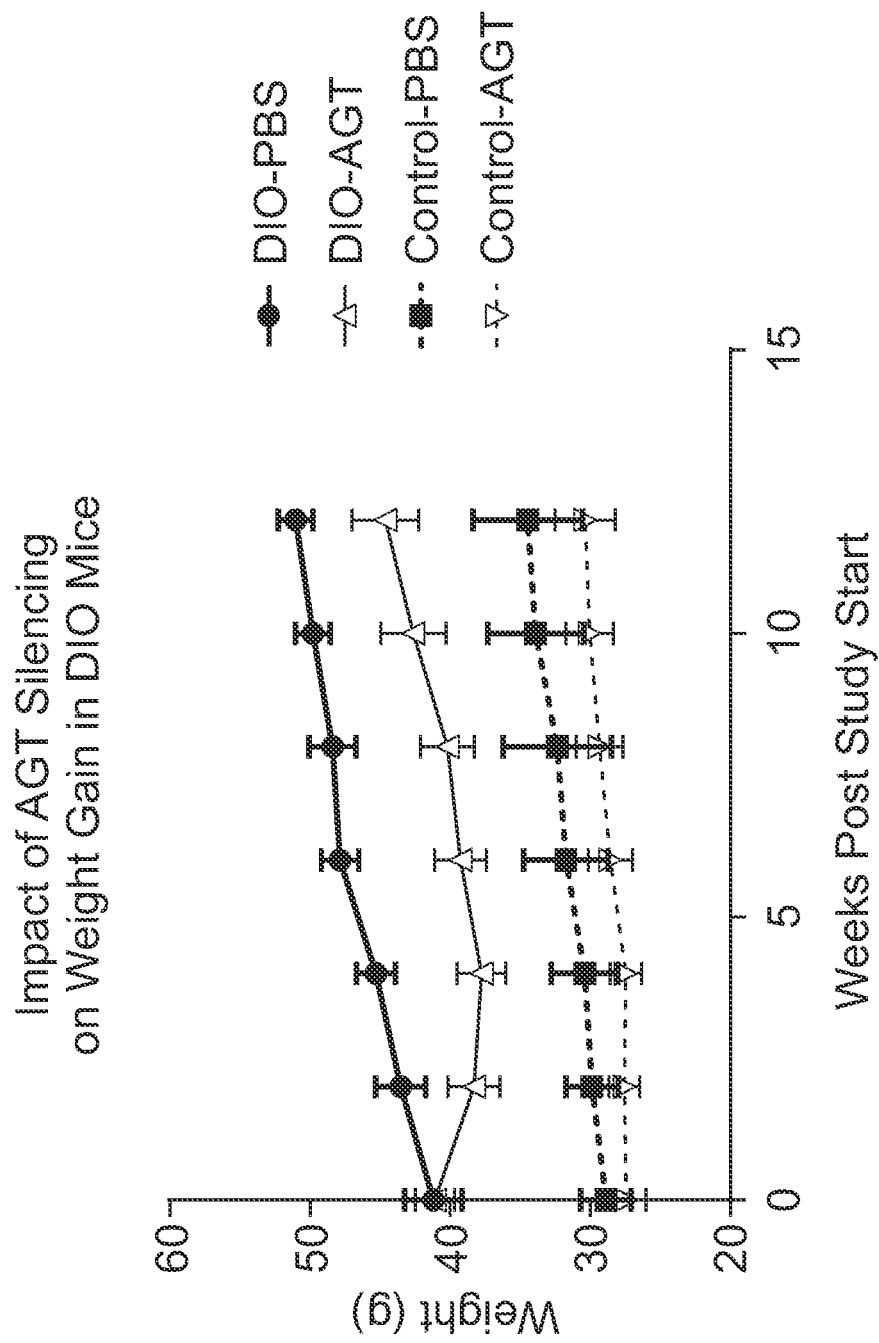
FIG. 8A is a graph showing average body weights of high fat fed diet induced obesity (DIO) mice or normal chow fed mice (n=5 per group) treated with either an AGT dsRNA agent or PBS.

Treatment with the AGT dsRNA agent was effective at significantly decreasing weight gain as compared to the PBS treated DIO mice, as determined by two-way repeated measures ANOVA in the DIO mice, starting at two weeks post first dose and maintained throughout the study (FIG. 8A). In an analysis comparing starting weights, the DIO+ AGT dsRNA group did not gain weight relative to starting weight until the last time-point. Prior to the final time point, mice either lost weight relative to start weight (weeks 2, 4, 6), or there was no difference in weight (weeks 8, 10). No significant difference in weight was observed between the PBS and AGT dsRNA agent chow fed mice until weeks 10 and 12 of the study.

Figure 8B:
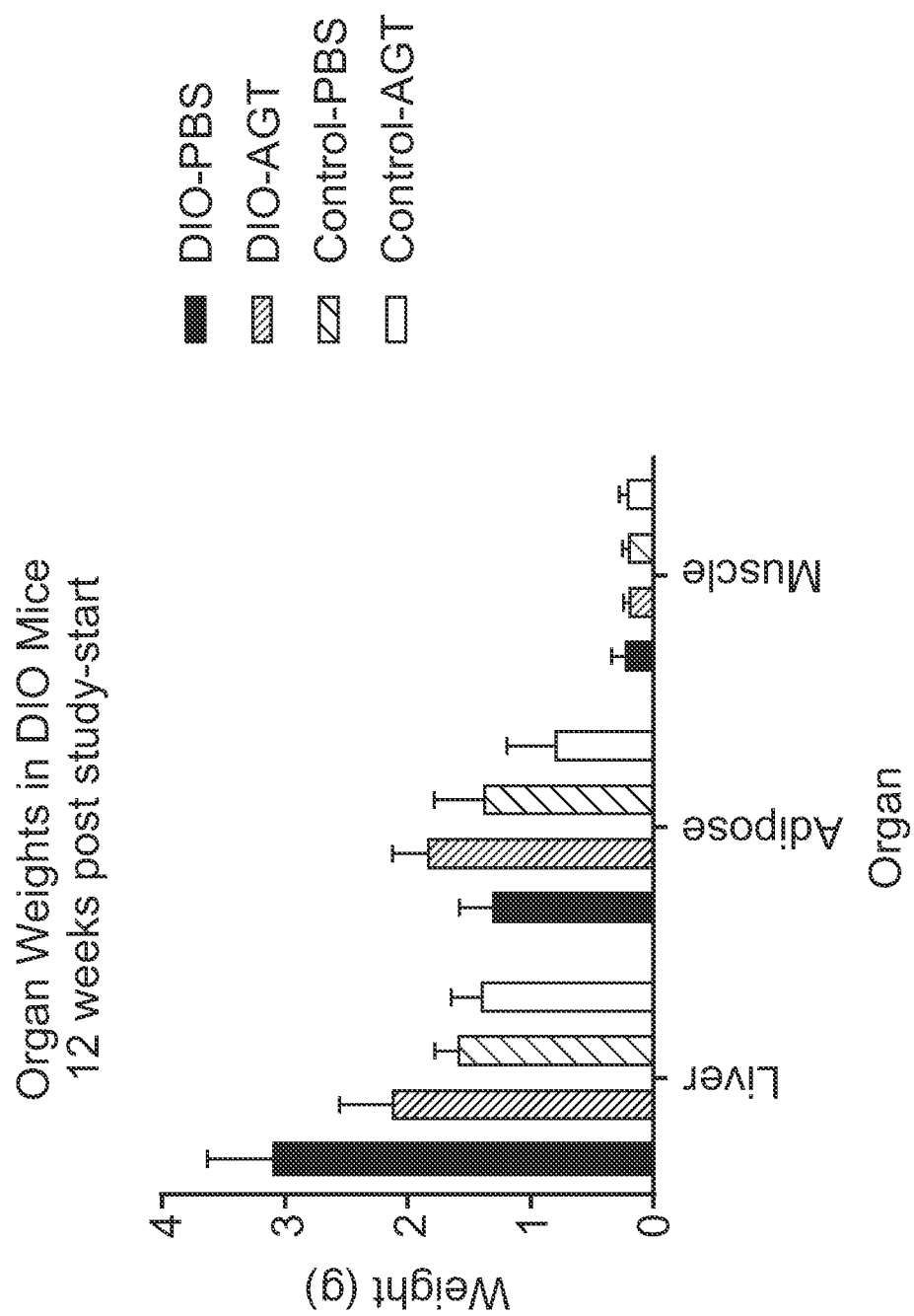
FIG. 8B is a graph showing terminal liver, adipose, and muscle weights (n=5 per group) of high fat fed diet induced obesity (DIO) mice or normal chow fed mice treated with either an AGT dsRNA agent or PBS.

Organ weights were determined at the end of the study to assess the effect of treatment with the AGT dsRNA agent on the location of fat deposition. Liver weights of the AGT dsRNA agent treated DIO mice were significantly lower than the PBS treated DIO mice (FIG. 8B). No significant difference in liver weight was observed between the AGT dsRNA agent and PBS treated normal chow fed mice. Adipose tissue (epidydimal) weight was statistically higher in the DIO+AGT siRNA group than the DIO+PBS, while the opposite was true for the normal-weight animals. There was no significant difference in calf muscle weights across all four groups.

Figure 9A:
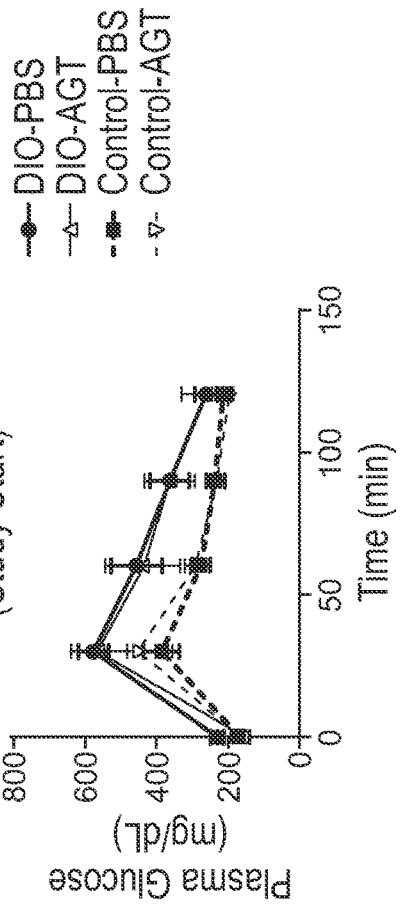
FIG. 9A is a graph showing the changes in plasma glucose levels (mg/dL) in high fat fed diet induced obesity (DIO) mice or normal chow fed mice (n=5 per group) treated with either an AGT dsRNA agent or PBS at week 0 prior to first treatment dose.
Figure 9C:
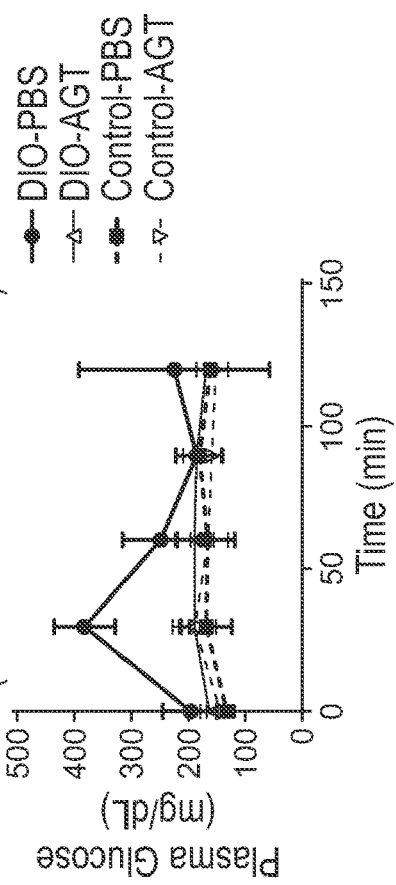
FIG. 9C is a graph showing the plasma glucose levels (mg/dL) in high fat fed diet induced obesity (DIO) mice or normal chow fed mice (n=5 per group) treated with either an AGT dsRNA agent or PBS at week 12 of the experiment.
Figure 9B:
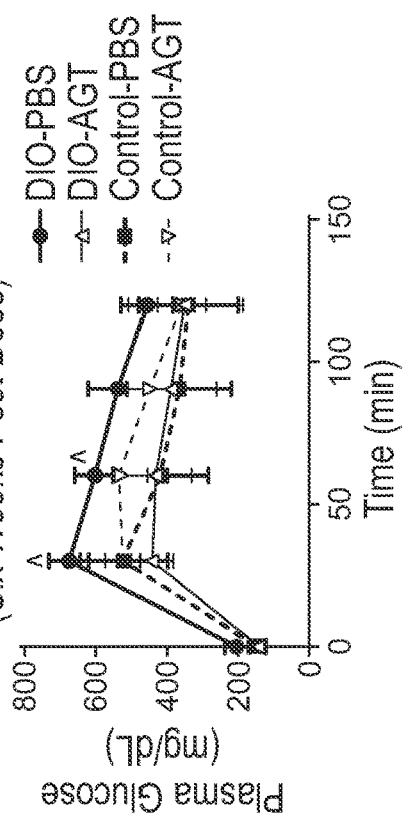
FIG. 9B is a graph showing the plasma glucose levels (mg/dL) in high fat fed diet induced obesity (DIO) mice or normal chow fed mice (n=5 per group) treated with either an AGT dsRNA agent or PBS at week 6 of the experiment.

Glucose tolerance tests were performed at week 0 (predose), week 6, and week 12 using a standard protocol. Blood glucose was measured at predose, 30, 60, 90, and 120 minutes post bolus intraperitoneal glucose dose administration using an AlphaTRAK®2 glucometer (Abbott Animal Health). The results are shown in FIGS. 9A-9C. At week 0, DIO mice had decreased glucose tolerance as compared to the chow fed controls. By six weeks, a significance difference was observed in multiple comparisons post-test between the AGT dsRNA agent treated DIO mice and the PBS treated DIO mice. At twelve weeks, and excluding one DIO+PBS animal whose values were above the glucometer limit, there continued to be a significant difference between AGT dsRNA agent treated DIO mice and the PBS treated DIO mice. Additionally, the data from DIO+AGT siRNA group were not different from either control group (AGT dsRNA agent treated or PBS treated chow fed mice) at six or twelve weeks.

Example 8. Treatment of NASH with an AGT dsRNA Agent in a High Fat High Fructose Mouse Model A high fat-high fructose (HF HFr) fed mouse model of NASH (Softic et al. J Clin Invest 127 (11):4059-4074, 2017, incorporated herein by reference) was used to demonstrate the efficacy of AGT siRNA to treat NASH and signs of metabolic disorder.

Six to eight weeks-old C57BL/6 male mice obtained from Jackson Laboratories were fed a high fat diet containing 60% of calories as fat plus 30% fructose in water (Hf Hfr diet) for 12 weeks prior to treatment with an AGT dsRNA agent or PBS (control) in order to induce NASH or fed a standard chow and water diet. Food and water were provided ad libitum. Starting at week 12, HF HFr fed mice were subcutaneously administered a 10 mg/kg dose of a dsRNA agent targeted to AGT every other week for a total of four doses. Two weeks after the final dose (at week 20), livers were harvested, RNA was isolated, and AGT knockdown in liver was determined by RT-qPCR using the method described above. A 93% decrease in liver AGT mRNA was observed in the AGT dsRNA agent treated Hf Hfr fed mice as compared to the PBS treated HF HFr fed mice.

Figure 10A:
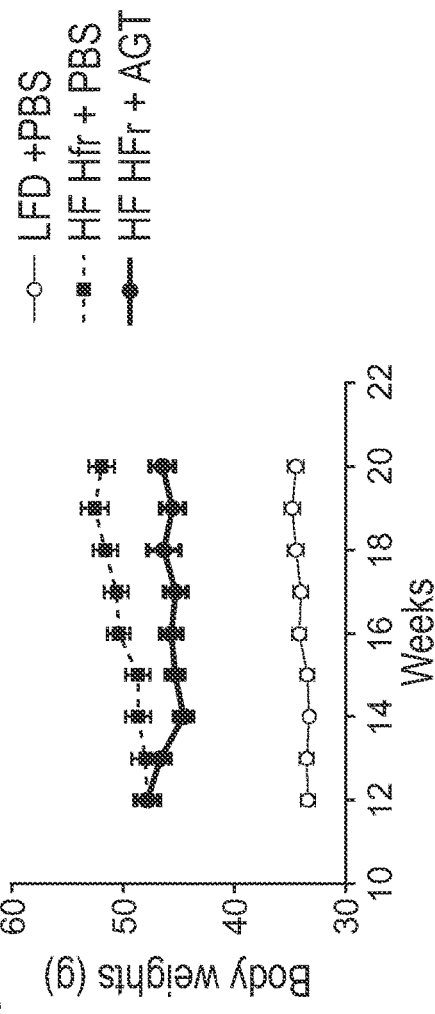
FIG. 10A is a graph showing average body weights of high fat high fructose (HF HFr) fed mice treated with either an AGT dsRNA agent or PBS, or normal chow fed (LFD) mice.
Figure 10B:
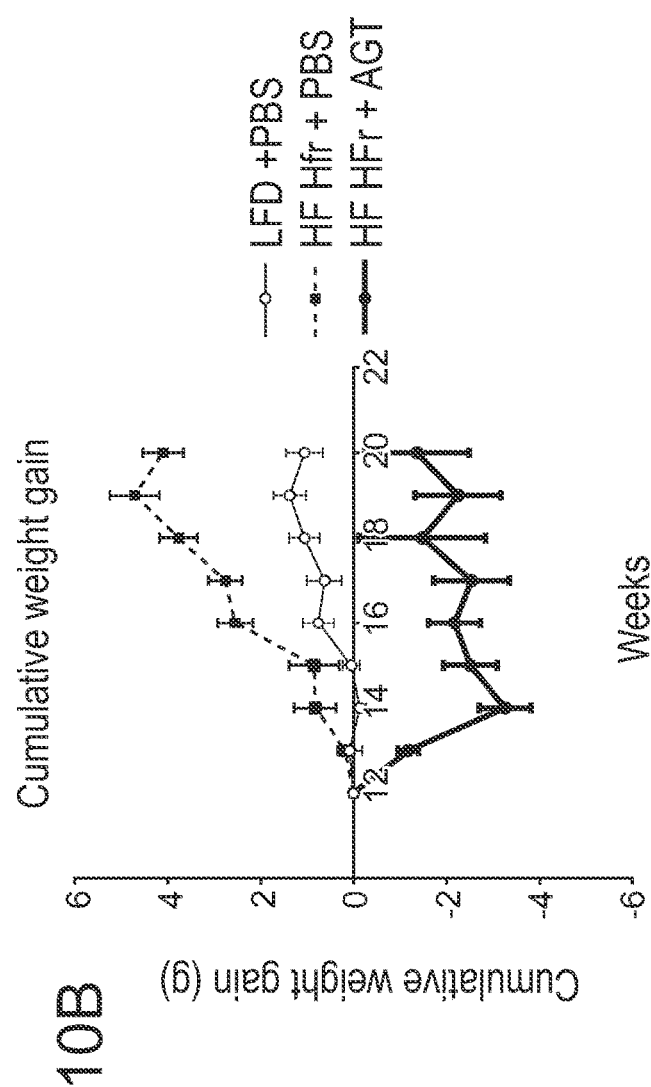
FIG. 10B is a graph showing average cumulative weight gain of high fat high fructose (HF HFr) fed mice treated with either an AGT dsRNA agent or PBS, or normal chow fed (LFD) mice.

As expected, body weight (FIG. 10A), cumulative weight gain (FIG. 10B), and terminal liver weight were significantly higher in the HF HFr fed control mice as compared to chow fed mice at all time points. Treatment with the AGT dsRNA agent in the HF HFr mice lost weight from week 12 till week 20 which resulted in a significant decrease in terminal body weight as compared to the control treated mice (p=0.0023). No significant difference in terminal liver weights was observed.

Serum and liver lipids and glucose, and serum insulin were assessed to determine the effect of the dsRNA agent in the HF HFr model. At week 20, serum triglycerides and glucose levels were substantially the same across all three groups (normal chow, HF HFr dsRNA, HF HFr control). Serum cholesterol and insulin levels were about the same in both HF Hfr groups, and significantly higher than in the chow fed group, as expected. Treatment with the AGT dsRNA agent was demonstrated to significantly decrease serum non-esterified fatty acids (NEFA) (p=0.01). In liver, cholesterol was elevated in both HF HFr groups as compared to normal chow control, but again, no significant decrease was observed after treatment with the AGT dsRNA agent. A significant decrease in liver triglycerides (p=0.017) and free fatty acids (p=0.001) was observed in the AGT dsRNA agent treated group as compared to the control treated group. A possible trend towards decreased thiobarbituric acid (TBA), an indicator of lipid oxidation, was seen in the AGT dsRNA treated group.

Figure 11A:
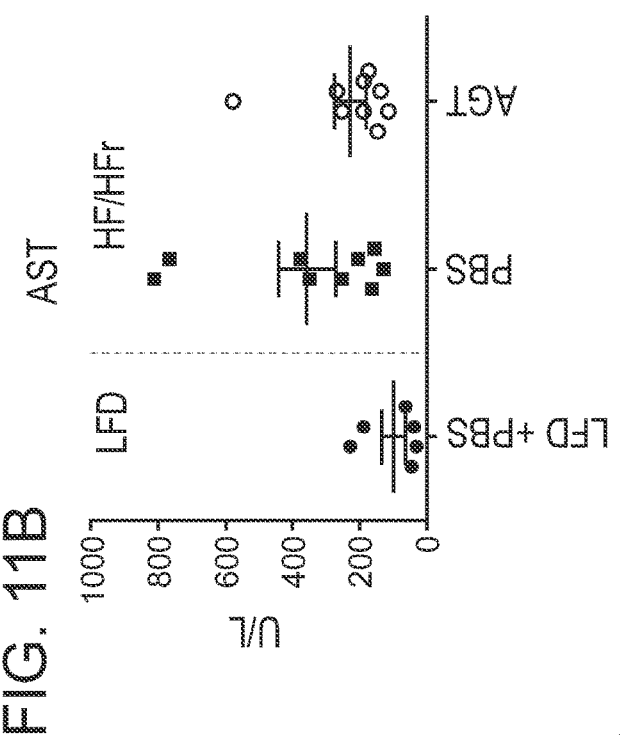
FIGS. 11A-11C are graphs showing serum liver enzymes in high fat high fructose (HF HFr) fed mice treated with either an AGT dsRNA agent or PBS, or normal chow fed (LFD) mice at week 20 of the experiment.
Figure 11B:
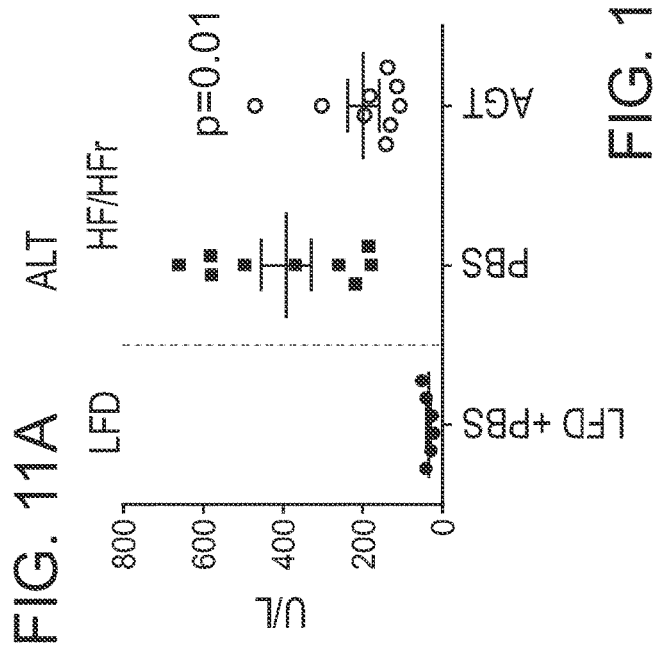
Figure 11C:
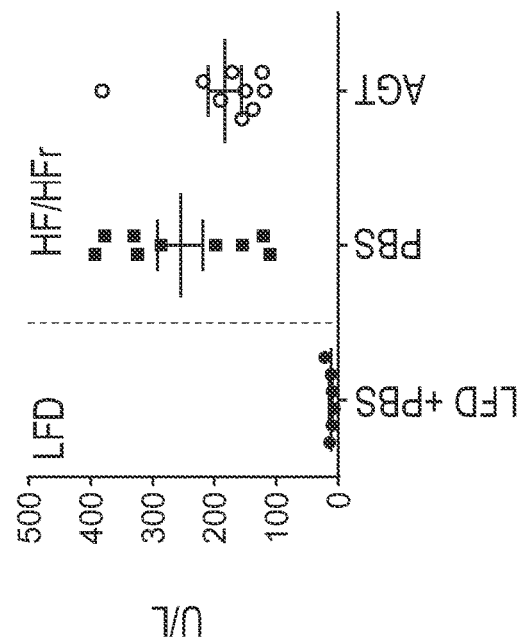

Liver injury was indicated by a significant increase in serum alanine aminotransferase (ALT), aspartate aminotransferase (AST), and glutamate dehydrogenase (GLDH) levels in the control treated Hf Hfr mice as compared to chow fed mice. Treatment with the AGT dsRNA agent resulted in a significant decrease in ALT (p=0.01) (FIG. 11A) with a trend towards decreased AST (FIG. 11B) and GLDH (FIG. 11C) as compared to control treated HF HFr mice.

Liver injury was also assessed by histopathology and NAS scores. As expected, the HF HFr diet induced significant steatosis, balloon degeneration, and lobular inflammation resulting in an increase in the overall NAS score as compared to chow fed mice. Treatment with the AGT dsRNA agent resulted in a significant decrease in balloon degeneration (p=0.04) with a trend towards decreased lobular inflammation resulting in a significant decrease in the overall NAS score (p=0.01) in the AGT dsRNA agent treated HF HFr fed animals as compared to the control treated HF HFr fed animals.

These data demonstrate that treatment with the AGT dsRNA agent is effective in ameliorating some of the signs of NASH. Notably, treatment with the AGT dsRNA agent was effective in reducing weight and liver injury enzymes, with a significant reduction in ALT and a slight reduction in AST and GLDH. Reductions in lobular inflammation and ballooning scores were also observed, bringing down the overall NAS score.

EQUIVALENTS

Those skilled in the art will recognize, or be able to ascertain using no more than routine experimentation, many equivalents to the specific embodiments and methods described herein. Such equivalents are intended to be encompassed by the scope of the following claims.

We claim:

1. A double stranded RNA (dsRNA) agent, or a salt thereof, for inhibiting expression of angiotensinogen (AGT) in a cell, comprising a sense strand and an antisense strand forming a double stranded region,
   wherein the sense strand comprises the nucleotide sequence 5'-gsuscaucCfaCfAfAfugagaguaca-3' (SEQ ID NO:482) and the antisense strand comprises the nucleotide sequence 5'-usGfsuac(Tgn)cucauu-gUfgGfaugacsgsa-3' (SEQ ID NO:666),
   wherein a, g, c, and u are 2'-O-methyl (2'-OMe) A, G, C, and U, respectively; Af, Gf, Cf and Uf are 2'-fluoro A, G, C and U, respectively; s is a phosphorothioate linkage; and (Tgn) is a thymidine-glycol nucleic acid (GNA) S-Isomer.

2. The dsRNA agent, or salt thereof, of claim 1, further comprising a ligand.

3. The dsRNA agent, or salt thereof, of claim 2, wherein the ligand is conjugated to the 3' end of the sense strand of the dsRNA agent, or salt thereof.

4. The dsRNA agent, or salt thereof, of claim 2, wherein the ligand is an N-acetylgalactosamine (GalNAc) derivative.

5. The dsRNA agent, or salt thereof, of claim 2, wherein the ligand is one or more GalNAc derivatives attached through a monovalent, bivalent, or trivalent branched linker.

6. The dsRNA agent, or salt thereof, of claim 4, wherein the ligand is

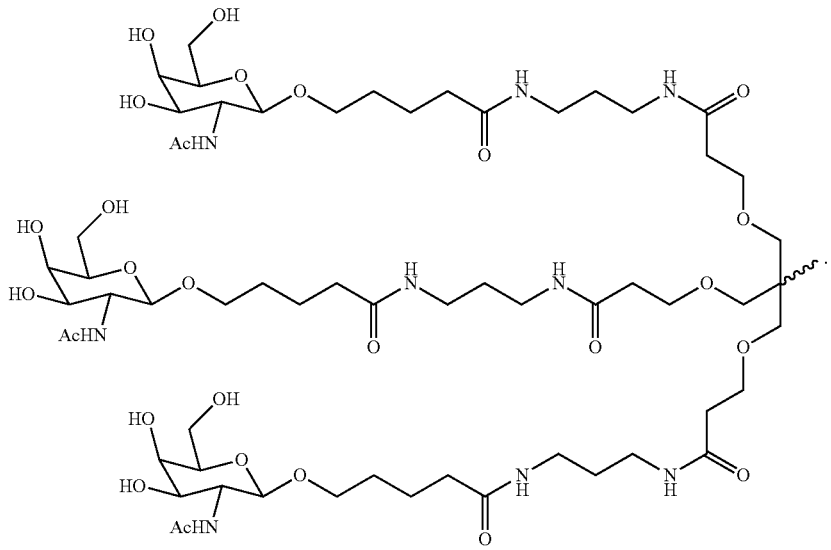

7. The dsRNA agent, or salt thereof, of claim 6, wherein the dsRNA agent, or salt thereof, is conjugated to the ligand as shown in the following schematic

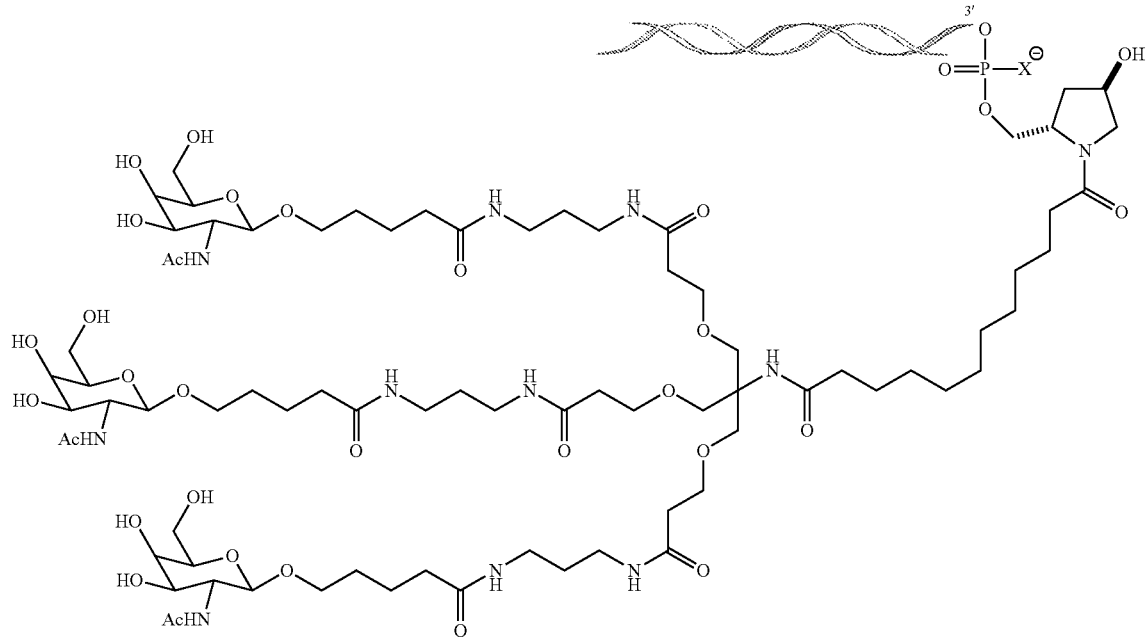

and, wherein X is O or S.

8. The dsRNA agent, or salt thereof, of claim 7, wherein the X is O.

9. A double stranded RNA (dsRNA) agent, or a salt thereof, for inhibiting expression of angiotensinogen (AGT) in a cell, comprising a sense strand and an antisense strand forming a double stranded region, wherein the sense strand comprises the nucleotide sequence 5'-gsuscaucCfaCfAfAfugagaguaca-3' (SEQ ID NO:482) and the antisense strand comprises the nucleotide sequence 5'-usGfsuac(Tgn)cucauu-gUfgGfaugacsgsa-3' (SEQ ID NO:666), wherein a, g, c, and u are 2'-O-methyl (2'-OMe) A, G, C, and U, respectively; Af, Gf, Cf and Uf are 2'-fluoro A, G, C and U, respectively; s is a phosphorothioate linkage; and (Tgn) is a thymidine-glycol nucleic acid (GNA)S-Isomer; and wherein the 3'-end of the sense strand is conjugated to a ligand as shown in the following schematic

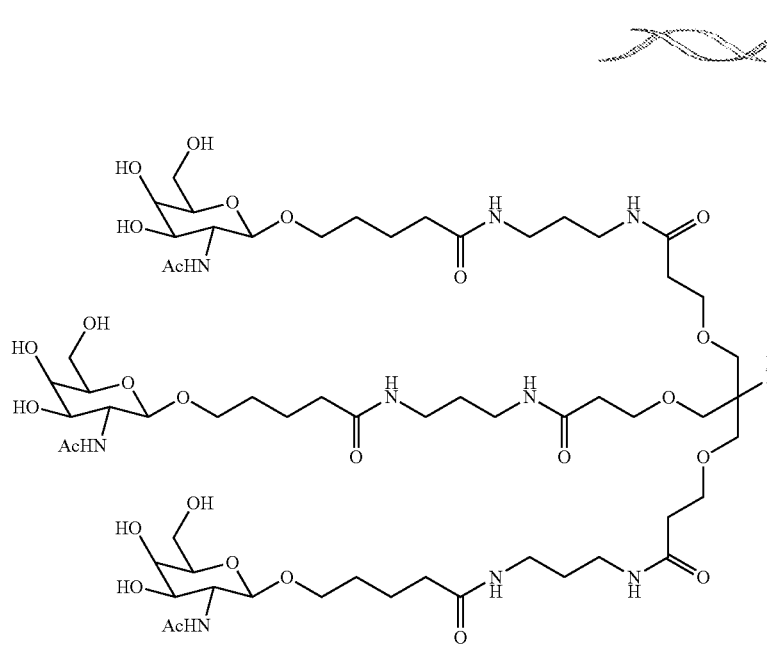
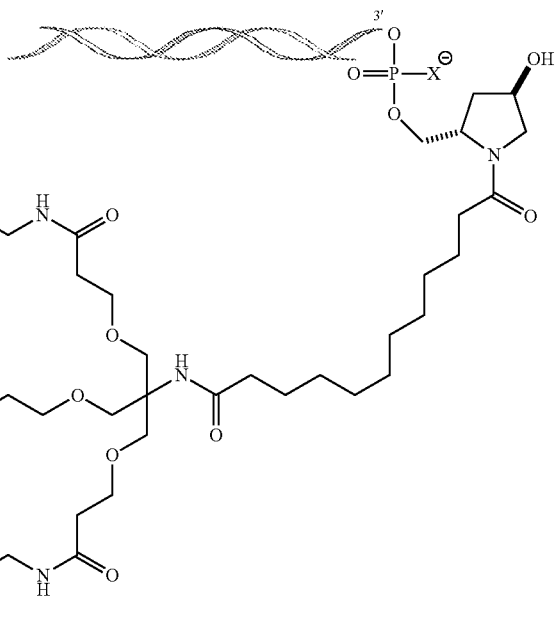

wherein X is O.

10. The dsRNA agent, or a salt thereof, of claim 9, which is in a salt form.

11. A pharmaceutical composition for inhibiting expression of a gene encoding AGT comprising the dsRNA agent, or salt thereof, of claim 1.

12. A pharmaceutical composition for inhibiting expression of a gene encoding AGT comprising the dsRNA agent, or salt thereof, of claim 9.

13. A double stranded RNA (dsRNA) agent, or a salt thereof, for inhibiting expression of angiotensinogen (AGT) in a cell, comprising a sense strand and an antisense strand forming a double stranded region, wherein the sense strand consists of the nucleotide sequence 5'-gsuscaucCfaCfAfAfugagaguaca-3' (SEQ ID NO:482) and the antisense strand consists of the nucleotide sequence 5'-usGfsuac(Tgn)cucauu-gUfgGfaugacsgsa-3' (SEQ ID NO:666), wherein a, g, c, and u are 2'-O-methyl (2'-OMe) A, G, C, and U, respectively; Af, Gf, Cf and Uf are 2'-fluoro A, G, C and U, respectively; s is a phosphorothioate linkage; and (Tgn) is a thymidine-glycol nucleic acid (GNA)S-Isomer; and wherein the 3'-end of the sense strand is conjugated to a ligand as shown in the following schematic

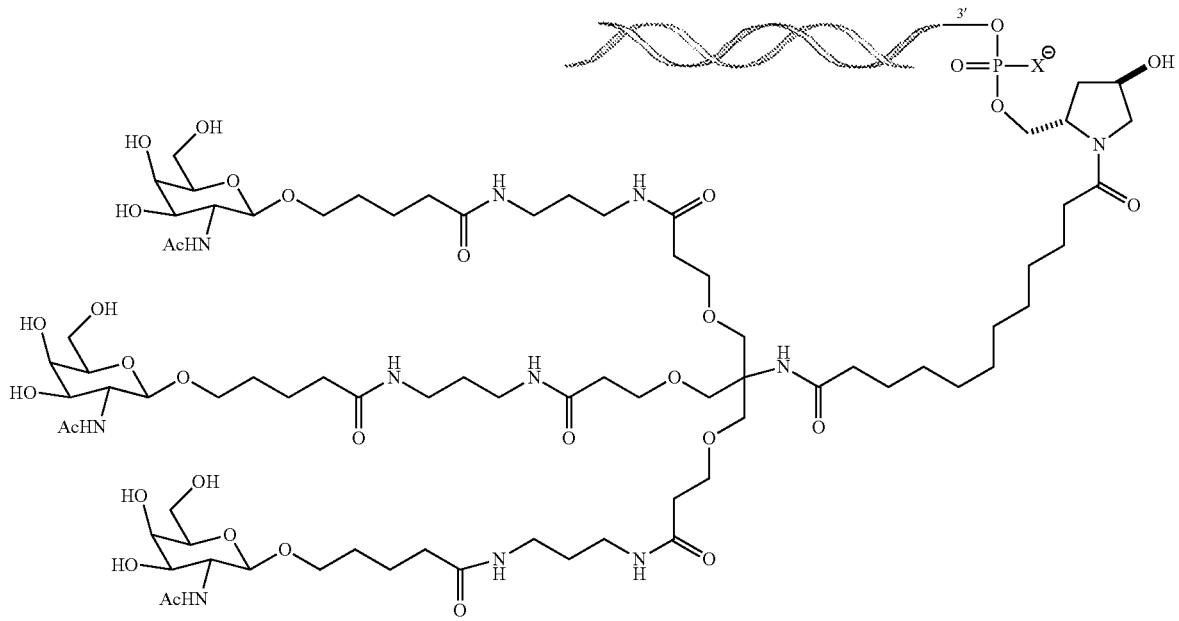

wherein X is O.

14. The dsRNA agent, or a salt thereof, of claim 13, which is in a salt form.

15. A pharmaceutical composition for inhibiting expression of a gene encoding AGT comprising the dsRNA agent, or salt thereof, of claim 13.

* * * * *

SEQUENCE LISTING

<160> NUMBER OF SEQ ID NOS: 960

<210> SEQ ID NO 1
<211> LENGTH: 2587
<212> TYPE: DNA
<213> ORGANISM: Homo sapiens

<400> SEQUENCE: 1

| | | | | | |
|---|---|---|---|---|---|
| atcccatgag | cgggcagcag | ggtcagaagt | ggcccccgtg | ttgcctaagc | aagactctcc | 60 |
| cctgccctct | gccctctgca | cctccggcct | gcatgtccct | gtggcctctt | ggggtacat | 120 |
| ctcccggggc | tgggtcagaa | ggcctgggtg | gttggcctca | ggctgtcaca | cacctaggga | 180 |
| gatgctcccg | tttctgggaa | ccttggcccc | gactcctgca | aacttcggta | aatgtgtaac | 240 |
| tcgaccctgc | accggctcac | tctgttcagc | agtgaaactc | tgcatcgatc | actaagactt | 300 |
| cctggaagag | gtcccagcgt | gagtgtcgct | tctggcatct | gtccttctgg | ccagcctgtg | 360 |
| gtctggccaa | gtgatgtaac | cctcctctcc | agcctgtgca | caggcagcct | gggaacagct | 420 |
| ccatccccac | ccctcagcta | taaatagggc | atcgtgaccc | ggccggggga | agaagctgcc | 480 |
| gttgttctgg | gtactacagc | agaagggtat | gcggaagcga | gcaccccagt | ctgagatggc | 540 |
| tcctgccggt | gtgagcctga | gggccaccat | cctctgcctc | ctggcctggg | ctggcctggc | 600 |
| tgcaggtgac | cgggtgtaca | tacacccctt | ccacctcgtc | atccacaatg | agagtacctg | 660 |
| tgagcagctg | gcaaaggcca | atgccgggaa | gcccaaagac | cccaccttca | tacctgctcc | 720 |
| aattcaggcc | aagacatccc | ctgtggatga | aaaggcccta | caggaccagc | tggtgctagt | 780 |
| cgctgcaaaa | cttgacaccg | aagacaagtt | gagggccgca | atggtcggga | tgctggccaa | 840 |
| cttcttgggc | ttccgtatat | atggcatgca | cagtgagcta | tggggcgtgg | tccatggggc | 900 |
| caccgtcctc | tccccaacgg | ctgtctttgg | caccctggcc | tctctctatc | tgggagcctt | 960 |
| ggaccacaca | gctgacaggc | tacaggcaat | cctgggtgtt | ccttggaagg | acaagaactg | 1020 |
| cacctcccgg | ctggatgcgc | acaaggtcct | gtctgccctg | caggctgtac | agggcctgct | 1080 |
| agtggcccag | gcagggctg | atagccaggc | ccagctgctg | ctgtccacgg | tggtgggcgt | 1140 |
| gttcacagcc | ccaggcctgc | acctgaagca | gccgtttgtg | cagggcctgg | ctctctatac | 1200 |
| ccctgtggtc | ctcccacgct | ctctggactt | cacagaactg | gatgttgctg | ctgagaagat | 1260 |
| tgacaggttc | atgcaggctg | tgacaggatg | gaagactggc | tgctccctga | tgggagccag | 1320 |
| tgtggacagc | accctggctt | tcaacaccta | cgtccacttc | caagggaaga | tgaagggctt | 1380 |
| ctccctgctg | gccgagcccc | aggagttctg | ggtggacaac | agcacctcag | tgtctgttcc | 1440 |
| catgctctct | ggcatgggca | ccttccagca | ctggagtgac | atccaggaca | acttctcggt | 1500 |
| gactcaagtg | cccttcactg | agagcgcctg | cctgctgctg | atccagcctc | actatgcctc | 1560 |
| tgacctggac | aaggtggagg | gtctcacttt | ccagcaaaac | tccctcaact | ggatgaagaa | 1620 |
| actatctccc | cggaccatcc | acctgaccat | gccccaactg | gtgctgcaag | gatcttatga | 1680 |
| cctgcaggac | ctgctcgccc | aggctgagct | gcccgccatt | ctgcacaccg | agctgaacct | 1740 |
| gcaaaaattg | agcaatgacc | gcatcagggt | ggggaggtg | ctgaacagca | ttttttttga | 1800 |
| gcttgaagcg | gatgagagag | agcccacaga | gtctacccaa | cagcttaaca | agcctgaggt | 1860 |
| cttggaggtg | accctgaacc | gcccattcct | gtttgctgtg | tatgatcaaa | gcgccactgc | 1920 |
| cctgcacttc | ctgggccgcg | tggccaaccc | gctgagcaca | gcatgaggcc | agggccccag | 1980 |
| aacacagtgc | ctggcaaggc | ctctgcccct | ggctttgag | gcaaaggcca | gcagcagata | 2040 |
| acaaccccgg | acaaatcagc | gatgtgtcac | ccccagtctc | ccacctttc | ttctaatgag | 2100 |

```
tcgactttga gctggaaagc agccgtttct ccttggtcta agtgtgctgc atggagtgag    2160
cagtagaagc ctgcagcggc acaaatgcac ctcccagttt gctgggttta ttttagagaa    2220
tgggggtggg gaggcaagaa ccagtgttta gcgcgggact actgttccaa aaagaattcc    2280
aaccgaccag cttgtttgtg aaacaaaaaa gtgttccctt ttcaagttga gaacaaaaat    2340
tgggttttaa aattaaagta tacatttttg cattgccttc ggtttgtatt tagtgtcttg    2400
aatgtaagaa catgacctcc gtgtagtgtc tgtaatacct tagttttttc cacagatgct    2460
tgtgattttt gaacaatacg tgaaagatgc aagcacctga atttctgttt gaatgcggaa    2520
ccatagctgg ttatttctcc cttgtgttag taataaacgt cttgccacaa taagcctcca    2580
aaaaaaa                                                              2587

<210> SEQ ID NO 2
<211> LENGTH: 2587
<212> TYPE: DNA
<213> ORGANISM: Homo sapiens

<400> SEQUENCE: 2
ttttttttgg aggcttattg tggcaagacg tttattacta acacaaggga gaaataacca      60
gctatggttc cgcattcaaa cagaaattca ggtgcttgca tctttcacgt attgttcaaa     120
aatcacaagc atctgtggaa aaaactaagg tattacagac actacacgga ggtcatgttc     180
ttacattcaa gacactaaat acaaaccgaa ggcaatgcaa aaatgtatac tttaatttta     240
aaacccaatt tttgttctca acttgaaaag ggaacacttt tttgtttcac aaacaagctg     300
gtcggttgga attcttttttg aacagtagt cccgcgctaa acactggttc ttgcctcccc     360
acccccattc tctaaaataa acccagcaaa ctgggaggtg catttgtgcc gctgcaggct     420
tctactgctc actccatgca gcacacttag accaaggaga aacggctgct ttccagctca     480
aagtcgactc attagaagaa aaggtgggag actgggggtg acacatcgct gatttgtccg     540
gggttgttat ctgctgctgg cctttgcctc aaaggccagg ggcagaggcc ttgccaggca     600
ctgtgttctg gggccctggc ctcatgctgt gctcagcggg ttggccacgc ggcccaggaa     660
gtgcagggca gtggcgcttt gatcatacac agcaaacagg aatgggcggt tcagggtcac     720
ctccaagacc tcaggcttgt taagctgttg ggtagactct gtgggctctc tctcatccgc     780
ttcaagctca aaaaaaatgc tgttcagcac ctcccccacc ctgatgcggt cattgctcaa     840
tttttgcagg ttcagctcgg tgtgcagaat ggcgggcagc tcagcctggg cgagcaggtc     900
ctgcaggtca taagatcctt gcagcaccag ttggggcatg tcaggtgga tggtccgggg      960 agatagtttc ttcatccagt tgagggagtt ttgctggaaa gtgagaccct ccaccttgtc    1020
caggtcagag gcatagtgag gctggatcag cagcaggcag gcgctctcag tgaagggcac    1080
ttgagtcacc gagaagttgt cctggatgtc actccagtgc tggaaggtgc ccatgccaga    1140
gagcatggga acagacactg aggtgctgtt gtccacccag aactcctggg gctcggccag    1200
cagggagaag cccttcatct tcccttggaa gtggacgtag gtgttgaaag ccagggtgct    1260
gtccacactg gctcccatca gggagcagcc agtcttccat cctgtcacag cctgcatgaa    1320
cctgtcaatc ttctcagcag caacatccag ttctgtgaag tccagagagc gtgggaggac    1380
cacaggggta tagagagcca ggccctgcac aaacggctgc ttcaggtgca ggcctggggc    1440
tgtgaacacg cccaccaccg tggacagcag cagctgggcc tggctatcag ccctgccctg    1500
ggccactagc aggccctgta cagcctgcag ggcagacagg accttgtgcg catccagccg    1560
```

| | |
|---|---|
| ggaggtgcag ttcttgtcct tccaaggaac acccaggatt gcctgtagcc tgtcagctgt | 1620 |
| gtggtccaag gctcccagat agagagaggc cagggtgcca agacagccg ttggggagag | 1680 |
| gacggtggcc ccatggacca cgccccatag ctcactgtgc atgccatata tacggaagcc | 1740 |
| caagaagttg gccagcatcc cgaccattgc ggccctcaac ttgtcttcgg tgtcaagttt | 1800 |
| tgcagcgact agcaccagct ggtcctgtag ggccttttca tccacagggg atgtcttggc | 1860 |
| ctgaattgga gcaggtatga aggtggggtc tttgggcttc ccggcattgg cctttgccag | 1920 |
| ctgctcacag gtactctcat tgtggatgac gaggtggaag gggtgtatgt acacccggtc | 1980 |
| acctgcagcc aggccagccc aggccaggag gcagaggatg gtggccctca ggctcacacc | 2040 |
| ggcaggagcc atctcagact ggggtgctcg cttccgcata cccttctgct gtagtaccca | 2100 |
| gaacaacggc agcttcttcc cccggccggg tcacgatgcc ctatttatag ctgaggggtg | 2160 |
| gggatggagc tgttcccagg ctgcctgtgc acaggctgga gaggagggtt acatcacttg | 2220 |
| gccagaccac aggctggcca gaaggacaga tgccagaagc gacactcacg ctgggacctc | 2280 |
| ttccaggaag tcttagtgat cgatgcagag tttcactgct gaacagagtg agccggtgca | 2340 |
| gggtcgagtt acacatttac gaagtttgc aggagtcggg gccaaggttc ccagaaacgg | 2400 |
| gagcatctcc ctaggtgtgt gacagcctga ggccaaccac ccaggccttc tgacccagcc | 2460 |
| ccgggagatg taccccaag aggccacagg gacatgcagg ccggaggtgc agagggcaga | 2520 |
| gggcagggga gagtcttgct taggcaacac ggggccact tctgaccctg ctgcccgctc | 2580 |
| atgggat | 2587 |

<210> SEQ ID NO 3
<211> LENGTH: 1834
<212> TYPE: DNA
<213> ORGANISM: Macaca fascicularis

<400> SEQUENCE: 3

| | |
|---|---|
| aagaagctgc cattgttctg ggtactacag cagaagggta tgcagaagcg agcaccccag | 60 |
| tccgagatgg ctcctgccag cgtgagcctg agggccacca tcctctgcct cctggcctgg | 120 |
| gctggcctgg ccacaggtga ccgggtgtac atacacccct tccacctcgt catccacaat | 180 |
| gagagtacct gtgagcagct ggcaaaggcc gatgctggga agcccaaaga tcccaccttc | 240 |
| acacctgttc cgatacaggc caagacgtct cctgtggatg aaaaggccct gcaggaccag | 300 |
| ctagtgctgg ttgccgcaaa actcgacacc gaggacaagt tgagagccgc gatggtcggg | 360 |
| atgctggcca acttcttggg cttccgtata tatggcatgc acagtgagct atggggcgtg | 420 |
| gtccatgggg ccaccatcct ctccccaacg gctgtctttg gcaccctggc ctctctctac | 480 |
| ctgggagcgt tggaccacac agccgacagg ctacaggcaa tcctgggcgt cccttggaag | 540 |
| gacaagaact gcacctcccg gctggatgcg cacaaggtcc tctctgccct gcaggctgta | 600 |
| cagggcctgc tggtggccca gggcagggct gacggccagt cccagctgct gttgtccaca | 660 |
| gtggtgggtc tcttcacagc cccagatctg cacctgaagc agccgtttgt gcagggcctg | 720 |
| gctctctatg cccctgtggt cctcccacgc tctctggact tcacagacct ggaagtcgct | 780 |
| gctgagaaga ttgacaggtt catgcaggct gtgacaggat ggaagattag cagccccctg | 840 |
| acgggagcca gtgcggacag cacctggtt ttcaacacct acgtccattt ccaagggaag | 900 |
| atgagggact tcttcctgct ggctgagccc caggagttct gggtggacaa cagcacctca | 960 |
| gtgtctgtcc ccatgctgtc tggcgtgggc accttccagc actggagcga cgcccaggac | 1020 |
| aacttctcag tgactcaagt gcccttactg agagcgcct gcttgctgct gattcagcct | 1080 |

```
cactacgcct ctgacctgga caaggtggag ggtctcactt tccagcaaaa ctccctcaac   1140
tggatgaaga aactgtctcc ccgggccatc cacctgacca tgccccgact ggtgctgcga   1200
ggatcttatg acctgcagga cctgcttgcc caggctgagc tgcccgccat tctgggcacc   1260
gagctgaacc tgcaaaaatt gagcaatgac aacctcaggg tggggaaggt gctgaacagc   1320 attcttttg aactcgaagc ggatgagaga gagcccacag agtctacccg acagctgaac   1380
aggcctgagt tcttggaggt gaccctggac cgcccattcc tgtttgctgt gtatgatcaa   1440
agtgccactg ccctgcactt cctgggccgt gtggccaacc cgctgagccc agcatgaggc   1500
cagggcccca gaacacagcg cctggcaagg cctctgcccc tggcctttga ggcgaaggcc   1560
agcagcagat atgtaactct ggaaaaacca gcgatttgtc accccagtc tcccaccttt    1620 tcttctaatg agtcaacttc gagctggaaa gcagtcgttt ctccttggtc taagtggtgc   1680
tgcgtgagca gtaagaaacc tgtggcagca caaatgcgcc tcccaggttg ctgggtttat   1740
tttagagaat gggggtgggg aggcaagaac cagtgtttag cgcgggacca ccgttccaaa   1800
aagaattcca accgaccagc ttgtttgtga aaca                              1834

<210> SEQ ID NO 4
<211> LENGTH: 1834
<212> TYPE: DNA
<213> ORGANISM: Macaca fascicularis

<400> SEQUENCE: 4
tgtttcacaa acaagctggt cggttggaat tctttttgga acgtgggtcc cgcgctaaac   60
actggttctt gcctccccac ccccattctc taaaataaac ccagcaacct gggaggcgca   120
tttgtgctgc cacaggtttc ttactgctca cgcagcacca cttagaccaa ggagaaacga   180
ctgctttcca gctcgaagtt gactcattag aagaaaaggt gggagactgg gggtgacaaa   240
tcgctggttt ttccagagtt acatatctgc tgctggcctt cgcctcaaag gccaggggca   300
gaggccttgc caggcgctgt gttctggggc cctggcctca tgctgggctc agcgggttgg   360
ccacacggcc caggaagtgc agggcagtgg cactttgatc atacacagca aacaggaatg   420
ggcggtccag ggtcacctcc aagaactcag gcctgttcag ctgtcgggta gactctgtgg   480
gctctctctc atccgcttcg agttcaaaaa gaatgctgtt cagcaccttc cccaccctga   540
ggttgtcatt gctcaatttt tgcaggttca gctcggtgcc cagaatggcg ggcagctcag   600
cctgggcaag caggtcctgc aggtcataag atcctcgcag caccagtcgg ggcatggtca   660
ggtggatggc ccggggagac agtttcttca tccagttgag ggagttttgc tggaaagtga   720
gaccctccac cttgtccagg tcagaggcgt agtgaggctg aatcagcagc aagcaggcgc   780
tctcagtaaa gggcacttga gtcactgaga agttgtcctg ggcgtcgctc cagtgctgga   840
aggtgcccac gccagacagc atggggacag acactgaggt gctgttgtcc acccagaact   900 cctgggctc agccagcagg aagaagtccc tcatcttccc ttggaaatgg acgtaggtgt   960
tgaaaaccag ggtgctgtcc gcactggctc ccgtcagggg gctgctaatc ttccatcctg   1020
tcacagcctg catgaacctg tcaatcttct cagcagcgac ttccaggtct gtgaagtcca   1080
gagagcgtgg gaggaccaca ggggcataga gagccaggcc ctgcacaaac ggctgcttca   1140
ggtgcagatc tggggctgtg aagagaccca ccactgtgga caacagcagc tgggactggc   1200
cgtcagccct gccctgggcc accagcaggc cctgtacagc ctgcagggca gagaggacct   1260
tgtgcgcatc cagccgggag gtgcagttct tgtccttcca agggacgccc aggattgcct   1320
```

| | |
|---|---|
| gtagcctgtc ggctgtgtgg tccaacgctc ccaggtagag agaggccagg gtgccaaaga | 1380 |
| cagccgttgg ggagaggatg gtggcccat ggaccacgcc ccatagctca ctgtgcatgc | 1440 |
| catatatacg gaagcccaag aagttggcca gcatcccgac catcgcggct ctcaacttgt | 1500 |
| cctcggtgtc gagttttgcg gcaaccagca ctagctggtc ctgcagggcc ttttcatcca | 1560 |
| caggagacgt cttggcctgt atcggaacag gtgtgaaggt gggatctttg ggcttcccag | 1620 |
| catcggcctt tgccagctgc tcacaggtac tctcattgtg gatgacgagg tggaagggt | 1680 |
| gtatgtacac ccggtcacct gtggccaggc cagcccaggc caggaggcag aggatggtgg | 1740 |
| ccctcaggct cacgctggca ggagccatct cggactgggg tgctcgcttc tgcataccct | 1800 |
| tctgctgtag tacccagaac aatggcagct tctt | 1834 |

<210> SEQ ID NO 5
<211> LENGTH: 1856
<212> TYPE: DNA
<213> ORGANISM: Mus musculus

<400> SEQUENCE: 5

| | |
|---|---|
| gatagctgtg cttgtctagg ttggcgctga aggatacaca gaagcaaatg cacagatcgg | 60 |
| agatgactcc cacgggggca ggcctgaagg ccaccatctt ctgcatcttg acctgggtca | 120 |
| gcctgacggc tggggaccgc gtatacatcc accccttcca tctccttac cacaacaaga | 180 |
| gcacctgcgc ccagctggag aaccccagtg tggagacact cccagagtca acgttcgagc | 240 |
| ctgtgcccat tcaggccaag acctcccctg tgaatgagaa gaccctgcat gatcagctcg | 300 |
| tgctggccgc cgagaagcta gaggatgagg accggaagcg ggctgcccag gtcgcaatga | 360 |
| tcgccaactt cgtgggcttc cgcatgtaca agatgctgaa tgaggcagga agtggggcca | 420 |
| gtggggccat cctctcacca ccagctctct ttggcaccct ggtctcttc taccttggat | 480 |
| ccttagatcc cacggccagc cagctgcaga cgctgctgga tgtccctgtg aaggagggag | 540 |
| actgcacctc ccgactagat ggacacaagg tcctcgctgc cctgcgggcc attcagggct | 600 |
| tgctggtcac ccagggtggg agcagcagcc agacacccct gctacagtcc attgtggtgg | 660 |
| ggctcttcac tgctccaggc tttcgtctaa agcactcatt tgttcagagc ctggctctct | 720 |
| ttaccctgc cctcttccca cgctctctgg atttatccac tgacccagtt cttgccactg | 780 |
| agaaaatcaa caggttcata aaggctgtga cagggtggaa gatgaacttg ccactggagg | 840 |
| gggtcagtac agacagcacc ctactttca acacctacgt tcacttccaa ggaacgatga | 900 |
| gaggtttctc tcagctgcct ggagtccatg aattctgggt ggacaacagc atctcggtgt | 960 |
| ctgtgcccat gatctccggc actggcaact tccagcactg gagtgacacc cagaacaact | 1020 |
| tctccgtgac gtgcgtgccc ctaggtgaga gagccacccct gctgctcatc cagccccact | 1080 |
| gcacctcaga tctcgacagg gtggaggccc tcatcttccg gaacgacctc ctgacttgga | 1140 |
| tagagaaccc gcctcctcgg gccatccgcc tgactctgcc ccagctggaa atccgaggat | 1200 |
| cctacaatct gcaggacctg ctggctgagg acaagctgcc cacccttttg ggtgcggagg | 1260 |
| caaatctgaa caacattggt gacaccaacc cccgagtggg agaggttctc aatagcatcc | 1320 |
| tcctcgaact caaagcagga gaggaggaac agccgaccac gtcgtccag cagcctggct | 1380 |
| caccggaggc actggatgtg accctgagca gccccttcct gttcgccatc tacgagcagg | 1440 |
| actcaggcac gctgcacttt ctgggcagag tgaataaccc ccagagtgtg gtgtgaggcc | 1500 |
| ttgtgcctag ccatggagac aaggccggtg tcggagaacc gttctgggca aaactcagtg | 1560 |
| ctgtcacccc tggctcccca tcacgccttg tagcgcggca gaggccgtct ccttggagac | 1620 |

```
tgcgctgacc gagaataaat gatgagcagc agagcctcct gggatgtggg tttgtttgga    1680
tactggggtg acagccagaa gctggcactc tgcacaggac tgccactctg aagaaattt     1740 ggaccaaaaa actgtttgtg acaccaaaaa gcaccccccc tttttttat ttgaggacag     1800 aaattgggtt ttaacattaa aatgcacatt atcccttaa aaaaaaaaaa aaaaaa         1856
```

<210> SEQ ID NO 6
<211> LENGTH: 1856
<212> TYPE: DNA
<213> ORGANISM: Mus musculus

<400> SEQUENCE: 6

```
tttttttttt tttttttaa ggggataatg tgcattttaa tgttaaaacc caatttctgt     60
cctcaaataa aaaaaggggg gggtgctttt tggtgtcaca aacagttttt tggtccaaat    120
ttcttccaga gtggcagtcc tgtgcagagt gccagcttct ggctgtcacc ccagtatcca    180
aacaaaccca catcccagga ggctctgctg ctcatcattt attctcggtc agcgcagtct    240
ccaaggagac ggcctctgcc gcgctacaag gcgtgatggg gagccagggg tgacagcact    300
gagttttgcc cagaacggtt ctccgacacc ggccttgtct ccatggctag cacaaggcc     360 tcacaccaca ctctgggggt tattcactct gcccagaaag tgcagcgtgc ctgagtcctg    420
ctcgtagatg cgaacagga agggctgct cagggtcaca tccagtgcct ccggtgagcc      480
aggctgctgg acagacgtgg tcggctgttc ctcctctcct gctttgagtt cgaggaggat    540
gctattgaga acctctccca ctcggggtt ggtgtcacca atgttgttca gatttgcctc     600
cgcacccaaa agggtgggca gcttgtcctc agccagcagg tcctgcagat tgtaggatcc    660
tcggatttcc agctggggca gagtcaggcg gatggcccga ggaggcgggt tctctatcca    720
agtcaggagg tcgttccgga agatgagggc ctccaccctg tcgagatctg aggtgcagtg    780
gggctggatg agcagcaggg tggctctctc acctaggggc acgcacgtca cggagaagtt    840
gttctgggtg tcactccagt gctggaagtt gccagtgccg gagatcatgg gcacagacac    900
cgagatgctg ttgtccaccc agaattcatg gactccaggc agctgagaga aacctctcat    960
cgttccttgg aagtgaacgt aggtgttgaa aagtaggggtg ctgtctgtac tgaccccctc   1020
cagtggcaag ttcatcttcc accctgtcac agcctttatg aacctgttga ttttctcagt    1080
ggcaagaact gggtcagtgg ataaatccag agagcgtggg aagagggcag gggtaaagag    1140
agccaggctc tgaacaaatg agtgctttag acgaaagcct ggagcagtga agagcccac     1200 cacaatggac tgtagcaggg gtgtctggct gctgctccca ccctgggtga ccagcaagcc    1260
ctgaatggcc cgcagggcag cgaggacctt gtgtccatct agtcgggagg tgcagtctcc    1320
ctccttcaca gggacatcca gcagcgtctg cagctggctg gccgtgggat ctaaggatcc    1380
aaggtagaaa gagaccaggg tgccaaagag agctggtggt gagaggatgg ccccactggc    1440
cccacttcct gcctcattca gcatcttgta catgcggaag cccacgaagt tggcgatcat    1500
tgcgacctgg gcagcccgct tccggtcctc atcctctagc ttctcggcgg ccagcacgag    1560
ctgatcatgc agggtcttct cattcacagg ggaggtcttg gcctgaatgg gcacaggctc    1620
gaacgttgac tctgggagtg tctccacact ggggttctcc agctgggcgc aggtgctctt    1680
gttgtggtaa aggagatgga aggggtggat gtatacgcgg tccccagccg tcaggctgac    1740
ccaggtcaag atgcagaaga tggtggcctt caggcctgcc ccgtgggag tcatctccga     1800 tctgtgcatt tgcttctgtg tatccttcag cgccaaccta gacaagcaca gctatc        1856
```

<210> SEQ ID NO 7
<211> LENGTH: 1958
<212> TYPE: DNA
<213> ORGANISM: Rattus norvegicus

<400> SEQUENCE: 7

| | | | | | |
|---|---|---|---|---|---|
| ccttgctcca | tcttggctaa | gcctggattc | ccatggtccc | ccgacctggg | tcctccccca | 60 |
| gcctctgtac | agagtagcct | gggaatagat | ccatcttcac | cccctcgagt | ataaataagg | 120 |
| ctgcttggtt | caccagggga | tagctgtgct | tgtctgggct | ggagctaaag | gacacacaga | 180 |
| agcaagtcca | cagatccgtg | atgactccca | cggggggcagg | cctgaaggcc | accatcttct | 240 |
| gcatcctgac | ctgggtcagc | ctgacagctg | ggaccgcgt | atacatccac | ccctttcatc | 300 |
| tcctctacta | cagcaagagc | acctgcgccc | agctggagaa | ccccagtgtg | gagacgctcc | 360 |
| cagagccaac | ctttgagcct | gtgcccattc | aggccaagac | ctccccgtg | gatgagaaga | 420 |
| ccctgcgaga | taagctcgtg | ctggccactg | agaagctaga | ggctgaggat | cggcagcgag | 480 |
| ctgcccaggt | cgcgatgatt | gccaacttca | tgggtttccg | catgtacaag | atgctgagtg | 540 |
| aggcaagagg | tgtagccagt | ggggccgtcc | tctctccacc | ggccctcttt | ggcaccctgg | 600 |
| tctctttcta | ccttggatcg | ttggatccca | cggccagcca | gttgcaggtg | ctgctgggcg | 660 |
| tccctgtgaa | ggagggagac | tgcacctccc | ggctggacgg | acataaggtc | ctcactgccc | 720 |
| tgcaggctgt | tcagggcttg | ctggtcaccc | agggtggaag | cagcagccag | acaccctgc | 780 |
| tacagtccac | cgtggtgggc | ctcttcactg | ccccaggctt | gcgcctaaaa | cagccatttg | 840 |
| ttgagagctt | gggtcccttc | accccgcca | tcttccctcg | ctctctggac | ttatccactg | 900 |
| acccagttct | tgctgcccag | aaaatcaaca | ggtttgtgca | ggctgtgaca | gggtggaaga | 960 |
| tgaacttgcc | actagagggg | gtcagcacgg | acagcaccct | attttcaac | acctacgttc | 1020 |
| acttccaagg | gaagatgaga | ggcttctccc | agctgactgg | gctccatgag | ttctgggtgg | 1080 |
| acaacagcac | ctcagtgtct | gtgcccatgc | tctcgggcac | tggcaacttc | cagcactgga | 1140 |
| gtgacgccca | gaacaacttc | tccgtgacac | gcgtgcccct | gggtgagagt | gtcaccctgc | 1200 |
| tgctgatcca | gccccagtgc | gcctcagatc | tcgacagggt | ggaggtcctc | gtcttccagc | 1260 |
| acgacttcct | gacttggata | agaacccgc | ctcctcgggc | catccgtctg | accctgccgc | 1320 |
| agctggaaat | tcggggatcc | tacaacctgc | aggacctgct | ggctcaggcc | aagctgtcta | 1380 |
| ccctttttggg | tgctgaggca | aatctgggca | agatgggtga | caccaacccc | cgagtgggag | 1440 |
| aggttctcaa | cagcatcctc | cttgaactcc | aagcaggcga | ggaggagcag | cccacagagt | 1500 |
| ctgcccagca | gcctggctca | cccgaggtgc | tggacgtgac | cctgagcagt | ccgttcctgt | 1560 |
| tcgccatcta | cgagcgggac | tcaggtgcgc | tgcactttct | gggcagagtg | gataaccccc | 1620 |
| aaaatgtggt | gtgatgcctc | ctgtgtagcc | atggagacaa | ggccagcgtc | agagagctat | 1680 |
| cctgggcaaa | aatcagtgcc | ttcacccctg | gcttcccgtc | actccttcca | gcaaggcaga | 1740 |
| ggccgtctcc | ttggagatgg | cgctaactga | gaataaatga | tgagcagcag | cctcctgggg | 1800 |
| tgtgggtttg | tttggacact | ggggtgagag | ccaggagctg | gcactctgta | taggaggact | 1860 |
| gccatcctgg | aaaaaaaaaa | tggaccaaac | aactgtttgt | gaaataaaaa | aaaaaaatt | 1920 |
| cccttttttat | ttgaaaaaaa | aaaaaaaaaa | aaaaaaaa | | | 1958 |

<210> SEQ ID NO 8
<211> LENGTH: 1958
<212> TYPE: DNA
<213> ORGANISM: Rattus norvegicus

<400> SEQUENCE: 8

```
tttttttttt tttttttttt tttttcaaat aaaaagggaa tttttttttt tttatttcac      60
aaacagttgt ttggtccatt ttttttttcc aggatggcag tcctcctata cagagtgcca     120
gctcctggct ctcaccccag tgtccaaaca aacccacacc ccaggaggct gctgctcatc     180
atttattctc agttagcgcc atctccaagg agacggcctc tgccttgctg aaggagtga     240
cgggaagcca ggggtgaagg cactgatttt tgcccaggat agctctctga cgctggcctt     300
gtctccatgg ctacacagga ggcatcacac cacattttgg gggttatcca ctctgcccag     360
aaagtgcagc gcacctgagt cccgctcgta gatggcgaac aggaacggac tgctcagggt     420
cacgtccagc acctcgggtg agccaggctg ctgggcagac tctgtgggct gctcctcctc     480
gcctgcttgg agttcaagga ggatgctgtt gagaacctct cccactcggg ggttggtgtc     540
acccatcttg cccagatttg cctcagcacc caaaagggta gacagcttgg cctgagccag     600
caggtcctgc aggttgtagg atccccgaat ttccagctgc ggcagggtca gacgatggc     660
ccgaggaggc gggttcttta ccaagtcag gaagtcgtgc tggaagacga ggacctccac     720
cctgtcgaga tctgaggcgc actggggctg gatcagcagc agggtgacac tctcacccag     780
gggcacgcgt gtcacggaga agttgttctg ggcgtcactc cagtgctgga agttgccagt     840
gcccgagagc atgggcacag acactgaggt gctgttgtcc acccagaact catggagccc     900
agtcagctgg gagaagcctc tcatcttccc ttggaagtga acgtaggtgt tgaaaaatag     960
ggtgctgtcc gtgctgaccc cctctagtgg caagttcatc ttccaccctg tcacagcctg    1020
cacaaacctg ttgattttct gggcagcaag aactgggtca gtggataagt ccagagagcg    1080
agggaagatg gcggggtga agggacccaa gctctcaaca aatggctgtt ttaggcgcaa    1140
gcctggggca gtgaagaggc ccaccacggt ggactgtagc aggggtgtct ggctgctgct    1200
tccaccctgg gtgaccagca agccctgaac agcctgcagg gcagtgagga ccttatgtcc    1260
gtccagccgg gaggtgcagt ctccctcctt cacagggacg cccagcagca cctgcaactg    1320
gctggccgtg ggatccaacg atccaaggta gaaagagacc agggtgccaa agagggccgg    1380
tggagagagg acggccccac tggctacacc tcttgcctca ctcagcatct tgtacatgcg    1440
gaaacccatg aagttggcaa tcatcgcgac ctgggcagct cgctgccgat cctcagcctc    1500
tagcttctca gtggccagca cgagcttatc tcgcagggtc ttctcatcca cggggaggt    1560
cttggcctga atgggcacag gctcaaaggt tggctctggg agcgtctcca cactggggtt    1620
ctccagctgg gcgcaggtgc tcttgctgta gtagaggaga tgaaaggggt ggatgtatac    1680
gcggtcccca gctgtcaggc tgacccaggt caggatgcag aagatggtgg ccttcaggcc    1740
tgccccgtg ggagtcatca cggatctgtg gacttgcttc tgtgtgtcct ttagctccag    1800
cccagacaag cacagctatc ccctggtgaa ccaagcagcc ttatttatac tcgaggggt    1860
gaagatggat ctattcccag gctactctgt acagaggctg ggggaggacc caggtcgggg    1920
gaccatggga atccaggctt agccaagatg gagcaagg                            1958
```

<210> SEQ ID NO 9
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

-continued

```
<400> SEQUENCE: 9
uguacucuca uuguggauga cga                                              23

<210> SEQ ID NO 10
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 10
gucauccaca augagaguac a                                                21

<210> SEQ ID NO 11
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 11
uguactcuca uuguggauga cga                                              23

<210> SEQ ID NO 12
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 12
gucauccaca augagaguac a                                                21

<210> SEQ ID NO 13
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 13
ucucccaccu uuucuucuaa u                                                21

<210> SEQ ID NO 14
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 14
auuagaagaa aaggugggag acu                                              23
```

```
<210> SEQ ID NO 15
<211> LENGTH: 16
<212> TYPE: PRT
<213> ORGANISM: Unknown
<220> FEATURE:
<221> NAME/KEY: source
<223> OTHER INFORMATION: /note="Description of Unknown:
      RFGF peptide"

<400> SEQUENCE: 15

Ala Ala Val Ala Leu Leu Pro Ala Val Leu Leu Ala Leu Leu Ala Pro
1               5                   10                  15

<210> SEQ ID NO 16
<211> LENGTH: 11
<212> TYPE: PRT
<213> ORGANISM: Unknown
<220> FEATURE:
<221> NAME/KEY: source
<223> OTHER INFORMATION: /note="Description of Unknown:
      RFGF analogue peptide"

<400> SEQUENCE: 16

Ala Ala Leu Leu Pro Val Leu Leu Ala Ala Pro
1               5                   10

<210> SEQ ID NO 17
<211> LENGTH: 13
<212> TYPE: PRT
<213> ORGANISM: Human immunodeficiency virus

<400> SEQUENCE: 17

Gly Arg Lys Lys Arg Arg Gln Arg Arg Arg Pro Pro Gln
1               5                   10

<210> SEQ ID NO 18
<211> LENGTH: 16
<212> TYPE: PRT
<213> ORGANISM: Drosophila sp.

<400> SEQUENCE: 18

Arg Gln Ile Lys Ile Trp Phe Gln Asn Arg Arg Met Lys Trp Lys Lys
1               5                   10                  15

<210> SEQ ID NO 19
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 19
cuuacgcuga guacuucgat t                                            21

<210> SEQ ID NO 20
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
```

```
<221> NAME/KEY: source
<223> OTHER INFORMATION: /note="Description of Combined DNA/RNA
      Molecule: Synthetic oligonucleotide"

<400> SEQUENCE: 20
ucgaaguacu cagcguaagt t                                              21

<210> SEQ ID NO 21
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 21
cacaaugaga guaccuguga a                                              21

<210> SEQ ID NO 22
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 22
gucucccacc uuuucuucua a                                              21

<210> SEQ ID NO 23
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 23 acuuccagc aaaacucccu a                                               21

<210> SEQ ID NO 24
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 24
ccucaacugg augaagaaac u                                              21

<210> SEQ ID NO 25
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 25
cuguuugcug uguaugauca a                                              21
```

```
<210> SEQ ID NO 26
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 26
uuugcugugu augaucaaag a                                              21

<210> SEQ ID NO 27
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 27
ccgaccagcu uguuugugaa a                                              21

<210> SEQ ID NO 28
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 28
uccaaccgac cagcuuguuu a                                              21

<210> SEQ ID NO 29
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 29
ccauuccugu uugcugugua u                                              21

<210> SEQ ID NO 30
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 30
caccuuuucu ucuaaugagu a                                              21

<210> SEQ ID NO 31
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

<400> SEQUENCE: 31
guuugcugug uaugaucaaa a                                          21

<210> SEQ ID NO 32
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 32
gcugagaaga uugacagguu a                                          21

<210> SEQ ID NO 33
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 33
uuccagcaaa acucccucaa a                                          21

<210> SEQ ID NO 34
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 34
ugcugagaag auugacaggu u                                          21

<210> SEQ ID NO 35
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 35
ucucacuuuc cagcaaaacu a                                          21

<210> SEQ ID NO 36
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 36
uccacaauga gaguaccugu a                                          21

<210> SEQ ID NO 37
<211> LENGTH: 21
<212> TYPE: RNA
<213> ORGANISM: Artificial Sequence

```
<220> FEATURE:
<221> NAME/KEY: source
<223> OTHER INFORMATION: /note="Description of Artificial Sequence:
      Synthetic oligonucleotide"

<400> SEQUENCE: 37
ccaccucguc auccacaaug a                                              21

<210> SEQ ID NO 38
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 38
ucacuuucca gcaaaacucc a                                              21

<210> SEQ ID NO 39
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 39
ucccucaacu ggaugaagaa a                                              21

<210> SEQ ID NO 40
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 40
gagaguaccu gugagcagcu a                                              21

<210> SEQ ID NO 41
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 41
agaauuccaa ccgaccagcu u                                              21

<210> SEQ ID NO 42
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 42
cauuccuguu ugcuguguau a                                              21
```

<210> SEQ ID NO 43
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 43
gaauuccaac cgaccagcuu a                                           21

<210> SEQ ID NO 44
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 44
cauccacaau gagaguaccu a                                           21

<210> SEQ ID NO 45
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 45
cccauuccug uuugcugugu a                                           21

<210> SEQ ID NO 46
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 46
cuggguuuau uuuagagaau a                                           21

<210> SEQ ID NO 47
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 47
gcuggguuua uuuuagagaa u                                           21

<210> SEQ ID NO 48
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 48
auggcaugca cagugagcua u                                           21

<210> SEQ ID NO 49
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 49
gagagagccc acagagucua a                                           21

<210> SEQ ID NO 50
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 50
gcaagaacca guguuuagcg a                                           21

<210> SEQ ID NO 51
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 51
ccagcaaaac ucccucaacu a                                           21

<210> SEQ ID NO 52
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 52
caccucguca uccacaauga a                                           21

<210> SEQ ID NO 53
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 53
cgucauccac aaugagagua a                                           21

<210> SEQ ID NO 54
<211> LENGTH: 21
<212> TYPE: RNA

```
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 54
cucccacgcu cucuggacuu a                                              21

<210> SEQ ID NO 55
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 55
aacucccuca acuggaugaa a                                              21

<210> SEQ ID NO 56
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 56
ugagaagauu gacagguuca u                                              21

<210> SEQ ID NO 57
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 57
ccucgucauc cacaaugaga a                                              21

<210> SEQ ID NO 58
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 58
gagaagauug acagguucau a                                              21

<210> SEQ ID NO 59
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 59
cuucuugggc uuccguauau a                                              21
```

<210> SEQ ID NO 60
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 60
uccaccucgu cauccacaau a                                              21

<210> SEQ ID NO 61
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 61
agauugacag guucaugcag a                                              21

<210> SEQ ID NO 62
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 62
cucccucaac uggaugaaga a                                              21

<210> SEQ ID NO 63
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 63
aaugagagua ccugugagca a                                              21

<210> SEQ ID NO 64
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 64
ccaccuuuuc uucuaaugag u                                              21

<210> SEQ ID NO 65
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:

Synthetic oligonucleotide"

<400> SEQUENCE: 65
cgaccagcuu guuugugaaa a                    21

<210> SEQ ID NO 66
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 66
accuuuucuu cuaaugaguc a                    21

<210> SEQ ID NO 67
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 67
gucauccaca augagaguac a                    21

<210> SEQ ID NO 68
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 68
cacaaugaga guaccuguga a                    21

<210> SEQ ID NO 69
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 69
gucucccacc uuuucuucua a                    21

<210> SEQ ID NO 70
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 70
acuuuccagc aaaacucccu a                    21

<210> SEQ ID NO 71
<211> LENGTH: 21

```
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 71
ccucaacugg augaagaaac u                                            21

<210> SEQ ID NO 72
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 72
cuguuugcug uguaugauca a                                            21

<210> SEQ ID NO 73
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 73
uuugcugugu augaucaaag a                                            21

<210> SEQ ID NO 74
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 74
ccgaccagcu uguuugugaa a                                            21

<210> SEQ ID NO 75
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 75
uccaaccgac cagcuuguuu a                                            21

<210> SEQ ID NO 76
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 76
```

```
ccauuccugu uugcugugua u                                              21
```

<210> SEQ ID NO 77
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 77

```
caccuuuucu ucuaaugagu a                                              21
```

<210> SEQ ID NO 78
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 78

```
guuugcugug uaugaucaaa a                                              21
```

<210> SEQ ID NO 79
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 79

```
gcugagaaga uugacagguu a                                              21
```

<210> SEQ ID NO 80
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 80

```
uuccagcaaa acucccucaa a                                              21
```

<210> SEQ ID NO 81
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 81

```
ugcugagaag auugacaggu u                                              21
```

<210> SEQ ID NO 82
<211> LENGTH: 21
<212> TYPE: RNA
<213> ORGANISM: Artificial Sequence
<220> FEATURE:
<221> NAME/KEY: source

```
<223> OTHER INFORMATION: /note="Description of Artificial Sequence:
      Synthetic oligonucleotide"

<400> SEQUENCE: 82
ucucacuuuc cagcaaaacu a                                              21

<210> SEQ ID NO 83
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 83
uccacaauga gaguaccugu a                                              21

<210> SEQ ID NO 84
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 84
ccaccucguc auccacaaug a                                              21

<210> SEQ ID NO 85
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 85
ucacuuucca gcaaaacucc a                                              21

<210> SEQ ID NO 86
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 86
ucccucaacu ggaugaagaa a                                              21

<210> SEQ ID NO 87
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 87
gagaguaccu gugagcagcu a                                              21

<210> SEQ ID NO 88
```

```
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 88
agaauuccaa ccgaccagcu u                                              21

<210> SEQ ID NO 89
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 89
cauuccuguu ugcuguguau a                                              21

<210> SEQ ID NO 90
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 90
gaauuccaac cgaccagcuu a                                              21

<210> SEQ ID NO 91
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 91
cauccacaau gagaguaccu a                                              21

<210> SEQ ID NO 92
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 92
cccauuccug uuugcugugu a                                              21

<210> SEQ ID NO 93
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 93
```
cuggguuuau uuuagagaau a                                              21

<210> SEQ ID NO 94
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 94
gcuggguuua uuuagagaa u                                               21

<210> SEQ ID NO 95
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 95
auggcaugca cagugagcua u                                              21

<210> SEQ ID NO 96
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 96
gagagagccc acagagucua a                                              21

<210> SEQ ID NO 97
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 97
gcaagaacca guguuuagcg a                                              21

<210> SEQ ID NO 98
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 98
ccagcaaaac ucccucaacu a                                              21

<210> SEQ ID NO 99
<211> LENGTH: 21
<212> TYPE: RNA
<213> ORGANISM: Artificial Sequence
<220> FEATURE:

<221> NAME/KEY: source
<223> OTHER INFORMATION: /note="Description of Artificial Sequence:
      Synthetic oligonucleotide"

<400> SEQUENCE: 99
caccucguca uccacaauga a                                      21

<210> SEQ ID NO 100
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 100
cgucauccac aaugagagua a                                      21

<210> SEQ ID NO 101
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 101
cucccacgcu cucuggacuu a                                      21

<210> SEQ ID NO 102
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 102
aacucccuca acuggaugaa a                                      21

<210> SEQ ID NO 103
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 103
ugagaagauu gacagguuca u                                      21

<210> SEQ ID NO 104
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 104
ccucgucauc cacaaugaga a                                      21

```
<210> SEQ ID NO 105
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 105
gagaagauug acagguucau a                                              21

<210> SEQ ID NO 106
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 106
cuucuugggc uuccguauau a                                              21

<210> SEQ ID NO 107
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 107
uccaccucgu cauccacaau a                                              21

<210> SEQ ID NO 108
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 108
agauugacag guucaugcag a                                              21

<210> SEQ ID NO 109
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 109
cucccucaac uggaugaaga a                                              21

<210> SEQ ID NO 110
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

```
<400> SEQUENCE: 110
aaugagagua ccugugagca a                                              21

<210> SEQ ID NO 111
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 111
ccaccuuuuc uucuaaugag u                                              21

<210> SEQ ID NO 112
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 112
cgaccagcuu guuugugaaa a                                              21

<210> SEQ ID NO 113
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 113
accuuuucuu cuaaugaguc a                                              21

<210> SEQ ID NO 114
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 114
gucauccaca augagaguac a                                              21

<210> SEQ ID NO 115
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 115
cacaaugaga guaccuguga a                                              21

<210> SEQ ID NO 116
<211> LENGTH: 21
<212> TYPE: RNA
<213> ORGANISM: Artificial Sequence
```

```
<220> FEATURE:
<221> NAME/KEY: source
<223> OTHER INFORMATION: /note="Description of Artificial Sequence:
      Synthetic oligonucleotide"

<400> SEQUENCE: 116
gucucccacc uuucuucua a                                              21

<210> SEQ ID NO 117
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 117 acuuccagc aaaacucccu a                                              21

<210> SEQ ID NO 118
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 118
ccucaacugg augaagaaac u                                             21

<210> SEQ ID NO 119
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 119
cuguuugcug uguaugauca a                                             21

<210> SEQ ID NO 120
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 120
uuugcugugu augaucaaag a                                             21

<210> SEQ ID NO 121
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 121
ccgaccagcu uguuugugaa a                                             21
```

```
<210> SEQ ID NO 122
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 122
uccaaccgac cagcuuguuu a                                              21

<210> SEQ ID NO 123
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 123
ccauuccugu uugcugugua u                                              21

<210> SEQ ID NO 124
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 124
caccuuuucu ucuaaugagu a                                              21

<210> SEQ ID NO 125
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 125
guuugcugug uaugaucaaa a                                              21

<210> SEQ ID NO 126
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 126
gcugagaaga uugacagguu a                                              21

<210> SEQ ID NO 127
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

```
<400> SEQUENCE: 127
uuccagcaaa acucccucaa a                                              21

<210> SEQ ID NO 128
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 128
ugcugagaag auugacaggu u                                              21

<210> SEQ ID NO 129
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 129
ucucacuuuc cagcaaaacu a                                              21

<210> SEQ ID NO 130
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 130
uccacaauga gaguaccugu a                                              21

<210> SEQ ID NO 131
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 131
ccaccucguc auccacaaug a                                              21

<210> SEQ ID NO 132
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 132
ucacuuucca gcaaaacucc a                                              21

<210> SEQ ID NO 133
<211> LENGTH: 21
<212> TYPE: RNA
```

```
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 133
ucccucaacu ggaugaagaa a                                              21

<210> SEQ ID NO 134
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 134
gagaguaccu gugagcagcu a                                              21

<210> SEQ ID NO 135
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 135
agaauuccaa ccgaccagcu u                                              21

<210> SEQ ID NO 136
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 136
cauuccuguu ugcuguguau a                                              21

<210> SEQ ID NO 137
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 137
gaauuccaac cgaccagcuu a                                              21

<210> SEQ ID NO 138
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 138
cauccacaau gagaguaccu a                                              21
```

<210> SEQ ID NO 139
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 139
cccauuccug uuugcugugu a                                              21

<210> SEQ ID NO 140
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 140
cuggguuuau uuuagagaau a                                              21

<210> SEQ ID NO 141
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 141
gcuggguuua uuuuagagaa u                                              21

<210> SEQ ID NO 142
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 142
auggcaugca cagugagcua u                                              21

<210> SEQ ID NO 143
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 143
gagagagccc acagagucua a                                              21

<210> SEQ ID NO 144
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:

-continued

Synthetic oligonucleotide"

<400> SEQUENCE: 144
gcaagaacca guguuuagcg a                                           21

<210> SEQ ID NO 145
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 145
ccagcaaaac ucccucaacu a                                           21

<210> SEQ ID NO 146
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 146
caccucguca uccacaauga a                                           21

<210> SEQ ID NO 147
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 147
cgucauccac aaugagagua a                                           21

<210> SEQ ID NO 148
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 148
cucccacgcu cucuggacuu a                                           21

<210> SEQ ID NO 149
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 149
aacucccuca acuggaugaa a                                           21

<210> SEQ ID NO 150
<211> LENGTH: 21

```
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 150
ugagaagauu gacagguuca u                                             21

<210> SEQ ID NO 151
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 151
ccucgucauc cacaaugaga a                                             21

<210> SEQ ID NO 152
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 152
gagaagauug acagguucau a                                             21

<210> SEQ ID NO 153
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 153
cuucuugggc uuccguauau a                                             21

<210> SEQ ID NO 154
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 154
uccaccucgu cauccacaau a                                             21

<210> SEQ ID NO 155
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 155
```
agauugacag guucaugcag a                                          21

<210> SEQ ID NO 156
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 156
cucccucaac uggaugaaga a                                          21

<210> SEQ ID NO 157
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 157
aaugagagua ccugugagca a                                          21

<210> SEQ ID NO 158
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 158
ccaccuuuuc uucuaaugag u                                          21

<210> SEQ ID NO 159
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 159
cgaccagcuu guuugugaaa a                                          21

<210> SEQ ID NO 160
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 160
accuuuucuu cuaaugaguc a                                          21

<210> SEQ ID NO 161
<211> LENGTH: 21
<212> TYPE: RNA
<213> ORGANISM: Artificial Sequence
<220> FEATURE:
<221> NAME/KEY: source -continued
<223> OTHER INFORMATION: /note="Description of Artificial Sequence:
      Synthetic oligonucleotide"

<400> SEQUENCE: 161
gucauccaca augagaguac a                                              21

<210> SEQ ID NO 162
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 162
cacaaugaga guaccuguga a                                              21

<210> SEQ ID NO 163
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 163
gucucccacc uuuucuucua a                                              21

<210> SEQ ID NO 164
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 164 acuuccagc aaaacucccu a                                               21

<210> SEQ ID NO 165
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 165
ccucaacugg augaagaaac u                                              21

<210> SEQ ID NO 166
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 166
cuguuugcug uguaugauca a                                              21

<210> SEQ ID NO 167

```
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 167
uuugcugugu augaucaaag a                                              21

<210> SEQ ID NO 168
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 168
ccgaccagcu uguuugugaa a                                              21

<210> SEQ ID NO 169
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 169
uccaaccgac cagcuuguuu a                                              21

<210> SEQ ID NO 170
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 170
ccauuccugu uugcugugua u                                              21

<210> SEQ ID NO 171
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 171
caccuuuucu ucuaaugagu a                                              21

<210> SEQ ID NO 172
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 172
```
guuugcugug uaugaucaaa a                                            21

<210> SEQ ID NO 173
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 173
gcugagaaga uugacagguu a                                            21

<210> SEQ ID NO 174
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 174
uuccagcaaa acucccucaa a                                            21

<210> SEQ ID NO 175
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 175
ugcugagaag auugacaggu u                                            21

<210> SEQ ID NO 176
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 176
ucucacuuuc cagcaaaacu a                                            21

<210> SEQ ID NO 177
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 177
uccacaauga gaguaccugu a                                            21

<210> SEQ ID NO 178
<211> LENGTH: 21
<212> TYPE: RNA
<213> ORGANISM: Artificial Sequence
<220> FEATURE:

```
<221> NAME/KEY: source
<223> OTHER INFORMATION: /note="Description of Artificial Sequence:
      Synthetic oligonucleotide"

<400> SEQUENCE: 178
ccaccucguc auccacaaug a                                              21

<210> SEQ ID NO 179
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 179
ucacuuucca gcaaaacucc a                                              21

<210> SEQ ID NO 180
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 180
ucccucaacu ggaugaagaa a                                              21

<210> SEQ ID NO 181
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 181
gagaguaccu gugagcagcu a                                              21

<210> SEQ ID NO 182
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 182
agaauuccaa ccgaccagcu u                                              21

<210> SEQ ID NO 183
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 183
cauuccuguu ugcuguguau a                                              21
```

```
<210> SEQ ID NO 184
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 184
gaauuccaac cgaccagcuu a                                            21

<210> SEQ ID NO 185
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 185
cauccacaau gagaguaccu a                                            21

<210> SEQ ID NO 186
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 186
cccauuccug uuugcugugu a                                            21

<210> SEQ ID NO 187
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 187
cuggguuuau uuuagagaau a                                            21

<210> SEQ ID NO 188
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 188
gcuggguuua uuuuagagaa u                                            21

<210> SEQ ID NO 189
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

```
<400> SEQUENCE: 189
auggcaugca cagugagcua u                                              21

<210> SEQ ID NO 190
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 190
gagagagccc acagagucua a                                              21

<210> SEQ ID NO 191
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 191
gcaagaacca guguuuagcg a                                              21

<210> SEQ ID NO 192
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 192
ccagcaaaac ucccucaacu a                                              21

<210> SEQ ID NO 193
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 193
caccucguca uccacaauga a                                              21

<210> SEQ ID NO 194
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 194
cgucauccac aaugagagua a                                              21

<210> SEQ ID NO 195
<211> LENGTH: 21
<212> TYPE: RNA
<213> ORGANISM: Artificial Sequence
```

-continued

```
<220> FEATURE:
<221> NAME/KEY: source
<223> OTHER INFORMATION: /note="Description of Artificial Sequence:
      Synthetic oligonucleotide"

<400> SEQUENCE: 195
cucccacgcu cucuggacuu a                                              21

<210> SEQ ID NO 196
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 196
aacucccuca acuggaugaa a                                              21

<210> SEQ ID NO 197
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 197
ugagaagauu gacagguuca u                                              21

<210> SEQ ID NO 198
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 198
ccucgucauc cacaaugaga a                                              21

<210> SEQ ID NO 199
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 199
gagaagauug acagguucau a                                              21

<210> SEQ ID NO 200
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 200
cuucuugggc uuccguauau a                                              21
```

<210> SEQ ID NO 201
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 201
uccaccucgu cauccacaau a                                              21

<210> SEQ ID NO 202
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 202
agauugacag guucaugcag a                                              21

<210> SEQ ID NO 203
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 203
cucccucaac uggaugaaga a                                              21

<210> SEQ ID NO 204
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 204
aaugagagua ccugugagca a                                              21

<210> SEQ ID NO 205
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 205
uucacaggua cucucauugu gga                                            23

<210> SEQ ID NO 206
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 206
uuagaagaaa agguggGaga cug                                               23

<210> SEQ ID NO 207
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 207
uagggaguuu ugcuggaaag uga                                               23

<210> SEQ ID NO 208
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 208 aguucuuca uccaguugag gga                                                23

<210> SEQ ID NO 209
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 209
uugaucauac acagcaaaca gga                                               23

<210> SEQ ID NO 210
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 210
ucuuugauca uacacagcaa aca                                               23

<210> SEQ ID NO 211
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 211
uuucacaaac aagcuggucg guu                                               23

<210> SEQ ID NO 212
<211> LENGTH: 23
<212> TYPE: RNA

```
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 212
uaaacaagcu ggucgguugg aau                                              23

<210> SEQ ID NO 213
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 213
auacacagca aacaggaaug ggc                                              23

<210> SEQ ID NO 214
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 214
uacucauuag aagaaaaggu ggg                                              23

<210> SEQ ID NO 215
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 215
uuuugaucau acacagcaaa cag                                              23

<210> SEQ ID NO 216
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 216
uaaccuguca aucuucucag cag                                              23

<210> SEQ ID NO 217
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 217
uuugagggag uuuugcugga aag                                              23
```

```
<210> SEQ ID NO 218
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 218
aaccugucaa ucuucucagc agc                                         23

<210> SEQ ID NO 219
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 219
uaguuuugcu ggaaagugag acc                                         23

<210> SEQ ID NO 220
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 220
uacagguacu cucauugugg aug                                         23

<210> SEQ ID NO 221
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 221
ucauugugga ugacgaggug gaa                                         23

<210> SEQ ID NO 222
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 222
uggaguuuug cuggaaagug aga                                         23

<210> SEQ ID NO 223
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
```

-continued

```
      Synthetic oligonucleotide"

<400> SEQUENCE: 223
uuucuucauc caguugaggg agu                                              23

<210> SEQ ID NO 224
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 224
uagcugcuca cagguacucu cau                                              23

<210> SEQ ID NO 225
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 225
aagcuggucg guuggaauuc uuu                                              23

<210> SEQ ID NO 226
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 226
uauacacagc aaacaggaau ggg                                              23

<210> SEQ ID NO 227
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 227
uaagcugguc gguuggaauu cuu                                              23

<210> SEQ ID NO 228
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 228
uagguacucu cauugugga gac                                               23

<210> SEQ ID NO 229
<211> LENGTH: 23
```

```
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 229
uacacagcaa acaggaaugg gcg                                           23

<210> SEQ ID NO 230
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 230
uauucucuaa aauaaaccca gca                                           23

<210> SEQ ID NO 231
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 231
auucucuaaa auaaacccag caa                                           23

<210> SEQ ID NO 232
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 232
auagcucacu gugcaugcca uau                                           23

<210> SEQ ID NO 233
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 233
uuagacucug ugggcucucu cuc                                           23

<210> SEQ ID NO 234
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 234
```

```
ucgcuaaaca cgguucuug ccu                                            23

<210> SEQ ID NO 235
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 235
uaguugaggg aguuuugcug gaa                                            23

<210> SEQ ID NO 236
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 236
uucauugugg augacgaggu gga                                            23

<210> SEQ ID NO 237
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 237
uuacucucau uguggaugac gag                                            23

<210> SEQ ID NO 238
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 238
uaaguccaga gagcguggga gga                                            23

<210> SEQ ID NO 239
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 239
uuucauccag uugagggagu uuu                                            23

<210> SEQ ID NO 240
<211> LENGTH: 23
<212> TYPE: RNA
<213> ORGANISM: Artificial Sequence
<220> FEATURE:
<221> NAME/KEY: source
```

```
<223> OTHER INFORMATION: /note="Description of Artificial Sequence:
      Synthetic oligonucleotide"

<400> SEQUENCE: 240
augaaccugu caaucuucuc agc                                              23

<210> SEQ ID NO 241
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 241
uucucauugu ggaugacgag gug                                              23

<210> SEQ ID NO 242
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 242
uaugaaccug ucaaucuucu cag                                              23

<210> SEQ ID NO 243
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 243
uauauacgga agcccaagaa guu                                              23

<210> SEQ ID NO 244
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 244
uauuguggau gacgaggugg aag                                              23

<210> SEQ ID NO 245
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 245
ucugcaugaa ccugucaauc uuc                                              23

<210> SEQ ID NO 246
```

```
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 246
uucuucaucc aguugaggga guu                                              23

<210> SEQ ID NO 247
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 247
uugcucacag guacucucau ugu                                              23

<210> SEQ ID NO 248
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 248
acucauuaga agaaaaggug gga                                              23

<210> SEQ ID NO 249
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 249
uuuucacaaa caagcugguc ggu                                              23

<210> SEQ ID NO 250
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 250
ugacucauua gaagaaaagg ugg                                              23

<210> SEQ ID NO 251
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 251
```
uguacucuca uuguggauga cga                                         23

<210> SEQ ID NO 252
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 252
uucacaggua cucucauugu gga                                         23

<210> SEQ ID NO 253
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 253
uuagaagaaa agguggaga cug                                          23

<210> SEQ ID NO 254
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 254
uagggaguuu ugcuggaaag uga                                         23

<210> SEQ ID NO 255
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 255
aguuucuuca uccaguugag gga                                         23

<210> SEQ ID NO 256
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 256
uugaucauac acagcaaaca gga                                         23

<210> SEQ ID NO 257
<211> LENGTH: 23
<212> TYPE: RNA
<213> ORGANISM: Artificial Sequence
<220> FEATURE:

```
<221> NAME/KEY: source
<223> OTHER INFORMATION: /note="Description of Artificial Sequence:
      Synthetic oligonucleotide"

<400> SEQUENCE: 257
ucuuugauca uacacagcaa aca                                           23

<210> SEQ ID NO 258
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 258
uuucacaaac aagcuggucg guu                                           23

<210> SEQ ID NO 259
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 259
uaaacaagcu ggucgguugg aau                                           23

<210> SEQ ID NO 260
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 260
auacacagca aacaggaaug ggc                                           23

<210> SEQ ID NO 261
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 261
uacucauuag aagaaaaggu ggg                                           23

<210> SEQ ID NO 262
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 262
uuuugaucau acacagcaaa cag                                           23
```

```
<210> SEQ ID NO 263
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 263
uaaccuguca aucuucucag cag                                               23

<210> SEQ ID NO 264
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 264
uuugagggag uuuugcugga aag                                               23

<210> SEQ ID NO 265
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 265
aaccugucaa ucuucucagc agc                                               23

<210> SEQ ID NO 266
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 266
uaguuuugcu ggaaagugag acc                                               23

<210> SEQ ID NO 267
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 267
uacagguacu cucauugugg aug                                               23

<210> SEQ ID NO 268
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

```
<400> SEQUENCE: 268
ucauugugga ugacgaggug gaa                                          23

<210> SEQ ID NO 269
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 269
uggaguuuug cuggaaagug aga                                          23

<210> SEQ ID NO 270
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 270
uuucuucauc caguugaggg agu                                          23

<210> SEQ ID NO 271
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 271
uagcugcuca cagguacucu cau                                          23

<210> SEQ ID NO 272
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 272
aagcuggucg guuggaauuc uuu                                          23

<210> SEQ ID NO 273
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 273
uauacacagc aaacaggaau ggg                                          23

<210> SEQ ID NO 274
<211> LENGTH: 23
<212> TYPE: RNA
<213> ORGANISM: Artificial Sequence
```

```
<220> FEATURE:
<221> NAME/KEY: source
<223> OTHER INFORMATION: /note="Description of Artificial Sequence:
      Synthetic oligonucleotide"

<400> SEQUENCE: 274
uaagcugguc gguuggaauu cuu                                              23

<210> SEQ ID NO 275
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 275
uagguacucu cauuguggau gac                                              23

<210> SEQ ID NO 276
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 276
uacacagcaa acaggaaugg gcg                                              23

<210> SEQ ID NO 277
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 277
uauucucuaa aauaaaccca gca                                              23

<210> SEQ ID NO 278
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 278
auucucuaaa auaaacccag caa                                              23

<210> SEQ ID NO 279
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 279
auagcucacu gugcaugcca uau                                              23
```

<210> SEQ ID NO 280
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 280
uuagacucug ugggcucucu cuc                                                23

<210> SEQ ID NO 281
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 281
ucgcuaaaca cugguucuug ccu                                                23

<210> SEQ ID NO 282
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 282
uaguugaggg aguuuugcug gaa                                                23

<210> SEQ ID NO 283
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 283
uucauugugg augacgaggu gga                                                23

<210> SEQ ID NO 284
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 284
uuacucucau uguggaugac gag                                                23

<210> SEQ ID NO 285
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

```
<400> SEQUENCE: 285
uaaguccaga gagcguggga gga                                              23

<210> SEQ ID NO 286
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 286
uuucauccag uugagggagu uuu                                              23

<210> SEQ ID NO 287
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 287
augaaccugu caaucuucuc agc                                              23

<210> SEQ ID NO 288
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 288
uucucauugu ggaugacgag gug                                              23

<210> SEQ ID NO 289
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 289
uaugaaccug ucaaucuucu cag                                              23

<210> SEQ ID NO 290
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 290
uauauacgga agcccaagaa guu                                              23

<210> SEQ ID NO 291
<211> LENGTH: 23
<212> TYPE: RNA
```

```
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 291
uauuguggau gacgaggugg aag                                              23

<210> SEQ ID NO 292
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 292
ucugcaugaa ccugucaauc uuc                                              23

<210> SEQ ID NO 293
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 293
uucuucaucc aguugaggga guu                                              23

<210> SEQ ID NO 294
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 294
uugcucacag guacucucau ugu                                              23

<210> SEQ ID NO 295
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 295
acucauuaga agaaaaggug gga                                              23

<210> SEQ ID NO 296
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 296
uuuucacaaa caagcugguc ggu                                              23
```

```
<210> SEQ ID NO 297
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 297
ugacucauua gaagaaaagg ugg                                           23

<210> SEQ ID NO 298
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 298
uguacucuca uuguggauga cga                                           23

<210> SEQ ID NO 299
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 299
uucacaggua cucucauugu gga                                           23

<210> SEQ ID NO 300
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 300
uuagaagaaa agugggaga cug                                            23

<210> SEQ ID NO 301
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 301
uagggaguuu ugcuggaaag uga                                           23

<210> SEQ ID NO 302
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
```

-continued

Synthetic oligonucleotide"

<400> SEQUENCE: 302
aguuucuuca uccaguugag gga            23

<210> SEQ ID NO 303
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 303
uugaucauac acagcaaaca gga            23

<210> SEQ ID NO 304
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 304
ucuuugauca uacacagcaa aca            23

<210> SEQ ID NO 305
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 305
uuucacaaac aagcuggucg guu            23

<210> SEQ ID NO 306
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 306
uaaacaagcu ggucgguugg aau            23

<210> SEQ ID NO 307
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 307
auacacagca aacaggaaug ggc            23

<210> SEQ ID NO 308
<211> LENGTH: 23

```
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 308
uacucauuag aagaaaaggu ggg                                          23

<210> SEQ ID NO 309
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 309
uuuugaucau acacagcaaa cag                                          23

<210> SEQ ID NO 310
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 310
uaaccuguca aucuucucag cag                                          23

<210> SEQ ID NO 311
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 311
uuugagggag uuuugcugga aag                                          23

<210> SEQ ID NO 312
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 312
aaccugucaa ucuucucagc agc                                          23

<210> SEQ ID NO 313
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 313
```
uaguuuugcu ggaaagugag acc                                    23

<210> SEQ ID NO 314
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 314
uacagguacu cucauugugg aug                                    23

<210> SEQ ID NO 315
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 315
ucauugugga ugacgaggug gaa                                    23

<210> SEQ ID NO 316
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 316
uggaguuuug cuggaaagug aga                                    23

<210> SEQ ID NO 317
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 317
uuucuucauc caguugaggg agu                                    23

<210> SEQ ID NO 318
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 318
uagcugcuca cagguacucu cau                                    23

<210> SEQ ID NO 319
<211> LENGTH: 23
<212> TYPE: RNA
<213> ORGANISM: Artificial Sequence
<220> FEATURE:
<221> NAME/KEY: source

```
<223> OTHER INFORMATION: /note="Description of Artificial Sequence:
      Synthetic oligonucleotide"

<400> SEQUENCE: 319
aagcuggucg guuggaauuc uuu                                              23

<210> SEQ ID NO 320
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 320
uauacacagc aaacaggaau ggg                                              23

<210> SEQ ID NO 321
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 321
uaagcugguc gguuggaauu cuu                                              23

<210> SEQ ID NO 322
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 322
uagguacucu cauuguggau gac                                              23

<210> SEQ ID NO 323
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 323
uacacagcaa acaggaaugg gcg                                              23

<210> SEQ ID NO 324
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 324
uauucucuaa aauaaaccca gca                                              23

<210> SEQ ID NO 325
```

```
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 325
auucucuaaa auaaacccag caa                                              23

<210> SEQ ID NO 326
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 326
auagcucacu gugcaugcca uau                                              23

<210> SEQ ID NO 327
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 327
uuagacucug ugggcucucu cuc                                              23

<210> SEQ ID NO 328
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 328
ucgcuaaaca cugguucuug ccu                                              23

<210> SEQ ID NO 329
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 329
uaguugaggg aguuuugcug gaa                                              23

<210> SEQ ID NO 330
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 330
```
uucauugugg augacgaggu gga                                          23

<210> SEQ ID NO 331
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 331
uuacucucau uguggaugac gag                                          23

<210> SEQ ID NO 332
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 332
uaaguccaga gagcguggga gga                                          23

<210> SEQ ID NO 333
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 333
uuucauccag uugagggagu uuu                                          23

<210> SEQ ID NO 334
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 334
augaaccugu caaucuucuc agc                                          23

<210> SEQ ID NO 335
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 335
uucucauugu ggaugacgag gug                                          23

<210> SEQ ID NO 336
<211> LENGTH: 23
<212> TYPE: RNA
<213> ORGANISM: Artificial Sequence
<220> FEATURE:

<221> NAME/KEY: source
<223> OTHER INFORMATION: /note="Description of Artificial Sequence:
      Synthetic oligonucleotide"

<400> SEQUENCE: 336
uaugaaccug ucaaucuucu cag                                              23

<210> SEQ ID NO 337
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 337
uauauacgga agcccaagaa guu                                              23

<210> SEQ ID NO 338
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 338
uauuguggau gacgaggugg aag                                              23

<210> SEQ ID NO 339
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 339
ucugcaugaa ccugucaauc uuc                                              23

<210> SEQ ID NO 340
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 340
uucuucaucc aguugaggga guu                                              23

<210> SEQ ID NO 341
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 341
uugcucacag guacucucau ugu                                              23

```
<210> SEQ ID NO 342
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 342
acucauuaga agaaaaggug gga                                          23

<210> SEQ ID NO 343
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 343
uuuucacaaa caagcugguc ggu                                          23

<210> SEQ ID NO 344
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 344
ugacucauua gaagaaaagg ugg                                          23

<210> SEQ ID NO 345
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 345
uguacucuca uuggauga cga                                            23

<210> SEQ ID NO 346
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 346
uucacaggua cucucauugu gga                                          23

<210> SEQ ID NO 347
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

-continued

<400> SEQUENCE: 347
uuagaagaaa agugggaga cug                                                    23

<210> SEQ ID NO 348
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 348
uagggaguuu ugcuggaaag uga                                                   23

<210> SEQ ID NO 349
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 349
aguuucuuca uccaguugag gga                                                   23

<210> SEQ ID NO 350
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 350
uugaucauac acagcaaaca gga                                                   23

<210> SEQ ID NO 351
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 351
ucuuugauca uacacagcaa aca                                                   23

<210> SEQ ID NO 352
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 352
uuucacaaac aagcuggucg guu                                                   23

<210> SEQ ID NO 353
<211> LENGTH: 23
<212> TYPE: RNA
<213> ORGANISM: Artificial Sequence

```
<220> FEATURE:
<221> NAME/KEY: source
<223> OTHER INFORMATION: /note="Description of Artificial Sequence:
      Synthetic oligonucleotide"

<400> SEQUENCE: 353
uaaacaagcu ggucgguugg aau                                              23

<210> SEQ ID NO 354
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 354
auacacagca aacaggaaug ggc                                              23

<210> SEQ ID NO 355
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 355
uacucauuag aagaaaaggu ggg                                              23

<210> SEQ ID NO 356
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 356
uuuugaucau acacagcaaa cag                                              23

<210> SEQ ID NO 357
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 357
uaaccuguca aucuucucag cag                                              23

<210> SEQ ID NO 358
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 358
uuugagggag uuuugcugga aag                                              23
```

```
<210> SEQ ID NO 359
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 359
aaccugucaa ucuucucagc agc                                              23

<210> SEQ ID NO 360
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 360
uaguuuugcu ggaaagugag acc                                              23

<210> SEQ ID NO 361
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 361
uacagguacu cucauugugg aug                                              23

<210> SEQ ID NO 362
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 362
ucauugugga ugacgaggug gaa                                              23

<210> SEQ ID NO 363
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 363
uggaguuuug cuggaaagug aga                                              23

<210> SEQ ID NO 364
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

```
<400> SEQUENCE: 364
uuucuucauc caguugaggg agu                                            23

<210> SEQ ID NO 365
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 365
uagcugcuca cagguacucu cau                                            23

<210> SEQ ID NO 366
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 366
aagcuggucg guuggaauuc uuu                                            23

<210> SEQ ID NO 367
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 367
uauacacagc aaacaggaau ggg                                            23

<210> SEQ ID NO 368
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 368
uaagcugguc gguuggaauu cuu                                            23

<210> SEQ ID NO 369
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 369
uagguacucu cauugugaau gac                                            23

<210> SEQ ID NO 370
<211> LENGTH: 23
<212> TYPE: RNA
```

```
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 370
uacacagcaa acaggaaugg gcg                                              23

<210> SEQ ID NO 371
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 371
uauucucuaa aauaaaccca gca                                              23

<210> SEQ ID NO 372
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 372
auucucuaaa auaaacccag caa                                              23

<210> SEQ ID NO 373
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 373
auagcucacu gugcaugcca uau                                              23

<210> SEQ ID NO 374
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 374
uuagacucug ugggcucucu cuc                                              23

<210> SEQ ID NO 375
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 375
ucgcuaaaca cugguucuug ccu                                              23
```

```
<210> SEQ ID NO 376
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 376
uaguugaggg aguuuugcug gaa                                            23

<210> SEQ ID NO 377
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 377
uucauugugg augacgaggu gga                                            23

<210> SEQ ID NO 378
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 378
uuacucucau uguggaugac gag                                            23

<210> SEQ ID NO 379
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 379
uaaguccaga gagcguggga gga                                            23

<210> SEQ ID NO 380
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 380
uuucauccag uugagggagu uuu                                            23

<210> SEQ ID NO 381
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
```

-continued

Synthetic oligonucleotide"

<400> SEQUENCE: 381
augaaccugu caaucuucuc agc                                       23

<210> SEQ ID NO 382
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 382
uucucauugu ggaugacgag gug                                       23

<210> SEQ ID NO 383
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 383
uaugaaccug ucaaucuucu cag                                       23

<210> SEQ ID NO 384
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 384
uauauacgga agcccaagaa guu                                       23

<210> SEQ ID NO 385
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 385
uauuguggau gacgaggugg aag                                       23

<210> SEQ ID NO 386
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 386
ucugcaugaa ccugucaauc uuc                                       23

<210> SEQ ID NO 387
<211> LENGTH: 23

```
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 387
uucuucaucc aguugaggga guu                                              23

<210> SEQ ID NO 388
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 388
uugcucacag guacucucau ugu                                              23

<210> SEQ ID NO 389
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 389
cacaaugaga guaccuguga a                                                21

<210> SEQ ID NO 390
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 390
gucucccacc uuuucuucua a                                                21

<210> SEQ ID NO 391
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 391 acuuccagc aaaacucccu a                                                 21

<210> SEQ ID NO 392
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 392
```
ccucaacugg augaagaaac u                      21

<210> SEQ ID NO 393
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 393
cuguuugcug uguaugauca a                      21

<210> SEQ ID NO 394
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 394
uuugcugugu augaucaaag a                      21

<210> SEQ ID NO 395
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 395
ccgaccagcu uguuugugaa a                      21

<210> SEQ ID NO 396
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 396
uccaaccgac cagcuuguuu a                      21

<210> SEQ ID NO 397
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 397
ccauuccugu uugcugugua u                      21

<210> SEQ ID NO 398
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
          Synthetic oligonucleotide"

<400> SEQUENCE: 398
caccuuuucu ucuaaugagu a                                              21

<210> SEQ ID NO 399
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 399
guuugcugug uaugaucaaa a                                              21

<210> SEQ ID NO 400
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 400
gcugagaaga uugacagguu a                                              21

<210> SEQ ID NO 401
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 401
uuccagcaaa acucccucaa a                                              21

<210> SEQ ID NO 402
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 402
ugcugagaag auugacaggu u                                              21

<210> SEQ ID NO 403
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 403
ucucacuuuc cagcaaaacu a                                              21

<210> SEQ ID NO 404

```
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 404
uccacaauga gaguaccugu a                                              21

<210> SEQ ID NO 405
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 405
ccaccucguc auccacaaug a                                              21

<210> SEQ ID NO 406
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 406
ucacuuucca gcaaaacucc a                                              21

<210> SEQ ID NO 407
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 407
ucccucaacu ggaugaagaa a                                              21

<210> SEQ ID NO 408
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 408
gagaguaccu gugagcagcu a                                              21

<210> SEQ ID NO 409
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 409
```
agaauuccaa ccgaccagcu u                                             21

<210> SEQ ID NO 410
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 410
cauuccuguu ugcuguguau a                                             21

<210> SEQ ID NO 411
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 411 gaauccaac cgaccagcuu a                                              21

<210> SEQ ID NO 412
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 412
cauccacaau gagaguaccu a                                             21

<210> SEQ ID NO 413
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 413
cccauuccug uuugcugugu a                                             21

<210> SEQ ID NO 414
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 414
cuggguuuau uuuagagaau a                                             21

<210> SEQ ID NO 415
<211> LENGTH: 21
<212> TYPE: RNA
<213> ORGANISM: Artificial Sequence
<220> FEATURE:

```
<221> NAME/KEY: source
<223> OTHER INFORMATION: /note="Description of Artificial Sequence:
      Synthetic oligonucleotide"

<400> SEQUENCE: 415
gcuggguuua uuuuagagaa u                                              21

<210> SEQ ID NO 416
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 416
auggcaugca cagugagcua u                                              21

<210> SEQ ID NO 417
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 417
gagagagccc acagagucua a                                              21

<210> SEQ ID NO 418
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 418
gcaagaacca guguuuagcg a                                              21

<210> SEQ ID NO 419
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 419
ccagcaaaac ucccucaacu a                                              21

<210> SEQ ID NO 420
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 420
caccucguca uccacaauga a                                              21
```

```
<210> SEQ ID NO 421
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 421
cgucauccac aaugagagua a                                              21

<210> SEQ ID NO 422
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 422
cucccacgcu cucuggacuu a                                              21

<210> SEQ ID NO 423
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 423
aacucccuca acuggaugaa a                                              21

<210> SEQ ID NO 424
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 424
ugagaagauu gacagguuca u                                              21

<210> SEQ ID NO 425
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 425
ccucgucauc cacaaugaga a                                              21

<210> SEQ ID NO 426
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

```
<400> SEQUENCE: 426
gagaagauug acagguucau a                                              21

<210> SEQ ID NO 427
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 427
cuucuugggc uuccguauau a                                              21

<210> SEQ ID NO 428
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 428
uccaccucgu cauccacaau a                                              21

<210> SEQ ID NO 429
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 429
agauugacag guucaugcag a                                              21

<210> SEQ ID NO 430
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 430
cucccucaac uggaugaaga a                                              21

<210> SEQ ID NO 431
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 431
aaugagagua ccugugagca a                                              21

<210> SEQ ID NO 432
<211> LENGTH: 21
<212> TYPE: RNA
<213> ORGANISM: Artificial Sequence
```

```
<220> FEATURE:
<221> NAME/KEY: source
<223> OTHER INFORMATION: /note="Description of Artificial Sequence:
      Synthetic oligonucleotide"

<400> SEQUENCE: 432
ccaccuuuuc uucuaaugag u                                              21

<210> SEQ ID NO 433
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 433
cgaccagcuu guuguguaaa a                                              21

<210> SEQ ID NO 434
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 434
accuuuucuu cuaaugaguc a                                              21

<210> SEQ ID NO 435
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 435
gucauccaca augagaguac a                                              21

<210> SEQ ID NO 436
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 436
cacaaugaga guaccuguga a                                              21

<210> SEQ ID NO 437
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 437
gucucccacc uuuucuucua a                                              21
```

<210> SEQ ID NO 438
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 438 acuuccagc aaaacucccu a                        21

<210> SEQ ID NO 439
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 439
ccucaacugg augaagaaac u                        21

<210> SEQ ID NO 440
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 440
cuguuugcug uguaugauca a                        21

<210> SEQ ID NO 441
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 441
uuugcugugu augaucaaag a                        21

<210> SEQ ID NO 442
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 442
ccgaccagcu uguuugugaa a                        21

<210> SEQ ID NO 443
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 443
uccaaccgac cagcuuguuu a                                      21

<210> SEQ ID NO 444
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 444
ccauuccugu uugcugugua u                                      21

<210> SEQ ID NO 445
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 445
caccuuuucu ucuaaugagu a                                      21

<210> SEQ ID NO 446
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 446
guuugcugug uaugaucaaa a                                      21

<210> SEQ ID NO 447
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 447
gcugagaaga uugacagguu a                                      21

<210> SEQ ID NO 448
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 448
uuccagcaaa acucccucaa a                                      21

<210> SEQ ID NO 449
<211> LENGTH: 21
<212> TYPE: RNA

```
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 449
ugcugagaag auugacaggu u                                               21

<210> SEQ ID NO 450
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 450
ucucacuuuc cagcaaaacu a                                               21

<210> SEQ ID NO 451
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 451
uccacaauga gaguaccugu a                                               21

<210> SEQ ID NO 452
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 452
ccaccucguc auccacaaug a                                               21

<210> SEQ ID NO 453
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 453
ucacuuucca gcaaaacucc a                                               21

<210> SEQ ID NO 454
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 454
ucccucaacu ggaugaagaa a                                               21
```

```
<210> SEQ ID NO 455
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 455
gagaguaccu gugagcagcu a                                              21

<210> SEQ ID NO 456
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 456
agaauuccaa ccgaccagcu u                                              21

<210> SEQ ID NO 457
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 457
cauuccuguu ugcuguguau a                                              21

<210> SEQ ID NO 458
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 458
gaauuccaac cgaccagcuu a                                              21

<210> SEQ ID NO 459
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 459
cauccacaau gagaguaccu a                                              21

<210> SEQ ID NO 460
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
```

-continued

Synthetic oligonucleotide"

<400> SEQUENCE: 460
cccauuccug uuugcugugu a                                    21

<210> SEQ ID NO 461
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 461
cuggguuuau uuuagagaau a                                    21

<210> SEQ ID NO 462
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 462 gcugguuua uuuuagagaa u                                     21

<210> SEQ ID NO 463
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 463
auggcaugca cagugagcua u                                    21

<210> SEQ ID NO 464
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 464
gagagagccc acagagucua a                                    21

<210> SEQ ID NO 465
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 465
gcaagaacca guguuuagcg a                                    21

<210> SEQ ID NO 466
<211> LENGTH: 21

```
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 466
ccagcaaaac ucccucaacu a                                           21

<210> SEQ ID NO 467
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 467
caccucguca uccacaauga a                                           21

<210> SEQ ID NO 468
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 468
cgucauccac aaugagagua a                                           21

<210> SEQ ID NO 469
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 469
cucccacgcu cucuggacuu a                                           21

<210> SEQ ID NO 470
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 470
aacucccuca acuggaugaa a                                           21

<210> SEQ ID NO 471
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 471
```
ugagaagauu gacagguuca u                                        21

<210> SEQ ID NO 472
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 472
ccucgucauc cacaaugaga a                                        21

<210> SEQ ID NO 473
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 473
gagaagauug acagguucau a                                        21

<210> SEQ ID NO 474
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 474
cuucuugggc uuccguauau a                                        21

<210> SEQ ID NO 475
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 475
uccaccucgu cauccacaau a                                        21

<210> SEQ ID NO 476
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 476
agauugacag guucaugcag a                                        21

<210> SEQ ID NO 477
<211> LENGTH: 21
<212> TYPE: RNA
<213> ORGANISM: Artificial Sequence
<220> FEATURE:
<221> NAME/KEY: source

```
<223> OTHER INFORMATION: /note="Description of Artificial Sequence:
      Synthetic oligonucleotide"

<400> SEQUENCE: 477
cucccucaac uggaugaaga a                                             21

<210> SEQ ID NO 478
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 478
aaugagagua ccugugagca a                                             21

<210> SEQ ID NO 479
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 479
ccaccuuuuc uucuaaugag u                                             21

<210> SEQ ID NO 480
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 480
cgaccagcuu guuugugaaa a                                             21

<210> SEQ ID NO 481
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 481
accuuuucuu cuaaugaguc a                                             21

<210> SEQ ID NO 482
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 482
gucauccaca augagaguac a                                             21

<210> SEQ ID NO 483
```

```
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 483
cacaaugaga guaccuguga a                                              21

<210> SEQ ID NO 484
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 484
gucucccacc uuucuucua a                                               21

<210> SEQ ID NO 485
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 485 acuuccagc aaaacuccu a                                                21

<210> SEQ ID NO 486
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 486
ccucaacugg augaagaaac u                                              21

<210> SEQ ID NO 487
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 487
cuguuugcug uguaugauca a                                              21

<210> SEQ ID NO 488
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 488
```
uuugcugugu augaucaaag a                                          21

<210> SEQ ID NO 489
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 489
ccgaccagcu uguuugugaa a                                          21

<210> SEQ ID NO 490
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 490
uccaaccgac cagcuuguuu a                                          21

<210> SEQ ID NO 491
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 491
ccauuccugu uugcugugua u                                          21

<210> SEQ ID NO 492
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 492
caccuuuucu ucuaaugagu a                                          21

<210> SEQ ID NO 493
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 493
guuugcugug uaugaucaaa a                                          21

<210> SEQ ID NO 494
<211> LENGTH: 21
<212> TYPE: RNA
<213> ORGANISM: Artificial Sequence
<220> FEATURE:

<221> NAME/KEY: source
<223> OTHER INFORMATION: /note="Description of Artificial Sequence:
      Synthetic oligonucleotide"

<400> SEQUENCE: 494
gcugagaaga uugacagguu a                                              21

<210> SEQ ID NO 495
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 495
uuccagcaaa acucccucaa a                                              21

<210> SEQ ID NO 496
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 496
ugcugagaag auugacaggu u                                              21

<210> SEQ ID NO 497
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 497
ucucacuuuc cagcaaaacu a                                              21

<210> SEQ ID NO 498
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 498
uccacaauga gaguaccugu a                                              21

<210> SEQ ID NO 499
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 499
ccaccucguc auccacaaug a                                              21

```
<210> SEQ ID NO 500
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 500
ucacuuucca gcaaaacucc a                                              21

<210> SEQ ID NO 501
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 501
ucccucaacu ggaugaagaa a                                              21

<210> SEQ ID NO 502
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 502
gagaguaccu gugagcagcu a                                              21

<210> SEQ ID NO 503
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 503
agaauuccaa ccgaccagcu u                                              21

<210> SEQ ID NO 504
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 504
cauuccuguu ugcuguguau a                                              21

<210> SEQ ID NO 505
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

```
<400> SEQUENCE: 505
gaauuccaac cgaccagcuu a                                              21

<210> SEQ ID NO 506
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 506
cauccacaau gagaguaccu a                                              21

<210> SEQ ID NO 507
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 507
cccauuccug uuugcugugu a                                              21

<210> SEQ ID NO 508
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 508 cugguuuau uuuagagaau a                                               21

<210> SEQ ID NO 509
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 509
gcuggguuua uuuuagagaa u                                              21

<210> SEQ ID NO 510
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 510
auggcaugca cagugagcua u                                              21

<210> SEQ ID NO 511
<211> LENGTH: 21
<212> TYPE: RNA
<213> ORGANISM: Artificial Sequence
```

```
<220> FEATURE:
<221> NAME/KEY: source
<223> OTHER INFORMATION: /note="Description of Artificial Sequence:
      Synthetic oligonucleotide"

<400> SEQUENCE: 511
gagagagccc acagagucua a                                              21

<210> SEQ ID NO 512
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 512
gcaagaacca guguuuagcg a                                              21

<210> SEQ ID NO 513
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 513
ccagcaaaac ucccucaacu a                                              21

<210> SEQ ID NO 514
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 514
caccucguca uccacaauga a                                              21

<210> SEQ ID NO 515
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 515
cgucauccac aaugagagua a                                              21

<210> SEQ ID NO 516
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 516
cucccacgcu cucuggacuu a                                              21
```

<210> SEQ ID NO 517
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 517
aacucccuca acuggaugaa a                                              21

<210> SEQ ID NO 518
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 518
ugagaagauu gacagguuca u                                              21

<210> SEQ ID NO 519
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 519
ccucgucauc cacaaugaga a                                              21

<210> SEQ ID NO 520
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 520
gagaagauug acagguucau a                                              21

<210> SEQ ID NO 521
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 521
cuucuugggc uuccguauau a                                              21

<210> SEQ ID NO 522
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

```
<400> SEQUENCE: 522
uccaccucgu cauccacaau a                                       21

<210> SEQ ID NO 523
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 523
agauugacag guucaugcag a                                       21

<210> SEQ ID NO 524
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 524
cucccucaac uggaugaaga a                                       21

<210> SEQ ID NO 525
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 525
aaugagagua ccugugagca a                                       21

<210> SEQ ID NO 526
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 526
ccaccuuuuc uucuaaugag u                                       21

<210> SEQ ID NO 527
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 527
cgaccagcuu guuugugaaa a                                       21

<210> SEQ ID NO 528
<211> LENGTH: 21
<212> TYPE: RNA
```

```
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 528
accuuuucuu cuaaugaguc a                                           21

<210> SEQ ID NO 529
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 529
gucauccaca augagaguac a                                           21

<210> SEQ ID NO 530
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 530
cacaaugaga guaccuguga a                                           21

<210> SEQ ID NO 531
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 531
gucucccacc uuuucuucua a                                           21

<210> SEQ ID NO 532
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 532 acuuccagc aaaacucccu a                                            21

<210> SEQ ID NO 533
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 533
ccucaacugg augaagaaac u                                           21
```

```
<210> SEQ ID NO 534
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 534
cuguuugcug uguaugauca a                                          21

<210> SEQ ID NO 535
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 535
uuugcugugu augaucaaag a                                          21

<210> SEQ ID NO 536
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 536
ccgaccagcu uguuugugaa a                                          21

<210> SEQ ID NO 537
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 537
uccaaccgac cagcuuguuu a                                          21

<210> SEQ ID NO 538
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 538
ccauuccugu uugcugugua u                                          21

<210> SEQ ID NO 539
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
```

-continued

Synthetic oligonucleotide"

<400> SEQUENCE: 539
caccuuuucu ucuaaugagu a                                           21

<210> SEQ ID NO 540
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 540
guuugcugug uaugaucaaa a                                           21

<210> SEQ ID NO 541
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 541
gcugagaaga uugacagguu a                                           21

<210> SEQ ID NO 542
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 542
uuccagcaaa acucccucaa a                                           21

<210> SEQ ID NO 543
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 543
ugcugagaag auugacaggu u                                           21

<210> SEQ ID NO 544
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 544
ucucacuuuc cagcaaaacu a                                           21

<210> SEQ ID NO 545
<211> LENGTH: 21

```
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 545
uccacaauga gaguaccugu a                                              21

<210> SEQ ID NO 546
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 546
ccaccucguc auccacaaug a                                              21

<210> SEQ ID NO 547
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 547
ucacuuucca gcaaaacucc a                                              21

<210> SEQ ID NO 548
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 548
ucccucaacu ggaugaagaa a                                              21

<210> SEQ ID NO 549
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 549
gagaguaccu gugagcagcu a                                              21

<210> SEQ ID NO 550
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 550
```
agaauuccaa ccgaccagcu u        21

<210> SEQ ID NO 551
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 551
cauuccuguu ugcuguguau a        21

<210> SEQ ID NO 552
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 552
gaauuccaac cgaccagcuu a        21

<210> SEQ ID NO 553
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 553
cauccacaau gagaguaccu a        21

<210> SEQ ID NO 554
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 554
cccauuccug uuugcugugu a        21

<210> SEQ ID NO 555
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 555
cuggguuuau uuuagagaau a        21

<210> SEQ ID NO 556
<211> LENGTH: 21
<212> TYPE: RNA
<213> ORGANISM: Artificial Sequence
<220> FEATURE:
<221> NAME/KEY: source

```
<223> OTHER INFORMATION: /note="Description of Artificial Sequence:
      Synthetic oligonucleotide"

<400> SEQUENCE: 556
gcuggguuua uuuuagagaa u                                           21

<210> SEQ ID NO 557
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 557
auggcaugca cagugagcua u                                           21

<210> SEQ ID NO 558
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 558
gagagagccc acagagucua a                                           21

<210> SEQ ID NO 559
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 559
gcaagaacca guguuuagcg a                                           21

<210> SEQ ID NO 560
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 560
ccagcaaaac ucccucaacu a                                           21

<210> SEQ ID NO 561
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 561
caccucguca uccacaauga a                                           21

<210> SEQ ID NO 562
```

```
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 562
cgucauccac aaugagagua a                                            21

<210> SEQ ID NO 563
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 563
cucccacgcu cucuggacuu a                                            21

<210> SEQ ID NO 564
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 564
aacucccuca acuggaugaa a                                            21

<210> SEQ ID NO 565
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 565
ugagaagauu gacagguuca u                                            21

<210> SEQ ID NO 566
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 566
ccucgucauc cacaaugaga a                                            21

<210> SEQ ID NO 567
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 567
```
gagaagauug acagguucau a                                        21

<210> SEQ ID NO 568
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 568
cuucuugggc uuccguauau a                                        21

<210> SEQ ID NO 569
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 569
uccaccucgu cauccacaau a                                        21

<210> SEQ ID NO 570
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 570
agauugacag guucaugcag a                                        21

<210> SEQ ID NO 571
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 571
cucccucaac uggaugaaga a                                        21

<210> SEQ ID NO 572
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 572
aaugagagua ccugugagca a                                        21

<210> SEQ ID NO 573
<211> LENGTH: 23
<212> TYPE: RNA
<213> ORGANISM: Artificial Sequence
<220> FEATURE:

```
<221> NAME/KEY: source
<223> OTHER INFORMATION: /note="Description of Artificial Sequence:
      Synthetic oligonucleotide"

<400> SEQUENCE: 573
uucacaggua cucucauugu gga                                               23

<210> SEQ ID NO 574
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 574
uuagaagaaa agguggaga cug                                                23

<210> SEQ ID NO 575
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 575
uagggaguuu ugcuggaaag uga                                               23

<210> SEQ ID NO 576
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 576
aguuucuuca uccaguugag gga                                               23

<210> SEQ ID NO 577
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 577
uugaucauac acagcaaaca gga                                               23

<210> SEQ ID NO 578
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 578
ucuuugauca uacacagcaa aca                                               23
```

```
<210> SEQ ID NO 579
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 579
uuucacaaac aagcuggucg guu                                          23

<210> SEQ ID NO 580
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 580
uaaacaagcu ggucgguugg aau                                          23

<210> SEQ ID NO 581
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 581
auacacagca aacaggaaug ggc                                          23

<210> SEQ ID NO 582
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 582
uacucauuag aagaaaaggu ggg                                          23

<210> SEQ ID NO 583
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 583
uuuugaucau acacagcaaa cag                                          23

<210> SEQ ID NO 584
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

```
<400> SEQUENCE: 584
uaaccuguca aucuucucag cag                                              23

<210> SEQ ID NO 585
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 585
uuugagggag uuuugcugga aag                                              23

<210> SEQ ID NO 586
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 586
aaccugucaa ucuucucagc agc                                              23

<210> SEQ ID NO 587
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 587
uaguuuugcu ggaaagugag acc                                              23

<210> SEQ ID NO 588
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 588
uacagguacu cucauugugg aug                                              23

<210> SEQ ID NO 589
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 589 ucauuggga ugacgaggug gaa                                               23

<210> SEQ ID NO 590
<211> LENGTH: 23
<212> TYPE: RNA
<213> ORGANISM: Artificial Sequence
```

```
-continued

<220> FEATURE:
<221> NAME/KEY: source
<223> OTHER INFORMATION: /note="Description of Artificial Sequence:
      Synthetic oligonucleotide"

<400> SEQUENCE: 590
uggaguuuug cuggaaagug aga                                              23

<210> SEQ ID NO 591
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 591
uuucuucauc caguugaggg agu                                              23

<210> SEQ ID NO 592
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 592
uagcugcuca cagguacucu cau                                              23

<210> SEQ ID NO 593
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 593
aagcuggucg guuggaauuc uuu                                              23

<210> SEQ ID NO 594
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 594
uauacacagc aaacaggaau ggg                                              23

<210> SEQ ID NO 595
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 595
uaagcugguc gguuggaauu cuu                                              23
```

```
<210> SEQ ID NO 596
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 596
uagguacucu cauugguggau gac                                         23

<210> SEQ ID NO 597
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 597
uacacagcaa acaggaaugg gcg                                          23

<210> SEQ ID NO 598
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 598
uauucucuaa aauaaaccca gca                                          23

<210> SEQ ID NO 599
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 599
auucucuaaa auaaacccag caa                                          23

<210> SEQ ID NO 600
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 600
auagcucacu gugcaugcca uau                                          23

<210> SEQ ID NO 601
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

```
<400> SEQUENCE: 601
uuagacucug ugggcucucu cuc                                          23

<210> SEQ ID NO 602
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 602
ucgcuaaaca cugguucuug ccu                                          23

<210> SEQ ID NO 603
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 603
uaguugaggg aguuuugcug gaa                                          23

<210> SEQ ID NO 604
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 604
uucauugugg augacgaggu gga                                          23

<210> SEQ ID NO 605
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 605
uuacucucau uguggaugac gag                                          23

<210> SEQ ID NO 606
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 606
uaaguccaga gagcguggga gga                                          23

<210> SEQ ID NO 607
<211> LENGTH: 23
<212> TYPE: RNA
```

```
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 607
uuucauccag uugagggagu uuu                                             23

<210> SEQ ID NO 608
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 608
augaaccugu caaucuucuc agc                                             23

<210> SEQ ID NO 609
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 609
uucucauugu ggaugacgag gug                                             23

<210> SEQ ID NO 610
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 610
uaugaaccug ucaaucuucu cag                                             23

<210> SEQ ID NO 611
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 611
uauauacgga agcccaagaa guu                                             23

<210> SEQ ID NO 612
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 612 uauugggau gacgaggugg aag                                              23
```

```
<210> SEQ ID NO 613
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 613
ucugcaugaa ccugucaauc uuc                                            23

<210> SEQ ID NO 614
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 614
uucuucaucc aguugaggga guu                                            23

<210> SEQ ID NO 615
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 615
uugcucacag guacucucau ugu                                            23

<210> SEQ ID NO 616
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 616
acucauuaga agaaaaggug gga                                            23

<210> SEQ ID NO 617
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 617
uuuucacaaa caagcugguc ggu                                            23

<210> SEQ ID NO 618
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
```

-continued

Synthetic oligonucleotide"

<400> SEQUENCE: 618
ugacucauua gaagaaaagg ugg                                    23

<210> SEQ ID NO 619
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 619
uguacucuca uuguggauga cga                                    23

<210> SEQ ID NO 620
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 620
uucacaggua cucucauugu gga                                    23

<210> SEQ ID NO 621
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 621
uuagaagaaa aggugggaga cug                                    23

<210> SEQ ID NO 622
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 622
uagggaguuu ugcuggaaag uga                                    23

<210> SEQ ID NO 623
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 623
aguuucuuca uccaguugag gga                                    23

<210> SEQ ID NO 624
<211> LENGTH: 23

```
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 624
uugaucauac acagcaaaca gga                                            23

<210> SEQ ID NO 625
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 625
ucuuugauca uacacagcaa aca                                            23

<210> SEQ ID NO 626
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 626
uuucacaaac aagcuggucg guu                                            23

<210> SEQ ID NO 627
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 627
uaaacaagcu ggucgguugg aau                                            23

<210> SEQ ID NO 628
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 628
auacacagca aacaggaaug ggc                                            23

<210> SEQ ID NO 629
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 629
```

-continued uacucauuag aagaaaaggu ggg    23

<210> SEQ ID NO 630
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 630
uuuugaucau acacagcaaa cag    23

<210> SEQ ID NO 631
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 631
uaaccuguca aucuucucag cag    23

<210> SEQ ID NO 632
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 632
uuugagggag uuuugcugga aag    23

<210> SEQ ID NO 633
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 633
aaccugucaa ucuucucagc agc    23

<210> SEQ ID NO 634
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 634
uaguuuugcu ggaaagugag acc    23

<210> SEQ ID NO 635
<211> LENGTH: 23
<212> TYPE: RNA
<213> ORGANISM: Artificial Sequence
<220> FEATURE:
<221> NAME/KEY: source -continued
<223> OTHER INFORMATION: /note="Description of Artificial Sequence:
      Synthetic oligonucleotide"

<400> SEQUENCE: 635
uacagguacu cucauugugg aug                                              23

<210> SEQ ID NO 636
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 636
ucauugugga ugacgaggug gaa                                              23

<210> SEQ ID NO 637
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 637
uggaguuuug cuggaaagug aga                                              23

<210> SEQ ID NO 638
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 638
uuucuucauc caguugaggg agu                                              23

<210> SEQ ID NO 639
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 639
uagcugcuca cagguacucu cau                                              23

<210> SEQ ID NO 640
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 640
aagcuggucg guuggaauuc uuu                                              23

<210> SEQ ID NO 641

```
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 641
uauacacagc aaacaggaau ggg                                                 23

<210> SEQ ID NO 642
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 642
uaagcugguc gguuggaauu cuu                                                 23

<210> SEQ ID NO 643
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 643
uagguacucu cauuguggau gac                                                 23

<210> SEQ ID NO 644
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 644
uacacagcaa acaggaaugg gcg                                                 23

<210> SEQ ID NO 645
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 645
uauucucuaa aauaaaccca gca                                                 23

<210> SEQ ID NO 646
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 646
```
auucucuaaa auaaacccag caa                                           23

<210> SEQ ID NO 647
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 647
auagcucacu gugcaugcca uau                                           23

<210> SEQ ID NO 648
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 648
uuagacucug ugggcucucu cuc                                           23

<210> SEQ ID NO 649
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 649
ucgcuaaaca cugguucuug ccu                                           23

<210> SEQ ID NO 650
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 650
uaguugaggg aguuuugcug gaa                                           23

<210> SEQ ID NO 651
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 651
uucauugugg augacgaggu gga                                           23

<210> SEQ ID NO 652
<211> LENGTH: 23
<212> TYPE: RNA
<213> ORGANISM: Artificial Sequence
<220> FEATURE:

```
<221> NAME/KEY: source
<223> OTHER INFORMATION: /note="Description of Artificial Sequence:
      Synthetic oligonucleotide"

<400> SEQUENCE: 652
uuacucucau uguggaugac gag                                           23

<210> SEQ ID NO 653
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 653
uaaguccaga gagcguggga gga                                           23

<210> SEQ ID NO 654
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 654
uuucauccag uugagggagu uuu                                           23

<210> SEQ ID NO 655
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 655
augaaccugu caaucuucuc agc                                           23

<210> SEQ ID NO 656
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 656
uucucauugu ggaugacgag gug                                           23

<210> SEQ ID NO 657
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 657
uaugaaccug ucaaucuucu cag                                           23
```

```
<210> SEQ ID NO 658
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 658
uauauacgga agcccaagaa guu                                              23

<210> SEQ ID NO 659
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 659
uauuguggau gacgaggugg aag                                              23

<210> SEQ ID NO 660
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 660
ucugcaugaa ccugucaauc uuc                                              23

<210> SEQ ID NO 661
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 661
uucuucaucc aguugaggga guu                                              23

<210> SEQ ID NO 662
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 662
uugcucacag guacucucau ugu                                              23

<210> SEQ ID NO 663
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
```

```
<221> NAME/KEY: source
<223> OTHER INFORMATION: /note="Description of Combined DNA/RNA
      Molecule: Synthetic oligonucleotide"

<400> SEQUENCE: 663
acucatuaga agaaaaggug gga                                              23

<210> SEQ ID NO 664
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 664
uuuucacaaa caagcugguc ggu                                              23

<210> SEQ ID NO 665
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 665
ugacucauua gaagaaaagg ugg                                              23

<210> SEQ ID NO 666
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 666
uguactcuca uuguggauga cga                                              23

<210> SEQ ID NO 667
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 667
uucacaggua cucucauugu gga                                              23

<210> SEQ ID NO 668
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 668
```
uuagaagaaa aggugggaga cug                23

<210> SEQ ID NO 669
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
    Synthetic oligonucleotide"

<400> SEQUENCE: 669
uagggaguuu ugcuggaaag uga                23

<210> SEQ ID NO 670
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
    Synthetic oligonucleotide"

<400> SEQUENCE: 670 aguucuuca uccaguugag gga                23

<210> SEQ ID NO 671
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
    Synthetic oligonucleotide"

<400> SEQUENCE: 671
uugaucauac acagcaaaca gga                23

<210> SEQ ID NO 672
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
    Synthetic oligonucleotide"

<400> SEQUENCE: 672
ucuuugauca uacacagcaa aca                23

<210> SEQ ID NO 673
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
    Synthetic oligonucleotide"

<400> SEQUENCE: 673
uuucacaaac aagcuggucg guu                23

<210> SEQ ID NO 674
<211> LENGTH: 23
<212> TYPE: RNA
<213> ORGANISM: Artificial Sequence
<220> FEATURE:

```
<221> NAME/KEY: source
<223> OTHER INFORMATION: /note="Description of Artificial Sequence:
      Synthetic oligonucleotide"

<400> SEQUENCE: 674
uaaacaagcu ggucgguugg aau                                          23

<210> SEQ ID NO 675
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 675
auacacagca aacaggaaug ggc                                          23

<210> SEQ ID NO 676
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 676
uacucauuag aagaaaaggu ggg                                          23

<210> SEQ ID NO 677
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 677
uuuugaucau acacagcaaa cag                                          23

<210> SEQ ID NO 678
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 678
uaacctguca aucuucucag cag                                          23

<210> SEQ ID NO 679
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 679
```
uuugagggag uuuugcugga aag				23

<210> SEQ ID NO 680
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 680
aaccugucaa ucuucucagc agc				23

<210> SEQ ID NO 681
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 681
uaguutugcu ggaaagugag acc				23

<210> SEQ ID NO 682
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 682
uacagguacu cucauugugg aug				23

<210> SEQ ID NO 683
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 683
ucauugugga ugacgaggug gaa				23

<210> SEQ ID NO 684
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 684
uggagtuuug cuggaaagug aga                                              23

<210> SEQ ID NO 685
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 685
uuucutcauc caguugaggg agu                                              23

<210> SEQ ID NO 686
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 686
uagcugcuca cagguacucu cau                                              23

<210> SEQ ID NO 687
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 687
aagcuggucg guuggaauuc uuu                                              23

<210> SEQ ID NO 688
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 688
uauacacagc aaacaggaau ggg                                              23

<210> SEQ ID NO 689
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 689
uaagctgguc gguuggaauu cuu                                              23

```
<210> SEQ ID NO 690
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 690
uagguacucu cauugugggau gac                                              23

<210> SEQ ID NO 691
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 691
uacacagcaa acaggaaugg gcg                                               23

<210> SEQ ID NO 692
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 692
uauuctcuaa aauaaaccca gca                                               23

<210> SEQ ID NO 693
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 693
auucucuaaa auaaacccag caa                                               23

<210> SEQ ID NO 694
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 694
auagctcacu gugcaugcca uau                                               23
```

```
<210> SEQ ID NO 695
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 695
uuagacucug ugggcucucu cuc                                        23

<210> SEQ ID NO 696
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 696
ucgcuaaaca cugguucuug ccu                                        23

<210> SEQ ID NO 697
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 697
uaguugaggg aguuuugcug gaa                                        23

<210> SEQ ID NO 698
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 698
uucautgugg augacgaggu gga                                        23

<210> SEQ ID NO 699
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 699
uuacucucau uuggaugac gag                                         23

<210> SEQ ID NO 700
<211> LENGTH: 23
<212> TYPE: RNA
<213> ORGANISM: Artificial Sequence
```

```
-continued

<220> FEATURE:
<221> NAME/KEY: source
<223> OTHER INFORMATION: /note="Description of Artificial Sequence:
      Synthetic oligonucleotide"

<400> SEQUENCE: 700
uaaguccaga gagcguggga gga                                              23

<210> SEQ ID NO 701
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 701
uuucatccag uugagggagu uuu                                              23

<210> SEQ ID NO 702
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 702
augaaccugu caaucuucuc agc                                              23

<210> SEQ ID NO 703
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 703
uucucauugu ggaugacgag gug                                              23

<210> SEQ ID NO 704
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 704
uaugaaccug ucaaucuucu cag                                              23

<210> SEQ ID NO 705
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

```
<400> SEQUENCE: 705
uauauacgga agcccaagaa guu                                        23

<210> SEQ ID NO 706
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 706
uauugtggau gacgaggugg aag                                        23

<210> SEQ ID NO 707
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 707
ucugcaugaa ccugucaauc uuc                                        23

<210> SEQ ID NO 708
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 708
uucuucaucc aguugaggga guu                                        23

<210> SEQ ID NO 709
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 709
uugcucacag guacucucau ugu                                        23

<210> SEQ ID NO 710
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 710
```
acucauuaga agaaaaggug gga                                      23

<210> SEQ ID NO 711
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 711
uuuucacaaa caagcugguc ggu                                      23

<210> SEQ ID NO 712
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 712
ugacucauua gaagaaaagg ugg                                      23

<210> SEQ ID NO 713
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 713
uguacucuca uuguggauga cga                                      23

<210> SEQ ID NO 714
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 714
uucacaggua cucucauugu gga                                      23

<210> SEQ ID NO 715
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 715
uuagaagaaa aggugggaga cug                                      23

<210> SEQ ID NO 716
<211> LENGTH: 23
<212> TYPE: RNA
<213> ORGANISM: Artificial Sequence
<220> FEATURE:

```
<221> NAME/KEY: source
<223> OTHER INFORMATION: /note="Description of Artificial Sequence:
      Synthetic oligonucleotide"

<400> SEQUENCE: 716
uagggaguuu ugcuggaaag uga                                          23

<210> SEQ ID NO 717
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 717
aguuuctuca uccaguugag gga                                          23

<210> SEQ ID NO 718
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 718
uugaucauac acagcaaaca gga                                          23

<210> SEQ ID NO 719
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 719
ucuuugauca uacacagcaa aca                                          23

<210> SEQ ID NO 720
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 720
uuucacaaac aagcuggucg guu                                          23

<210> SEQ ID NO 721
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 721
```
uaaacaagcu ggucgguugg aau                                               23

<210> SEQ ID NO 722
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 722
auacacagca aacaggaaug ggc                                               23

<210> SEQ ID NO 723
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 723
uacucauaag aagaaaaggu ggg                                               23

<210> SEQ ID NO 724
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 724
uuuugatcau acacagcaaa cag                                               23

<210> SEQ ID NO 725
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 725
uaaccuguca aucuucucag cag                                               23

<210> SEQ ID NO 726
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 726
uuugagggag uuuugcugga aag        23

<210> SEQ ID NO 727
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 727
aaccugtcaa ucuucucagc agc        23

<210> SEQ ID NO 728
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 728
uaguuutgcu ggaaagugag acc        23

<210> SEQ ID NO 729
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 729
uacaggtacu cucauugugg aug        23

<210> SEQ ID NO 730
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 730
ucauugtgga ugacgaggug gaa        23

<210> SEQ ID NO 731
<211> LENGTH: 23
<212> TYPE: DNA
<213> ORGANISM: Artificial Sequence

```
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 731 uggaguuug cuggaaagug aga                                        23

<210> SEQ ID NO 732
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 732
uuucuucauc caguugaggg agu                                       23

<210> SEQ ID NO 733
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 733
uagcugcuca cagguacucu cau                                       23

<210> SEQ ID NO 734
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 734
aagcuggucg guuggaauuc uuu                                       23

<210> SEQ ID NO 735
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 735
uauacacagc aaacaggaau ggg                                       23

<210> SEQ ID NO 736
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

```
<400> SEQUENCE: 736
uaagcugguc gguuggaauu cuu                                          23

<210> SEQ ID NO 737
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 737
uagguacucu cauuguggau gac                                          23

<210> SEQ ID NO 738
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 738
uacacagcaa acaggaaugg gcg                                          23

<210> SEQ ID NO 739
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 739
uauucucuaa aauaaaccca gca                                          23

<210> SEQ ID NO 740
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 740
auucuctaaa auaaacccag caa                                          23

<210> SEQ ID NO 741
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 741
auagcucacu gugcaugcca uau                                          23
```

```
<210> SEQ ID NO 742
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 742
uuagactcug ugggcucucu cuc                                           23

<210> SEQ ID NO 743
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 743
ucgcuaaaca cugguucuug ccu                                           23

<210> SEQ ID NO 744
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 744
uaguugaggg aguuuugcug gaa                                           23

<210> SEQ ID NO 745
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 745
uucauugugg augacgaggu gga                                           23

<210> SEQ ID NO 746
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 746
uuacuctcau uguggaugac gag                                           23

<210> SEQ ID NO 747
```

```
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 747
uaaguccaga gagcguggga gga                                                23

<210> SEQ ID NO 748
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 748
uuucauccag uugagggagu uuu                                                23

<210> SEQ ID NO 749
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 749
augaaccugu caaucuucuc agc                                                23

<210> SEQ ID NO 750
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 750
uucucatugu ggaugacgag gug                                                23

<210> SEQ ID NO 751
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 751
uaugaaccug ucaaucuucu cag                                                23

<210> SEQ ID NO 752
<211> LENGTH: 23
<212> TYPE: RNA
<213> ORGANISM: Artificial Sequence
<220> FEATURE:
<221> NAME/KEY: source
```

```
<223> OTHER INFORMATION: /note="Description of Artificial Sequence:
      Synthetic oligonucleotide"

<400> SEQUENCE: 752
uauauacgga agcccaagaa guu                                              23

<210> SEQ ID NO 753
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 753
uauuguggau gacgaggugg aag                                              23

<210> SEQ ID NO 754
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 754
ucugcatgaa ccugucaauc uuc                                              23

<210> SEQ ID NO 755
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 755
uucuucaucc aguugaggga guu                                              23

<210> SEQ ID NO 756
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 756
uugcucacag guacucucau ugu                                              23

<210> SEQ ID NO 757
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 757
```

```
uccacaauga gaguaccugu gag                                              23

<210> SEQ ID NO 758
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 758
cagucuccca ccuuuucuuc uaa                                              23

<210> SEQ ID NO 759
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 759
ucacuuucca gcaaaacucc cuc                                              23

<210> SEQ ID NO 760
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 760
ucccucaacu ggaugaagaa acu                                              23

<210> SEQ ID NO 761
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 761
uccuguuugc uguguaugau caa                                              23

<210> SEQ ID NO 762
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 762
uguuugcugu guaugaucaa agc                                              23

<210> SEQ ID NO 763
<211> LENGTH: 23
<212> TYPE: RNA
<213> ORGANISM: Artificial Sequence
<220> FEATURE:
<221> NAME/KEY: source
```

```
<223> OTHER INFORMATION: /note="Description of Artificial Sequence:
      Synthetic oligonucleotide"

<400> SEQUENCE: 763
aaccgaccag cuuguuugug aaa                                              23

<210> SEQ ID NO 764
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 764
auuccaaccg accagcuugu uug                                              23

<210> SEQ ID NO 765
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 765
gcccauuccu guuugcugug uau                                              23

<210> SEQ ID NO 766
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 766
cccaccuuuu cuucuaauga guc                                              23

<210> SEQ ID NO 767
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 767
cuguuugcug uguaugauca aag                                              23

<210> SEQ ID NO 768
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 768
cugcugagaa gauugacagg uuc                                              23

<210> SEQ ID NO 769
```

```
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 769
cuuuccagca aaacuccuc aac                                            23

<210> SEQ ID NO 770
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 770
gcugcugaga agauugacag guu                                           23

<210> SEQ ID NO 771
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 771
ggucucacuu uccagcaaaa cuc                                           23

<210> SEQ ID NO 772
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 772
cauccacaau gagaguaccu gug                                           23

<210> SEQ ID NO 773
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 773
uuccaccucg ucauccacaa uga                                           23

<210> SEQ ID NO 774
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 774
```
ucucacuuuc cagcaaaacu ccc                                            23

<210> SEQ ID NO 775
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 775
acucccucaa cuggaugaag aaa                                            23

<210> SEQ ID NO 776
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 776
augagaguac cugugagcag cug                                            23

<210> SEQ ID NO 777
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 777
aaagaauucc aaccgaccag cuu                                            23

<210> SEQ ID NO 778
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 778
cccauuccug uuugcugugu aug                                            23

<210> SEQ ID NO 779
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 779
aagaauucca accgaccagc uug                                            23

<210> SEQ ID NO 780
<211> LENGTH: 23
<212> TYPE: RNA
<213> ORGANISM: Artificial Sequence
<220> FEATURE:

```
<221> NAME/KEY: source
<223> OTHER INFORMATION: /note="Description of Artificial Sequence:
      Synthetic oligonucleotide"

<400> SEQUENCE: 780
gucauccaca augagaguac cug                                              23

<210> SEQ ID NO 781
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 781
cgcccauucc uguuugcugu gua                                              23

<210> SEQ ID NO 782
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 782
ugcuggguuu auuuuagaga aug                                              23

<210> SEQ ID NO 783
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 783
uugcuggguu uauuuuagag aau                                              23

<210> SEQ ID NO 784
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 784
auauggcaug cacagugagc uau                                              23

<210> SEQ ID NO 785
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 785
gagagagagc ccacagaguc uac                                              23
```

```
<210> SEQ ID NO 786
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 786
aggcaagaac caguguuuag cgc                                            23

<210> SEQ ID NO 787
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 787
uuccagcaaa acucccucaa cug                                            23

<210> SEQ ID NO 788
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 788
uccaccucgu cauccacaau gag                                            23

<210> SEQ ID NO 789
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 789
cucgucaucc acaaugagag uac                                            23

<210> SEQ ID NO 790
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 790
uccucccacg cucucuggac uuc                                            23

<210> SEQ ID NO 791
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

```
<400> SEQUENCE: 791
aaaacucccu caacuggaug aag                                          23

<210> SEQ ID NO 792
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 792
gcugagaaga uugacagguu cau                                          23

<210> SEQ ID NO 793
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 793
caccucguca uccacaauga gag                                          23

<210> SEQ ID NO 794
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 794
cugagaagau ugacagguuc aug                                          23

<210> SEQ ID NO 795
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 795
aacuucuugg gcuuccguau aua                                          23

<210> SEQ ID NO 796
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 796
cuuccaccuc gucauccaca aug                                          23

<210> SEQ ID NO 797
<211> LENGTH: 23
<212> TYPE: RNA
<213> ORGANISM: Artificial Sequence
```

```
-continued

<220> FEATURE:
<221> NAME/KEY: source
<223> OTHER INFORMATION: /note="Description of Artificial Sequence:
      Synthetic oligonucleotide"

<400> SEQUENCE: 797
gaagauugac agguucaugc agg                                             23

<210> SEQ ID NO 798
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 798
aacucccuca acuggaugaa gaa                                             23

<210> SEQ ID NO 799
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 799
acaaugagag uaccugugag cag                                             23

<210> SEQ ID NO 800
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 800
ucccaccuuu ucuucuaaug agu                                             23

<210> SEQ ID NO 801
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 801
accgaccagc uuguuuguga aac                                             23

<210> SEQ ID NO 802
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 802
ccaccuuuuc uucuaaugag ucg                                             23
```

```
<210> SEQ ID NO 803
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 803
ucgucaucca caaugagagu acc                                              23

<210> SEQ ID NO 804
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 804
uccacaauga gaguaccugu gag                                              23

<210> SEQ ID NO 805
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 805
cagucuccca ccuuuucuuc uaa                                              23

<210> SEQ ID NO 806
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 806
ucacuuucca gcaaaacucc cuc                                              23

<210> SEQ ID NO 807
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 807
ucccucaacu ggaugaagaa acu                                              23

<210> SEQ ID NO 808
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

```
<400> SEQUENCE: 808
uccuguuugc uguguaugau caa                                              23

<210> SEQ ID NO 809
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 809
uguuugcugu guaugaucaa agc                                              23

<210> SEQ ID NO 810
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 810
aaccgaccag cuuguuugug aaa                                              23

<210> SEQ ID NO 811
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 811
auuccaaccg accagcuugu uug                                              23

<210> SEQ ID NO 812
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 812
gcccauuccu guuugcugug uau                                              23

<210> SEQ ID NO 813
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 813
cccaccuuuu cuucuaauga guc                                              23

<210> SEQ ID NO 814
<211> LENGTH: 23
<212> TYPE: RNA
```

```
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 814
cuguuugcug uguaugauca aag                                              23

<210> SEQ ID NO 815
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 815
cugcugagaa gauugacagg uuc                                              23

<210> SEQ ID NO 816
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 816
cuuuccagca aaacucccuc aac                                              23

<210> SEQ ID NO 817
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 817
gcugcugaga agauugacag guu                                              23

<210> SEQ ID NO 818
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 818
ggucucacuu uccagcaaaa cuc                                              23

<210> SEQ ID NO 819
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 819
cauccacaau gagaguaccu gug                                              23
```

<210> SEQ ID NO 820
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 820
uuccaccucg ucauccacaa uga                                         23

<210> SEQ ID NO 821
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 821
ucucacuuuc cagcaaaacu ccc                                         23

<210> SEQ ID NO 822
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 822
acucccucaa cuggaugaag aaa                                         23

<210> SEQ ID NO 823
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 823
augagaguac cugugagcag cug                                         23

<210> SEQ ID NO 824
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 824
aaagaauucc aaccgaccag cuu                                         23

<210> SEQ ID NO 825
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:

Synthetic oligonucleotide"

<400> SEQUENCE: 825
cccauuccug uuugcugugu aug					23

<210> SEQ ID NO 826
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 826
aagaauucca accgaccagc uug					23

<210> SEQ ID NO 827
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 827
gucauccaca augagaguac cug					23

<210> SEQ ID NO 828
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 828
cgcccauucc uguuugcugu gua					23

<210> SEQ ID NO 829
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 829
ugcuggguuu auuuuagaga aug					23

<210> SEQ ID NO 830
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 830
uugcuggguu uauuuuagag aau					23

<210> SEQ ID NO 831
<211> LENGTH: 23

```
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 831
auauggcaug cacagugagc uau                                            23

<210> SEQ ID NO 832
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 832
gagagagagc ccacagaguc uac                                            23

<210> SEQ ID NO 833
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 833
aggcaagaac caguguuuag cgc                                            23

<210> SEQ ID NO 834
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 834
uuccagcaaa acucccucaa cug                                            23

<210> SEQ ID NO 835
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 835
uccaccucgu cauccacaau gag                                            23

<210> SEQ ID NO 836
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 836
```
cucgucaucc acaaugagag uac                                          23

<210> SEQ ID NO 837
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 837
uccucccacg cucucuggac uuc                                          23

<210> SEQ ID NO 838
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 838
aaaacucccu caacuggaug aag                                          23

<210> SEQ ID NO 839
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 839
gcugagaaga uugacagguu cau                                          23

<210> SEQ ID NO 840
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 840
caccucguca uccacaauga gag                                          23

<210> SEQ ID NO 841
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 841
cugagaagau ugacagguuc aug                                          23

<210> SEQ ID NO 842
<211> LENGTH: 23
<212> TYPE: RNA
<213> ORGANISM: Artificial Sequence
<220> FEATURE:
<221> NAME/KEY: source

```
<223> OTHER INFORMATION: /note="Description of Artificial Sequence:
      Synthetic oligonucleotide"

<400> SEQUENCE: 842
aacuucuugg gcuuccguau aua                                              23

<210> SEQ ID NO 843
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 843
cuuccaccuc gucauccaca aug                                              23

<210> SEQ ID NO 844
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 844
gaagauugac agguucaugc agg                                              23

<210> SEQ ID NO 845
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 845
aacucccuca acuggaugaa gaa                                              23

<210> SEQ ID NO 846
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 846
acaaugagag uaccugugag cag                                              23

<210> SEQ ID NO 847
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 847
ucccaccuuu ucuucuaaug agu                                              23

<210> SEQ ID NO 848
```

```
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 848
accgaccagc uuguuguga aac                                                 23

<210> SEQ ID NO 849
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 849
ccaccuuuuc uucuaaugag ucg                                                23

<210> SEQ ID NO 850
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 850
ucgucaucca caaugagagu acc                                                23

<210> SEQ ID NO 851
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 851
uccacaauga gaguaccugu gag                                                23

<210> SEQ ID NO 852
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 852
cagucuccca ccuuuucuuc uaa                                                23

<210> SEQ ID NO 853
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 853
```
ucacuuucca gcaaaacucc cuc                                              23

<210> SEQ ID NO 854
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 854
ucccucaacu ggaugaagaa acu                                              23

<210> SEQ ID NO 855
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 855
uccuguuugc uguguaugau caa                                              23

<210> SEQ ID NO 856
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 856
uguuugcugu guaugaucaa agc                                              23

<210> SEQ ID NO 857
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 857
aaccgaccag cuuguuugug aaa                                              23

<210> SEQ ID NO 858
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 858
auuccaaccg accagcuugu uug                                              23

<210> SEQ ID NO 859
<211> LENGTH: 23
<212> TYPE: RNA
<213> ORGANISM: Artificial Sequence
<220> FEATURE:

```
<221> NAME/KEY: source
<223> OTHER INFORMATION: /note="Description of Artificial Sequence:
      Synthetic oligonucleotide"

<400> SEQUENCE: 859
gcccauuccu guuugcugug uau                                           23

<210> SEQ ID NO 860
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 860
cccaccuuuu cuucuaauga guc                                           23

<210> SEQ ID NO 861
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 861
cuguuugcug uguaugauca aag                                           23

<210> SEQ ID NO 862
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 862
cugcugagaa gauugacagg uuc                                           23

<210> SEQ ID NO 863
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 863
cuuuccagca aaacucccuc aac                                           23

<210> SEQ ID NO 864
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 864
gcugcugaga agauugacag guu                                           23
```

```
<210> SEQ ID NO 865
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 865
ggucucacuu uccagcaaaa cuc                                          23

<210> SEQ ID NO 866
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 866
cauccacaau gagaguaccu gug                                          23

<210> SEQ ID NO 867
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 867
uuccaccucg ucauccacaa uga                                          23

<210> SEQ ID NO 868
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 868
ucucacuuuc cagcaaaacu ccc                                          23

<210> SEQ ID NO 869
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 869
acucccucaa cuggaugaag aaa                                          23

<210> SEQ ID NO 870
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

```
<400> SEQUENCE: 870
augagaguac cugugagcag cug                                        23

<210> SEQ ID NO 871
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 871
aaagaauucc aaccgaccag cuu                                        23

<210> SEQ ID NO 872
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 872
cccauuccug uuugcugugu aug                                        23

<210> SEQ ID NO 873
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 873
aagaauucca accgaccagc uug                                        23

<210> SEQ ID NO 874
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 874
gucauccaca augagaguac cug                                        23

<210> SEQ ID NO 875
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 875
cgcccauucc uguuugcugu gua                                        23

<210> SEQ ID NO 876
<211> LENGTH: 23
<212> TYPE: RNA
<213> ORGANISM: Artificial Sequence
```

```
<220> FEATURE:
<221> NAME/KEY: source
<223> OTHER INFORMATION: /note="Description of Artificial Sequence:
      Synthetic oligonucleotide"

<400> SEQUENCE: 876
ugcuggguuu auuuuagaga aug                                           23

<210> SEQ ID NO 877
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 877
uugcuggguu uauuuuagag aau                                           23

<210> SEQ ID NO 878
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 878
auauggcaug cacagugagc uau                                           23

<210> SEQ ID NO 879
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 879
gagagagagc ccacagaguc uac                                           23

<210> SEQ ID NO 880
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 880
aggcaagaac caguguuuag cgc                                           23

<210> SEQ ID NO 881
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 881
uuccagcaaa acucccucaa cug                                           23
```

<210> SEQ ID NO 882
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 882
uccaccucgu cauccacaau gag                                              23

<210> SEQ ID NO 883
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 883
cucgucaucc acaaugagag uac                                              23

<210> SEQ ID NO 884
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 884
uccucccacg cucucuggac uuc                                              23

<210> SEQ ID NO 885
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 885
aaaacuuccu caacuggaug aag                                              23

<210> SEQ ID NO 886
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 886
gcugagaaga uugacagguu cau                                              23

<210> SEQ ID NO 887
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 887
caccucguca uccacaauga gag                                            23

<210> SEQ ID NO 888
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 888
cugagaagau ugacagguuc aug                                            23

<210> SEQ ID NO 889
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 889
aacuucuugg gcuuccguau aua                                            23

<210> SEQ ID NO 890
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 890
cuuccaccuc gucauccaca aug                                            23

<210> SEQ ID NO 891
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 891
gaagauugac agguucaugc agg                                            23

<210> SEQ ID NO 892
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 892
aacucccuca acuggaugaa gaa                                            23

<210> SEQ ID NO 893
<211> LENGTH: 23
<212> TYPE: RNA

```
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 893
acaaugagag uaccugugag cag                                              23

<210> SEQ ID NO 894
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 894
ucccaccuuu ucuucuaaug agu                                              23

<210> SEQ ID NO 895
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 895
accgaccagc uuguuuguga aac                                              23

<210> SEQ ID NO 896
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 896
ccaccuuuuc uucuaaugag ucg                                              23

<210> SEQ ID NO 897
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 897
ucgucaucca caaugagagu acc                                              23

<210> SEQ ID NO 898
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 898
uccacaauga gaguaccugu gag                                              23
```

```
<210> SEQ ID NO 899
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 899
cagucuccca ccuuuucuuc uaa                                              23

<210> SEQ ID NO 900
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 900
ucacuuucca gcaaaacucc cuc                                              23

<210> SEQ ID NO 901
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 901
ucccucaacu ggaugaagaa acu                                              23

<210> SEQ ID NO 902
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 902
uccuguuugc uguguaugau caa                                              23

<210> SEQ ID NO 903
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 903
uguuugcugu guaugaucaa agc                                              23

<210> SEQ ID NO 904
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
```

-continued

Synthetic oligonucleotide"

<400> SEQUENCE: 904
aaccgaccag cuuguuugug aaa                          23

<210> SEQ ID NO 905
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 905
auuccaaccg accagcuugu uug                          23

<210> SEQ ID NO 906
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 906
gcccauuccu guuugcugug uau                          23

<210> SEQ ID NO 907
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 907
cccaccuuuu cuucuaauga guc                          23

<210> SEQ ID NO 908
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 908
cuguuugcug uguaugauca aag                          23

<210> SEQ ID NO 909
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 909
cugcugagaa gauugacagg uuc                          23

<210> SEQ ID NO 910
<211> LENGTH: 23

```
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 910
cuuuccagca aacucccuc aac                                              23

<210> SEQ ID NO 911
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 911
gcugcugaga agauugacag guu                                             23

<210> SEQ ID NO 912
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 912
ggucucacuu uccagcaaaa cuc                                             23

<210> SEQ ID NO 913
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 913
cauccacaau gagaguaccu gug                                             23

<210> SEQ ID NO 914
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 914
uuccaccucg ucauccacaa uga                                             23

<210> SEQ ID NO 915
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 915
```
ucucacuuuc cagcaaaacu ccc          23

<210> SEQ ID NO 916
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 916
acucccucaa cuggaugaag aaa          23

<210> SEQ ID NO 917
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 917
augagaguac cugugagcag cug          23

<210> SEQ ID NO 918
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 918
aaagaauucc aaccgaccag cuu          23

<210> SEQ ID NO 919
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 919
cccauuccug uuugcugugu aug          23

<210> SEQ ID NO 920
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 920
aagaauucca accgaccagc uug          23

<210> SEQ ID NO 921
<211> LENGTH: 23
<212> TYPE: RNA
<213> ORGANISM: Artificial Sequence
<220> FEATURE:
<221> NAME/KEY: source -continued

```
<223> OTHER INFORMATION: /note="Description of Artificial Sequence:
      Synthetic oligonucleotide"

<400> SEQUENCE: 921
gucauccaca augagaguac cug                                              23

<210> SEQ ID NO 922
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 922
cgcccauucc uguuugcugu gua                                              23

<210> SEQ ID NO 923
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 923
ugcuggguuu auuuuagaga aug                                              23

<210> SEQ ID NO 924
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 924
uugcuggguu uauuuuagag aau                                              23

<210> SEQ ID NO 925
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 925
auauggcaug cacagugagc uau                                              23

<210> SEQ ID NO 926
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 926
gagagagagc ccacagaguc uac                                              23

<210> SEQ ID NO 927
```

```
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 927
aggcaagaac caguguuuag cgc                                                23

<210> SEQ ID NO 928
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 928
uuccagcaaa acucccucaa cug                                                23

<210> SEQ ID NO 929
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 929
uccaccucgu cauccacaau gag                                                23

<210> SEQ ID NO 930
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 930
cucgucaucc acaaugagag uac                                                23

<210> SEQ ID NO 931
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 931
uccucccacg cucucuggac uuc                                                23

<210> SEQ ID NO 932
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 932
```
aaaacucccu caacuggaug aag                                                   23

<210> SEQ ID NO 933
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 933
gcugagaaga uugacagguu cau                                                   23

<210> SEQ ID NO 934
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 934
caccucguca uccacaauga gag                                                   23

<210> SEQ ID NO 935
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 935
cugagaagau ugacagguuc aug                                                   23

<210> SEQ ID NO 936
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 936
aacuucuugg gcuuccguau aua                                                   23

<210> SEQ ID NO 937
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 937
cuuccaccuc gucauccaca aug                                                   23

<210> SEQ ID NO 938
<211> LENGTH: 23
<212> TYPE: RNA
<213> ORGANISM: Artificial Sequence
<220> FEATURE:

```
<221> NAME/KEY: source
<223> OTHER INFORMATION: /note="Description of Artificial Sequence:
      Synthetic oligonucleotide"

<400> SEQUENCE: 938
gaagauugac agguucaugc agg                                            23

<210> SEQ ID NO 939
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 939
aacucccuca acuggaugaa gaa                                            23

<210> SEQ ID NO 940
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 940
acaaugagag uaccugugag cag                                            23

<210> SEQ ID NO 941
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 941
gucauccaca augagaguac a                                              21

<210> SEQ ID NO 942
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 942
cacaaugaga guaccuguga a                                              21

<210> SEQ ID NO 943
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 943
gucucccacc uuuucuucua a                                              21
```

```
<210> SEQ ID NO 944
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 944
ccucaacugg augaagaaac u                                              21

<210> SEQ ID NO 945
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 945
ccucgucauc cacaaugaga a                                              21

<210> SEQ ID NO 946
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 946
gucauccaca augagaguac a                                              21

<210> SEQ ID NO 947
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 947
gucauccaca augagaguac a                                              21

<210> SEQ ID NO 948
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 948
gucauccaca augagaguac a                                              21

<210> SEQ ID NO 949
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

```
<400> SEQUENCE: 949
gucucccacc uuucuucua a                                                21

<210> SEQ ID NO 950
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 950
cacaaugaga guaccuguga a                                               21

<210> SEQ ID NO 951
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 951
uguacucuca uuguggauga cga                                             23

<210> SEQ ID NO 952
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 952
uucacaggua cucucauugu gga                                             23

<210> SEQ ID NO 953
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 953
uuagaagaaa aggugggaga cug                                             23

<210> SEQ ID NO 954
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 954
aguutcuuca uccaguugag gga                                             23
```

```
<210> SEQ ID NO 955
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 955
uucucauugu ggaugacgag gug                                            23

<210> SEQ ID NO 956
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 956
ugtacucuca uuguggauga cga                                            23

<210> SEQ ID NO 957
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 957
uguacucuca uuguggauga cga                                            23

<210> SEQ ID NO 958
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 958
uguacuctca uuguggauga cga                                            23

<210> SEQ ID NO 959
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 959
uuagaagaaa aggugggaga cug                                            23

<210> SEQ ID NO 960
```

```
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 960
uucacaggua cucucauugu gga                                           23
```